(12) United States Patent
Cantin et al.

(10) Patent No.: US 7,714,004 B2
(45) Date of Patent: May 11, 2010

(54) INDANE ACETIC ACID DERIVATIVES AND THEIR USE AS PHARMACEUTICAL AGENTS, INTERMEDIATES, AND METHOD OF PREPARATION

(75) Inventors: Louis-David Cantin, Hamden, CT (US); Soongyu Choi, Skillman, NJ (US); Roger B. Clark, Lexington, MA (US); Martin F. Hentemann, Hamden, CT (US); Xin Ma, Bethany, CT (US); Joachim Rudolph, Guilford, CT (US); Sidney X. Liang, Bethany, CT (US); Christiana Akuche, Hamden, CT (US); Rico C. Lavoie, Cheshire, CT (US); Libing Chen, Milford, CT (US); Dyuti Majumdar, Cambridge, MA (US); Philip L. Wickens, Wallingford, CT (US)

(73) Assignee: Bayer Pharmaceuticals Corporation, West Haven, CT (US)

( * ) Notice: Subject to any disclaimer, the term of this patent is extended or adjusted under 35 U.S.C. 154(b) by 862 days.

(21) Appl. No.: 10/537,630

(22) PCT Filed: Dec. 19, 2003

(86) PCT No.: PCT/US03/40842

§ 371 (c)(1),
(2), (4) Date: Jun. 3, 2005

(87) PCT Pub. No.: WO2004/058174

PCT Pub. Date: Jul. 15, 2004

(65) Prior Publication Data

US 2006/0084680 A1    Apr. 20, 2006

Related U.S. Application Data

(60) Provisional application No. 60/435,310, filed on Dec. 20, 2002.

(51) Int. Cl.
*A61K 31/426*   (2006.01)
*C07D 277/20*   (2006.01)

(52) U.S. Cl. ...................... 514/365; 548/202
(58) Field of Classification Search ................ 514/319, 514/567, 569; 546/205; 562/498
See application file for complete search history.

(56) References Cited

U.S. PATENT DOCUMENTS 6,828,335 B2 * 12/2004 Lowe et al. ................. 514/340

FOREIGN PATENT DOCUMENTS

| EP | 0298465 | 1/1989 |
|----|---------|--------|
| WO | 03011842 | 2/2003 |
| WO | 03089418 | 10/2003 |

OTHER PUBLICATIONS

Examination Report corresponding to European Application No. 03800063.4 dated Mar. 18, 2009.

* cited by examiner

*Primary Examiner*—Kamal A Saeed
*Assistant Examiner*—Kristin Bianchi
(74) *Attorney, Agent, or Firm*—Myers Bigel Sibley & Sajovec, PA

(57) ABSTRACT

This invention relates to novel indane acetic acid derivatives which are useful in the treatment of diseases such as diabetes, obesity, hyperlipidemia, and atherosclerotic diseases. The invention also relates to intermediates useful in preparation of indane acetic derivatives and to methods of preparation.

34 Claims, No Drawings

INDANE ACETIC ACID DERIVATIVES AND THEIR USE AS PHARMACEUTICAL AGENTS, INTERMEDIATES, AND METHOD OF PREPARATION

This application claims benefit of U.S. Provisional Application Ser. No. 60/435,310, filed Dec. 20, 2002, the contents of which are incorporated herein by reference in their entirety.

FIELD OF THE INVENTION

This invention is directed to indane acetic acid derivatives and their use in pharmaceutical compositions for the treatment of diseases such as diabetes, obesity, hyperlipidemia, and atherosclerotic disease. The invention is also directed to intermediates useful in preparation of indane acetic derivatives and to methods of preparation.

BACKGROUND OF THE INVENTION

Type 2 diabetes is the more common form of diabetes, with 90-95% of hyperglycemic patients experiencing this form of the disease. In type 2 diabetes, there appears to be a reduction in the pancreatic β-cell mass, several distinct defects in insulin secretion, and a decrease in tissue sensitivity to insulin. The symptoms and consequences of this form of diabetes include fatigue, frequent urination, thirst, blurred vision, frequent infections and slow healing of sores, diabetic nerve damage, retinopathy, micro and macro blood vessel damage, and heart and renal disease.

Resistance to the metabolic actions of insulin is one of the key features of type 2 diabetes. Insulin resistance is characterized by impaired uptake and utilization of glucose in insulin-sensitive target organs, for example, adipocytes and skeletal muscle, and by impaired inhibition of hepatic glucose output. Functional insulin deficiency, insulin resistance in the periphery, and the failure of insulin to suppress hepatic glucose output results in fasting hyperglycemia. Pancreatic β-cells compensate for the insulin resistance by secreting increased levels of insulin. However, the β-cells are unable to maintain this high output of insulin, and eventually, the glucose-induced insulin secretion falls, leading to the deterioration of glucose homeostasis and to the subsequent development of overt diabetes. Hyperinsulinemia is also linked to insulin resistance, hypertriglyceridemia, low high-density lipoprotein (HDL) cholesterol, and increased plasma concentration of low-density lipoproteins (LDL). The association of insulin resistance and hyperinsulinemia with these metabolic disorders has been termed "Syndrome X," and has been strongly linked to an increased risk of hypertension and coronary artery disease.

Obesity is an excessive accumulation of adipose tissue. Excess adipose tissue is associated with the development of serious medical conditions, for example, type 2 diabetes, hypertension, coronary artery disease, hyperlipidemia, obesity, and certain malignancies. The adipocyte may also influence glucose homeostasis through the production of tumor necrosis factor α (TNFα) and other molecules.

Atherosclerotic disease is known to be caused by a number of factors, for example, hypertension, diabetes, low levels of HDL, and high levels of LDL. Atherosclerotic-related diseases include cardiovascular disease, coronary heart disease (CHD), cerebrovascular disease, and peripheral vessel disease. Coronary heart disease includes CHD death, myocardial infarction, and coronary revascularization. Cerebrovascular disease includes ischemic or hemorrhagic stroke, and transient ischemic attacks.

Accordingly, despite the presence of some pharmaceuticals that are used to treat these diseases, there remains a need for new pharmaceuticals that are both safe and effective agents for the treatment of the disease, and for useful methods to prepare them.

The present invention relates to compounds which are useful in the treatment of diabetes and related disorders such as Syndrome X, impaired glucose tolerance, impaired fasting glucose, and hyperinsulinemia; obesity; atherosclerotic disease, dyslipidemia, and related disorders such as hypertriglyceridemia, low HDL cholesterol, and hypercholesteremia; cardiovascular disease; and cerebrovascular disease.

DESCRIPTION OF THE INVENTION

The invention provides indane acetic acid derivatives of Formula (I)

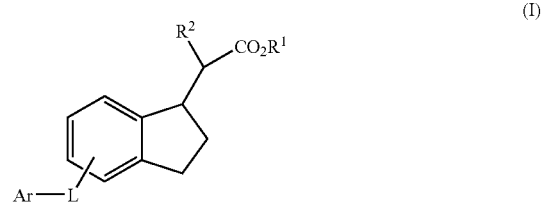

(I)

wherein
R$^1$ and R$^2$ are independently H, C$_1$-C$_6$ alkyl, or C$_3$-C$_6$ cycloalkyl;
L is a linker and selected from
—(CH$_2$)$_m$—X—,
—Y—(CH$_2$)$_n$—X—,
and

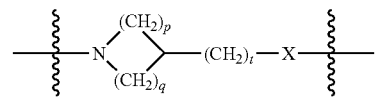

wherein
X is selected from the group O, S, S(═O), and S(═O)$_2$,
Y is selected from the group O, NR$^5$, S, S(═O), and S(═O)$_2$,
m is 1, 2, or 3,
n is 2, 3, or 4,
t is 0 or 1,
p is 0, 1, 2, or 3,
q is 1, 2, 3, or 4,
wherein the sum of p and q is 1, 2, 3, or 4;
Ar is selected from the group phenyl and a 6-membered heteroaryl ring containing up to three N atoms,
said Ar being optionally substituted at any available position by 1 to 5 independently selected R$^3$ groups, and optionally fused to a 5- or 6-membered saturated carbocyclic ring, a 5- or 6-membered unsaturated carbocyclic ring, or
a 5- or 6-membered heterocyclic ring containing up to 3 additional heteroatoms selected from N, O, and S, wherein
said fused ring may be optionally substituted at any available position by 1 to 4 independently selected $R^4$ groups;

$R^3$ is selected from
hydroxy,
SH,
halo,
CN,
$NO_2$,
$C(=O)OH$,
$C(=O)-OC_1-C_6$ alkyl,
$C(=O)-OC_3-C_6$ cycloalkyl,
$NR^6R^7$,
$C(=O)NR^6R^7$,
$C(=S)NR^6R^7$,
$C_1-C_6$ alkyl optionally substituted with halo, OH, $NR^6R^7$, or $C_1-C_6$ alkoxy,
$C_1-C_6$ haloalkyl,
$C_1-C_6$ alkoxy,
$C_1-C_6$ thioalkyl,
$C_2-C_6$ alkenyl,
$C_1-C_6$ haloalkoxy,
$C_3-C_8$ cycloalkyl,
$C_3-C_8$ cycloalkoxy,
phenoxy optionally substituted on the phenyl ring with halo, $C_1-C_6$ alkyl, or $C_1-C_6$ alkoxy, and
a mono or bicyclic ring radical selected from the group consisting of
a) phenyl optionally fused to
a 5- or 6-membered saturated or partially unsaturated carbocyclic ring, or
a 5- or 6-membered saturated or partially unsaturated heterocyclic ring containing from 1-3 heteroatoms selected from N, O, and S,
b) a 5- or 6-membered heterocyclic ring radical containing up to 4 heteroatoms selected from N, O, or S, optionally fused to
a 5- or 6-membered saturated or partially unsaturated carbocyclic ring, or
a 5- or 6-membered saturated or partially unsaturated heterocyclic ring containing from 1-3 heteroatoms selected from N, O, and S,
said mono or bicyclic ring radical being optionally substituted with up to 5 groups independently selected from
halo,
hydroxy,
oxo,
CN,
$C_1-C_6$ alkyl optionally substituted with halo, OH, $NR^6R^7$, or $C_1-C_6$ alkoxy,
$C_1-C_6$ haloalkyl,
$C_1-C_6$ alkoxy,
$C_1-C_6$ thioalkyl,
$C_1-C_6$ haloalkoxy,
$C_3-C_8$ cycloalkyl,
$C_3-C_8$ cycloalkoxy,
$C_1-C_6$ acyl,
$C(=O)OH$,
$CH_2C(=O)OH$,
$NR^6R^7$,
$C(=O)NR^6R^7$,
$C(=O)OC_1-C_6$ alkyl, and
$C(=O)OC_3-C_6$ cycloalkyl;

$R^4$ is selected from
oxo,
hydroxy,
halo,
CN,
$NR^6R^7$,
$C_1-C_6$ alkyl optionally substituted with OH, $NR^6R^7$, or $C_1-C_6$ alkoxy,
$C_1-C_6$ haloalkyl,
$C_1-C_6$ alkoxy,
$C_1-C_6$ thioalkyl,
$C_1-C_6$ haloalkoxy,
$C_3-C_8$ cycloalkyl, and
$C_3-C_8$ cycloalkoxy;

$R^5$ is selected from
H,
$C_1-C_6$ alkyl optionally substituted with $C_3-C_6$ cycloalkyl,
$C_1-C_6$ acyl,
benzyl optionally substituted with halo, $C_1-C_6$ alkoxy, $(C_1-C_6)$alkyl, CN, $NH_2$, $N[(C_1-C_3)alkyl]_2$, $NO_2$, or $CF_3$,
$C_3-C_6$ cycloalkyl, and
$C(=O)OC_1-C_6$ alkyl;

$R^6$ and $R^7$ are independently selected from
H,
$C_1-C_6$ alkyl optionally substituted with $C_3-C_6$ cycloalkyl,
$C_1-C_6$ acyl,
benzyl optionally substituted with halo, $C_1-C_6$ alkoxy, $(C_1-C_6)$alkyl, CN, $NH_2$, $N[(C_1-C_3)alkyl]_2$, $NO_2$, or $CF_3$,
$C_3-C_6$ cycloalkyl, and
phenyl optionally substituted with halo, $C_1-C_6$ alkoxy, $(C_1-C_6)$alkyl, CN, $N[(C_1-C_3)alkyl]_2$, $NO_2$, or $CF_3$, or $R^6$ and $R^7$ may be taken together with the nitrogen atom to which they are attached to form a 5- or 6-membered heterocyclic ring optionally interrupted by $NR^5$ or O;

and the pharmacologically acceptable esters and salts thereof;
provided that when L is $-Y-(CH_2)_n-X-$, X is O, Y is O, and Ar is phenyl; then $R^3$ cannot be a hydroxy group in the meta position relative to the attachment point of L on the phenyl ring.

DEFINITIONS

The terms identified above have the following meaning throughout: The term "halo" means F, Cl, Br, or I.

The term "$C_1-C_6$ alkyl" means a straight or branched saturated hydrocarbon carbon chain of from 1 to about 6 carbon atoms, respectively. Examples of such groups include methyl, ethyl, isopropyl, sec-butyl, 2-methylpentyl, n-hexyl, and the like.

The term "$C_2-C_6$ alkenyl" means a straight or branched unsaturated hydrocarbon carbon chain of from 2 to about 6 carbon atoms. Examples of such groups include vinyl, allyl, isopropenyl, 2-butenyl, 3ethyl-2-butenyl, 4-hexenyl, and the like.

The term "$C_1-C_6$ haloalkyl" means a $C_1-C_6$ alkyl group substituted by 1 to 3 halogen atoms or fluorine up to the perfluoro level. Examples of such groups include trifluoromethyl, tetrafluoroethyl, 1,2-dichloropropyl, 5-bromopentyl, 6-iodohexyl, and the like.

The terms "$C_3$-$C_6$ cycloalkyl" and "$C_3$-$C_8$ cycloalkyl" mean a saturated carbocyclic ring system of from 3 to about 6 carbon atoms or from 3 to about 8 carbon atoms, respectively. Examples of such groups include cyclopropyl, cyclobutyl, cyclopentyl, cyclohexyl, and the like.

The term "$C_1$-$C_6$ acyl" means a $C_1$-$C_6$ alkyl group attached at the carbonyl carbon atom. The radical is attached to the rest of the molecule at the carbonyl bearing carbon atom. Examples of such groups include acetyl, propionyl, n-butanoyl, 2-methylpentantoyl, and the like.

The term "$C_1$-$C_6$ alkoxy" means a linear or branched saturated carbon group having from 1 to about 6 C atoms, said carbon group being attached to an O atom. The O atom is the point of attachment of the alkoxy substituent to the rest of the molecule. Such groups include, but are not limited to, methoxy, ethoxy, n-propoxy, isopropoxy, and the like.

The term "$C_1$-$C_6$ thioalkyl" means a linear or branched saturated carbon group having from 1 to about 6 C atoms, said carbon group being attached to an S atom. The S atom is the point of attachment of the thioalkyl substituent to the rest of the molecule. Such groups include, for example, methylthio, propylthio, hexylthio, and the like.

The term "$C_1$-$C_6$ haloalkoxy" means a $C_1$-$C_6$ alkoxy group further substituted on C with 1 to 3 halogen atoms or fluorine up to the perfluoro level.

The term "$C_3$-$C_8$ cycloalkoxy" means a $C_3$-$C_8$ cycloalkyl group attached to an O atom. The O atom is the point of attachment of the cycloalkoxy group with the rest of the molecule.

The term "phenoxy" means a phenyl group attached to an O atom. The O atom is the point of attachment of the phenoxy group to the rest of the molecule.

The term "6-membered heteroaryl ring" means a 6-membered monocyclic heteroaromatic ring radical containing 1-5 carbon atoms and up to the indicated number of N atoms. Examples of 6-membered heteroaryl rings are pyridyl, pyrimidyl, pyridazinyl, pyrazinyl, triazinyl, and the like.

The term "5- or 6-membered heterocyclic ring" means a 5 or 6-membered ring containing 1-5 C atoms and up to the indicated number of N, O, and S atoms, and may be aromatic, partially saturated, or fully saturated.

The term "optionally substituted" means that, unless indicated otherwise, the moiety so modified may have from one to up to the number of the substituents indicated, provided the resulting substitution is chemically feasible as recogized in the art. Each substituent may replace any H atom on the moiety so modified as long as the replacement is chemically possible and chemically stable. For example, a chemically unstable compound would be one where each of two substituents is bonded to a single C atom through each substituents heteroatom. Another example of a chemically unstable compound would be one where an alkoxy group is bonded to the unsaturated carbon of an alkene to form an enol ether. When there are two or more substituents on any moiety, each substituent is chosen independently of the other substituent so that, accordingly, the substituents can be the same or different.

When the 5-or 6-membered heterocyclic ring is attached to the rest of the molecule as a substituent, it becomes a radical. Examples of 5- or 6-membered heteroaryl ring radicals are furyl, pyrrolyl, thienyl, pyrazolyl, isoxazolyl, imidazolyl, oxazolyl, thiazolyl, isothiazolyl, triazolyl, thiadiazolyl, oxadiazolyl, pyridyl, pyrimidyl, pyridazinyl, pyrazinyl, triazinyl, and the like. Examples of partially unsaturated 5- or 6-membered heterocyclic ring radicals include dihydropyrano, pyrrolinyl, pyrazolinyl, imidazolinyl, dihydrofuryl, and the like. Examples of saturated 5- or 6-membered heterocyclic ring radicals include pyrrolidinyl, tetrahydropyridyl, piperidinyl, morpholinyl, tetrahydrofuryl, tetrahydrothienyl, piperazinyl, and the like. The point of attachment of the radical may be from any available C or N atom of the ring to the rest of the molecule.

When the 5-or 6-membered heterocyclic ring is fused to another ring contained in the rest of the molecule, it forms a bicyclic ring. Examples of such 5- and 6-heterocyclic fused rings include pyrrolo, furo, pyrido, piperido, thieno, and the like. The point of fusion is at any available face of the heterocyclic ring and parent molecule.

The linker L is substituted at either the 4- or 5 carbon atom (as shown below) of the indane ring in Formula (I), replacing a H atom.

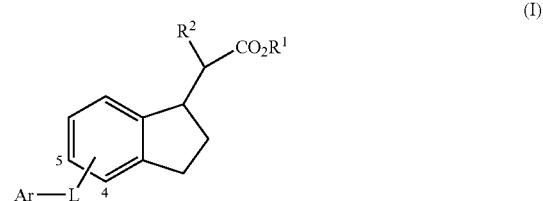

(I)

The compounds described in Tables 1-19 are intended to be representative examples of the invention, and it will be understood that the scope of the invention is not limited by the scope of the examples. Those skilled in the art will recognize that the invention may be practiced with variations on the disclosed structures, materials, compositions and methods, and such variations are regarded as within the ambit of the invention.

A salt of a compound of Formula (I) may be prepared in situ during the final isolation and purification of a compound or by separately reacting the purified compound in its free base form with a suitable organic or inorganic acid and isolating the salt thus formed. Likewise, when the compound of Formula (I) contains a carboxylic acid moiety, (e.g., $R^1$=H), a salt of said compound of Formula (I) may be prepared by separately reacting it with a suitable inorganic or organic base and isolating the salt thus formed. The term "pharmaceutically acceptable salt" refers to a relatively non-toxic, inorganic or organic acid addition salt of a compound of the present invention (see, e.g., Berge et al., J. Pharm. Sci. 66:1-19, 1977).

Representative salts of the compounds of Formula (I) include the conventional non-toxic salts and the quaternary ammonium salts which are formed, for example, from inorganic or organic acids or bases by means well known in the art. For example, such acid addition salts include acetate, adipate, alginate, ascorbate, aspartate, benzoate, benzenesulfonate, bisulfate, butyrate, citrate, camphorate, camphorsulfonate, cinnamate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, itaconate, lactate, maleate, mandelate, methanesulfonate, 2-naphthalenesulfonate, nicotinate, nitrate, oxalate, pamoate, pectinate, persulfate, 3-phenylpropionate, picrate, pivalate, propionate, succinate, sulfonate, tartrate, thiocyanate, tosylate, undecanoate, and the like.

Base salts include, for example, alkali metal salts such as potassium and sodium salts, alkaline earth metal salts such as calcium and magnesium salts, and ammonium salts with organic bases such as dicyclohexylamine, ethanolamine, and N-methyl-D-glucamine. Additionally, basic nitrogen containing groups in the conjugate base may be quaternized with such agents as lower alkyl halides such as methyl, ethyl, propyl, and butyl chlorides, bromides and iodides; dialkyl sulfates like dimethyl, diethyl, and dibutyl sulfate; diamyl sulfates; long chain halides such as decyl, lauryl, myristyl, and strearyl chlorides, bromides and iodides; aralkyl halides like benzyl and phenethyl bromides, and the like.

The esters of Formula (I) in the present invention are non-toxic, pharmaceutically acceptable esters, for example, alkyl esters such as methyl, ethyl, propyl, isopropyl, butyl, isobutyl, or pentyl esters. Additional esters such as, for example, methyl ester or phenyl-$C_1$-$C_5$ alkyl may be used. The compound of Formula (I) may be esterified by a variety of conventional procedures including reacting the appropriate anhydride, carboxylic acid, or acid chloride with the alcohol group of the Formula (I) compound. The appropriate anhydride may be reacted with the alcohol in the presence of a base to facilitate acylation such as 1,8-bis[dimethylamino]naphthalene or N,N-dimethylaminopyridine. An appropriate carboxylic acid may be reacted with the alcohol in the presence of a dehydrating agent such as dicyclohexylcarbodiimide, 1-[3-dimethylaminopropyl]-3-ethylcarbodiimide, or other water soluble dehydrating agents which are used to drive the reaction by the removal of water, and optionally, an acylation catalyst. Esterification may also be effected using the appropriate carboxylic acid in the presence of trifluoroacetic anhydride and optionally, pyridine, or in the presence of N,N-carbonyldiimidazole with pyridine. Reaction of an acid chloride with the alcohol may be carried out with an acylation catalyst such as DMAP or pyridine.

One skilled in the art would readily know how to successfully carry out these as well as other methods of esterification of alcohols.

Additionally, sensitive or reactive groups on the compound of Formula (I) may need to be protected and deprotected during any of the above methods for forming esters. Protecting groups in general may be added and removed by conventional methods well known in the art (see, e.g., T. W. Greene and P. G. M. Wuts, *Protective Groups in Organic Synthesis*; Wiley: New York, (1999)).

The compounds of Formula (I) may contain one or more asymmetric centers, depending upon the location and nature of the various substituents desired. Asymmetric carbon atoms may be present in the (R) or (S) configuration. Preferred isomers are those with the absolute configuration which produces the compound of Formula (I) with the more desirable biological activity. In certain instances, asymmetry may also be present due to restricted rotation about a given bond, for example, the central bond adjoining two aromatic rings of the specified compounds.

Substituents on a ring may also be present in either cis or trans form, and a substituent on a double bond may be present in either Z or E form.

It is intended that all isomers (including enantiomers and diastereomers), either by nature of asymmetric centers or by restricted rotation as described above, as separated, pure or partially purified isomers or racemic mixtures thereof, be included within the scope of the instant invention. The purification of said isomers and the separation of said isomeric mixtures may be accomplished by standard techniques known in the art.

The particular process to be utilized in the preparation of the compounds of this invention depends upon the specific compound desired. Such factors as the selection of the specific moiety, and the specific substituents possible at various locations on the molecule, all play a role in the path to be followed in the preparation of the specific compounds of this invention. Those factors are readily recognized by one of ordinary skill in the art.

Reaction Schemes

In general, the compounds used in this invention may be prepared by standard techniques known in the art, by known processes analogous thereto, and/or by the processes described herein, using starting materials which are either commercially available or producible according to routine, conventional chemical methods. The following preparative reaction schemes are presented to aid the reader in the synthesis of the compounds of the present invention. Unless otherwise specifically defined within a scheme, the groups Ar, $R^1$—$R^7$, X, Y, L, m, n, p, q, and t are as defined hereinabove. The use of "lg", and "lg'" are used to indicate certain leaving groups which are appropriate for the reaction conditions described and have the same meaning throughout. Specifically, the designation "lg" includes groups such as halo, mesylate, tosylate, and the combination of OH/$PPh_3$/ADDP; the designation "lg'" includes such groups as halo, mesylate, tosylate, and the like. The use of "pg" is used to indicate the presence of a standard protecting group which is appropriate for the reaction conditions described and has the same meaning throughout. Specifically, the designation "pg" includes such groups as Boc, Bn, TBDMS, and the like.

Reaction Scheme 1 is particularly useful for the preparation of Formula (I) compounds in which L is —Y—$(CH_2)_n$—X—; X is O; and Y is O, S, or $NR^5$. In this Scheme, a compound of Formula (IV) is prepared either by the basic coupling a compound of Formula (II), for example a phenol, thiophenol, or aniline, with a compound of Formula (III), for example, a dibromoalkane. Alternatively a compound of Formula (VI), for example, a bromo or iodoarene, can be reacted with an alcohol, alkyl amine, or thiol, wherein the alkyl group is also substituted by an optionally protected alcohol (Formula VII), catalyzed by base and/or a palladium catalyst such as Pd(OAc)$_2$/BINAP. The intermediate of Formula (IV) is then allowed to react with a hydroxyindane of Formula (V) with a base when required, such as $Cs_2CO_3$, to give the compound of Formula (Ia); hydrolysis gives the corresponding acid derivative of Formula (Ib). Hydroxyindane compounds of Formula (V) are either commercially available or prepared as described in WO2003/011842A1, and in the examples described hereinbelow.

Reaction Scheme 1

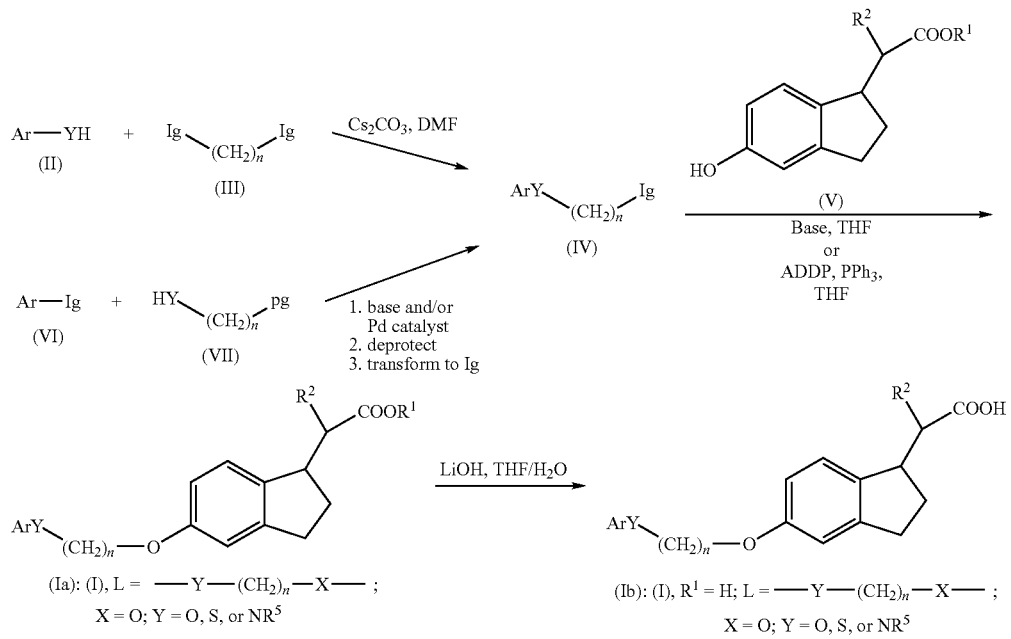

Reaction Scheme 2a is variation of Reaction Scheme 1, also useful for preparation of Formula (I) compounds in which L is —Y—$(CH_2)_n$—X—; X is O; and Y is O, S, or $NR^5$. In this Scheme, the compound of Formula (III) is first allowed to react with the hydroxyindane of Formula (V) in the presence of a base when required, such as $Cs_2CO_3$ to form the intermediate of Formula (VIII). This intermediate is then allowed to react with the Ar—YH compound also in the presence of a base when required, such as $Cs_2CO_3$, to form the compound of Formula (Ia) as described for Reaction Scheme 1.

Reaction Scheme 2a

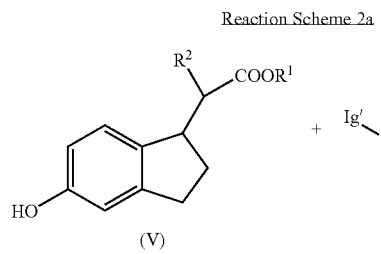

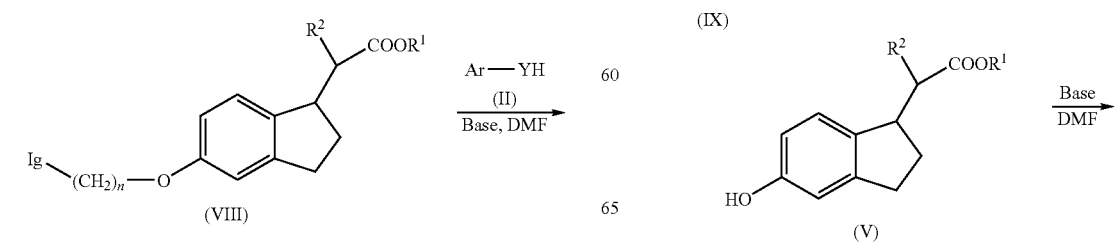

-continued

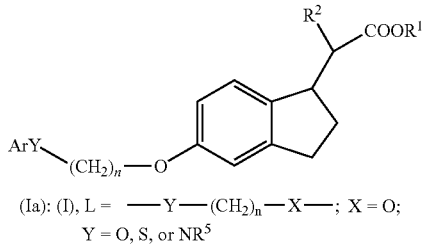

Reaction Scheme 2b is a further variation for the preparation of the above described Formula (Ia) compounds in which the hydroxyindane of Formula (V) is first allowed to react with the compound of Formula (IX) in the presence of a base when required, such as $Cs_2CO_3$, to provide the intermediate of Formula (X). Following deprotection, coupling with the Formula (XI) compound in the presence of base and/or in the presence of a palladium catalyst (e.g., $Pd(OAc)_2$/BINAP), provides the Formula (Ia) product.

Reaction Scheme 2b

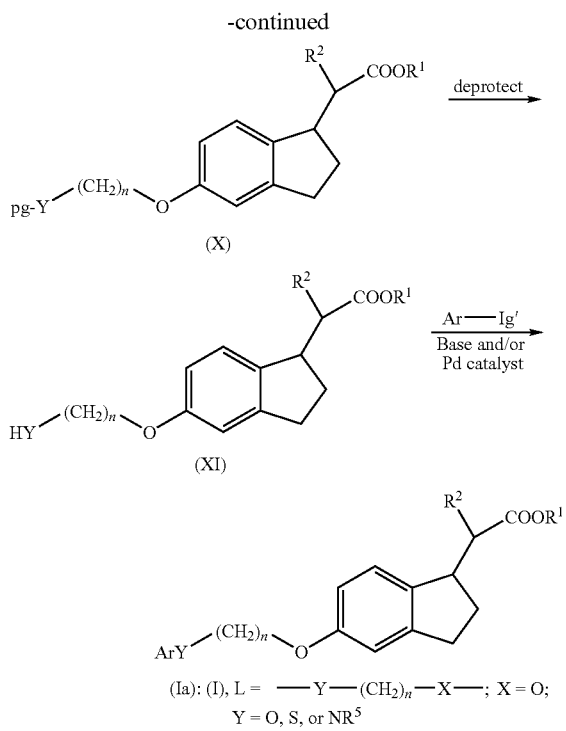

Reaction Schemes 3-18 illustrate other specific methods of preparation of Formula (I) compounds, which are, in general variations of Reaction Schemes 1-3 or methods analogous thereto.

Reaction Scheme 3 illustrates a more specific preparation of compounds of Formula (I) in which Ar is substituted pyridyl, L is —Y—(CH$_2$)$_n$—X—, and X and Y are O. This represents an example of Reaction Scheme 2a in which the Ar—YH compound of Formula (II) is the hydroxypyridine compound of Formula (IIa). Reaction of (IIa) with the Formula (VIII) indane intermediate under basic conditions (e.g., Cs$_2$CO$_3$) gives the ester product of Formula (Ic) and hydrolysis as described above provides the acid of Formula (Id). Compounds prepared by this method appear in Examples 246-247 below and in Table 9a.

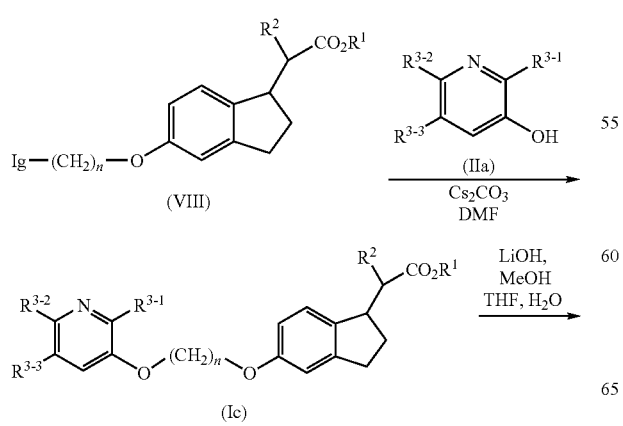

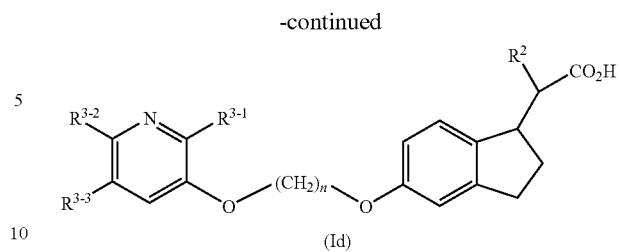

Reaction Scheme 4 illustrates the specific preparation of compounds of Formula (I) in which Ar is substituted pyridyl, L is —Y—CH$_2$)$_n$—X—, X and Y are O, and n is 2. This a specific example of Reaction Scheme 2a and Reaction Scheme 3 in which the coupling of (VIIIa) and (IIa) is carried out under Mitsunobu conditions. Compounds prepared by this method appear in Examples 248-251 below and in Table 9a.

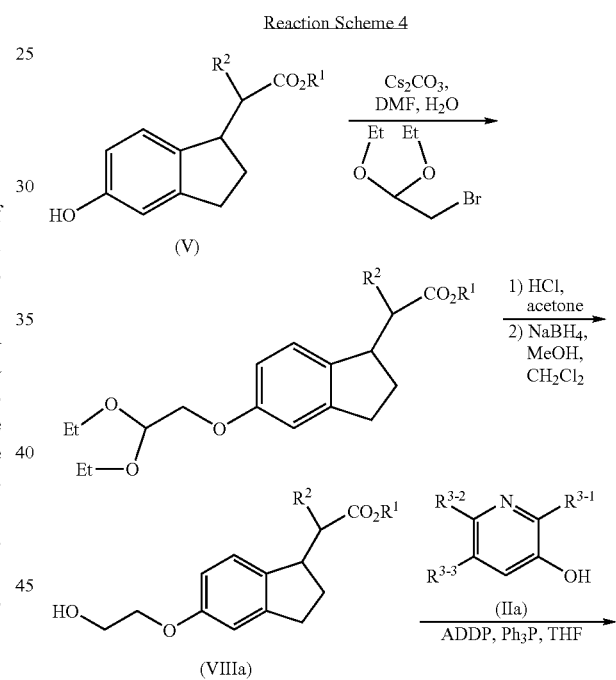

Reaction Scheme 5 illustrates the synthesis of Formula (I) compounds in which Ar is substituted 5-thiazolylpyridinyl, L is —Y—(CH$_2$)$_n$—X—, and X is O. This represents a more specific example of Reaction Scheme 1 in which the coupling of (IVa) and (V) is carried out under Mitsunobu conditions.

The cyano substitutent on the pyridine ring is then further converted into a thiazole ring in two steps, giving the compounds of Formula (Ig) and (Ih). Compounds prepared by this method are shown in Examples 257-261 and in Table 10a below.

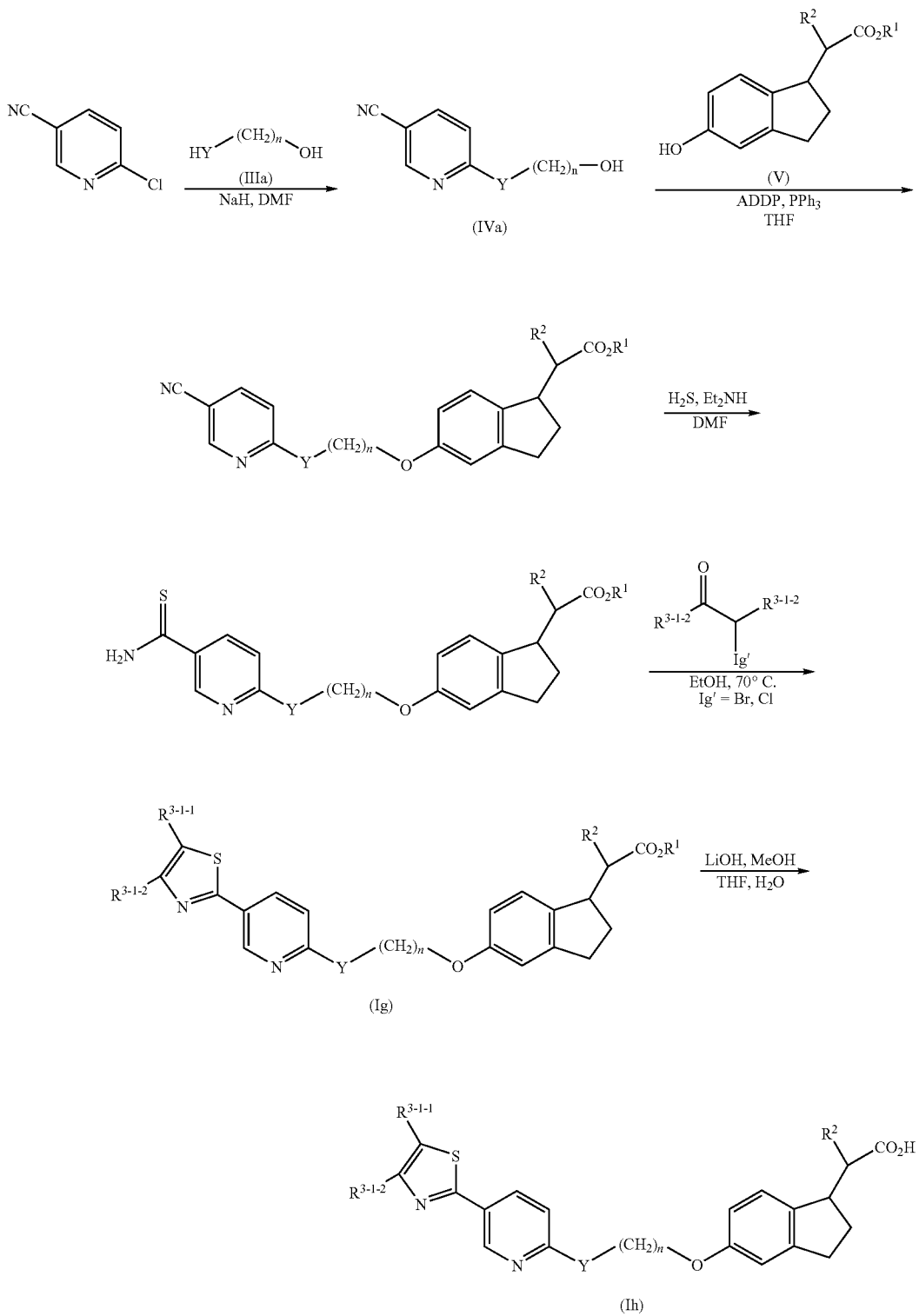

Reaction Scheme 5

Reaction Scheme 6 illustrates specific synthesis of Formula (I) compounds in which Ar is substituted 5-thiazolylpyridinyl, L is —Y—CH$_2$)$_n$—O—, Y is NR$^5$, and n is 3. The 5-thiazolyl substituent is prepared in the same fashion as in Reaction Scheme 5 above. Compounds prepared by this method are shown in Examples 262-268 and in Table 10a below.
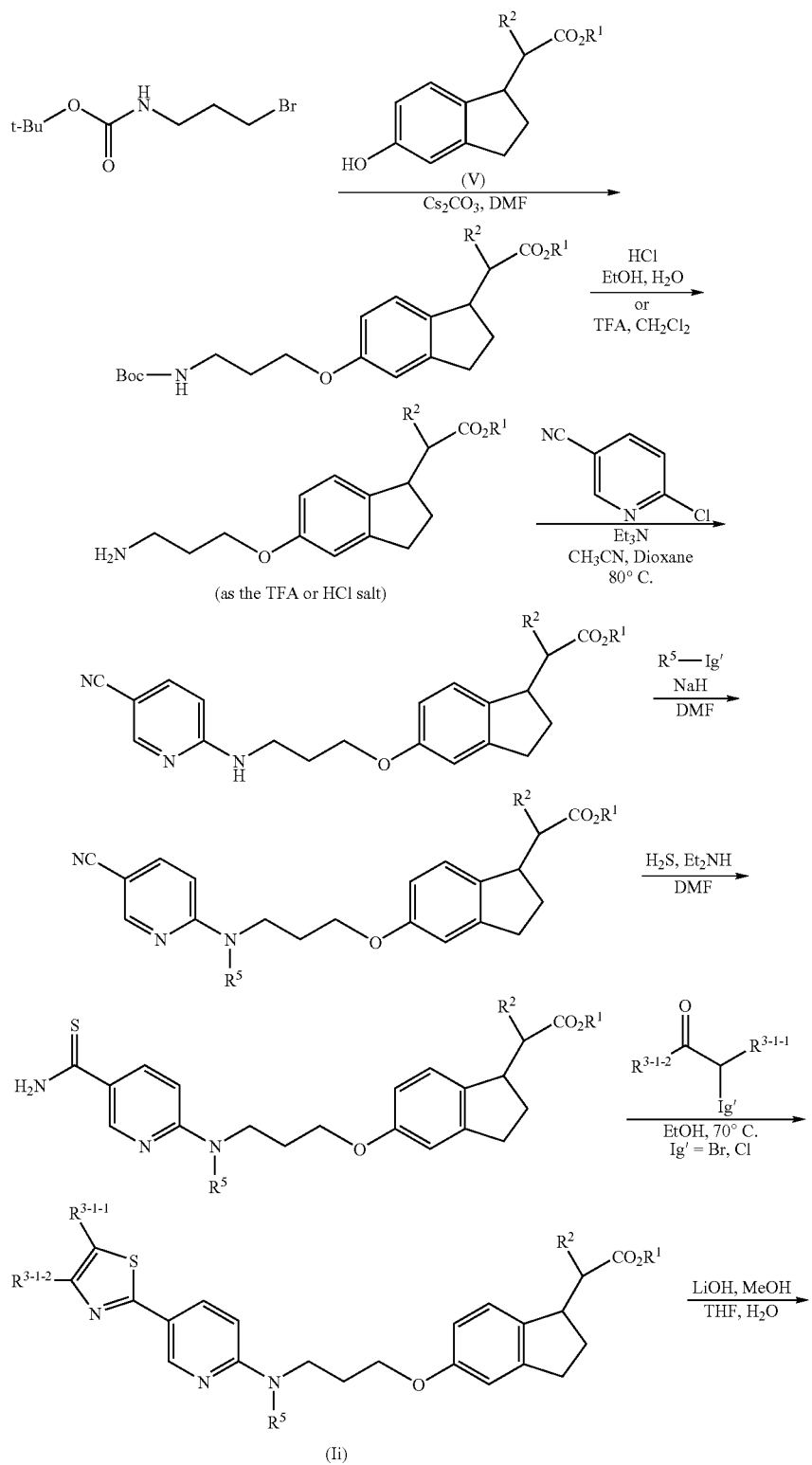
Reaction Scheme 6

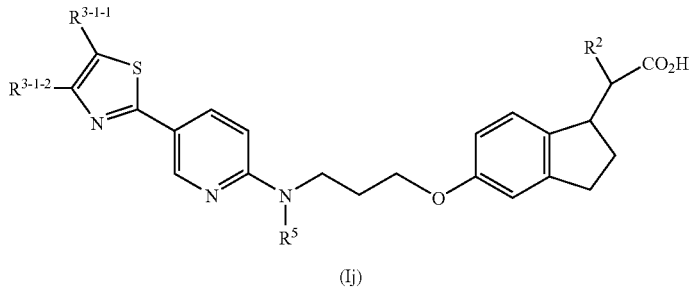

(Ij)

Reaction Scheme 7 illustrates the specific synthesis of Formula (I) compounds in which Ar is substituted pyrimidinyl, L is —Y—CH$_2$)$_n$—O—, and Y is NR$^5$. The coupling of the bromopyrimidine intermediate formed in the intitial coupling is N-alkylated to give the N—R$^5$ group, and then further elaborated using Suzuki coupling conditions to provide the compounds of Formula (Ik) and (Im). Compounds prepared by this method are shown in Examples 281-283 and in Table 11a below.

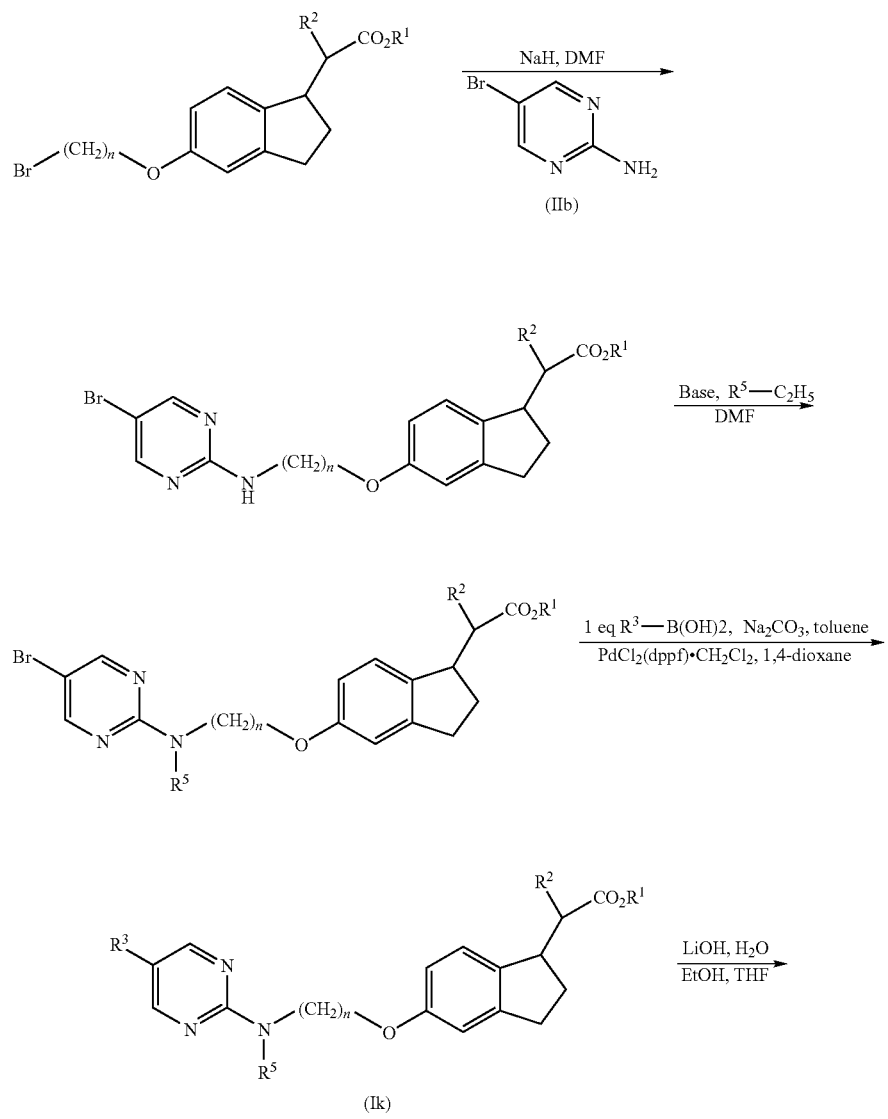

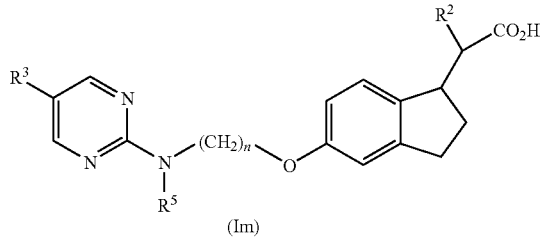

Reaction Scheme 8 illustrates the specific synthesis of Formula (I) compounds in which Ar is 4-phenyl substituted pyrimidinyl, L is —Y—(CH$_2$)$_n$—O—, Y is NR$^5$, and n is 3. This is a variation of Reaction Scheme 7 in which the Suzuki reation is carried prior to the coupling of the indane compound Formula (V) to the Ar—Y—(CH$_2$)$_3$—OH compound of Formula (IVb). Compounds prepared by this method are shown in Examples 290-293 and in Table 12a below.

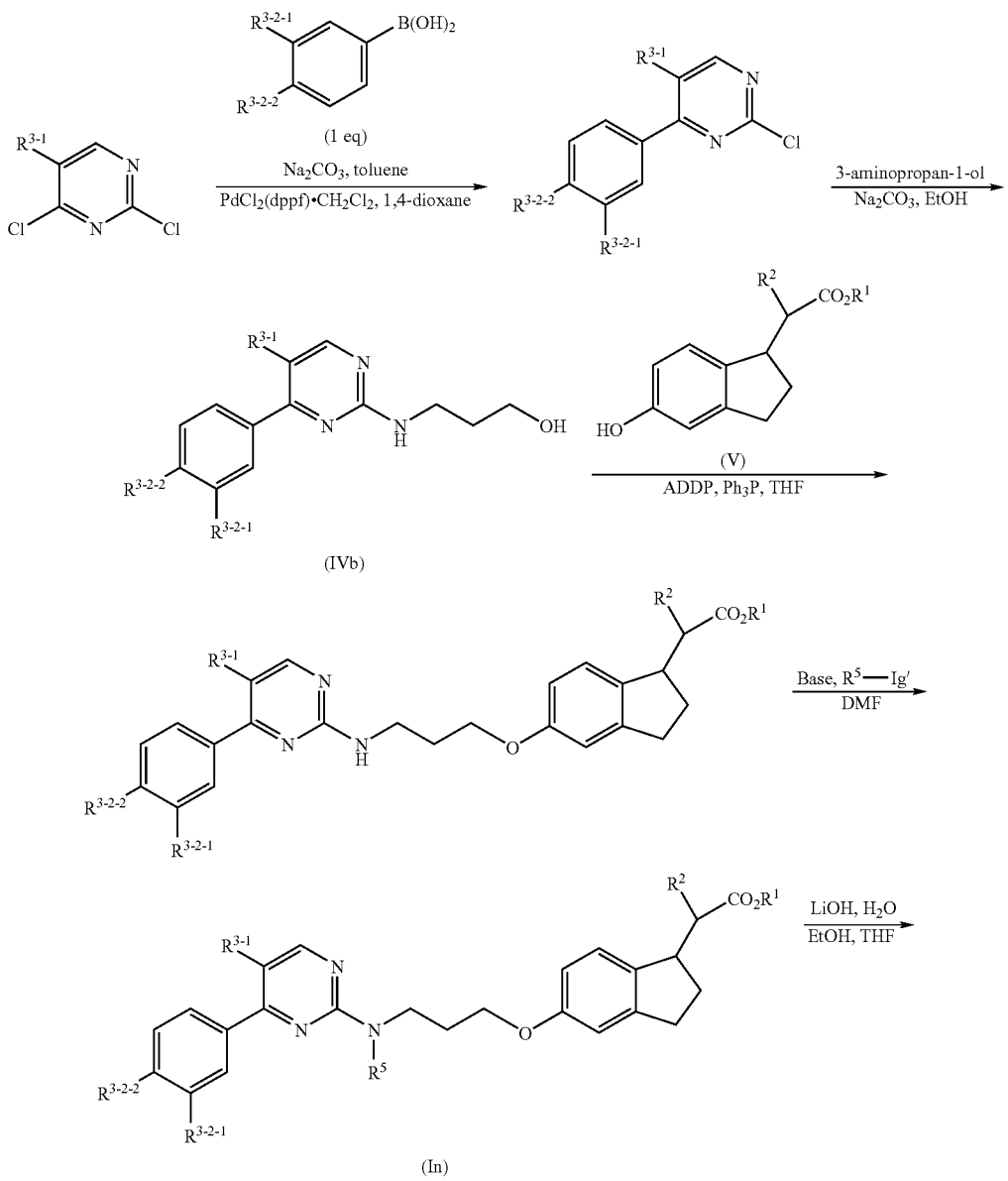

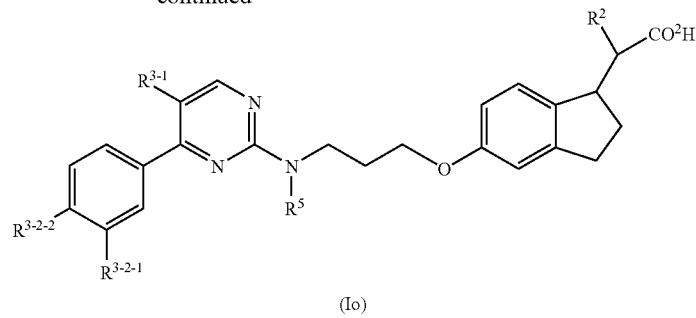

(Io)

Reaction Scheme 9 illustrates a specific synthesis of Formula (I) compounds similar to Reaction Scheme 10, in which Ar is phenyl substituted pyridyl, L is —Y—$(CH_2)_n$—O—, and Y is $NR^5$. It should be noted that the first step of the reaction sequence may generate a mixture of two possible regioisomers. In these cases, the mixture was separated at different stages of the reaction sequence. Compounds prepared by this method are shown in Examples 301-314 and in Table 13a below.

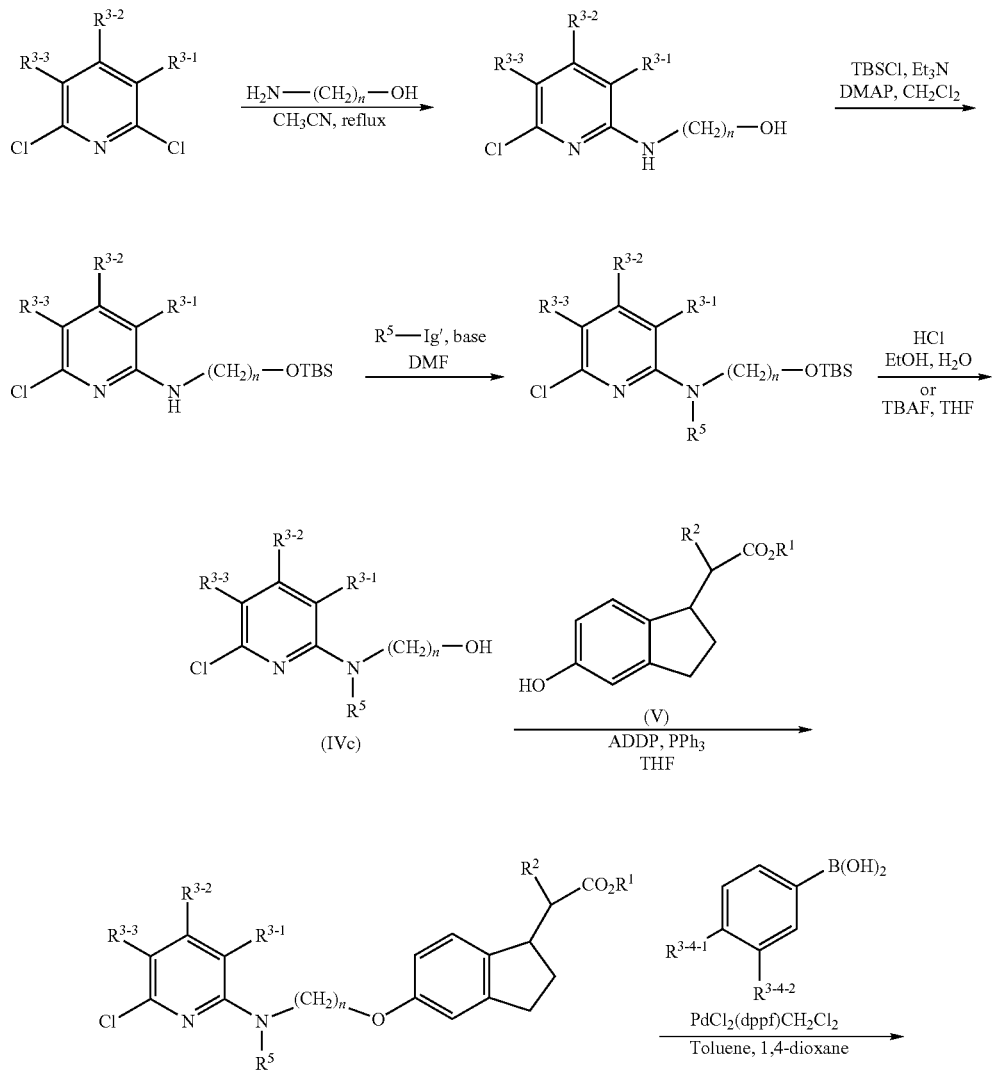

Reaction Scheme 9

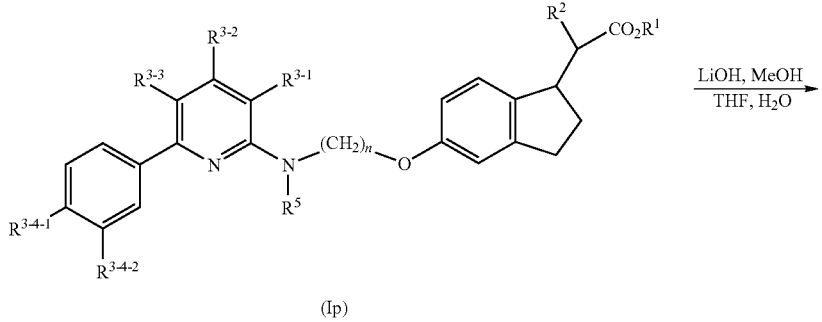

(Ip)

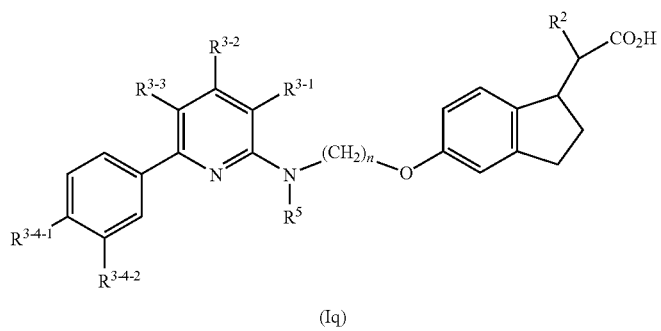

(Iq)

Reaction Scheme 10 illustrates a further synthesis of Formula (I) compounds in which Ar is phenyl substituted pyridyl, L is —Y—(CH$_2$)$_n$—O—, and Y is NR$^5$. This Scheme represents a variation in the synthesis of the Formula (Ip) compound of Reaction Scheme 9 in which the Suzuki reaction step is carried out first. Compounds prepared by this method are shown in Examples 315-320 and in Table 13a below. Hydrolysis of the ester of Formula (Ip), prepared by Reaction Scheme 10, to the acid of Formula (Iq) can be carried out as described in Reaction Scheme 9.

Reaction Scheme 10

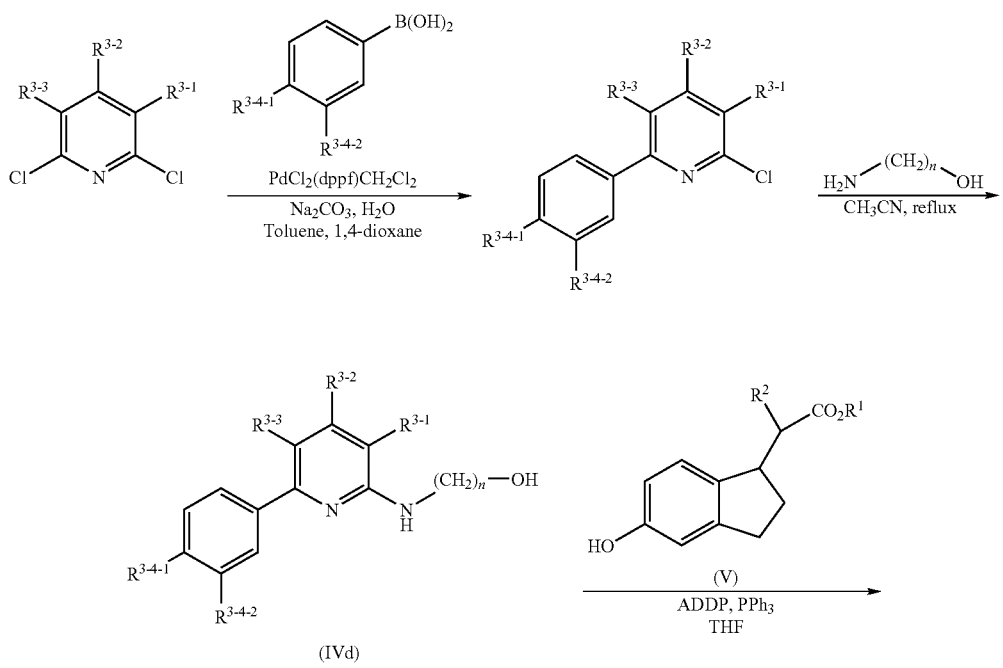

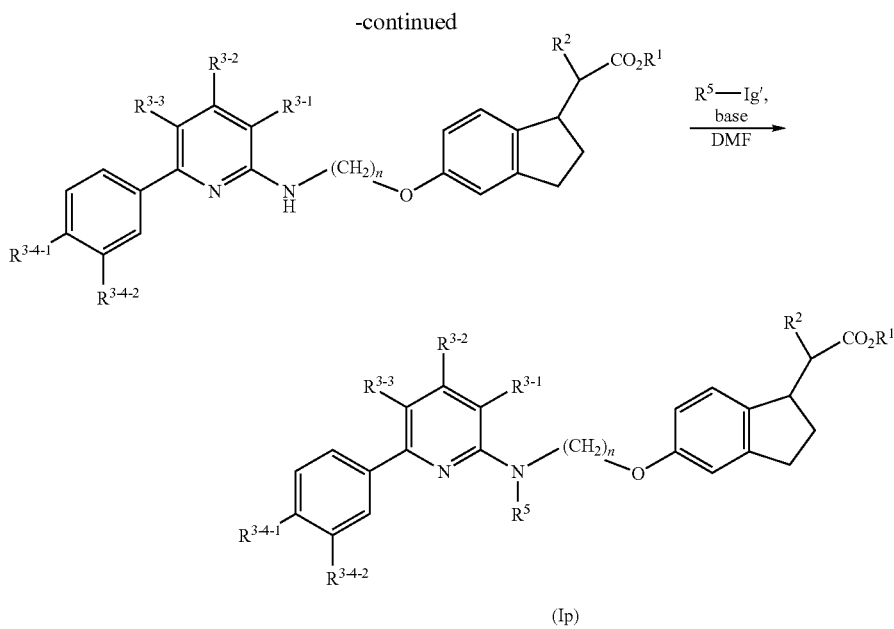

(Ip)

Reaction Scheme 11 illustrates a synthesis of Formula (I) compounds in which Ar is substituted pyrimidyl, L is —Y—(CH$_2$)$_n$—O—, and Y is NR$^5$. This represents the preparation of compounds in which the point of attachment of the pyrimidyl group to the the linker is the 4 (or 6) position rather than the 2-position as described in Reaction Schemes 7 and 8. Compounds prepared by this method are shown in Examples 339-346 and in Tables 14a and 15a below, and Examples 297-300 in Table 12a.

Reaction Scheme 11

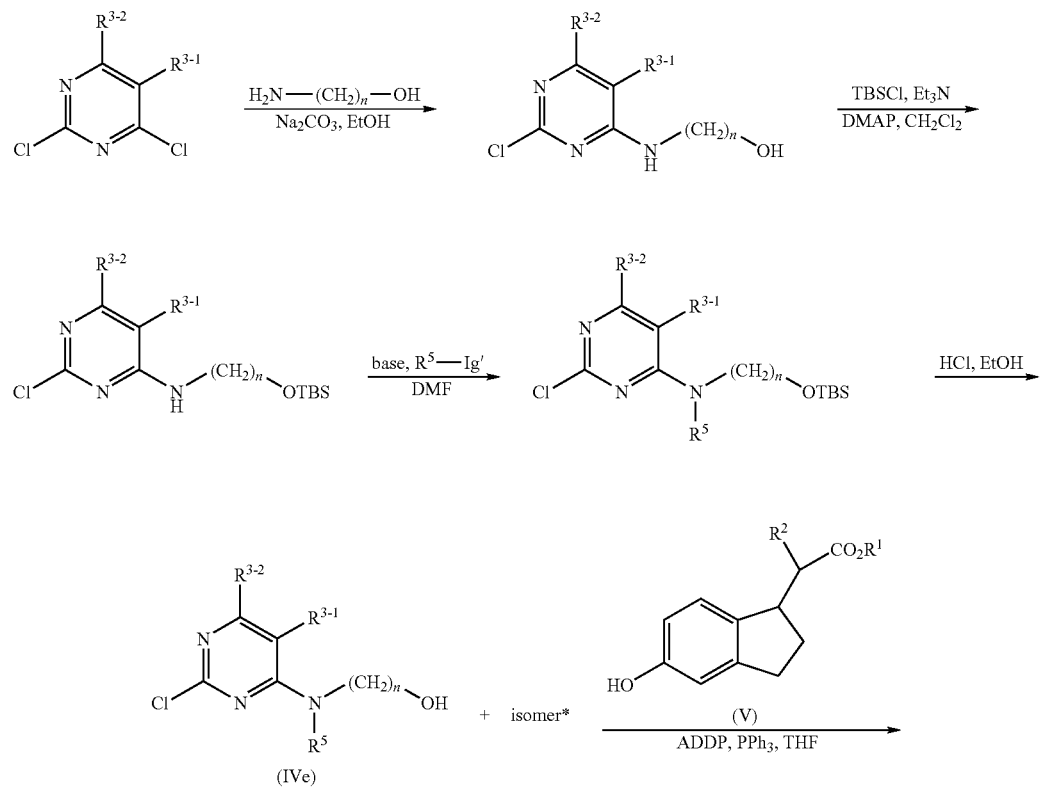

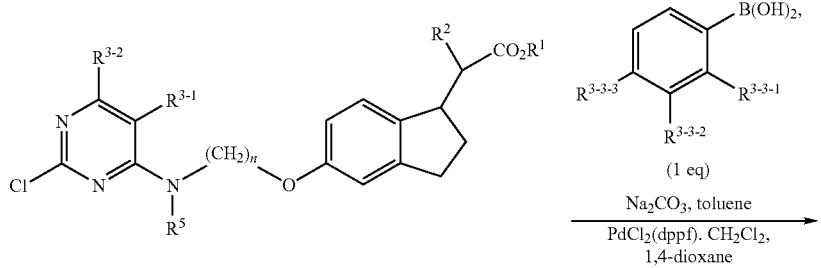

(1 eq)

Na₂CO₃, toluene
PdCl₂(dppf).CH₂Cl₂,
1,4-dioxane

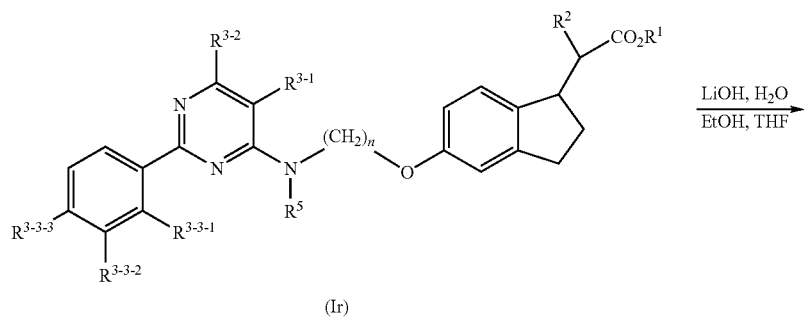

(Ir)

LiOH, H₂O
EtOH, THF

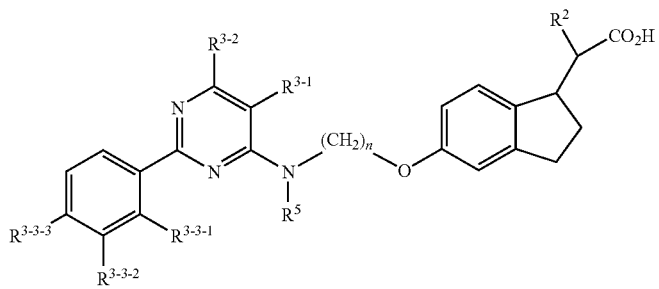

(Is)

*When $R^{3-1}$ = CF₃ and $R^{3-2}$ = H, the product is obtained as a 1:1 mixture with the regioisomer below:

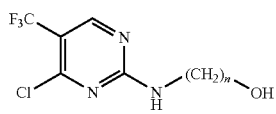

Reaction Scheme 12 illustrates an additional synthesis of Formula (I) compounds in which Ar is substituted pyrimidyl, $R^1$ and $R^2$ are H, L is —Y—$(CH_2)_n$—O—, and Y is $NR^5$. Compounds prepared by this method are shown in Examples 408-410 and in Table 16a.

Reaction Scheme 12

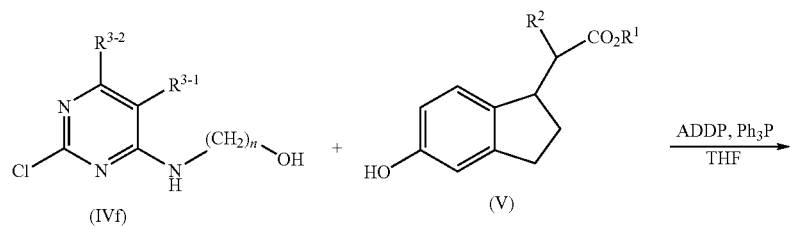

ADDP, Ph₃P
THF

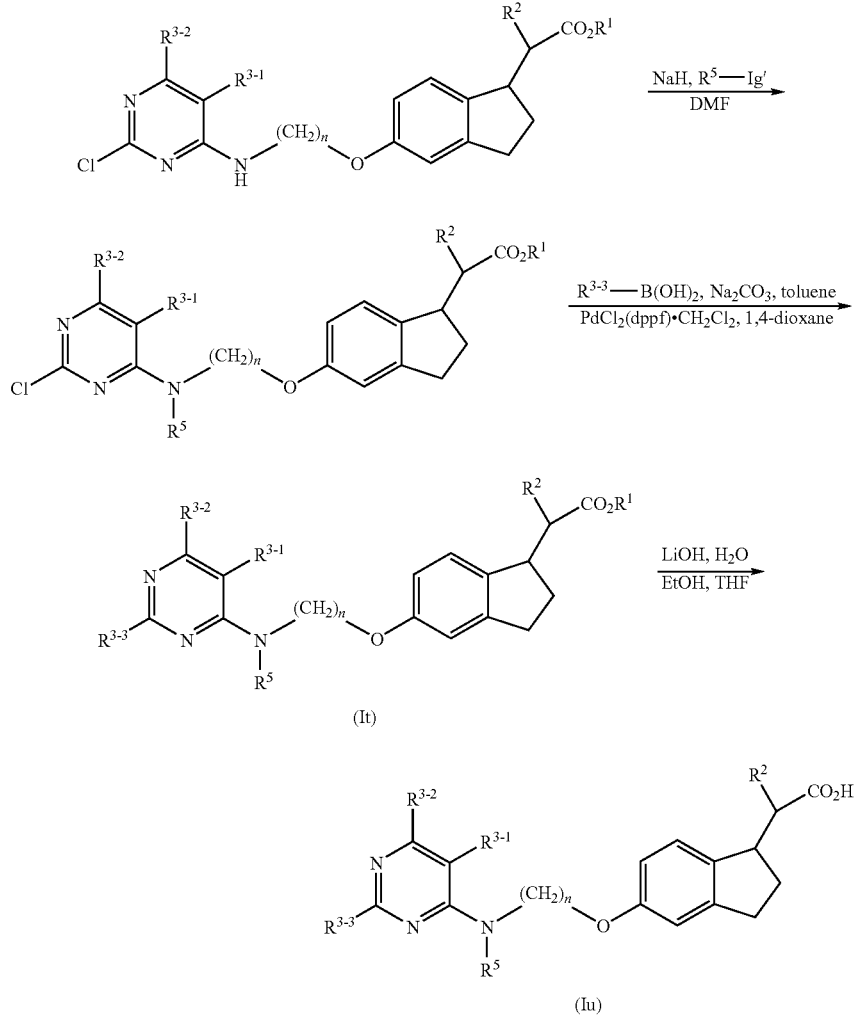
Reaction Scheme 13 illustrates the synthesis of Formula (I) compounds in which Ar is substituted pyrimidyl, L is —Y—(CH$_2$)$_n$—O—, and Y is O. Compounds prepared by this method are shown in Examples 438-439.
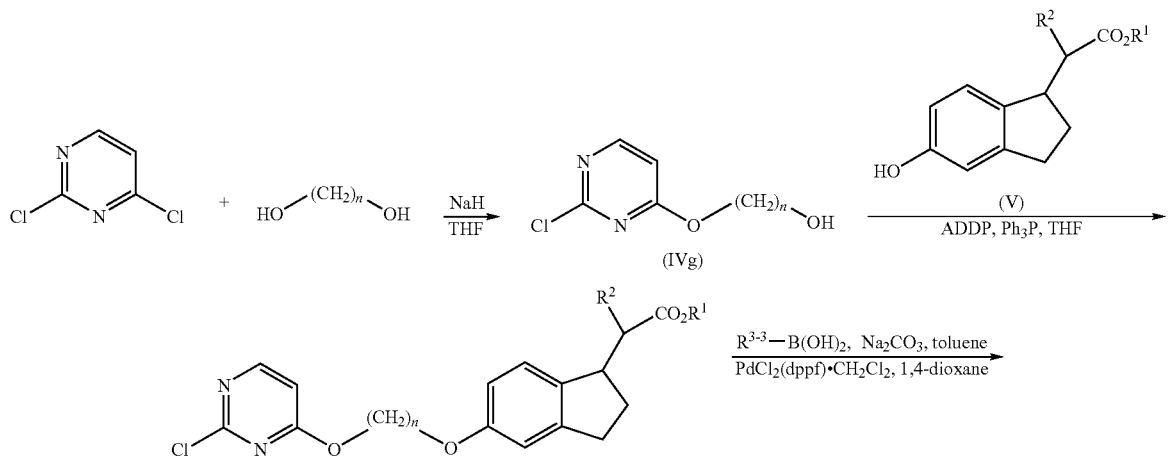

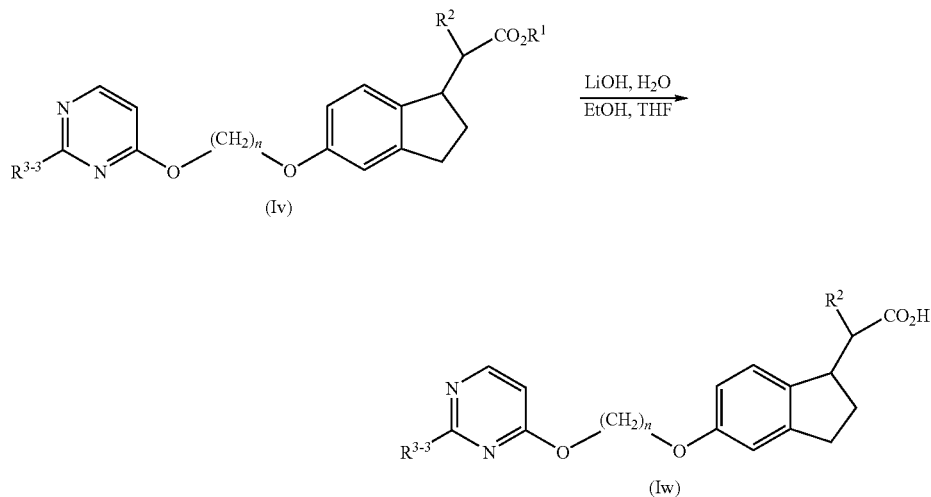
Reaction Scheme 14 illustrates the synthesis of Formula (I) compounds in which Ar is substituted pyrimidyl, L is —Y—$(CH_2)_n$—O—, and Y is $NR^5$. Compounds prepared by this method are shown in Examples 440-446 and in Table 17a below.
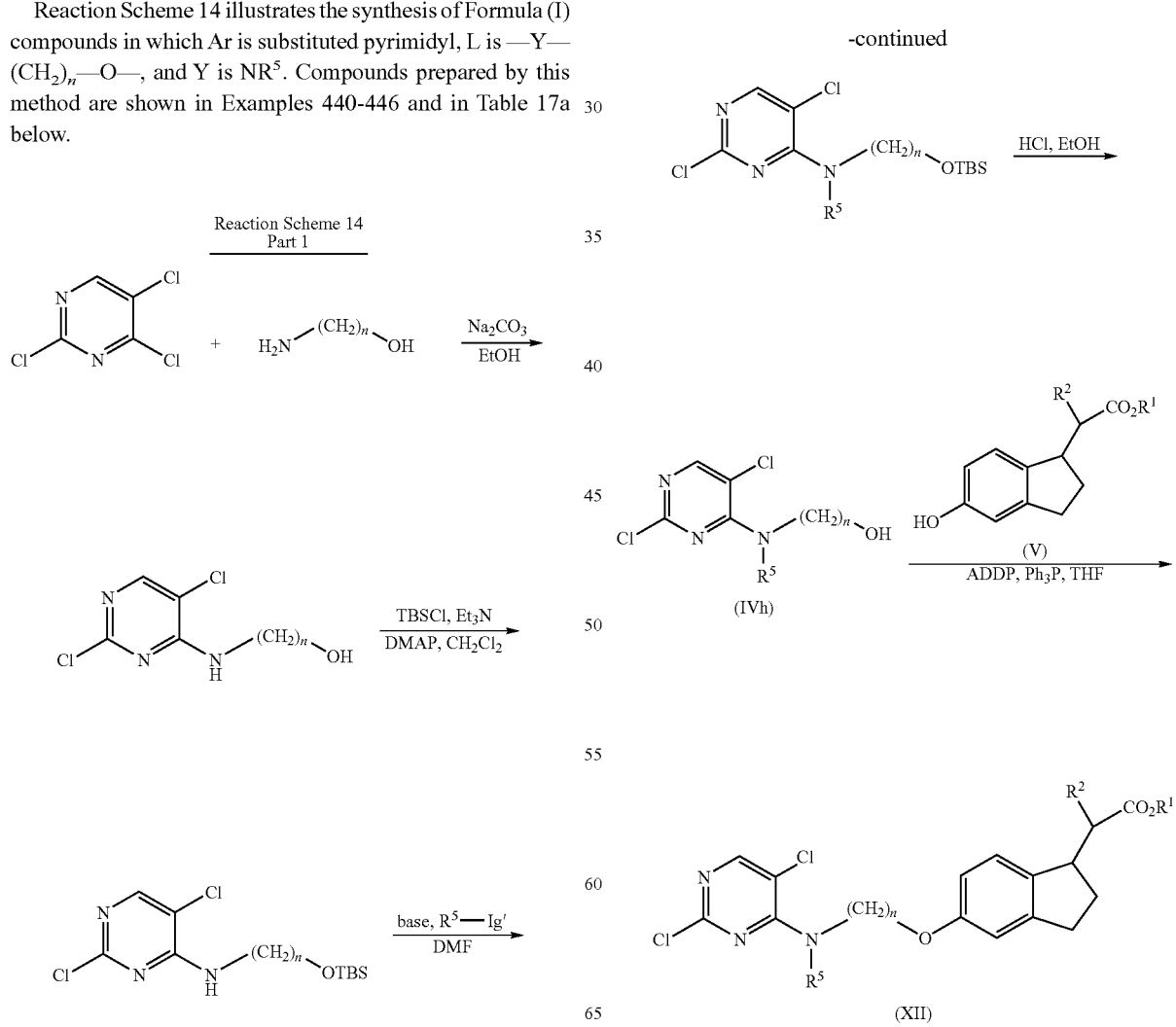

Part 2
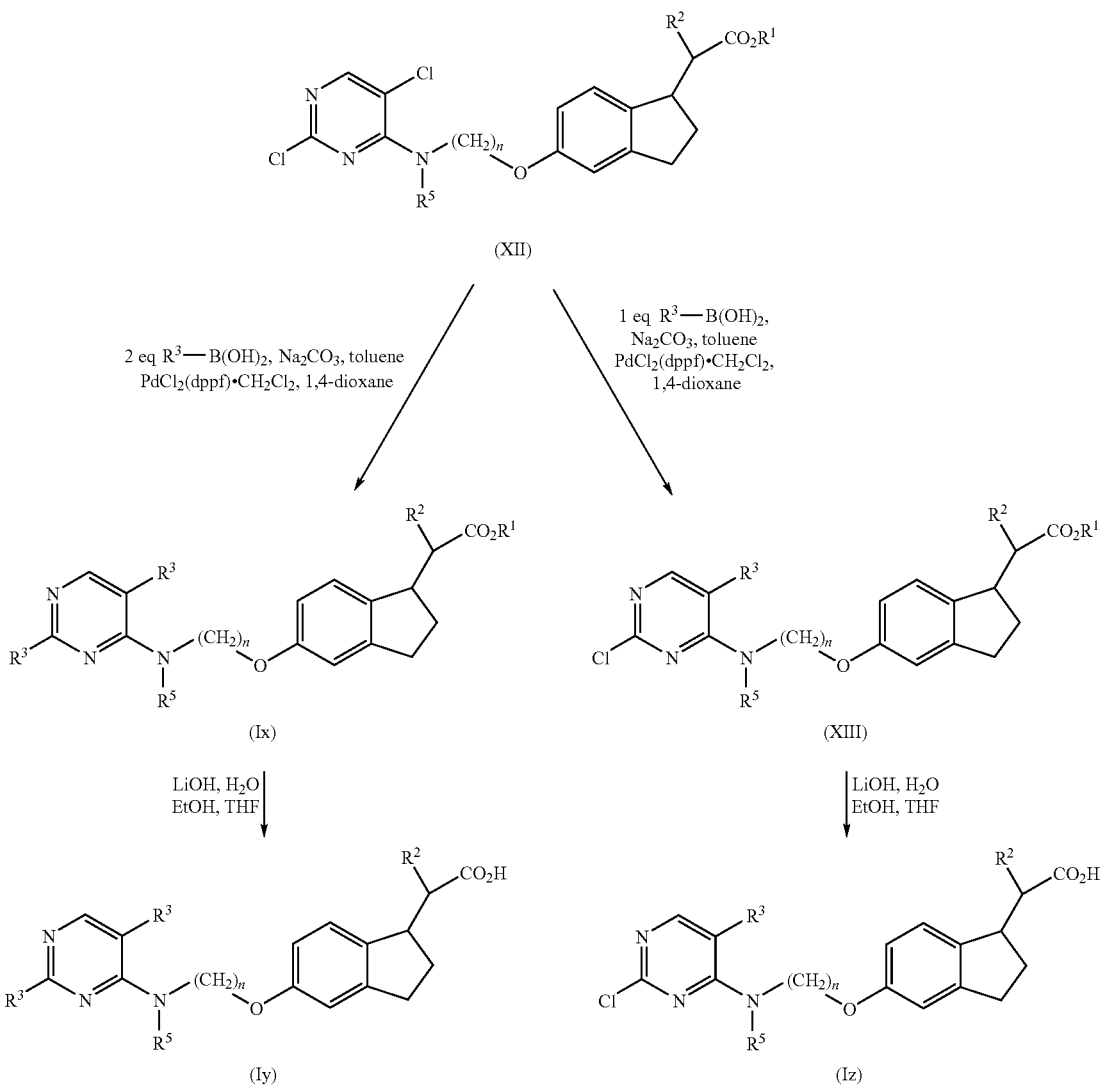
Reaction Scheme 15 illustrates the synthesis of Formula (I) compounds in which Ar is phenyl substituted pyrimidyl, L is
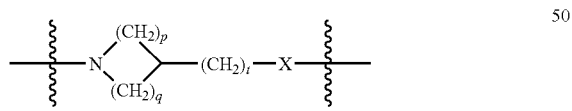
and X is O.
Compounds prepared by this method are shown in Examples 458-460, 467, and 468, and in Table 18a below.
Reaction Scheme 15
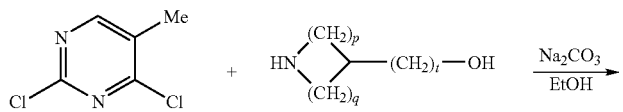

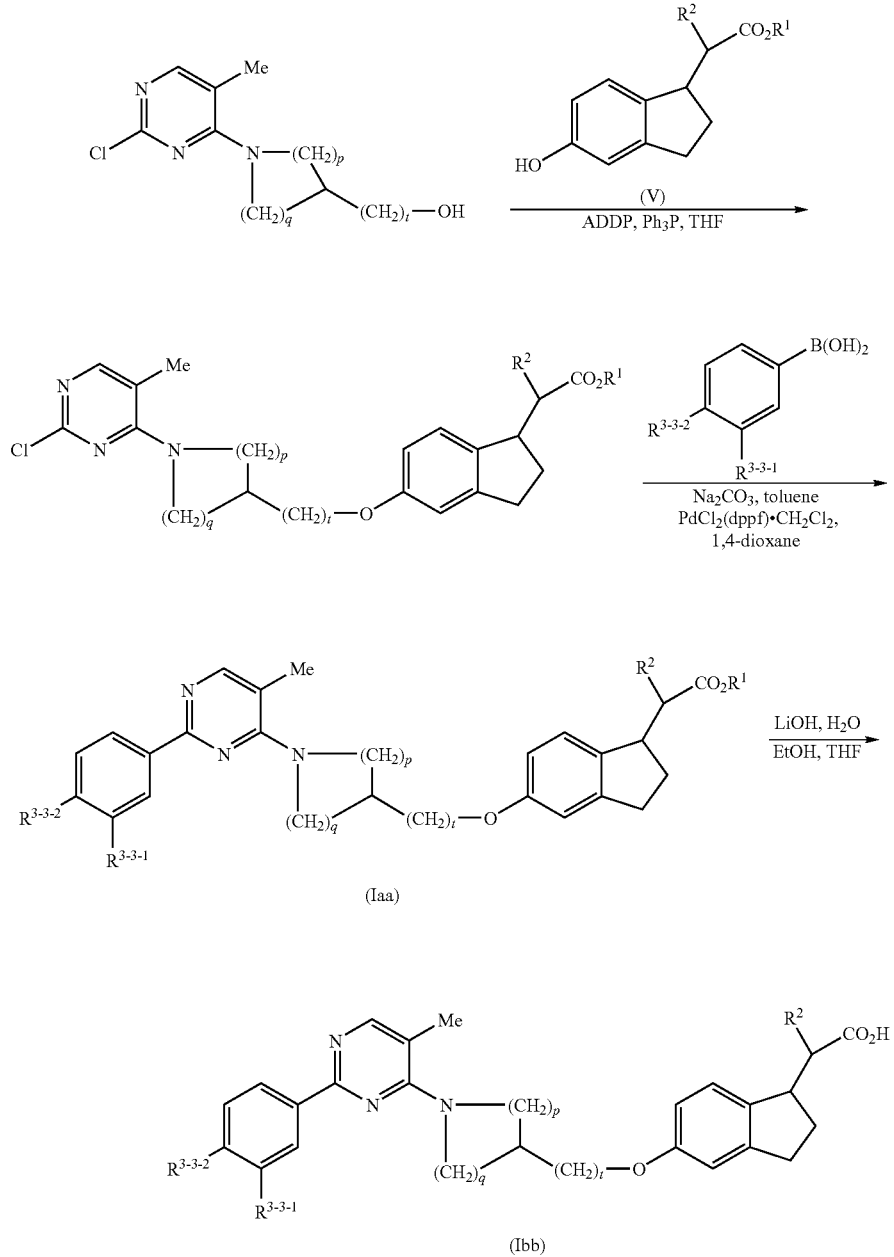
Reaction Scheme 16 illustrates the synthesis of Formula (I) compounds in which Ar is substituted pyridyl, L is —CH$_2$)$_m$—X—, m is 2, and X is O. Compounds prepared by this method are shown in Examples 469-473 and Table 19a below.
Reaction Scheme 16
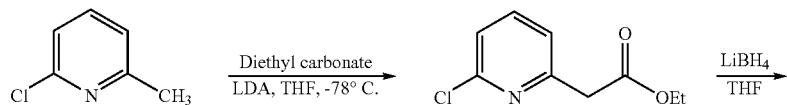

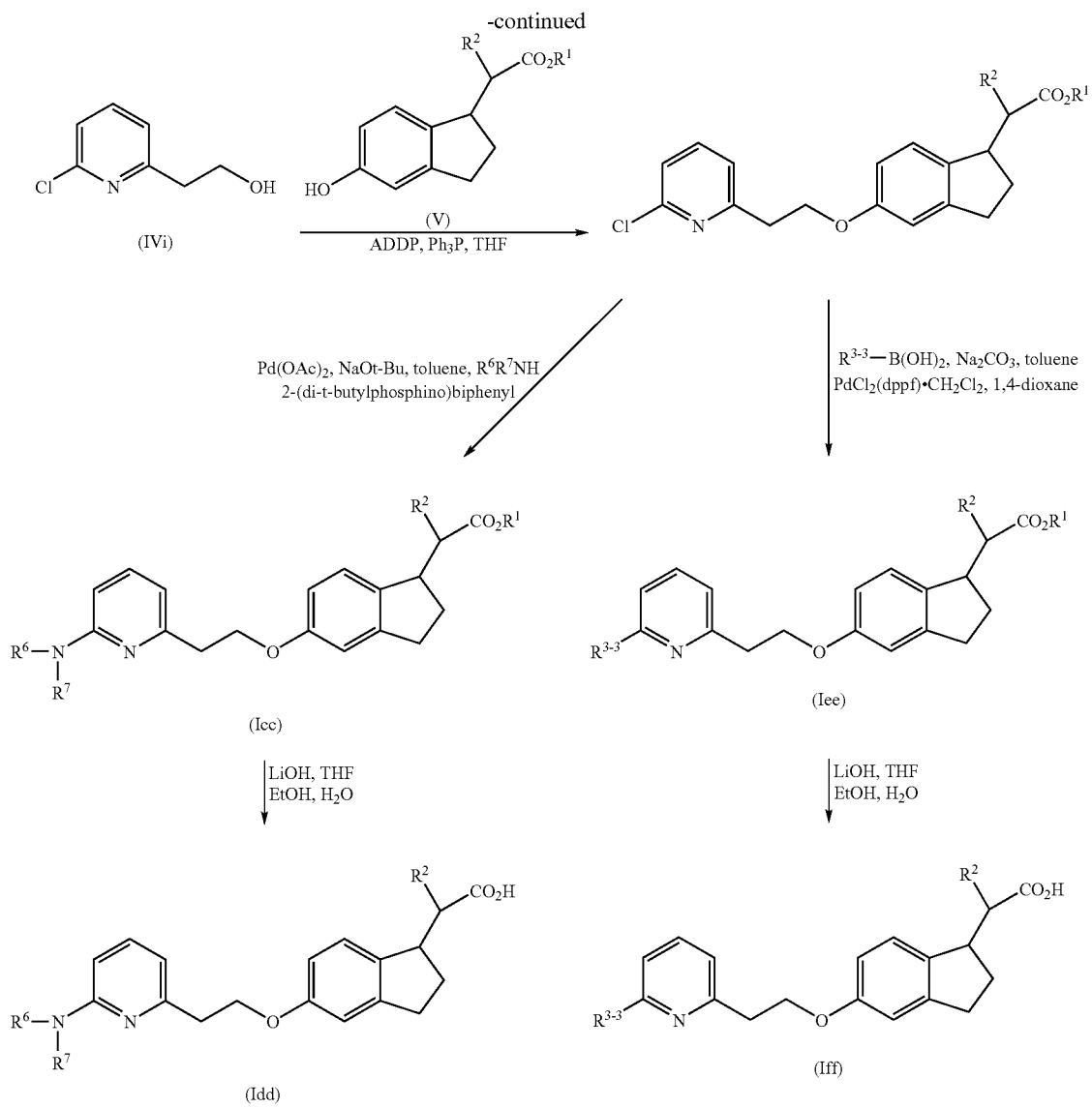
Reaction Scheme 17 illustrates an alternate synthesis of Formula (I) compounds in which Ar is substituted pyridyl, L is —CH$_2$)$_m$—X—, m is 2 and X is O. Compounds prepared by this method are shown in Examples 474-482 and Table 19a below.

-continued
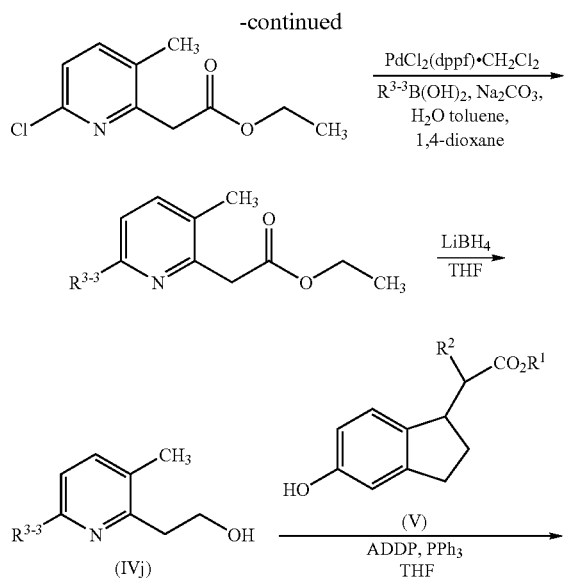
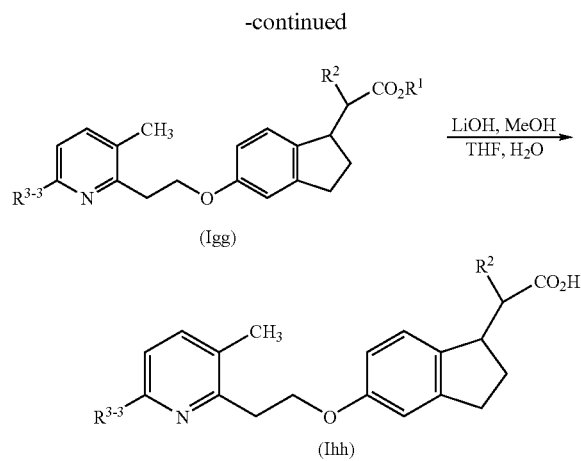
Reaction Scheme 18 illustrates the synthesis of Formula (I) compounds in which Ar is thiazolyl substituted phenyl, L is —Y(CH$_2$)$_n$—X—, X is S, and Y is O. Compounds prepared by this method are shown in Examples 504-510 below.
Reaction Scheme 18
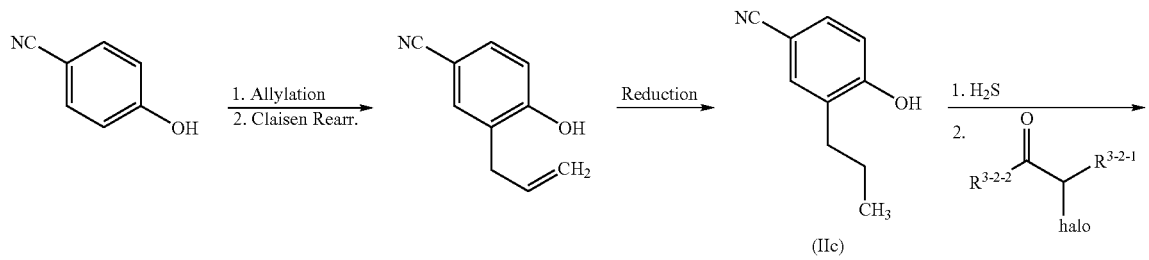
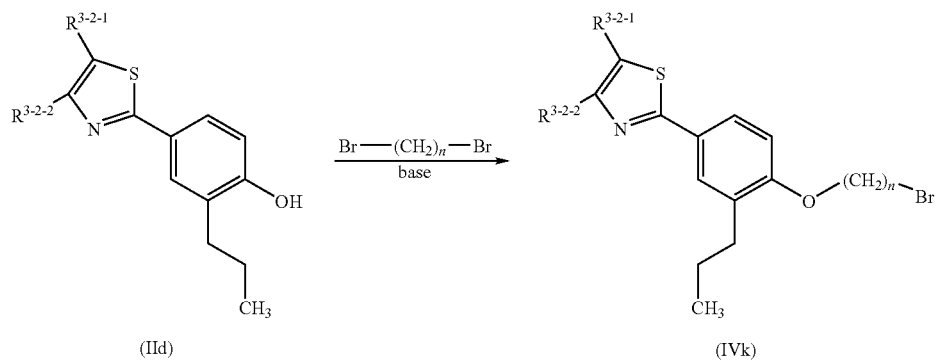
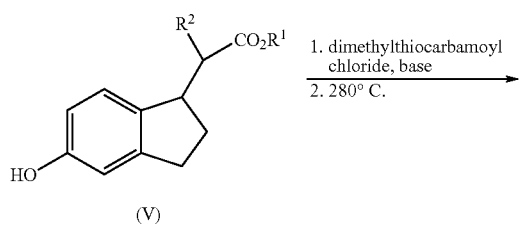

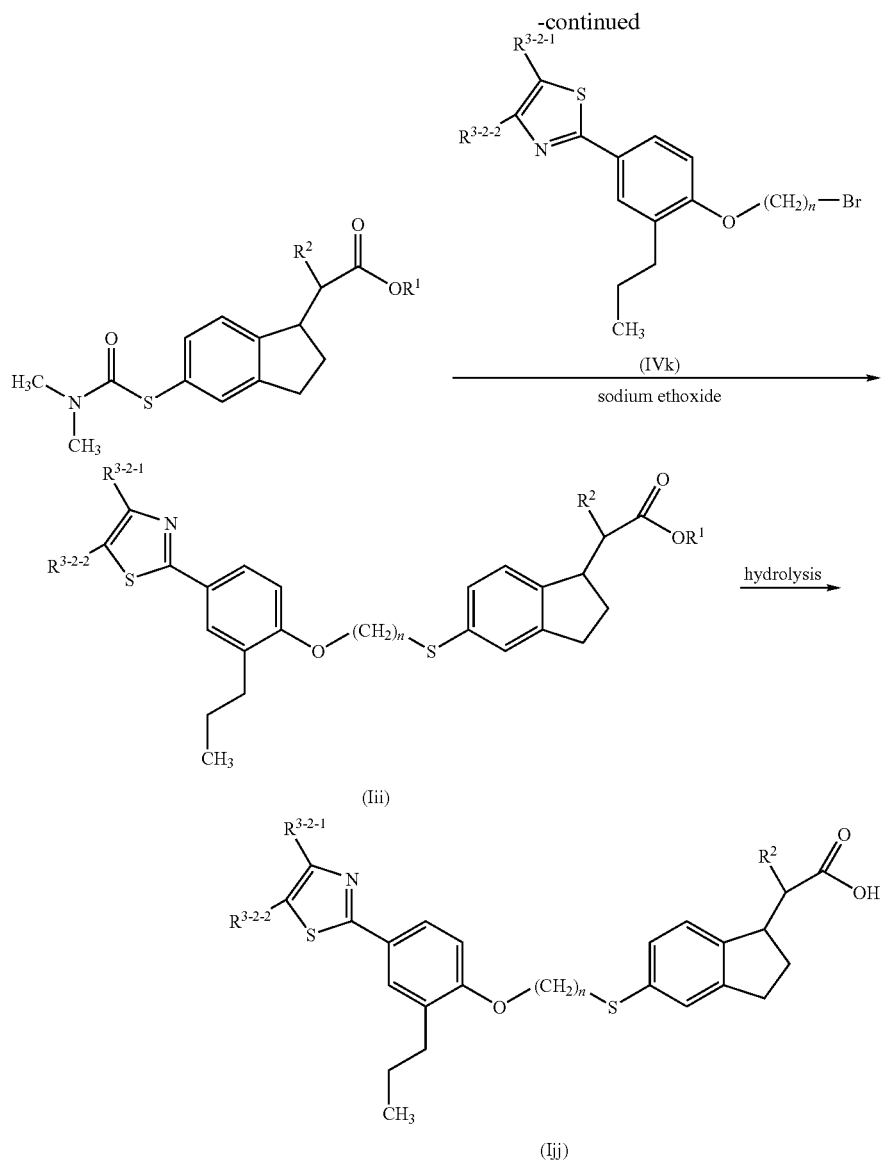

The preparation of Formula (I) compounds in which X and/or Y are S(=O) or S(=O)$_2$, can be prepared by standard oxidation of the corresponding Formula (I) compounds in which X and/or Y are S, using one [for S(=O)] or two [for S(=O)$_2$] equivalents of an oxidizing agent such as m-chloroperbenzoic acid in an inert solvent.

Preparation of Starting Materials

Starting materials are either commericially available or prepared by standard methods. Two specific methods are illustrated in Reactions Schemes 19 and 20 below.

The specific method of preparation of compounds of Formula (IIc), used in the preparation of Formula (I) compounds in which Ar is benzisoxazolyl and X is O, is shown in Reaction Scheme 19. In this Scheme, the benzisoxazole ring is prepared in two steps from a readily available 2-hydroxyacetophenone, via oxime formation and cyclization using either DAST or Mitsunobu conditions.

Reaction Scheme 19

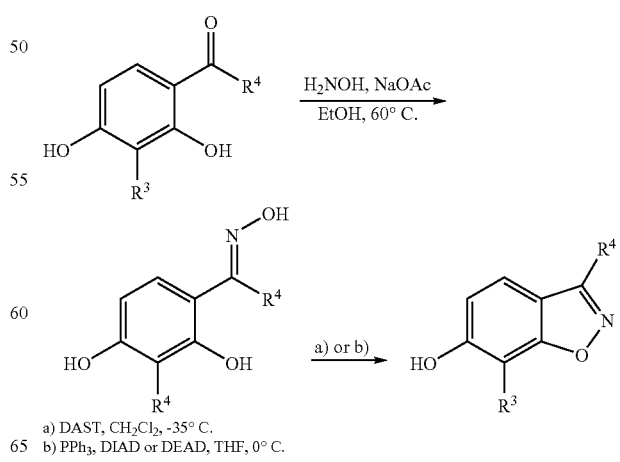

a) DAST, CH$_2$Cl$_2$, -35° C.
b) PPh$_3$, DIAD or DEAD, THF, 0° C.

Reaction Scheme 20 illustrates the synthesis of starting materials of Formula (IIh) used in the preparation of Formula (I) compounds in which Ar is n-propyl-substituted phenyl and Y is O. This Scheme represents a general method, more specifically described in Reaction Scheme 18 for Formula (IIc) where $R^3$=CN. A phenol of Formula (IIf) is converted to the O-propenyl compound which is allowed to undergo a Claisen rearrangement to the 2-propenyl phenol of Formula (IIg). Reduction of the propenyl substituent to a propyl substituent is carried out under standard hydrogenation conditions to give the Formula (IIh) compound.

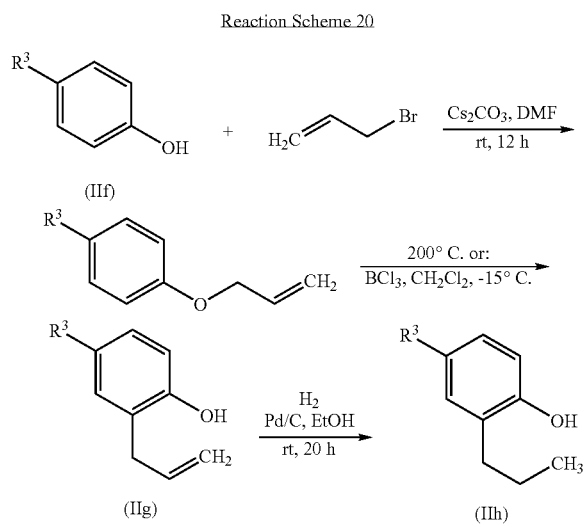

Reaction Scheme 20

The following specific examples are presented to illustrate the invention described herein, but should not be construed as limiting the scope of the invention in any way.

General Experimental Methods

Air and moisture sensitive liquids and solutions were transferred via syringe or cannula, and introduced into reaction vessels through rubber septa. Commercial grade reagents and solvents were used without further purification. The term "concentration under reduced pressure" refers to use of a Buchi rotary evaporator at approximately 15 mm of Hg. All temperatures are reported uncorrected in degrees Celsius (° C.). Column chromatography (flash chromatography) was preferably performed on a Biotage system using 32-63 micron, 60 Å, silica gel pre-packed cartridges. Purification using preparative reversed-phase HPLC chromatography were accomplished using a Gilson 215 system, using a YMC Pro-C18 AS-342 (150×20 mm I.D.) column. Typically, the mobile phase used was a mixture of H$_2$O (A) and MeCN (B). The water could be mixed or not with 0.1% TFA. A typical gradient was:

| Time [min] | A: % | B: % | Flow [mL/min] |
|---|---|---|---|
| 0.50 | 90.0 | 10.0 | 1.0 |
| 11.00 | 0.0 | 100.0 | 1.0 |
| 14.00 | 0.0 | 100.0 | 1.0 |
| 15.02 | 100.0 | 0.0 | 1.0 |

Chiral analytical HPLC experiments were performed using one of the two following methods using a Varian Pro Star 1200:

A: Column: Chiracel AD, 4.6 (I.D.)×250 mm
Mobile Phase: A: 0.1% TFA in hexanes; B: 0.1% TFA in i-PrOH;
Isocratic: 95% A (5% B), 20 min.
Flow Rate: 1.5 mL/min
Detector (UV): 284 nm
B: Column: Chiracel AD, 4.6 (I.D.)×250 mm
Mobile Phase: A: 0.1% TFA in hexanes; B: 0.1% TFA in i-PrOH
Isocratic: 95% A (5% B), 25 min.
Flow Rate: 1.0 mL/min
Detector (UV): 284 nm Electron impact mass spectra (EI-MS or GC-MS) were obtained with a Hewlett Packard 5989A mass spectrometer equipped with a Hewlett Packard 5890 Gas Chromatograph with a J & W DB-5 column (0.25 uM coating; 30 m×0.25 mm). The ion source was maintained at 250° C. and spectra were scanned from 50-800 amu at 2 sec per scan.

High pressure liquid chromatography-electrospray mass spectra (LC-MS) were obtained using a Hewlett-Packard 1100 HPLC equipped with a quaternary pump, a variable wavelength detector set at 254 nm, a YMC pro C-18 column (2×23 mm, 120A), and a Finnigan LCQ ion trap mass spectrometer with electrospray ionization. Spectra were scanned from 120-1200 amu using a variable ion time according to the number of ions in the source. The eluents were A: 2% acetonitrile in water with 0.02% TFA, and B: 2% water in acetonitrile with 0.018% TFA. Gradient elution from 10% to 95% B over 3.5 min at a flowrate of 1.0 mL/min was used with an initial hold of 0.5 min and a final hold at 95% B of 0.5 min. Total run time was 6.5 min. For consistency in characterizaton data, the retention time (RT) is reported in min at the apex of the peak as detected by the UV-Vis detector set at 254 nm.

Routine one-dimensional NMR spectroscopy was performed on 300 or 400 MHz Varian Mercury-plus spectrometers. The samples were dissolved in deuterated solvents obtained from Cambridge Isotope Labs, and transferred to 5 mm ID Wilmad NMR tubes. The spectra were acquired at 293 K. The chemical shifts were recorded on the ppm scale and were referenced to the appropriate residual solvent signals, such as 2.49 ppm for DMSO-d$_6$, 1.93 ppm for CD$_3$CN, 3.30 ppm for CD$_3$OD, 5.32 ppm for CD$_2$Cl$_2$, and 7.26 ppm for CDCl$_3$ for $^1$H spectra, and 39.5 ppm for DMSO-d$_6$, 1.3 ppm for CD$_3$CN, 49.0 ppm for CD$_3$OD, 53.8 ppm for CD$_2$Cl$_2$, and 77.0 ppm for CDCl$_3$ for $^{13}$C spectra. General methods of preparation are illustrated in the reaction schemes, and by the specific preparative examples that follow.

ABBREVIATIONS AND ACRONYMS

When the following abbreviations are used throughout the disclosure, they have the following meaning:
Ac acetyl
AcOH acetic acid
ADDP 1,1'-[azodicarbonyl]dipiperidine
AMU Atomic Mass Unit
Bn benzyl
Boc t-butoxycarbonyl
Bu butyl
CDCl$_3$ deuterochloroform
Celite® registered trademark of Celite Corp. brand of diatomaceous earth
CI chemical ionization
d doublet
dd doublet of doublet
ddd doublet of doublet of doublet
de diastereomeric excess DAST (diethylamino) sulfur trifluoride
DEAD diethyl azodicarboxylate
DIA diisopropylamine
DIAD diisopropyl azodicarboxylate
DMAP 4-(N,N-dimethyl)amino pyridine
DME dimethoxyethane
DMF N,N-dimethyl formamide
DMSO dimethylsulfoxide
DMSO-$d_6$ dimethylsulfoxide-$d_6$
DOWEX® 66 Dowex hydroxide, weakly basic anion, macroporous, 25-50 mesh
dppf 1,1'-bis(diphenylphosphino)ferrocene
Drierite® anhydrous calcium sulfate (W. A. Hammond Drierite Co.)
ee enantiomeric excess
EI electron impact ionization
EI-MS electron impact-mass spectrometry
eq equivalent
Et ethyl
EtOH ethanol
EtOAc ethyl acetate
EtSH ethane thiol
g gram
GC-MS gas chromatography-mass spectrometry
h hour(s)
$^1$H NMR proton nuclear magnetic resonance
Hex hexanes
HPLC high performance liquid chromatography
LC-MS liquid chromatography/mass spectroscopy
LDA lithium diisopropylamide
m multiplet
M molar
m/z mass over charge
Me methyl
MeCN acetonitrile
mg milligram
MHz megahertz
min minute(s)
mol mole
mmol millimole
MS mass spectrometry
N normal
NMR nuclear magnetic resonance
NaOAc sodium acetate
Pd/C palladium on carbon
$PdC_2$(dppf).$CH_2Cl_2$ [1,1'-bis(diphenylphosphino)ferrocene]dichloropalladium (II) complex with dichloromethane (1:1)
Ph phenyl
$PPh_3$ triphenylphosphine
ppm parts per million
psi pounds per square inch
Pr propyl
q quartet
qt quintet
quant. quantitative
$R_f$ TLC retention factor
rt room temperature
RT retention time (HPLC)
s singlet
TBAF tetrabutyl ammonium fluoride
TBS tert-butyldimethylsilyl
TBSCl tert-butyidimethylsilyl chloride
TFA trifluoroacetic acid
THF tetrahydrofuran
TLC thin layer chromatography
TMS tetramethylsilyl
v/v volume per unit volume
vol volume
w/w weight per unit weight

PREPARATIVE EXAMPLES OF INDANE ACID DERIVATIVES

Example 1

Preparation of ethyl(5-methoxy-2,3-dihydro-1H-inden-1-ylidene)ethanoate

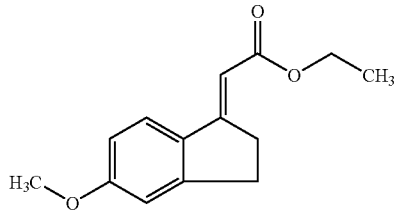

To a solution of 5-methoxyindanone (150 g, 0.91 mol) in anhydrous tetrahydrofuran (4.5 L), was added zinc (30 mesh, 103.64 g, 1.59 mol) and copper(I) chloride (4.53 g, 0.045 mol). The suspension was stirred under argon atmosphere and refluxed for 15 min; approximately a 25% portion of ethyl bromoacetate (133 mL, 1.18 mol) was added to the refluxing mixture in a slow dropwise fashion. After allowing to cool and stirring for 12 h at rt; TLC showed the presence of desired product. The remainder of ethyl bromoacetate was added dropwise; an exotherm was observed (internal temperature increased to 35° C.). After 4 h, TLC showed complete reaction. After the solids settled to the bottom of the flask, the liquid was siphoned off leaving a small amount behind to cover the solids. The flask was re-charged with 5-methoxyindanone (157.6 g, 1.86 mol total), anhydrous tetrahydrofuran (4.5 L), and zinc (80.92 g, 2.73 mol total). Ethyl bromoacetate (140 mL, 2.36 mol) was added dropwise. An exotherm was observed (internal temperature increased to 35° C.). When the stirred mixture was cooled to rt, TLC showed the reaction to be complete. The solids were allowed to settle and the liquid was siphoned off. The combined reaction solutions were concentrated under reduced pressure to a volume of about 2 L. The liquid was then poured into HCl (1 N aqueous solution, cooled in ice water) to bring the pH to 1. The product was extracted with ethyl acetate (2×1 L, 1×500 mL). The combined extracts were washed with water (1 L), brine (1 L), dried over $Na_2SO_4$, filtered, and concentrated under reduced pressure to afford a dark red oil which solidified gradually (438.3 g; theoretical yield=432 g). $^1$H NMR ($CDCl_3$): δ 7.5 (d, 1H), 6.8 (m, 2H), 6.2 (t, 1 H), 4.2 (q, 2H), 3.8 (s, 3H), 3.3 (m,2H), 3.0 (t, 2H), 1.3 (t, 3H). MS (CI) m/z 233 [M+H]$^+$.

Example 2

Preparation of ethyl(5-methoxy-2,3-dihydro-1H-inden-1-yl)acetate

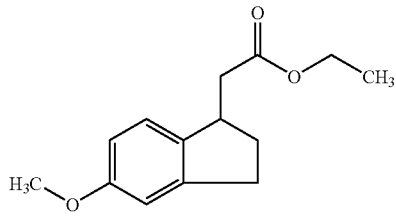

The crude product from Example 1 was dissolved in absolute ethanol (2.6 L) and hydrogenated at 40 psi of hydrogen over 10% palladium on carbon (21.6 g). Filtration through Celite® and concentration of the filtrate afforded the title compound: 433.3 g (99% yield for 2 steps) as a brown oil. $^1$H NMR (CDCl$_3$): δ 7.1 (dd, 1H), 6.8 (d, 1H), 6.7 (dd, 1H), 4.2 (q, 2H), 3.8 (s, 3H), 3.5 (m, 1H), 2.9 (m, 2H), 2.7 (dd, 1H), 2.4 (m, 2H), 1.7 (m, 1H), 1.3 (t, 3H). MS (CI) m/z 235 [M+H]$^+$.

Example 3

Preparation of (5-methoxy-2,3-dihydro-1H-inden-1-yl)acetic acid

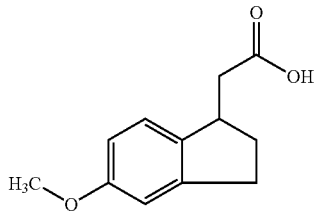

To a solution of the crude ester (416 g, 1.77 mol) prepared in Example 2 in EtOH (1 L), was added a solution of NaOH (142 g, 3.54 mol) in water (1.5 L). The reaction mixture was heated to reflux, during which time the color changed to dark red, and the reaction became homogeneous. After 1 h, the reaction was cooled to rt, and the EtOH was removed under reduced pressure. The remaining basic aqueous layer was washed with Et$_2$O (3×500 mL), then acidified with HCl (conc. aqueous solution) to pH~4 at which point an oily residue formed. The mixture was then extracted with Et$_2$O (4×500 mL), the combined extracts washed with water (2×300 mL) and brine, and then dried over Na$_2$SO$_4$. Filtration and evaporation of the solvents under reduced pressure gave the title compound (305 g, 83%) as a yellow solid after drying for 12 h under vacuum. $^1$H NMR (CDCl$_3$) δ 7.34 (d, 1H), 6.71 (s, 1H), 6.65 (dd, 1H), 3.71 (s, 3H), 3.47 (m, 1H), 2.80 (m, 3H), 2.35 (m, 2H), 1.71 (m, 1H). MS (CI) m/z 207 [M+H]$^+$.

Example 4

Preparation of [(1S)-5-methoxy-2,3-dihydro-1H-inden-1-yl]acetic acid

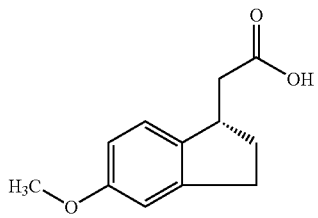

Method A. To a solution of the acid (341.0 g, 1.65 mol) prepared in Example 3 in acetone (8.2 L, reagent grade), was added (S)-(−)-α-methylbenzylamine (223.8 mL, 1.74 mol) dropwise at rt with stirring. A thick white precipitate formed during the addition. An additional 500 mL acetone was added and stirring continued for 1 h. The solids were collected by filtration, washed with acetone (300 mL), and dried under suction. The solids were then suspended in acetone (8.2 L) and warmed to reflux until all solids dissolved. The solution was cooled slowly over 12 h, during which time a white precipitate formed. The suspension was cooled to 0° C., then filtered, and the solids were washed with cold acetone (500 mL). After drying under suction, a sample analyzed by chiral analytical HPLC (Method A) showed an ee of 95%. The recrystallization process was repeated as described above using acetone (6.7 L) after which chiral analytical HPLC (Method A) analysis showed an ee of 99%. After drying under suction, 192 g salt were obtained. The salt was suspended in EtOAc (2 L) and HCl (1 L of a 1 N aqueous solution), and shaken in a separatory funnel, whereupon the salt dissolved. The organic layer was separated, washed with HCl (500 mL, 1 N aqueous solution), water (2×300 mL), and brine, then dried over Na$_2$SO$_4$. After filtration, the solvent was evaporated under reduced pressure, giving an oil which solidified upon standing. The title product (120.5 g, 35%) was obtained as an off-white solid after vacuum drying. $^1$H NMR (CDCl$_3$) δ 7.10 (d, 1H), 6.79 (d, 1H), 6.73 (dd, 1H), 3.79 (s, 3H), 3.55 (m, 1H), 2.89 (m, 2H), 2.79 (dd, 1H), 2.46 (dd, 1H), 2.43 (m, 1H), 1.80 (m, 1H). MS (ESI) m/z 207 [M+H]$^+$.

The absolute stereochemical assignment was done by single crystal X-Ray crystallography of a derivative containing the Evans' oxazolidinone chiral auxiliary.

Method B. As an alternative to Method A, the title compound may also be prepared via an enzymatic process. Thus, a mixture of the crude ester (500.0 g, 2.13 mol; 87% pure as determined by analytical HPLC) prepared in Example 2, in reagent grade acetone (1 L), a phosphate buffer (2.5 L, pH 7.0, 0.05 M) and water (2.5 L) was treated in one portion with Amano Lipase PS (150 g, Amano Enzymes), and the mixture was stirred vigorously at rt for 12 h. Chiral analytical HPLC analysis (Method A) of an aliquot (homogeneous aliquot prepared by dissolving an aliquot in i-PrOH followed by filtration) showed one peak corresponding to unreacted R-ester and another peak corresponding to desired S-acid. Only trace amounts of S-ester and R-acid were noted. Then, HCl (500 mL, 2 N aqueous solution) was added in one portion to the reaction mixture to ensure a pH~2, and the mixture was stirred for 20 min. The mixture was filtered and the solids washed with EtOAc (2×500 mL), then water (500 mL). The combined filtrates were further diluted with EtOAc (1 L), and the layers stirred together vigorously. Stirring was stopped and the layers allowed to separate. The resulting emulsion was broken by the addition of solid NaCl and stirring. The aqueous layer was removed, then extracted with EtOAc (3×1 L) in the same fashion. The combined organic extractions were washed with water (4×500 mL), and brine, then extracted with a Na$_2$CO$_3$ (8×500 mL, 5% aqueous solution). Chiral analytical HPLC (Method A) analysis of the organic layer showed that it contained none of the S-enantiomer acid. The combined Na$_2$CO$_3$ extracts were washed with EtOAc (2×1 L), then acidified to pH~2 by the addition of HCl (2 N aqueous solution). A white solid precipitated, accompanied by CO$_2$ evolution. The mixture was extracted with EtOAc (3×1 L). The combined extracts were washed with water (2×1 L) and brine, then dried over Na$_2$SO$_4$. Chiral analytical HPLC (Method A) analysis of this solution showed that the material had an ee of 98%. The solvent was evaporated under reduced pressure, giving an oil which solidified upon standing. The title product (172.9 g) was obtained as an off-white solid after vacuum drying, and then this material was recrystallized from boiling hexanes (8.8 L). After cooling for 12 h, light yellow needles were collected via filtration, washed with hexanes (200 mL), and dried under suction. The title product (146.9 g, 38% from crude starting ester) was obtained as light yellow needles after vacuum drying. $^1$H NMR results were the same as those for Example 3.

Example 5

Preparation of ethyl[(1S)-5-methoxy-2,3-dihydro-1H-inden-1-yl]acetate

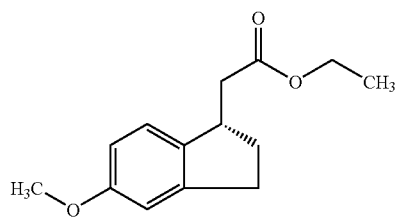

To a solution of the acid (305 g, 1.48 mol) prepared in Example 4 in 4.8 L absolute EtOH at rt under argon, was added chlorotrimethylsilane (413 mL, 3.25 mol) dropwise. An approximate 5° C. rise in temperature was noted during the addition. After stirring for 12 h, the EtOH was evaporated under reduced pressure, giving a bi-phasic liquid mixture. This mixture was diluted in ice-water (500 mL), then extracted with EtOAc (2×750 mL). The combined extracts were washed with water (3×300 mL), and then with a saturated aqueous solution of NaHCO$_3$ (200 mL). The organic phase was washed once more with water (300 mL), then brine, and dried over Na$_2$SO$_4$. The title compound (354 g, quant.) was obtained as a light yellow oil after solvent removal and vacuum drying. $^1$H NMR (CDCl$_3$) δ 7.07 (d, 1H), 6.78 (d, 1H), 6.71 (dd, 1H), 4.18 (q, 2H), 3.78 (s, 3H), 3.52 (m, 1H), 2.89 (m, 2H), 2.72 (dd, 1H), 2.37 (o, 2H), 1.74 (m, 1H), 1.28 (t, 3H). MS (CI) m/z 235 [M+H]$^+$.

Example 6

Preparation of ethyl[(1S)-5-hydroxy-2,3-dihydro-1H-inden-1-yl]acetate

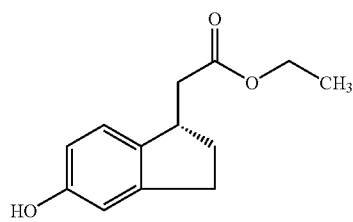

To a cold solution (ice water bath) of the compound (346 g, 1.48 mol) prepared in Example 5 in CH$_2$Cl$_2$ (4.2 L), was added AlCl$_3$ (984.6 g, 7.38 mol) portionwise under argon such that the reaction temperature was maintained below 10° C. The light brown suspension was stirred for 10 min, then EtSH (546 mL, 7.38 mol) was added dropwise at such a rate that the reaction temperature was maintained below 5° C. After 2.5 h of stirring below 10° C., the reaction mixture was slowly poured into 6 L ice water with strong agitation. The organic layer was separated, and the aqueous layer was extracted with CH$_2$Cl$_2$ (3×1 L). The combined CH$_2$Cl$_2$ layers were washed with water (2×1 L), then dried over Na$_2$SO$_4$. The solvent was removed under reduced pressure, giving a brown oil, which was filtered through a pad of silica gel (eluted with 0-10% EtOAc/Hexanes). Fractions were collected, and the title compound (314 g, 96%) was obtained as a thick yellow oil after solvent removal and vacuum drying. $^1$H NMR (CDCl$_3$) δ 6.92 (d, 1H), 6.62 (d, 1H), 6.55 (dd, 1H), 4.10 (q, 2H), 3.43 (q, 1H), 2.75 (m, 2H), 2.64 (dd, 1H), 2.31 (dd, 1H), 2.29 (m, 1H), 1.67 (m, 1H), 1.20 (t, 3H). MS (CI) m/z 221 [M+H]$^+$.

Example 7

Preparation of 4-methoxy-1-indanone

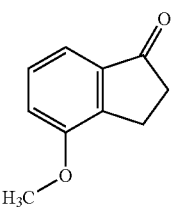

4-Hydroxy-1-indanone (5.0 g, 33.7 mmol) was dissolved in acetone (170 mL) and then potassium carbonate (9.0 g, 138.21 mmol) and MeI (9.6 g, 67.5 mmol) were added. The resulting suspension was heated to 50° C. and stirred for 3 days at which time the reaction mixture was concentrated under reduced pressure. The residue was partitioned between EtOAc and water. The organic phase was separated and the aqueous phase was extracted with EtOAc. The combined organic layers were dried over MgSO$_4$, filtered and concentrated under reduced pressure to give the title compound (5.4 g, 98%) as a yellow solid. GC-MS m/z [M+H]$^+$ 163.

Example 8

Preparation of ethyl(2E)-(4-methoxy-2,3-dihydro-1H-inden-1-ylidene)ethanoate

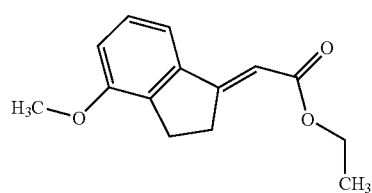

Triethyl phosphonoacetate (6.1 g, 27.4 mmol) was added to a suspension of NaH (1.1 g, 27.4 mmol, 60% dispersion in mineral oil) in THF (76 mL). The resulting solution was stirred at rt for 2 h at which time 4-methoxy-1-indanone (Example 7, 3.7 g, 22.8 mmol) was added and the reaction mixture heated at reflux for 18 h. The reaction was cooled to rt and partitioned between EtOAc and a saturated aqueous solution of NH$_4$Cl. The organic phase was separated and dried over MgSO$_4$, and then concentrated under reduced pressure. The crude product was purified by silica gel flash chromatography (8:1 Hexanes: EtOAc) to give the title compound as a yellow oil (3.4 g, 65%). GC-MS m/z [M+H]+ 233.

Example 9

Preparation of ethyl(4-hydroxy-2,3-dihydro-1H-inden-1-yl)acetate

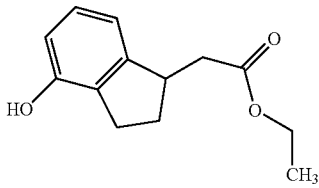

A round bottomed flask was flushed with argon and then charged with Pd(OH)$_2$ (316 mg, 10 wt %). The flask was evacuated and back-filled with argon, and then EtOH (5 mL) was added to the catalyst. Ethyl(2E)-(4-methoxy-2,3-dihydro-1H-inden-1-ylidene)ethanoate (Example 8, 3.2 g, 13.6 mmol) was added as a solution in EtOH (63 mL). Ammonium formate (4.3 g, 68 mmol) was added, and the reaction mixture was heated to 65° C. After 2 h, the reaction mixture was cooled and filtered through a pad of Celite®, and concentrated under reduced pressure. The reaction mixture was used without further purification according to the method outlined in Example 6 to give the title compound (2.3 g, 78%) as a yellow oil. $^1$H NMR (400 MHz, CDCl$_3$): δ 7.14 (t, 1H), 6.76 (d, 1H), 6.67 (d, 1H), 4.91 (br s, 1H), 4.19 (q, 2H), 3.60 (m, 1H), 2.85-2.88 (m, 1H), 2.76-2.80 (m, 2H), 2.19-2.26 (m, 2H), 1.76-1.82 (m, 1H), 1.26 (t, 3H); GC-MS m/z [M+H]+ 221.

Example 10

Preparation of methyl 2-(6-methoxy-1H-inden-3-yl)propanoate

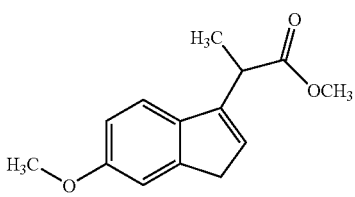

In an oven dried 3-neck 5.0 L flask fitted with a condenser, a thermometer, and an addition funnel was charged under argon, 5-methoxy-1-indanone (86.73 g, 0.52 mol) and THF (2.13 L). The mixture was stirred at rt and became an orange-colored solution. To this were added zinc granules (59.96 g, 0.92 mol, 30 mesh). The mixture was heated to ~50° C. with simultaneous addition of a solution of methyl-2-bromopropionate (88.80 g, 0.79 mol) in THF (393 mL). The reaction mixture was heated for a period of 20 h, after which heating was stopped and the reaction mixture cooled to rt followed by cooling on an ice bath. The mixture was then slowly quenched with HCl (3.3 L, 1 N aqueous solution) maintaining the internal temperature at ~188° C. The aqueous layer was extracted with EtOAc (3×500 mL). The organic layer was then washed with water (4×500 mL, a pH of ~4.5 achieved), brine (500 mL), and dried over Na$_2$SO$_4$. The solvent was removed under vacuum to give a dark brown colored oil. The crude product was purified by silica gel chromatography (1-8% EtOAc/hexane gradient) to give 54.09 g (52%) of the title compound as a dark brown oil. $^1$H NMR (400 MHz, DMSO-d$_6$): δ 7.25 (1H, d), 7.09 (1H, s), 6.87 (1H, dd), 6.24 (1H, s), 3.82 (1H, q), 3.75 (3H, s), 3.58 (3H, s), 3.30 (2H, s), 1.21 (3H, d); LC-MS: RT=3.00 min, (M+H)+: 233.0.

Example 11

Preparation of 2-(6-methoxy-1H-inden-3-yl)propanoic acid

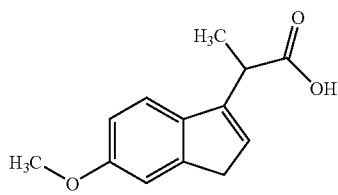

In a 1 L three-neck flask charged with NaOH (18.57 g, 0.464 mol) and water (216 mL), was slowly added (over 15-20 min) a solution of methyl 2-(6-methoxy-1H-inden-3-yl)propanoate (Example 10) (53.92 g, 0.232 mol) in MeOH (215 mL). During the addition, the reaction temperature increased to 38° C. To this mixture was added THF (108 mL) and then the mixture was heated to 40-45° C. for a period of 8 h and subsequently stirred at rt for 17 h. The solvent was removed under vacuum and the resulting aqueous mixture was extracted with CH$_2$Cl$_2$ (3×100 mL). The aqueous layer was acidified with HCl (38 mL, 37% aqueous solution) to pH~2.5 and extracted with EtOAc (3×100 mL). The combined organic layers were washed with water (4×150 mL) and brine (50 mL), dried over Na$_2$SO$_4$, and filtered. The solvent was evaporated under vacuum, and the resulting oil was dried under vacuum at 40-45° C. for 16-18 h to give 45.71 g (90%) of the title compound. $^1$H NMR (400 MHz, DMSO-d$_6$): δ 7.25 (1H, d), 7.05 (1H, s), 6.83 (1H, dd), 6.19 (1H, s), 3.73 (3H, s), 3.68 (1H, q), 3.30 (2H, s), 1.39 (3H, d); LC-MS: RT=2.43 min, (M+H)+: 219.1.

Example 12

Preparation of (2S)-2-[(1S)-5-methoxy-2,3-dihydro-1H-inden-1-yl]propanoic acid

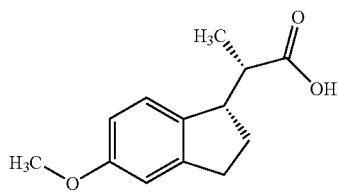

In a 1 L single neck flask was charged the racemic 2-(6-methoxy-1H-inden-3-yl)propanoic acid (Example 11) (41.9 g, 0.192 mol) and acetonitrile (629 mL). To this dark orange colored solution was added under stirring (R)-(+)-α-methyl-benzylamine (25.91 mL, 0.201 mol) slowly over a period of 10 min. The dark orange colored solution was then stirred at rt for 16-18 h. The resulting suspension was concentrated to dryness under vacuum to give 61.3 g of the 1:1 diastereomeric salt mixture. Under argon, ethanol (19 mL) was added to chlorotris(triphenylphosphine)rhodium(I) (2.0 g, 2.2 mmol). To this suspension was added a solution of the above 1:1 diastereomeric salt mixture (15.0 g, 0.044 mol) in a mixture of EtOH (116 mL) and THF (15 mL). This mixture was hydrogenated in a Parr apparatus under 60 psi at rt over a period of 17 h. The resulting suspension was cooled to 0-5° C. over a period of 30 min. The precipitate was filtered off and dried under vacuum at 40-45° C. for a period of 16-18 h to give the diastereomerically enriched salt (6.79 g, 45%) containing mainly the (S,S)-enantiomer of its anionic component [84% ee, chiral analytical HPLC, Method B]. The assignment of the absolute configuration is described in the following part. This crude salt was recrystallized by dissolution in MeCN (238 mL) under reflux condition. The resulting solution was cooled over 2 h and the precipitate filtered off, washed with MeCN (13 mL) and dried under vacuum at 40-45° C. to give the desired salt (5.19 g, 76% of mass recovered) having an ee of 98.14% (chiral analytical HPLC, Method B] reflecting the identical enantiomeric purity of the (S,S)-enantiomer of its anionic component. $^1$H NMR (of the salt) (400 MHz, DMSO-$d_6$): δ 7.35 (2H, d), 7.30 (2H, t), 7.19 (1H, m), 7.05 (1H, d), 6.73 (1H s), 6.65 (1H, dd), 4.07 (1H, q), 3.70 (3H, s), 3.40 (1H, q), 2.77 (2H, m), 2.58 (1H, q), 2.05 (1H, m), 1.75 (1H, m), 1.35 (3H, d), 0.87 (3H, d); Quattro Micro (Micromass)(-esi) (M–H)$^-$: 219 (free acid). The absolute stereochemistry of the title compound was determined to be (1S,2S) by single crystal x-ray crystallography of the (R)-(+)-α-methyl benzylamine salt. A dichloromethane solution of the diastereomerically pure salt was acidified by washing with 1N HCl followed by washing the organic layer with water. The organic layer was dried with Na$_2$SO$_4$ and concentrated to dryness to give the enantiomerically pure free acid, (2S)-2-[(1S)-5-methoxy-2,3-dihydro-1H-inden-1-yl]propanoic acid.

Example 13

Preparation of methyl(2S)-2-[(1S)-5-methoxy-2,3-dihydro-1H-inden-1yl]propanoate

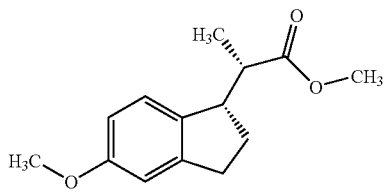

A suspension of (2S)-2-[(1S)-5-methoxy-2,3-dihydro-1H-inden-1-yl]propanoic acid (Example 12) (6.45 g, 0.029 mol), sodium bicarbonate (7.380 g, 0.088 mol), and iodomethane (5.5 mL, 0.088 mol) in DMF (60 mL) was stirred at rt for a period of 17 h. The completion of the reaction was achieved by addition of an additional amount of iodomethane (0.93 mL, 0.015 mol) and stirring for another 3 h at rt. The reaction mixture was poured into water (200 mL) and the aqueous layer was extracted with EtOAc (2×100 mL). The combined organic layers were washed with NaOH (1 N aqueous solution), water and brine, dried (Na$_2$SO$_4$), filtered, and concentrated to dryness under vacuum to give 5.70 g (84%) of the title compound. $^1$H NMR (400 MHz, DMSO-$d_6$) δ 6.96 (d, 1H), 6.77 (d, 1H), 6.67 (dd, 1H), 3.70 (s, 3H), 3.63 (s, 3H), 3.38 (q, 1H), 2.78 (m, 3H) 2.08 (m, 1H), 1.78 (m, 1H); LC-MS RT=3.10 min; (M+H)$^+$ 234.9.

Example 14

Preparation of methyl(2S)-2-[(1S)-5-hydroxy-2,3-dihydro-1H-inden-1-yl]propanoate

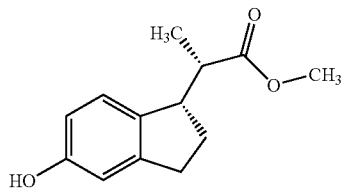

A solution of methyl(2S-2-[(1S)-5-methoxy-2,3-dihydro-1H-inden-1yl]propanoate (Example 13) (5.70 g, 0.024 mol) in CH$_2$Cl$_2$ (70 mL), under argon, was cooled to 0-5° C. and AlCl$_3$ (16.22 g, 0.122 mol) was added portion-wise while maintaining the temperature below 10° C. To this mixture was added EtSH (9.0 mL, 0.122 mol) and the resulting mixture was stirred at 0-5° C. for 4 h. The reaction mixture was then slowly poured into vigorously stirred ice-water (200 mL) and the aqueous layer was extracted with CH$_2$Cl$_2$. The combined organic layers were washed with water, brine, dried (Na$_2$SO$_4$), filtered, and concentrated to dryness under vacuum. The resulting crude product was purified by silica gel flash chromatography (gradient of 10-40% ethyl acetate/hexanes) to give 4.2 g (80%) of the title compound. $^1$H NMR (400 MHz, CDCl$_3$): δ 6.93 (d, 1H), 6.70 (s, 1H), 6.63 (dd, 1H), 3.72 (s, 3H), 3.50 (q, 1H), 2.83 (m, 3H), 2.19 (m, 1H), 1.90 (m, 1H), 1.08 (d, 3H); GC-MS: RT=8.60 min, (M+H)$^+$ 220.

Example 15

Preparation of (2S)-2-[(1S)-5-methoxy-2,3-dihydro-1H-inden-1-yl]propanoic acid and (2R)-2-[(1R)-5-methoxy-2,3-dihydro-1H-inden-1-yl]propanoic acid

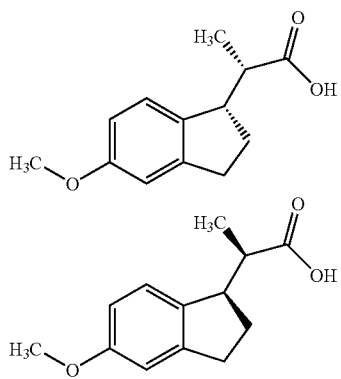

The starting acid (Example 11) was reacted under Wilkinson's hydrogenation conditions (60 psi) using 4.5 g starting material, 1.04 g catalyst, and 4.5 mL triethylamine in 45 mL ethanol and 5 mL THF (analogous procedure as for example 12). The standard extractive workup gave 3.22 g product. $^1$H NMR (400 MHz, DMSO-$d_6$) 0.87 (d, 3H), 1.75 (m, 1H), 2.04

(m, 1H), 3.66 (s, 3H), 6.65 (m, 1H), 6.76 (s, 1H), 7.04 (d, 1H) 12.18 (bs, 1H): LC-MS RT 2.41 min.

Example 16

Preparation of methyl(2S)-2-[(1S)-5-methoxy-2,3-dihydro-1H-inden-1-yl]propanoate and methyl(2R)-2-[(1R)-5-methoxy-2,3-dihydro-1H-inden-1-yl]propanoate

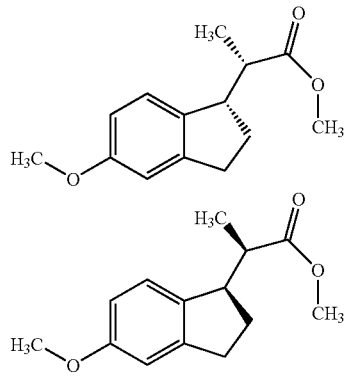

The compound was prepared by the reaction of 1.5 g starting acid (Example 15), 0.93 mL iodomethane, and 1.75 g sodium bicarbonate in 10 mL methanol under the esterification conditions as described in Example 13. Workup gave 1.53 g, 96%. $^1$H NMR (400 MHz), (CD$_2$Cl$_2$): δ 1.05 (d, 3H), 1.88 (m, 1H), 2.19 (m, 1H), 3.44 (m, 1H), 3.68 (s, 3H), 3.77 (s, 3H).

Example 17

Preparation of methyl(2S)-2-[(1S)-5-hydroxy-2,3-dihydro-1H-inden-1-yl]propanoate and methyl(2R)-2-[(1R)-5-hydroxy-2,3-dihydro-1H-inden-1-yl]propanoate

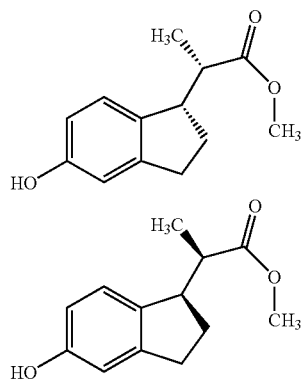

Using the demethylation conditions described in Example 14, and starting with Example 16 (1.53 g), AlCl$_3$ (4.35 g) and EtSH (2.4 mL) in CH$_2$Cl$_2$ (20 mL), 1.21 g of product (84%) were obtained. $^1$H NMR (CD$_2$Cl$_2$): δ 1.05 (d, 3H), 1.88 (m, 1H), 2.18 (m, 1H), 3.45 (m, 1H), 3.67 (s, 3H), 6.60 (m, 1H, aryl), 6.69 (s, 1H), 6.93 (d, 1H).

Example 18

Preparation of methyl 2-(6-methoxy-1H-inden-3-yl)butanoate

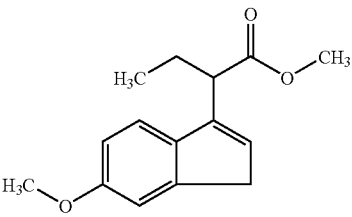

An oven dried 5-L four-necked round-bottomed flask was fitted with a thermometer, a condenser, an addition funnel, and a mechanical stirrer. Under an argon atmosphere, a suspension of 5-methoxy-1-indanone (80.0 g, 494 mmol), Zn powder (Lancaster, 56.2 g, 865 mmol) in THF (2 L, anhydrous) was stirred at 60° C. (internal temperature), while a solution of methyl bromobutyrate (134.1 g, 741 mmol) in THF (400 mL, anhydrous) was added slowly using an addition funnel. After completion of the addition, the reaction mixture was stirred at 60° C. (internal temperature) for 1 h. The reaction was followed by TLC analysis of aliquots following 1 N aqueous HCl workup. After the reaction was completed, it was cooled in an ice-water bath followed by slow addition of HCl (3 L, 1 N aqueous solution). The internal temperature was kept below 20° C. The mixture was then extracted with EtOAc (1 L). The organic layer was washed with water until a pH of 6.0-7.0 was reached, then with brine, dried over Na$_2$SO$_4$, and then filtered. The product (127 g,>99%), a yellow oil, was obtained after solvent removal and drying under vacuum. $^1$H NMR (300 MHz), (DMSO-d$_6$) δ 7.28 (d, 1H), 7.05 (d, 1H), 6.82 (dd, 1H), 6.22 (s, 1H), 3.72 (s, 3H), 3.60 (m, 1H), 3.58 (s, 3H), 3.28 (s, 2H), 1.95 (m, 1H), 1.80 (m, 1H), 0.88 (t, 3H).

Example 19

Preparation of 2-(6-methoxy-1H-inden-3-yl)butanoic acid

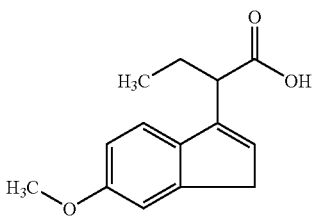

To a solution of the ester prepared in Example 18 (200.0 g, 813 mmol) in MeOH (2 L), was added a solution of KOH (91.0 g, 1.63 mol) in water (200 mL). The reaction mixture was stirred at 60° C. (internal temperature) for 2 h. TLC showed 70% conversion. A solution of KOH (45.0 g, 0.81 mol) in water (100 mL) was then slowly added to the reaction mixture. The reaction was complete in 1 h, after which the mixture was cooled to rt, and then the solvents were removed under reduced pressure. The residue was dissolved in water (3 L), and then washed with EtOAc (2×1 L). The aqueous layer was cooled in an ice-water bath, acidified with HCl (37% aqueous solution) to pH<3.0 and extracted with CH₂Cl₂ (3 L). The organic phase was washed with water (2×1 L), dried over Na₂SO₄, filtered, and then the filtrate was stirred with 30 g charcoal for 2 h. The charcoal was removed by filtration through a pad of Celite® to provide the title compound (175 g, 93%) as a light brown solid after solvent removal and drying under reduced pressure. ¹H NMR (300 MHz), (DMSO-d₆) δ12.20 (b, 1H), 7.30 (d, 1H), 7.06 (d, 1H), 6.82 (dd, 1H), 6.22 (s, 1H), 3.75 (s, 3H), 3.45 (t, 1H), 3.30 (s, 2H), 1.90 (m, 1H) 1.78 (m, 1H), 0.90 (t, 3H).

Example 20

Preparation of (2S)-2-(6-methoxy-1H-inden-3-yl)butanoic acid

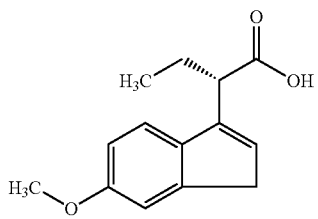

To a solution of the racemic indene acid prepared in Example 19 (300 g, 1.29 mol) in CH₃CN (4.5 L), was added quinine (324 g, 1.0 mol) at rt. The mixture was stirred for 1 h, and became a homogeneous solution. A small amount of the insoluble particles were removed by filtration through a microfiber filter under vacuum. The filtrate was then mechanically stirred under argon for 24 h, a precipitate formed, after which a small sample of the solid was taken and analyzed by chiral analytical HPLC (Method A), showing 76% ee. The agitation was continued for two additional days, after which the suspension was filtered. The solid collected was washed with CH₃CN (3×200 mL), and then dried under vacuum at 40° C. for 3 h. This solid was stirred with CH₃CN (4.5 L) at 70° C. until all solids went into solution. Heat was shut off, and the solution was allowed to cool to rt slowly. The resulting suspension was stirred at rt for 24 h and then filtered. The filter cake was washed with CH₃CN (3×250 mL) and dried under vacuum at 40° C. for 24 h. This quinine salt was collected as a white solid (254.6 g, 35.4% yield, 96.8% ee for the acid).

The quinine salt (544.3 g, 0.98 mol) was dissolved in CH₂Cl₂ (4.0 L) to obtain a clear solution. This solution was stirred vigorously with HCl (4.0 L of a 2N aqueous solution) in a 22-L round-bottomed flask with a bottom valve. After 30 min, the mixture was allowed to settle, the organic layer was separated and the aqueous layer was extracted with CH₂Cl₂ (1 L). The combined organic layers were washed with water (3×2.0 L) until a pH of 5.0-6.0 was reached, and then dried over Na₂SO₄. The product (230.8 g, 99%, 96.8% ee) was obtained as an off white solid after solvent removal and vacuum drying. The ¹H NMR spectrum was identical to that of the racemic material described in Example 19.

Treatment of the mother liquor in similar fashion gave the enriched R-isomer. Alternatively, the mother liquor could be subjected to aqueous basic conditions in order to effect racemization and recovery of racemic starting material.

The absolute configuration was determined after the following step (Example 21).

Example 21

Preparation of (2S)-2-[(1S)-5-methoxy-2,3-dihydro-1H-inden-1-yl]butanoic acid

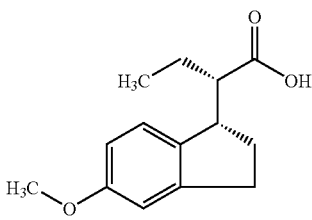

A solution of the product obtained in Example 20 (105 g, 453 mmol), ClRh(PPh₃)₃ (21.0 g, 22.7 mmol), and Et₃N (68.8 g, 679.5 mmol) in EtOH (945 mL) and THF (105 mL) was shaken in a 2-L pressure bottle under H₂ (60 psi) for 16 h. The solvents were removed under reduced pressure and the residue was taken up in a mixture of HCl (1.5 L, 1 N aqueous solution) and CH₂Cl₂ (1.5 L) and stirred. The aqueous layer was extracted with CH₂Cl₂ (2×250 mL). The combined organic layers were washed with HCl (1 L, 1 N aqueous solution) and stirred with NaOH (1 L, 1 N aqueous solution). The organic layer was extracted with NaOH (2×0.5 L, 1 N aqueous solution). The combined aqueous layer was washed with CH₂Cl₂ (2×250 mL), and acidified (pH 2.0-3.0) by a slow addition of HCl (37% aqueous solution) while maintaining the temperature below 15° C. The acidic mixture was extracted with CH₂Cl₂ (2×1.5 L). The combined organic phases were washed with water (2×0.5 L) until a pH of 5.0-6.0 was reached, and brine, dried over Na₂SO₄, filtered, and then concentrated under reduced pressure. The product (101.0 g, 95% yield, 96.8% ee) was obtained as a light yellow oil.

The absolute configuration of the title compound was determined by single crystal X-Ray crystallography of the corresponding (R)-(+)-α-methyl benzylamine salt.

¹H NMR (300 MHz), (DMSO-d₆) δ 12.20 (s, 1H), 7.04 (d, 1H), 6.78 (d, 1H), 6.66 (dd, 1H), 3.70 (s, 3H), 3.28 (m, 1H), 2.72 (m, 2H), 2.32 (m, 1H), 2.06 (m, 1H), 1.80 (m, 1H), 1.50 (m, 1H), 1.36 (m, 1H), 0.82 (t, 3H).

Example 22

Preparation of methyl(2S)-2-[(1S)-5-methoxy-2,3-dihydro-1H-inden-1-yl]butanoate

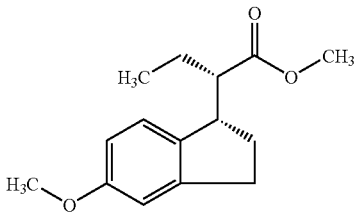

A suspension of the acid prepared in Example 21 (220.0 g, 0.94 mol), NaHCO₃ (237.0 g, 2.82 mol), CH₃I (200 g, 1.41 mol) in DMF (2.0 L) was stirred under argon at rt for 18 h.

Adding additional CH₃I (100 g, 0.71 mol) and stirring for an additional 24 h at rt caused completion of the reaction. The reaction mixture was poured into 4.0 L water, and extracted with EtOAc (2×2 L). The combined organic layers were sequentially washed with water (2×1 L), NaOH (1 L, 1 N aqueous solution), water (2×1 L), and brine (0.5 L). The organic phase was dried over Na₂SO₄, filtered, and concentrated under reduced pressure to afford the title compound (233 g, 99%) as a light yellow. ¹H NMR (300 MHz, DMSO-d₆) δ 6.90 (d, 1H), 6.78 (d, 1H), 6.66 (dd, 1H), 3.70 (s, 3H), 3.60 (s, 3H), 3.20 (m, 1H), 2.80 (m, 2H), 2.40 (m, 1H), 2.08 (m, 1H), 1.80 (m, 1H), 1.58 (m, 1H), 1.40 (m, 1H), 0.80 (t, 3H).

Example 23

Preparation of methyl(2S)-2-[(1S)-5-hydroxy-2,3-dihydro-1H-inden-1-yl]butanoate

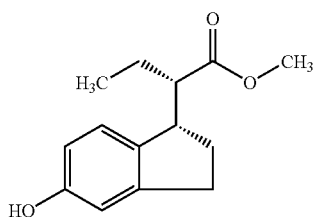

To a cold solution (ice water bath) of the compound prepared in Example 22 (233 g, 0.94 mol) in CH₂Cl₂ (2.5 L), was added AlCl₃ (630 g, 4.7 mol) slowly under argon. The internal temperature was kept below 20° C., and the color of the reaction turned purple. EtSH (345 mL, 4.7 mol) was added slowly via an addition funnel maintaining the internal temperature below 15° C. After 2 h of stirring at a temperature below 20° C., the reaction was completed and was slowly poured into ice-water (2.5 L) with strong agitation. The organic phase was separated, and the aqueous phases was extracted with CH₂Cl₂ (1 L) The combined organic phases were washed with water (4×1 L) until a pH of 6.0-7.0 was reached, and then dried over Na₂SO₄, filtered, concentrated under reduced pressure and then dried under vacuum to provide the title compound (216 g, 98%) as a white solid. ¹H NMR (300 MHz), (DMSO-d₆) δ 9.10 (s, 1H), 6.78 (d, 1H), 6.58 (d, 1H), 6.50 (dd, 1H), 3.60 (s, 3H), 3.20 (q, 1H), 2.70 (m, 2H), 2.40 (m, 1H), 2.08 (m, 1H), 1.80 (m, 1H), 1.50 (m, 2H), 0.80 (t, 3H).

Example 24

Preparation of 3-trifluoromethyl-7-propyl-6-hydroxy-benzisoxazole

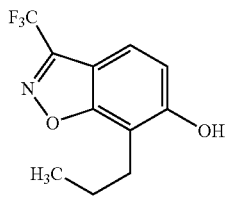

1-(2,4-Dihydroxy-3-propylphenyl)-2,2,2-trifluoroethanone oxime (4.2 g, 15.96 mmol, prepared by the method described in WO9728137) and PPh₃ (8.82 g, 33.6 mmol) were dissolved in THF (250 mL), and the mixture was cooled to 0° C. A solution of DEAD (5.02 mL, 32.0 mmol) in THF (150 mL) was slowly added over a period of 30 min. The reaction mixture was stirred for 1 h at 0° C. After addition of water (500 mL) and extraction with EtOAc (3×300 mL), the combined organic phases were washed with brine (300 mL), dried over Na₂SO₄, filtered, and concentrated under reduced pressure. The product was purified by silica gel flash chromatography (1:6 EtOAc/hexane) to yield 1.96 g (50%) of the title compound as a light yellow powder. ¹H NMR (300 MHz, CDCl₃): δ 1.00 (t, 3H), 1.73 (m, 2H), 2.88 (t, 2H), 5.34 (s, 1H), 6.93 (d, 1H), 7.48 (d, 1H).

Example 25

Preparation of 6-(2-bromoethoxy)-7-propyl-3-(trifluoromethyl)-1,2-benzisoxazole

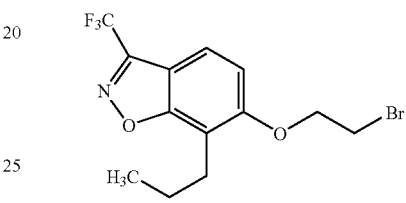

3-Trifluoromethyl-7-propyl-6-hydroxy-benzisoxazole (1 g, 4.1 mmol) prepared in Example 24, 1,2-dibromoethane (3.7 g, 18.3 mmol) and NaOH (6 M aqueous solution, 1 mL, 6.0 mmol) were combined and stirred under reflux for 4.5 h. A second portion of NaOH (6 M aqueous solution, 0.43 mL, 2.6 mmol) was added, and stirring under reflux was continued for 4 h. Upon cooling to rt, water (10 mL) was added and the mixture was extracted with CH₂Cl₂ (3×). The combined organic phases were washed with NaOH (5 M aqueous solution, 2×) and water (3×). The organic phase was dried over Na₂SO₄, filtered, and concentrated under reduced pressure. The crude product was purified by silica gel flash chromatography (EtOAc/hexanes (v/v) 1:9) to obtain 550 mg (38%) of the title compound as colorless crystals. ¹H NMR (300 MHz, CDCl₃): δ 0.99 (t, 3H), 1.72 (dt, 2H), 2.94 (t, 2H), 3.70 (t, 2H), 4.42 (t, 2H), 7.03 (d, 1H), 7.58 (d, 1H).

Example 26

Preparation of ((1S)-5-{2-[(3-methyl-7-propyl-1,2-benzisoxazol-6-yl)oxy]ethoxy}-2,3-dihydro-1H-inden-1-yl)acetic acid

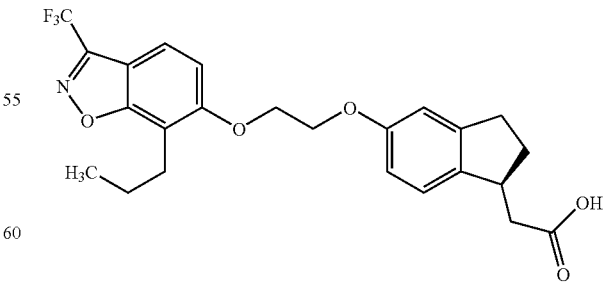

Ethyl[(1S)-5-hydroxy-2,3-dihydro-1H-inden-1-yl]acetate (Example 6) (62.4 mg, 0.28 mmol) was dissolved in DMF (5 mL), and Cs₂CO₃ (111 mg, 0.34 mmol) and 3 drops of water were added. 6-(2-bromoethoxy)-7-propyl-3-(trifluoromethyl)1,2-benzisoxazole (100 mg, 0.28 mmol) was added and the reaction mixture was stirred for 10 h at 60° C. The solvent was removed under reduced pressure, and the crude product was taken up in EtOAc, filtered through silica gel, and the filtrate was concentrated under reduced pressure. The crude product was dissolved in THF (2 mL), and LiOH (0.5 M aqueous solution, 0.9 mL) and MeOH (4 drops) were added. After stirring for 18 h at 50° C. the reaction mixture was concentrated under reduced pressure. Water and HCl (1 N aqueous solution) were added until the mixture was acidic which was followed by extraction using EtOAc. The product was purified by silica gel filtration (gradient 1:6 EtOAc/Hexane to 100% EtOAc), yielding 12 mg (9% over 2 steps) of the title compound as white crystals. $^1$H NMR (300 MHz, CD$_3$OD): δ 0.91 (t, 3H), 1.70 (m, 3H), 2.33 (m, 2H), 2.68 (m, 2H), 2.87 (m, 3H), 3.46 (m, 1H), 4.33 (m, 2H), 4.48 (m, 2H), 6.73 (dd, 1H), 6.82 (d, 1H), 7.11 (d, 1H), 7.34 (d, 1H), 7.67 (d, 1H).

Example 27

Preparation of 4-(allyloxy)benzonitrile

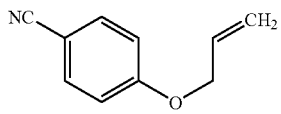

4-Hydroxybenzonitrile (30.0 g, 252 mmol), allyl bromide (39.6 g, 327 mmol), and Cs$_2$CO$_3$ (98.5 g, 302 mmol) were dissolved in DMF (900 mL), and water (1 mL) was added. After stirring for 12 h at rt, the reaction mixture was concentrated under reduced pressure, water was added, and the mixture was extracted with EtOAc (2×). The combined organic layers were washed with water and brine. The organic layer was dried over Na$_2$SO$_4$, filtered, and concentrated under reduced pressure yielding 40 g (100%) of the title compound as a white crystalline solid. $^1$H NMR (400 MHz, CDCl$_3$): δ 4.60 (d, 2H), 5.34 (d, 1H), 5.43 (d, 1H), 6.03 (m, 1H), 6.96 (d, 2H), 7.58 (d, 2H).

Example 28

Preparation of 3-allyl-4-hydroxybenzonitrile

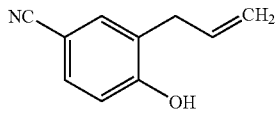

4-(Allyloxy)benzonitrile (40.0 g, 251.3 mmol) (Example 27) was heated under argon at 200° C. for 20 h. Upon cooling to rt, the product was purified via silica gel flash chromatography (EtOAc/hexane (v/v)=1:10 to EtOAc/hexane (v/v)=1:4 gradient), yielding 27.5 g (69%) of the title compound as a white crystalline solid. $^1$H NMR (400 MHz, CDCl$_3$): δ 3.44 (d, 2H), 5.18 (d, 1H), 5.24 (d, 1H), 5.99 (m, 1H), 6.05 (br, 1H), 6.89 (d, 1H), 7.46 (d, 2H).

Example 29

Preparation of 4-hydroxy-3-propylbenzonitrile

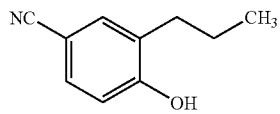

3-Allyl-4-hydroxybenzonitrile (20.0 g, 126 mmol) (Example 28) was dissolved in EtOH (320 mL) under argon. Pd/C (80 mg, 10%, Fluka) was added, and the reaction mixture was stirred under a hydrogen atmosphere (1 atm) at rt for 20 h. The catalyst was filtered off, and then the reaction mixture was concentrated under reduced pressure, yielding 20.2 g (99%) of the title compound as a slightly greenish oil. $^1$H NMR (400 MHz, CDCl$_3$): δ 0.95 (t, 3H), 1.63 (m, 2H), 2.56 (m, 2H), 6.86 (d, 1H), 7.30 (m, 2H).

Example 30

Preparation of 4-(benzyloxy)-3-propylbenzonitrile

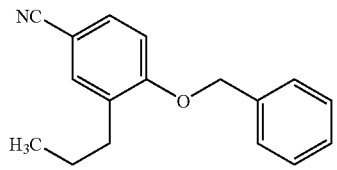

To a solution of 4-hydroxy-3-propylbenzonitrile (0.97 g, 6 mmol) (Example 29) in DMF (20 mL) were added 10 drops of water, benzyl bromide (2.05 g, 12 mmol), and Cs$_2$CO$_3$ (2.93 g, 9 mmol), and the mixture was stirred for 12 h at rt. The reaction mixture was concentrated under reduced pressure, and the residue was suspended in EtOAc and filtered. The precipitate was washed with more EtOAc. The combined filtrates were concentrated and purified by silica gel chromatography (EtOAc/hexanes (v/v)=1:19) to give 1.23 g (82%) of the title compound. $^1$H NMR (400 MHz, CDCl$_3$): δ 7.48-7.32 (m, 7H), 6.92 (d, 1H), 5.13 (s, 2H), 2.67 (t, 2H), 1.72-1.60 (m, 2H), 0.98 (t, 3H).

Example 31

Preparation of 4-(benzyloxy)-3-propylbenzenecarbothioamide

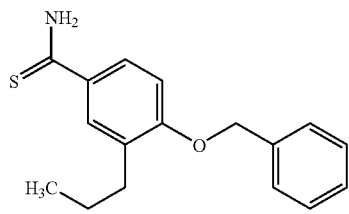

Through a solution of 4-(benzyloxy)-3-propylbenzonitrile (1.23 g, 4.91 mmol) (Example 30) in DMF (35 mL) was passed H₂S for 30 min at rt. Diethyl amine (0.76 mL, 7.36 mmol) was added and the solution was heated to 60° C. for 4 h. The mixture was cooled to rt, and the residual H₂S was removed by passing argon through the solution for 30 min. The reaction mixture was concentrated under reduced pressure, and the residue was filtered through a plug of silica and washed with EtOAc. Concentration of the filtrate under reduced pressure resulted in a yellow solid which was used in the next step without further purification.

Example 32

Preparation of 2-[4-(benzyloxy)-3-propylphenyl]-4-ethyl-1,3-thiazole

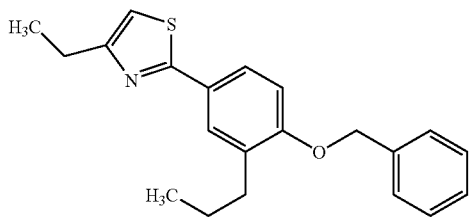

To a solution of 4-benzyloxy)-3-propylbenzenecarbothioamide (0.53 g, 1.86 mmol) (Example 31) in EtOH (70 mL) was added 1-bromo-2-butanone (0.47 g, 2.79 mmol), and the reaction was stirred for 3 h at 70° C. After the reaction was complete, the reaction mixture was concentrated under reduced pressure and the residue was saved. This procedure was repeated on a 1.1 g scale (based on thioamide). The two crude residues were combined and purified by silica gel chromatography (EtOAc/hexane (v/v)=1:9, then 100% EtOAc) to give 0.87 g (67% overall) of the title compound. ¹H NMR (400 MHz, CDCl₃):δ 7.72 (s, 1H), 7.67 (d, 1H), 7.45-7.28 (m, 5H), 6.88 (d, 1H), 6.76 (s, 1H), 5.12 (s, 2H), 4.09 (q, 2H), 2.84 (q, 2H), 2.75-2.66 (m, 2H), 1.30 (t, 3H), 0.93 (t, 3H).

Example 33

Preparation of 4-(4-ethyl-1,3-thiazol-2-yl)-2-propylphenol

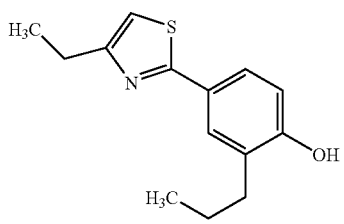

Under an atmosphere of argon, palladium on charcoal (0.10 g) was added to a solution of 2-[4-benzyloxy]-3-propylphenyl]-4-ethyl-1,3-thiazole (0.86 g, 2.53 mmol) (Example 32) and ammonium formate (1.28 g, 20.3 mmol) in EtOH (45 mL). The mixture was stirred at 40° C. for 2 h, and then cooled to rt. The solvent was evaporated and the material was suspended in EtOAc. This suspension was filtered through a small plug of silica gel and then concentrated to give a crude solid. The product was used in the next step without further purification. ¹H NMR (400 MHz, CDCl₃): δ 7.66 (s, 1H), 7.56 (d, 1H), 6.77-6.66 (m, 2H), 5.70-5.42 (br, 1H), 2.88-2.76 (m, 2H), 2.64-2.55 (m, 2H), 1.72-1.57 (q, 2H), 1.31 (t, 3H), 0.95 (t, 3H).

Example 34

Preparation of 2-[4-(2-bromoethoxy)-3-propylphenyl]-4-ethyl-1,3-thiazole

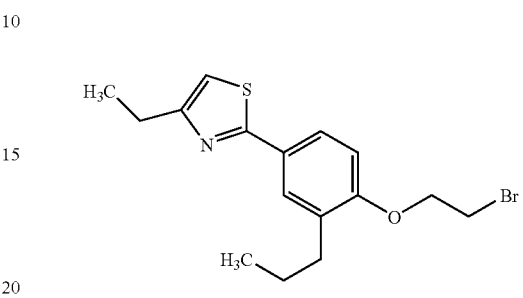

To a solution of 4-(4-ethyl-1,3-thiazol-2-yl)-2-propylphenol (0.24 g, 0.97 mmol) (Example 33) in DMF (2 mL, containing 1% v/v of water) was added 1,2-dibromoethane (1.09 g, 5.82 mmol), and the mixture was stirred at rt for 12 h. The reaction mixture was filtered, and the filtrate was concentrated under reduced pressure. The crude residue was suspended in EtOAc, filtered through a small plug of silica, and the filtrate was concentrated. The crude material was used in the next step without further purification. ¹H NMR (400 MHz, CDCl₃): δ 7.79-7.68 (m, 2H), 6.88-6.78 (m, 2H), 4.34 (t, 2H), 3.69 (t, 2H), 2.95-2.82 (m, 2H), 2.72-2.60 (m, 2H), 1.80-1.64 (m, 2H), 1.36 (t, 3H), 1.02 (t, 3H).

Example 35

Preparation of ethyl((1S)-5-{2-[4-(4-ethyl-1,3-thiazol-2-yl)-2-propylphenoxy]-ethoxy}-2,3-dihydro-1H-inden-1-yl)acetate

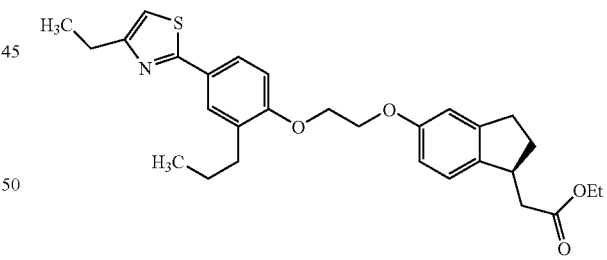

To a mixture of 2-[4-(2-bromoethoxy)-3-propylphenyl]-4-ethyl-1,3-thiazole (105 mg 0.30 mmol) (Example 34) and ethyl[(1S)-5-hydroxy-2,3-dihydro-1H-inden-1-yl]acetate (65 mg, 0.30 mmol) (Example 6) in DMF (4 mL, containing 1% v/v of water), was added Cs₂CO₃ (145 mg, 0.44 mmol), and the mixture was stirred for 24 h at rt. The reaction mixture was concentrated under reduced pressure, and the residue was suspended in EtOAc and filtered. The filtrate was concentrated and purified by silica gel chromatography (gradient: 100% hexane to 1:9 (v/v) EtOAc/hexane) to give 66 mg (41%) of the title compound as an oil. ¹H NMR (400 MHz, CDCl₃): δ 7.72-7.58 (m, 3H), 6.98 (d, 1H), 6.86-6.60 (m, 3H), 4.33-4.28 (br, 2H), 4.28-4.20 (br, 1H), 4.10 (q, 2H), 3.52-3.40

(m, 1H), 2.84 (m, 4H), 2.64 (dd, 1H), 2.58-2.50 (m, 3H), 2.40-2.24 (m, 2H), 1.72-1.50 (m, 3H), 1.26 (t, 3H), 1.20 (t, 3H), 0.84 (t, 3H).

Example 36

Preparation of ((1S)-5-{2-[4-(4-ethyl-1,3-thiazol-2-yl)-2-propylphenoxy]ethoxy}-2,3-dihydro-1H-inden-1-yl)acetic acid

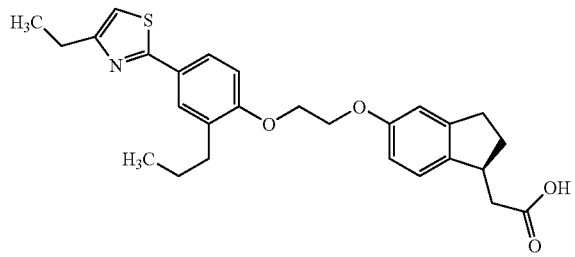

To a solution of ethyl((1S)-5-{2-[4-4-ethyl-1,3-thiazol-2-yl)-2-propylphenoxy]ethoxy}-2,3-dihydro-1H-inden-1-yl)acetate (18 mg, 0.04 mmol) (Example 35) in THF (1.2 mL), was added a solution of LiOH.H$_2$O (5 mg, 0.11 mmol) in H$_2$O (0.4 mL). The mixture was stirred for 12 h at rt. The reaction mixture was concentrated under reduced pressure, and the residue was suspended in a small volume of water. Then, HCl (1 N aqueous solution) was added until the solution was below pH 3. The aqueous layer was extracted with excess EtOAc, and the organic layer was dried, filtered and then concentrated to give the crude product. The residue was purified by HPLC (C$_{18}$ reverse phase column, using 0-80% CH$_3$CN in water) to give 2.2 mg (13%) of the title compound as a white solid. LC-MS: RT 3.78 min; (M+H)$^+$: 466.4.

Examples of compounds of Formula (Ikk) [Formula (I), where R$^2$ and R$^1$ are H, L is —Y—(CH$_2$)$_n$—X—, X and Y are O, and n is 2], as shown in Table 1a below, were made using procedures similar to those described in the previous Examples 1-36. All of the Ar—Y—H compounds [Formula (II) in Reaction Scheme 1] used as precursors were commercially available, unless otherwise noted.

TABLE 1a (Ikk)

| Ex. No | Ar | HPLC RT (min) | LC-MS [M + H]$^+$ |
|---|---|---|---|
| 37 | indol-5-yl | 2.87 | 352.2 |
| 38 | 2-methylindol-5-yl | 3.00 | 366.2 |
| 39 | indol-6-yl | 2.95 | 352.1 |
| 40 | indol-4-yl | 2.91 | 352.1 |
| 41 | 3-methylbenzofuran-6-yl | 3.33 | 367.5 |
| 42 | 2-methylbenzothiazol-5-yl | 2.93 | 384.3 |
| 43 | quinolin-6-yl | 2.02 | 364.2 |
| 44 | quinolin-7-yl | 2.08 | 364.3 |

TABLE 1b

IUPAC Names for Compounds in Table 1a

| Ex. No. | IUPAC Name |
|---|---|
| 37 | 2-[(1S)-5-(2-indol-5-yloxyethoxy)indanyl]acetic acid |
| 38 | 2-{(1S)-5-[2-(2-methylindol-5-yloxy)ethoxy]indanyl}acetic acid |
| 39 | 2-[(1S)-5-(2-indol-6-yloxyethoxy)indanyl]acetic acid |
| 40 | 2-[(1S)-5-(2-indol-4-yloxyethoxy)indanyl]acetic acid |

TABLE 1b-continued

IUPAC Names for Compounds in Table 1a

| Ex. No. | IUPAC Name |
|---|---|
| 41 | 2-{(1S)-5-[2-(3-methylbenzo[3,4-b]furan-6-yloxy)ethoxy]indanyl}acetic acid |
| 42 | 2-{(1S)-5-[2-(2-methylbenzothiazol-5-yloxy)ethoxy]indanyl}acetic acid |
| 43 | 2-[(1S)-5-(2-(6-quinolyloxy)ethoxy)indanyl]acetic acid |
| 44 | 2-[(1S)-5-(2-(7-quinolyloxy)ethoxy)indanyl]acetic acid |

Example 45

Preparation of ethyl[(1S)-5-(3-bromopropoxy)-2,3-dihydro-1H-inden-1-yl]acetate

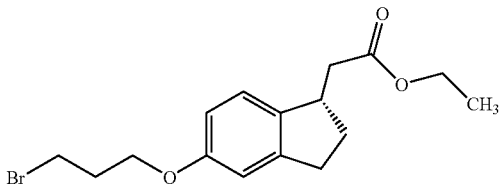

To a solution of ethyl[(1S)-5-hydroxy-2,3-dihydro-1H-inden-1-yl]acetate (0.166 g, 0.754 mmol) (Example 6) in DMF (0.5 mL, containing 1% v/v of water), were added 1,3-dibromopropane (0.27 mL, 2.64 mmol) and $Cs_2CO_3$ (0.295 g, 0.905 mmol). The mixture was stirred at rt for 13 h and then at 80° C. for 1 h. Upon cooling to rt, the reaction mixture was concentrated under reduced pressure. The residue was suspended in EtOAc, filtered, and the filter cake was washed with EtOAc. The combined filtrate was dried, concentrated and purified by silica gel chromatography (100% hexanes to EtOAc/hexane (v/v) 1:19 gradient) to give 153 mg (60%) of the title compound containing minor impurities. This material was used in later steps without further purification. $^1$H NMR (300 MHz, $CDCl_3$): δ 7.08 (d, 1H), 6.78 (s, 1H), 6.70 (dd, 1H), 4.19 (q, 2H), 4.08 (t, 2H), 3.60 (t, 2), 3.58-3.44 (m, 1H), 2.96-2.64 (m, 3H), 2.50-2.21 (m, 4H), 1.93-1.68 (m, 1H), 1.38 (t, 3H).

Example 46

Preparation of 5-(benzyloxy)-1-methyl-1H-indole

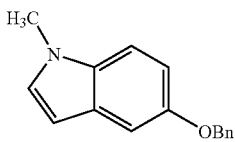

5-(Benzyloxy)-1H-indole (300 mg, 1.34 mmol) was dissolved in anhydrous DMF under an atmosphere of argon and cooled in a water bath. Sodium hydride (60% dispersion in mineral oil, 64.5 mg, 1.61 mmol) was added, and the mixture was stirred for 30 min. Iodomethane (247.9 mg, 1.75 mmol) was added and stirring was continued for 12 h at 40° C. The mixture was cooled to rt, 10 drops of water were added, and the reaction mixture was concentrated under reduced pressure. The residue was taken up in water and was extracted with EtOAc (2×). Purification by silica gel flash chromatography (EtOAc/hexane (v/v)=1:7) gave 254 mg (80%) of the title compound as a white crystalline solid. $^1$H NMR (400 MHz, $CDCl_3$): δ 3.78 (s, 3H), 5.11 (s, 2H), 6.40 (br, 1H), 6.94 (d, 1H), 7.00 (s, 1H), 7.17 (s, 1H), 7.20-7.48 (m, 6H).

Example 47

Preparation of 1-methyl-1H-indol-5-ol

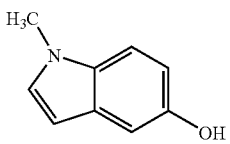

5-(Benzyloxy)-1-methyl-1H-indole (Example 46, 254 mg, 1.07 mmol) was dissolved in EtOH (15 mL) and 20% palladium (II) hydroxide on carbon (30.0 mg) was added. Ammonium formate (540 mg, 8.6 mmol) was added, and the mixture was stirred for 30 min at rt and subsequently for 2 h at 35° C. The catalyst was removed by filtration, and the filtrate was concentrated under reduced pressure. The residue was taken up in water, and the aqueous solution was extracted with EtOAc (2×). The combined organic phases were dried over $Na_2SO_4$, filtered, and concentrated under reduced pressure to provide 141 mg (90%) of the title compound as a white crystalline solid. $^1$H NMR (400 MHz, $CDCl_3$): δ 3.78 (s, 3H), 6.33 (br, 1H), 6.79 (d, 1H), 7.03 (br, 2H), 7.19 (d, 1H).

Example 48

Preparation of ethyl((1S)-5-{3-[(1-methyl-1H-indol-5-yl)oxy]propoxy}-2,3-dihydro-1H-inden-1-yl)acetate

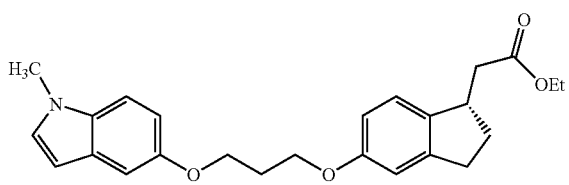

To a solution of 1-methyl-1H-indol-5-ol (44.0 mg, 0.30 mmol) (Example 47) and ethyl[(1S)-5-(3-bromopropoxy)-2,3-dihydro-1H-inden-1-yl]acetate (Example 45, 100 mg, 0.29 mmol) in DMF (4.0 mL) were added $Cs_2CO_3$ (114.6 mg, 0.35 mmol) and water (3 drops). The reaction mixture was stirred at 40° C. for 16 h, then cooled to rt, and concentrated under reduced pressure. Water was added and the aqueous layer was extracted with EtOAc (2×). The combined organic phases were dried over $Na_2SO_4$, filtered, and concentrated under reduced pressure. Purification by silica gel flash chromatography (EtOAc/Hexane (v/v)=1:13) yielded 55 mg (46%) of the title compound as a clear oil. $^1$H NMR (400 MHz, $CDCl_3$): δ 1.28 (t, 3H), 1.76 (m, 1H), 2.26 (m, 2H), 2.39 (m, 2H), 2.71 (dd, 1H), 2.88 (m, 2H), 3.50 (m, 1H), 3.78 (s, 3H), 4.18 (m, 6H), 6.38 (d, 1H), 6.72 (dd, 1H), 6.80 (s, 1H), 6.89 (d, 1H), 7.02 (s, 1H), 7.06 (d, 1H), 7.10 (s, 1H), 7.20 (d, 1H).

Example 49

Preparation of ((1S)-5-{3-[(1-methyl-1H-indol-5-yl)oxy]propoxy}-2,3-dihydro-1H-inden-1-yl)acetic acid

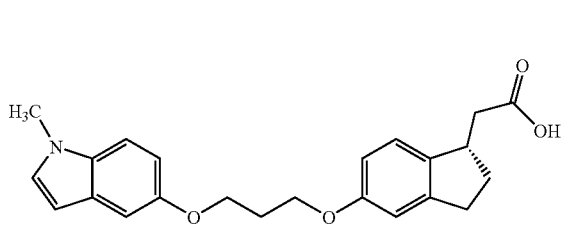

To a solution of ethyl((1S)-5-{3-[(1-methyl-1H-indol-5-yl)oxy]propoxy}-2,3-dihydro-1H-inden-1-yl)acetate (51 mg, 0.13 mmol) (Example 48) in THF (1.8 mL) was added LiOH.H$_2$O (6 mg, 0.15 mmol) in water (0.6 mL). The mixture was stirred for 12 h at rt, then the reaction mixture was concentrated under reduced pressure and the residue suspended in a small volume of water. The pH was adjusted to below 3 with HCl (1 N aqueous solution), and the aqueous layer was extracted with EtOAc. The organic layer was dried, filtered, and concentrated under reduced pressure to give 44 mg (93%) of the title compound as a solid. $^1$H NMR (400 MHz, CDCl$_3$): δ 7.10 (d, 1H), 7.05-6.96 (m, 2H), 6.93 (d, 1H), 6.81 (dd, 1H), 6.72 (s, 1H), 6.65 (dd, 1H), 6.32 (d, 1H), 4.18-4.00 (m, 4H), 3.69 (s, 3H), 3.52-3.40 (m, 1H), 2.92-2.65 (m, 3H), 2.42-2.24 (m, 2H), 2.22-2.10 (m, 2H), 1.78-1.62 (m, 1H); LC-MS RT=3.45 min, (M+H)$^+$ 380.1.

Example 50

Preparation of 4-methyl-1H-indol-5-ol

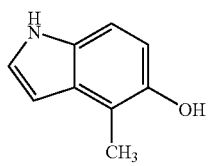

5-Methoxy-4-methyl-1H-indole (400.0 mg, 2.48 mmol) was dissolved in CH$_2$Cl$_2$ in an inert atmosphere, and the mixture was cooled to 5° C. Aluminium trichloride (1.65 g, 12.4 mmol) was added, and the reaction mixture was stirred for 5 min, at which point ethanethiol (770.8 mg, 12.4 mmol) was added dropwise. Stirring was continued for 2 h at 5° C. The mixture was poured into ice water (10 mL), stirred for 20 min, and then NaHCO$_3$ was added until a pH>7 was reached. The mixture was extracted with CH$_2$Cl$_2$ (4×), the combined organic phases dried over Na$_2$SO$_4$, filtered, and concentrated under reduced pressure. The residue was purified by silica gel flash chromatography (EtOAc/hexane (v/v) 1:5) to give 133 mg (36%) of the title compound as a white crystalline solid. $^1$H NMR (400 MHz, CDCl$_3$): δ 2.46 (s, 3H), 4.40 (br, 1H), 6.49 (s, 1H), 6.76 (d, 1H), 7.10 (d, 1H), 7.19 (s, 1H), 8.03 (br, 1H).

Example 51

Preparation of ethyl((1S)-5-{3-[(4-methyl-1H-indol-5-yl)oxy]propoxy}-2,3-dihydro-1H-inden-1-yl)acetate

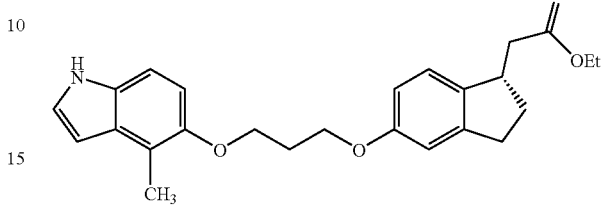

Using Examples 50 and 45 as starting materials, the product was prepared as described in Example 48. $^1$H NMR (400 MHz, CDCl$_3$): δ 1.30 (t, 3H), 1.76 (m, 1H), 2.28 (m, 2H), 2.41 (m, 2H), 2.47 (s, 3H), 2.69-2.94 (m, 3H), 3.52 (m, 1H), 4.20 (m, 6H), 6.51 (s, 1H), 6.76 (d, 1H), 6.82 (s, 1H), 6.91 (d, 1H), 7.09 (d, 1H), 7.16 (m, 2H), 8.10 (br, 1H).

Example 52

Preparation of ((1S)-5-{3-[(4-methyl-1H-indol-5-yl)oxy]propoxy}-2,3-dihydro-1H-inden-1-yl)acetic acid

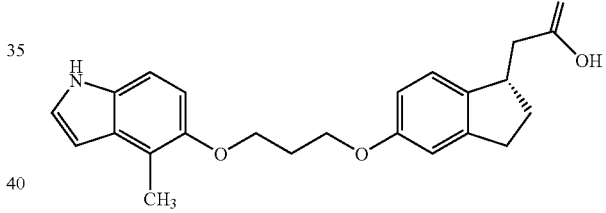

Using Example 51 as starting material, the product was prepared as described for Example 49. $^1$H NMR (400 MHz, CDCl$_3$): δ 8.06-7.98 (br, 1H), 7.22-7.14 (m, 2H), 7.08 (d, 1H), 6.90 (d, 1H), 6.80 (s, 1H), 6.74 (dd, 1H), 6.50 (s, 1H), 4.26-4.10 (m, 4H), 3.69-3.46 (m, 1H), 2.95-2.78 (m, 3H), 2.54-2.39 (m, 5H), 2.32-2.20 (m, 2H), 1.88-1.62 (m, 1H); LC-MS RT=3.17 min, (M+H)$^+$ 380.1.

Example 53

Preparation of 5-(allyloxy)-1H-indole

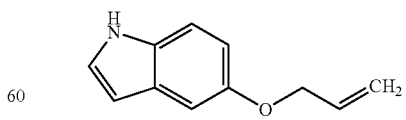

5-Hydroxy-1H-indole (500 mg, 3.76 mmol) and allyl bromide (499.7 mg, 4.13 mmol) were dissolved in DMF (15 mL), then Cs$_2$CO$_3$ (1.468 g, 4.51 mmol), and water (6 drops) were added. The reaction mixture was stirred at rt for 12 h, after which it was concentrated under reduced pressure, diluted with water, and the aqueous layer was extracted with EtOAc (2×). The combined organic phases were dried over Na$_2$SO$_4$, filtered, and concentrated under reduced pressure. Purification by silica gel flash chromatography (EtOAc/hexane (v/v)=1:11) gave 514 mg (79%) of the title compound as a light-yellow oil. $^1$H NMR (400 MHz, CDCl$_3$): δ 4.59 (d, 2H), 5.29 (d, 1H), 5.45 (d, 1H), 6.12 (m, 1H), 6.48 (d, 1H), 6.90 (d, 1H), 7.11 (s, 1H), 7.19 (s, 1H), 7.28 (m, 1H), 8.04 (br, 1H).

Example 54

Preparation of 4-allyl-1H-indol-5-ol

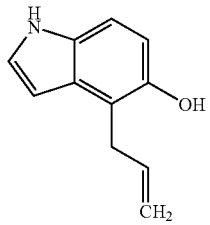

5-(Allyloxy)-1H-indole (514 mg, 2.97 mmol) (Example 53) was dissolved in 1,2,3,4-tetramethylbenzene (2.5 mL), and the reaction mixture was heated at 190° C. for 2 h. The mixture was cooled to rt and sonicated for 30 min. The mixture was then purified by silica gel column chromatography (EtOAc/hexane (v/v)=1:9) to give 361 mg (70%) of the title compound as a white crystalline solid. $^1$H NMR (400 MHz, CDCl$_3$): δ 3.68 (d, 2H), 5.13 (d, 1H), 5.18 (d, 1H), 6.07 (m, 1H), 6.45 (s, 1H), 6.79 (d, 1H), 7.12-7.18 (m, 2H), 8.06 (br, 1H).

Example 55

Preparation of 4-propyl-1H-indol-5-ol

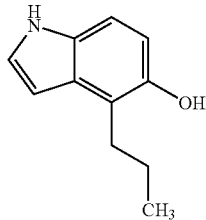

4-Allyl-1H-indol-5-ol (Example 54)120 mg, 0.69 mmol) was dissolved in EtOH (10 mL), and 20% palladium (II) hydroxide on carbon (20 mg) and ammonium formate (349.5 mg, 5.45 mmol) were added. After stirring for 30 min at rt, the mixture was heated to 40° C. for 2 h. After cooling to rt, the catalyst was removed by filtration, and the filtrate concentrated under reduced pressure. The residue was taken up in water, and the aqueous phase was extracted with EtOAc (2×). The combined organic phases were dried over Na$_2$SO$_4$, filtered, and concentrated under reduced pressure to give 91 mg (75%) of the title compound as a white solid. $^1$H NMR (400 MHz, CDCl$_3$): δ 1.04 (t, 3H), 2.74 (m, 2H), 2.88 (t, 2H), 6.49 (s, 1H), 6.75 (d, 1H), 7.10 (d, 1H), 7.18 (s, 1H), 8.00 (br, 1H).

Example 56

Preparation of ethyl((1S)-5-{3-[(4-propyl-1H-indol-5-yl)oxy]propoxy}-2,3-dihydro-1H-inden-1-yl)acetate

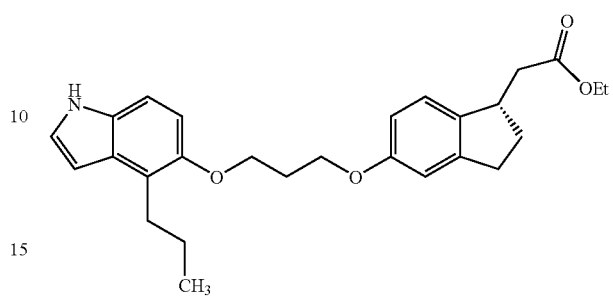

Using Examples 55 and 45 as starting material, the product was prepared as described in Example 48. $^1$H NMR (400 MHz, CDCl$_3$): δ 0.99 (t, 3H), 1.30 (t, 3H), 1.60-1.82 (m, 3H), 2.26 (m, 2H), 2.40 (m, 2H), 2.73 (dd, 1H), 2.88 (m, 4H), 3.52 (m, 1H), 4.19 (m, 6H), 6.49 (s, 1H), 6.72 (d, 1H), 6.80 (s, 1H), 6.90 (d, 1H), 7.05 (d, 1H), 7.17 (m, 2H), 8.00 (br, 1H).

Example 57

Preparation of ((1S)-5-{3-[(4-propyl-1H-indol-5-yl)oxy]propoxy}-2,3-dihydro-1H-inden-1-yl)acetic acid

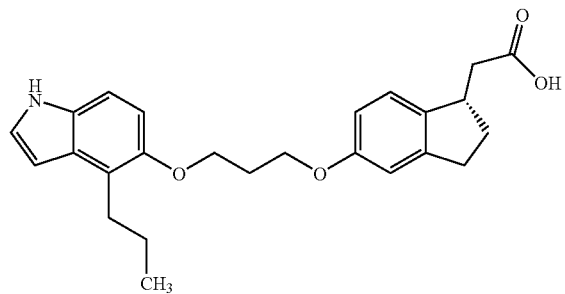

Using Example 56 as starting material, the product was prepared as described in Example 49. $^1$H NMR (400 MHz, CDCl$_3$): δ 8.00-7.84 (br, 1H), 7.16-7.06 (m, 2H), 7.01 (d, 1H), 6.81 (d, 1H), 6.70 (s, 1H), 6.66 (dd, 1H), 6.44-6.40 (m, 1H), 4.18-4.0 (m, 4H), 3.50-3.37 (m, 1H), 2.83-2.64 (m, 5H), 2.43-2.28 (m, 2H), 2.28-2.16 (m, 2H), 1.78-1.51 (m, 3H), 0.86 (t, 3H); LC-MS: RT=3.51 min, (M+H)$^+$ 408.0.

Example 58

Preparation of 4-allyl-5-(benzyloxy)-1H-indole

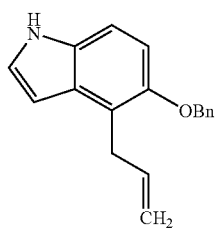

4-Allyl-1H-indol-5-ol (Example 54, 2.67 g, 15.4 mmol), benzyl bromide (2.90 g, 17.0 mmol), and Cs$_2$CO$_3$ (6.03 g, 18.5 mmol) were combined in DMF (50 mL), and water (15 drops) was added. After stirring for 12 h at rt, the reaction mixture was concentrated under reduced pressure. The residue was taken up in water, and the aqueous phase was extracted with EtOAc (2×). The combined organic phases were dried over $Na_2SO_4$, filtered, and concentrated under reduced pressure. Purification by silica gel flash chromatography (EtOAc/hexane (v/v)=1:7) gave 3.3 g (82%) of the title compound as a yellow oil. $^1$H NMR (400 MHz, $CDCl_3$): δ 3.74 (d, 2H), 5.00 (d, 1H), 5.09 (d, 1H), 5.10 (s, 2H), 6.07 (m, 1H), 6.55 (s, 1H), 6.98 (d, 1H), 7.20 (m, 2H), 7.31 (m, 1H), 7.38 (m, 2H), 7.48 (m, 2H), 8.03 (br, 1H).

Example 59

Preparation of 4-allyl-5-(benzyloxy)-1-methyl-1H-indole

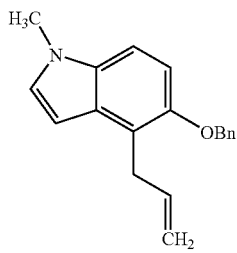

4-Allyl-5-(benzyloxy)-1H-indole (368.7 mg, 1.40 mmol) (Example 58) was dissolved in anhydrous DMF (12 mL) under an inert atmosphere, and the reaction mixture was cooled in an ice-water bath. Sodium hydride (60% in mineral oil) (181 mg, 1.68 mmol) was added, and the reaction mixture was stirred for an additional 30 min. Methyl iodide (278 mg, 1.96 mmol) was added and stirring at rt was continued for 30 min. The reaction mixture was heated to 40° C. for 12 h, cooled to rt, and water (10 drops) was added. The reaction mixture was concentrated under reduced pressure, after which water was added, and the aqueous phase was extracted with EtOAc (2×). The combined organic phases were dried over $Na_2SO_4$, filtered, and concentrated under reduced pressure. Purification by silica gel flash chromatography (EtOAc/hexane (v/v)=1:15) gave 259 mg (67%) of the title compound as an oil. $^1$H NMR (400 MHz, $CDCl_3$): δ 3.72 (m, 5H), 4.98 (d, 1H), 5.07 (d, 1H), 5.12 (s, 2H), 6.06 (m, 1H), 6.47 (s, 1H), 7.00 (d, 1H), 7.03 (s, 1H), 7.12 (d, 1H), 7.31 (m, 1H), 7.39 (m, 2H), 7.48 (m, 2H).

Example 60

Preparation of 1-methyl-4-propyl-1H-indol-5-ol

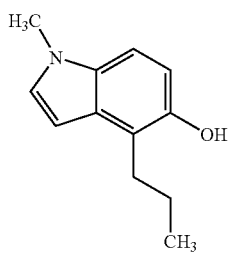

4-Allyl-5-(benzyloxy)-1-methyl-1H-indole (250.0 mg, 0.90 mmol) (Example 59) was dissolved in EtOH (15 mL), then 20% palladium (II) hydroxide on carbon (30 mg) was added, followed by ammonium formate (455 mg, 7.21 mmol). After stirring for 1 h at rt, the mixture was heated to 40° C. for 2.5 h. After cooling to rt, the catalyst was removed by filtration and the filtrate was concentrated under reduced pressure. Water was added to the residue, and the aqueous phase was extracted with EtOAc (2×). The combined organic phases were dried over $Na_2SO_4$, filtered, and concentrated under reduced pressure to give 150 mg (88%) of the title compound as an oil. $^1$H NMR (400 MHz, $CDCl_3$): δ 1.02 (t, 3H), 1.73 (m, 2H), 2.85 (t, 2H), 3.76 (s, 3H), 4.33 (br, 1H), 6.40 (s, 1H), 6.78 (d, 1H), 7.02 (m, 2H).

Example 61

Preparation of ethyl((1S)-5-{3-[(1-methyl-4-propyl-1H-indol-5-yl)oxy]propoxy}-2,3-dihydro-1H-inden-1-yl)acetate

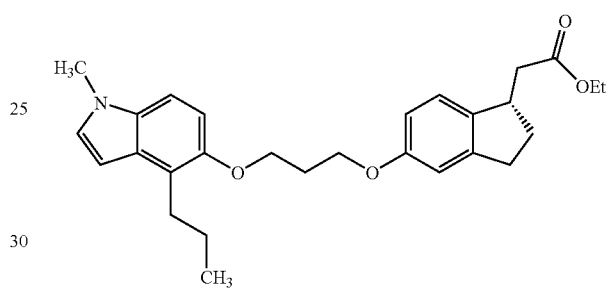

Using Example 60 as starting material, the title compound was prepared as described in Example 48. $^1$H NMR (400 MHz, $CDCl_3$): δ 0.97 (t, 3H), 1.29 (t, 3H), 1.68 (m, 2H), 1.77 (m, 1H), 2.28 (m, 2H), 2.39 (m, 2H), 2.72 (dd, 1H), 2.88 (m, 4H), 3.52 (m, 1H), 3.72 (s, 3H), 4.20 (m, 6H), 6.41 (s, 1H), 6.72 (dd, 1H), 6.80 (s, 1H), 6.93 (d, 1H), 7.01 (s, 1H), 7.08 (m, 2H).

Example 62

Preparation of ((1S)-5-{3-[(1-methyl-4-propyl-1H-indol-5-yl)oxy]propoxy}-2,3-dihydro-1H-inden-1-yl)acetic acid

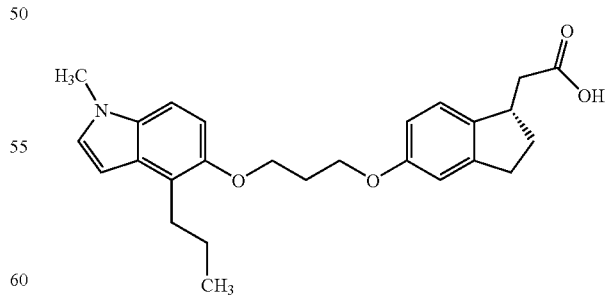

Using Examples 61 and 45 as starting material, the title compound was prepared as described in Example 49. $^1$H NMR (400 MHz, $CDCl_3$): δ 7.04-6.96 (m, 2H), 6.92 (d, 1H), 6.84 (d, 1H), 6.72 (s, 1H), 6.65 (dd, 1H), 6.32 (d, 1H), 4.18-4.02 (m, 4H), 3.68 (s, 3H), 3.52-3.40 (m, 1H), 2.88-2.64 (m, 5H), 2.46-2.30 (m, 2H), 2.22-2.14 (m, 2H), 1.78-1.52 (m, 3H), 0.88 (t, 3H); LC-MS: RT=3.88 min, (M+H)+ 422.1.

Example 63

Preparation of 6-(3-bromopropoxy)-3-methyl-1-benzofuran

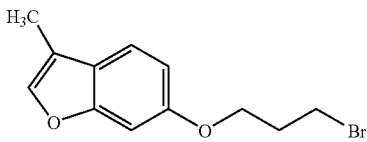

To a solution of 3-methyl-1-benzofuran-6-ol (0.20 g, 1.35 mmol) in NaOH (6 M aqueous solution, 0.25 mL) was added 1,3-dibromopropane (0.48 mL, 0.46 mmol), and the mixture was heated at 80° C. for 2 h. The reaction mixture was cooled to rt, and NaOH (6 M aqueous solution, 0.11 mL) was added. The reaction mixture was heated at 80° C. for 1 h, cooled to rt, and partitioned between $CH_2Cl_2$ and $NaHCO_3$ (saturated aqueous solution). The organic layer was dried, filtered, concentrated under reduced pressure, and purified by silica gel column chromatography (EtOAc/hexane (v/v)=1:19) to give 210 mg (58%) of the title compound containing minor impurities. This material was used in next step without further purification. $^1$H NMR (300 MHz, $CDCl_3$): δ 7.38 (d, 1H), 7.32 (s, 1H), 7.0 (s, 1H), 6.88 (dd, 1H), 4.14 (t, 2H), 3.62 (t, 2H), 2.40-2.28 (m, 2H), 2.20 (s, 3).

Example 64

Preparation of ethyl((1S)-5-{3-[(3-methyl-1-benzofuran-6-yl)oxy]propoxy}-2,3-dihydro-1H-inden-1-yl)acetate

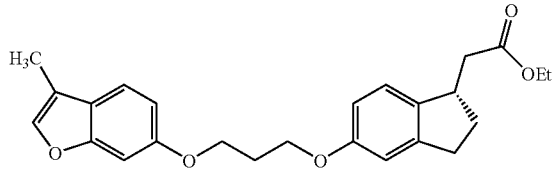

To a mixture of 6-(3-bromopropoxy)-3-methyl-1-benzofuran (87 mg, 0.32 mmol) (Example 63) and ethyl[(1S)-5-hydroxy-2,3-dihydro-1H-inden-1-yl]acetate (59 mg, 0.269 mmol) (Example 6) in DMF containing 1 vol % water (2.4 mL) was added $Cs_2CO_3$ (105 mg, 0.323 mmol). The mixture was stirred for 68 h at 80° C., and the reaction mixture cooled to rt, then concentrated under reduced pressure. The residue was suspended in EtOAc and filtered through a small plug of silica to give 119 mg (90%) of a light-yellow solid that was used in the next step without further purification.

Example 65

Preparation of ((1S)-5-{3-[(3-methyl-1-benzofuran-6-yl)oxy]propoxy}-2,3-dihydro-1H-inden-1-yl)acetic acid

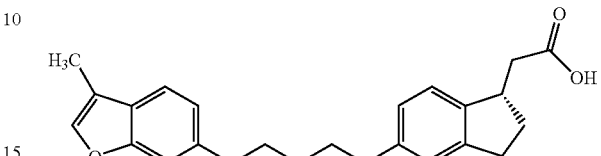

To a solution of ethyl((1S)-5-{3-[(3-methyl-1-benzofuran-6-yl)oxy]propoxy}-2,3-dihydro-1H-inden-1-yl)acetate (119 mg, 0.29 mmol) (Example 64) in THF (4.2 mL) was added a solution of $LiOH \cdot H_2O$ (15 mg, 0.35 mmol) in water (1.4 mL). The mixture was stirred for 4 h at 45° C. and then 12 h at rt. The reaction mixture was concentrated under reduced pressure, water was added, and the aqueous phase was washed with a small volume of $Et_2O$. The pH was adjusted to below 3 with HCl (1 N aqueous solution), and the aqueous phase was extracted with excess EtOAc. The combined EtOAc extracts were dried, filtered, and concentrated under reduced pressure to give 24 mg (22%) of the title compound as a solid. $^1$H NMR (300 MHz, $CDCl_3$): δ 7.44-7.22 (m, 2H), 7.08 (d, 1H), 6.98 (s, 1H), 6.89 (d, 1H), 6.80 (s, 1H), 6.72 (d, 1H), 4.32-4.04 (m, 4H), 3.63-3.44 (m, 1H), 2.98-2.76 (m, 3H), 2.58-2.37 (m, 2H), 2.37-2.14 (m, 5H), 1.88-1.70 (m, 1H); LC-MS: RT=3.53 min, (M+H)+ 381.1.

Example 66

Preparation of 1-(2,4-dihydroxy-3-propylphenyl)ethanone oxime

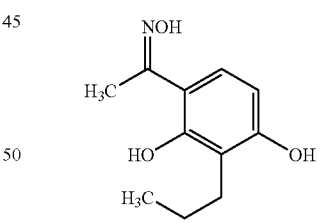

1-(2,4-dihydroxy-3-propylphenyl)ethanone (1.50 g, 7.72 mmol), hydroxylamine hydrochloride (1.61 g, 23.2 mmol), and anhydrous sodium acetate (1.90 g, 23.2 mmol) were combined in EtOH (30 mL) and stirred under reflux for 15 h. After cooling to rt, water (20 mL) was added, the EtOH was removed under reduced pressure and the aqueous phase was extracted with EtOAc (2×). The combined organic layers were dried over $Na_2SO_4$, filtered, and concentrated under reduced pressure to give 1.54 g (95%) of the title compound as a light-green solid. $^1$H NMR (400 MHz, $CDCl_3$): δ 0.93 (t, 3H), 1.52 (m, 2H), 2.23 (s, 3H), 2.60 (t, 2H), 6.32 (d, 2H), 7.12 (d, 2H).

Example 67

Preparation of
3-methyl-7-propyl-1,2-benzisoxazol-6-ol

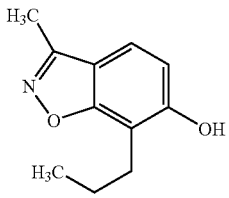

1-(2,4-dihydroxy-3-propylphenyl)ethanone oxime (400 mg, 1.91 mmol) (Example 66) was dissolved in CH$_2$Cl$_2$ and the solution was cooled to −35° C. under an atmosphere of argon. (Diethylamino)sulfur trifluoride (DAST) (647 mg, 4.01 mmol) was added dropwise and the solution was allowed to warm to −25° C. over 2 h. The mixture was quenched with NaHCO$_3$ (saturated aqueous solution). The organic phase separated and the aqueous phase extracted with CH$_2$Cl$_2$. The combined organic phases were dried over Na$_2$SO$_4$, filtered, and concentrated under reduced pressure. Purification by silica gel flash chromatography (EtOAc/hexane (v/v)=1:3) gave 282 mg (77%) of the title compound as a faintly red-colored solid. $^1$H NMR (400 MHz, CDCl$_3$): δ 0.95 (t, 3H), 1.67 (m, 2H), 2.56 (s, 3H), 2.79 (t, 2H), 6.76 (d, 1H), 7.19 (d, 1H).

Example 68

Preparation of ethyl((1S)-5-{3-[(3-methyl-7-propyl-1,2-benzisoxazol-6-yl)oxy]propoxy}-2,3-dihydro-1H-inden-1-yl)acetate

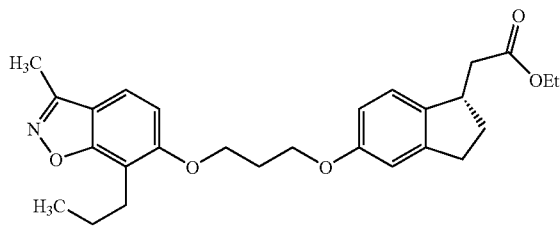

To a mixture of 3-methyl-7-propyl-1,2-benzisoxazol-6-l (269 mg, 1.01 mmol) (Example 67) and ethyl[(1S)-5-(3-bromopropoxy)-2,3-dihydro-1H-inden-1-yl]acetate (331 mg, 1.01 mmol) (Example 45) in DMF (8 mL, containing 1 vol % water) was added Cs$_2$CO$_3$ (661 mg, 2.03 mmol). The mixture was stirred for 16 h at rt, and then the reaction mixture was concentrated under reduced pressure. The residue was suspended in EtOAc and filtered through a small plug of silica to give 204 mg (39%) of the title compound as a white solid that was used in the next step without further purification.

Example 69

Preparation of [(1S)-5-{3-[(3-methyl-7-propyl-1,2-benzisoxazol-6-yl)oxy]propoxy}-2,3-dihydro-1H-inden-1-yl)acetic acid

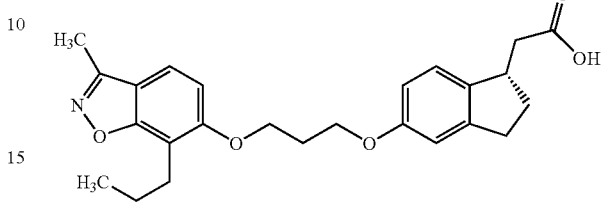

Using Example 68 as starting material, the title compound was prepared as described in Example 49 and purified by recrystallization from MeOH. $^1$H NMR (300 MHz, CDCl$_3$): δ 7.18 (d, 1H), 7.11 (d, 1H), 6.97 (d, 1H), 6.90 (s, 1H), 6.72 (dd, 1H), 4.24-4.10 (m, 4H), 3.60-3.44 (m, 1H), 2.96-2.74 (m, 5H), 2.60 (s, 3H), 2.52-2.36 (m, 2H), 2.34-2.20 (m, 2H), 1.84-1.70 (m, 1H), 1.70-1.52 (m, 2H), 0.92 (t, 3H); LC-MS: RT=4.09 min, (M+H)$^+$ 424.3.

Example 70

Preparation of
1-(2,4-dihydroxyphenyl)-2,2,2-trifluoroethanone oxime

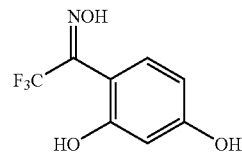

The title compound was prepared as described in Example 66 starting from the appropriately substituted and commercially available ketone. $^1$H NMR (300 MHz, DMSO-d$_6$): δ 6.26 (d, 1H), 6.32 (s, 1H), 6.82 (d, 1H). GC-MS [M+H]$^+$: 222.

Example 71

Preparation of
3-(trifluoromethyl)-1,2-benzisoxazol-6-ol

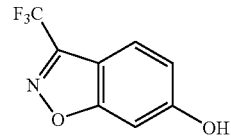

To a solution of 1-(2,4-dihydroxyphenyl)-2,2,2-trifluoroethanone oxime (Example 70, 0.25 g, 1.13 mmol) in THF (15 mL) was added triphenylphosphine (0.63 g, 2.4 mmol) and the mixture was cooled to 0° C. A solution of DEAD (0.48 mL, 2.3 mmol) in THF (10 mL) was slowly added while the temperature was kept at 0° C., after which the reaction mixture was stirred at 0-5° C. for 4 h. Water (30 mL) was added and the mixture was extracted with EtOAc (3×). The combined organic phases were washed with water and brine, dried over Na₂SO₄, filtered, and concentrated under reduced pressure. Purification by silica gel chromatography (EtOAc/hexane (v/v) 1:10 to 3:2 gradient) gave 0.23 g of the title compound with minor impurities. The material was used without further purification. GC-MS [M+H]⁺: 204.

Example 72

Preparation of ethyl[(1S)-5-(3-{[3-hydroxy-3-(trifluoromethyl)-2,3-dihydro-1,2-benzisoxazol-6-yl]oxy}propoxy)-2,3-dihydro-1H-inden-1-yl]acetate

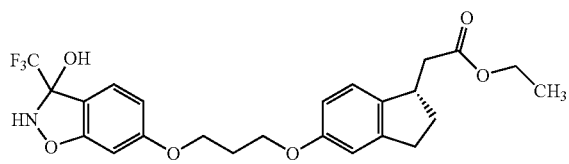

Using Example 71 as starting material, the title compound was prepared as described in Example 48. In the course of the reaction, addition of water to the isoxazole ring occurred, which produced the title compound. ¹H NMR (400 MHz, CDCl₃): δ 1.31 (t, 3H), 1.79 (m, 1H), 2.22 (m, 2H), 2.39 (m, 1H), 2.46 (dd, 1H), 2.73 (dd, 1H), 2.88 (m, 2H), 3.54 (m, 1H), 4.05 (t, 2H), 4.22 (m, 2H), 4.54 (t, 3H), 6.47 (d, 1H), 6.50 (dd, 1H), 6.69 (dd, 1H), 6.77 (s, 1H), 7.06 (d, 1H), 7.15 (d, 1H). LC-MS: RT 3.53 min, (M+H)⁺ 482.0.

Example 73

Preparation of [(1S)-5-(3-{[3-hydroxy-3-(trifluoromethyl)-2,3-dihydro-1,2-benzisoxazol-6-yl]oxy}propoxy)-2,3-dihydro-1H-inden-1-yl]acetic acid

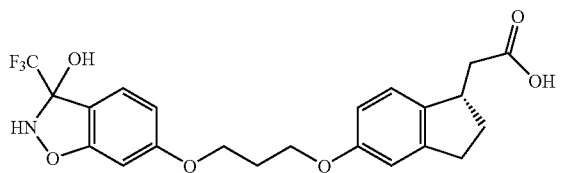

Using Example 72 as starting material, the title compound was prepared as described in Example 49. ¹H NMR (300 MHz, CDCl₃): δ 1.79 (m, 1H), 2.20 (m, 2H), 2.41 (m, 2H), 2.52 (m, 2H), 2.74 (dd, 1H), 2.84 (m, 2H), 3.52 (m, 1H), 4.02 (m, 2H), 4.53 (m, 2H), 6.41 (s, 1H), 6.48 (d, 1H), 6.68 (d, 1H), 6.77 (s, 1H), 7.07 (d, 1H), 7.17 (d, 1H); LC-MS: RT=3.01 min, (M+H)⁺ 454.0.

Examples of compounds of Formula (Imm) [Formula (I), where R² and R¹ are H, L is —Y—(CH₂)ₙ—X—, X and Y are O, and n is 3], as shown in Table 2a below, were made using procedures similar to those described in the previous Examples. All of the Ar—Y—H compounds [Formula (II) in Reaction Scheme 1] used as starting materials in Examples 74, 75, 77, 78, 84, and 85 were commercially available. The synthesis of the Ar—Y—H starting material used in Example 76 is described in Example 54. The benzisoxazoles employed in Examples 80-83 were synthesized as described in Examples 66-67. The oxazole employed in Example 79 was formed as a byproduct in the cyclodehydration reaction for the formation of the benzisoxazole employed in Example 80.

TABLE 2a (Imm)

Ar—O—(propoxy chain)—O—[indane-acetic acid]

| Ex. No | Ar | HPLC RT (min) | LC-MS [M + H]⁺ or NMR data |
|---|---|---|---|
| 74 | 1H-indol-5-yl | 3.13 | 366.0 |
| 75 | 2-methyl-1H-indol-5-yl | 3.16 | 380.2 |
| 76 | 4-allyl-1H-indol-5-yl | 3.40 | 406.0 |
| 77 | 1H-indol-6-yl | 3.19 | 366.2 |
| 78 | 1H-indol-4-yl | 3.07 | 366.2 |
| 79 | benzoxazol-6-yl | 3.28 | 368.1 |
| 80 | benzisoxazol-6-yl | 2.76 | 367.9 |

TABLE 2a-continued

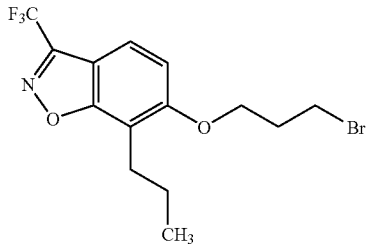

| Ex. No | Ar | HPLC RT (min) | LC-MS [M + H]+ or NMR data |
|---|---|---|---|
| 81 | H3C, benzisoxazole | 2.97 | 382.1 |
| 82 | H3C, methyl-benzisoxazole with CH3 | 3.84 | 396.3 |
| 83 | F3C, benzisoxazole with H3C-propyl | 4.18 | 477.9 |
| 84 | tetrahydronaphthyl | 4.51 | [a] |
| 85 | oxo-trihydronaphthyl | 3.90 | [b] |

[a] ¹H NMR (300 MHz, CDCl₃), δ 7.18-6.97 (m, 2H), 6.84-6.60 (m, 4H), 4.22-4.04 (m, 4H), 3.62-3.46 (m, 1H), 3.00-2.55 (m, 7H), 2.55-2.35 (m, 2H), 2.34-2.17 (m, 2H), 1.88-1.64 (m, 5H).
[b] ¹H NMR (300 MHz, CDCl₃), δ 7.65 (d, 1H), 7.28-7.20 (m, 1H), 7.10 (d, 1H), 7.04 (d, 1H), 6.90 (s, 1H), 6.72 (dd, 1H), 4.23-4.11 (m, 4H), 3.59-3.45 (m, 1H), 2.96-2.72 (m, 5H), 2.68-2.58 (m, 2H), 2.50-2.38 (m, 2H), 2.32-2.24 (m, 2H), 2.17-2.03 (m, 2H), 1.84-1.68 (m, 1H).

TABLE 2b

IUPAC Names for Compounds in Table 2a

| Ex. No. | IUPAC Name |
|---|---|
| 74 | 2-[(1S)-5-(3-indol-5-yloxypropoxy)indanyl]acetic acid |
| 75 | 2-{(1S)-5-[3-(2-methylindol-5-yloxy)propoxy]indanyl}acetic acid |
| 76 | 2-{(1S)-5-[3-(4-prop-2-enylindol-5-yloxy)propoxy]indanyl}acetic acid |
| 77 | 2-[(1S)-5-(3-indol-6-yloxypropoxy)indanyl]acetic acid |
| 78 | 2-[(1S)-5-(3-indol-4-yloxypropoxy)indanyl]acetic acid |
| 79 | 2-[(1S)-5-(3-benzoxazol-6-yloxypropoxy)indanyl]acetic acid |
| 80 | 2-[(1S)-5-(3-benzo[d]isoxazol-6-yloxypropoxy)indanyl]acetic acid |
| 81 | 2-{(1S)-5-[3-(3-methylbenzo[d]isoxazol-6-yloxy)propoxy]indanyl}acetic acid |
| 82 | 2-{(1S)-5-[3-(3,7-dimethylbenzo[d]isoxazol-6-yloxy)propoxy]indanyl}acetic acid |
| 83 | ((1S)-5-{3-[(3-methyl-7-propyl-1,2-benzisoxazol-6-yl)oxy]propoxy}-2,3-dihydro-1H-inden-1-yl)acetic acid |
| 84 | 2-[(1S)-5-(3-(5,6,7,8-tetrahydronaphthyloxy)propoxy)indanyl]acetic acid |
| 85 | 2-{(1S)-5-[3-(5-oxo(6,7,8-trihydronaphthyloxy))propoxy]indanyl}acetic acid |

Example 86

Preparation of 6-(3-bromopropoxy)-7-propyl-3-trifluoromethyl-1,2-benzo[d]-isoxazole

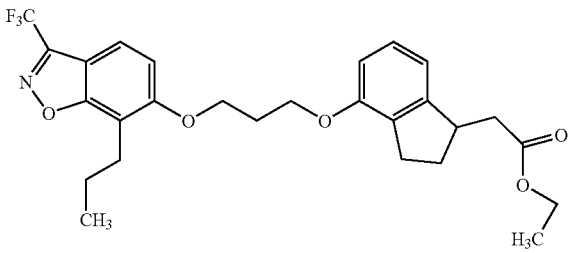

To a mixture of 3-trifluoromethyl-7-propyl-6-hydroxybenzisoxazole, (Example 24, 3.53 g, 14.4 mmol) and cesium carbonate (5.63 g, 17.3 mmol) in DMF (12 mL, containing 1% v/v of water), was added 1,3-dibromopropane (14.5 g, 72.0 mmol). The reaction mixture was stirred for 12 h at rt, and then the solvents were removed under reduced pressure. The residue was purified by silica gel flash chromatography (100% hexanes, then 2-5% EtOAc in hexanes) to give the product as a colorless oil (2.4 g, 46%). ¹H NMR (300 MHz, CDCl₃) δ 7.58 (d, 1H), 7.09 (d, 2H), 4.25 (t, 2H), 3.64 (t, 2H), 2.92 (t, 2H), 2.40 (m, 2H), 1.72 (m, 2H), 0.99 (t, 3H).

Example 87

Preparation of ethyl[4-(3-{[7-propyl-3-(trifluoromethyl)-1,2-benzisoxazol-6-yl]oxy}propoxy)-2,3-dihydro-1H-inden-1-yl]acetate Using Examples 86 and 9 as starting materials, the title compound was prepared using a similar procedure as the one described for Example 35 yielding 132 mg (85%) of material which was used in the next step without further purification.

$^1$H NMR (400 MHz, acetone-d$_6$): δ 7.71 (1H, d), 7.39 (1H, d), 1.15 (1H, t), 6.82-6.80 (2H, m), 4.45 (2H, t), 4.29 (2H, t), 4.13 (2H, q), 3.55-50 (1H, m), 2.96-2.85 (3H, m), 2.78-2.71 (2H, m), 2.42-2.30 (4H, m), 1.73-1.67 (3H, m), 1.24 (3H, t), 0.94 (3H, t); LC-MS: RT=3.47 min, (M+H)$^+$ 506.37.

Example 88

Preparation of [4-(3-{[7-propyl-3-(trifluoromethyl)-1,2-benzisoxazol-6-yl]oxy}propoxy)-2,3-dihydro-1H-inden-1-yl]acetic acid

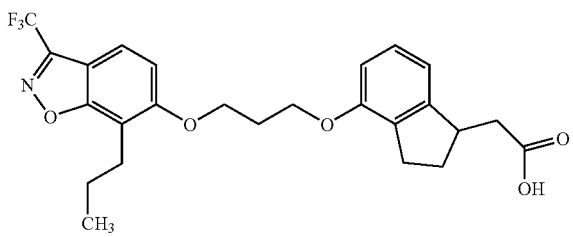

Using Example 87 as starting material, the title compound was prepared using a similar procedure as the one described for (Example 49). $^1$H NMR (400 MHz, acetone-d$_6$): δ 7.71 (1H, s), 7.39 (1H, d), 7.12 (1H, t), 6.85 (1H, d), 6.80 (1H, d), 4.45 (2H, t), 4.28 (2H, t), 3.54-3.51 (1H, m), 2.95-2.86 (3H, m), 2.79-2.70 (2H, m), 2.43-2.32 (4H, m), 1.78-1.67 (3H, M), 0.94 (3H, t); LC-MS RT=5.77 min, (M–H)$^+$ 476.

Example 89

Preparation of 1-(allyloxy)-4-(trifluoromethyl)benzene

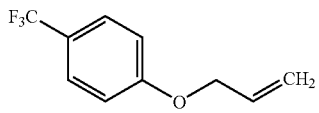

4-(Trifluoromethyl)phenol (1.50 g, 9.25 mmol), allyl bromide (14.55 9, 12.03 mmol), Cs$_2$CO$_3$ (3.62 g, 11.10 mmol), and water (15 drops) were combined in DMF (40 mL) and the mixture stirred for 12 h. The reaction mixture was then concentrated under reduced pressure, diluted with water, and extracted with EtOAc (2×). The combined organic phases were dried over Na$_2$SO$_4$, filtered, and concentrated under reduced pressure to give 0.96 g (51%) of the title compound as a light-yellow oil. $^1$H NMR (400 MHz, CDCl$_3$): δ 4.59 (d, 2H), 5.32 (d, 1H), 5.43 (d, 1 H), 6.05 (m, 1H), 6.97 (d, 2H), 7.53 (d, 2H).

Example 90

Preparation of 2-allyl-4-(trifluoromethyl)phenol

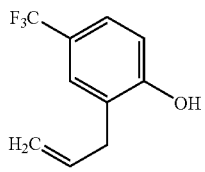

Under an atmosphere of argon, 1-(allyloxy)-4-trifluoromethyl)benzene (200 mg, 0.99 mmol) (Example 89) was dissolved in CH$_2$Cl$_2$ (anhydrous, 5 mL) and cooled to 15° C. Then, a solution of boron trichloride (1.04 mL, 1.04 mmol, 1 M in hexane) was added dropwise, and the reaction mixture was stirred for 2 h during which time the reaction mixture was allowed to warm to rt. The mixture was poured onto ice and extracted with EtOAc (2×). The combined organic phases were washed with NaHCO$_3$ (saturated aqueous solution), dried over Na$_2$SO$_4$, filtered, and concentrated under reduced pressure to afford the product as a yellow oil. This was used in the next step without further purification.

Example 91

Preparation of 2-propyl-4-(trifluoromethyl)phenol

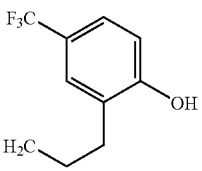

The crude 2-allyl(trifluoromethyl)phenol from Example 90 was dissolved in EtOH (5 mL), 10% Pd/C (20 mg) was added, and the mixture was stirred under an atmosphere of hydrogen at rt for 2 h. The catalyst was removed by filtration. The filtrate was concentrated under reduced pressure, and the residue was purified by silica gel flash chromatography (EtOAc/hexane (v/v) 1:10). This gave 91 mg (45% over 2 steps) of the title compound as a colorless oil. $^1$H NMR (400 MHz, CDCl$_3$): δ 1.00 (t, 3H), 1.68 (m, 2H), 2.61 (t, 2H), 5.14 (br, 1H), 6.80 (d, 1H), 7.32 (d, 1H), 7.36 (s, 1H).

Example 92

Preparation of ethyl ((1S)-5-{3-[2-propyl-4-(trifluoromethyl)phenoxy]propoxy}-2,3-dihydro-1H-inden-1-yl)acetate

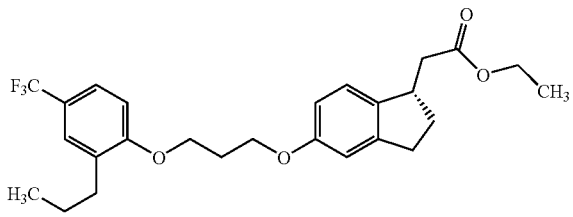

Using Examples 91 and 45 as starting materials, the title compound was prepared as described in Example 48. $^1$H NMR (400 MHz, CDCl$_3$): δ 0.95 (t, 3H), 1.29 (t, 3H), 1.60 (m, 2H), 1.76 (m, 1H), 2.29 (m, 2H), 2.39 (m, 2H), 2.61 (m, 2H), 2.72 (dd, 1H), 2.86 (m, 2H), 4.17 (m, 6H), 6.69 (d, 1H), 6.78 (s, 1H), 6.88 (d, 1H), 7.07 (d, 1H), 7.07 (d, 1H), 7.34 (s, 1H), 7.40 (d, 1H).

Example 93

Preparation of ((1S)-5-{3-[2-propyl-4-(trifluoromethyl)phenoxy]propoxy}-2,3-dihydro-1H-inden-1-yl)acetic acid

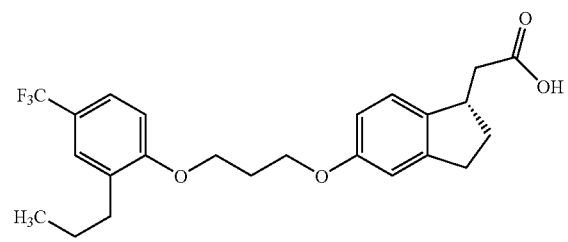

Using Example 92 as starting material, the title compound was prepared as described in Example 49. $^1$H NMR (400

MHz, CDCl$_3$): δ 7.40 (d, 1H), 7.34 (s, 1 H), 7.11 (d, 1H), 6.88 (d, 1H), 6.80 (s, 1H), 6.74 (dd, 1H), 4.26-4.12 (m, 4H), 3.60-3.50 (m, 1H), 2.96-2.78 (m, 3H), 2.68-2.59 (m, 2H), 2.52-2.39 (m, 2H), 2.35-2.26 (m, 2H), 1.88-1.72 (m, 1H), 1.68-1.54 (m, 2H), 0.96 (t, 3H).

Example 94

Preparation of ethyl {(1S)-5-[3-(4-iodophenoxy)propoxy]-2,3-dihydro-1H-inden-1-yl}acetate

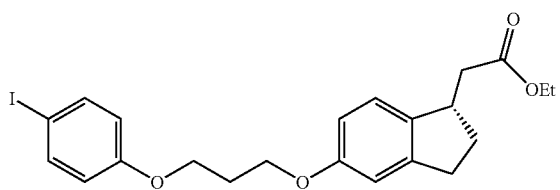

Using 4-iodophenol and Example 45 as starting materials, the title compound was prepared as described in Example 48. $^1$H NMR (400 MHz, CDCl$_3$): δ 7.54 (d, 2H), 7.06 (d, 1H), 6.80 (s, 1H), 6.72-6.64 (m, 3H), 4.23-4.06 (m, 6H), 3.58-3.46 (m, 1H), 2.94-2.78 (m, 2H), 2.72 (dd, 1H), 2.43-2.35 (m, 2H), 2.28-2.20 (m, 2H), 1.80-1.69 (m, 1H), 1.18 (t, 3H).

Example 95

Preparation of ethyl ((1S)-5-{3-[4-(3-thienyl)phenoxy]propoxy}-2,3-dihydro-1H-inden-1-yl)acetate

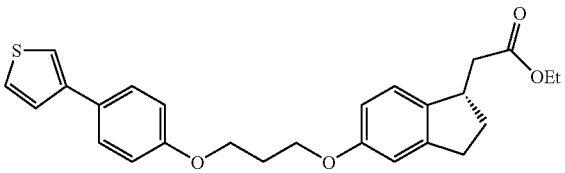

To a solution of thiophene-3-boronic acid (53 mg, 0.42 mmol), ethyl {(1 S)-5-[3-(4-iodophenoxy)propoxy]-2,3-dihydro-1H-inden-1-yl}acetate (50 mg, 0.10 mmol, Example 94) in toluene (1.8 mL), and 1,4-dioxane (0.45 mL), was added PdCl$_2$(dppf)-CH$_2$Cl$_2$ (7.6 mg, 0.01 mmol), and argon was passed through the mixture for 30 min. Then Na$_2$CO$_3$ (2 N aqueous solution, 0.50 mL) was added, and the mixture was heated to 75° C. for 48 h. The reaction was cooled to rt, and extracted with EtOAc (2×). The combined organic phases were washed with NaHCO$_3$ (saturated aqueous solution), dried, filtered and concentrated under reduced pressure. The residue was purified by preparative thin layer chromatography on silica gel to give 33 mg (73%) of the title compound as a colorless oil. $^1$H NMR (400 MHz, CDCl$_3$): δ 7.51 (d, 2H), 7.40-7.31 (m, 3H), 7.06 (d, 1H), 6.97 (d, 2H), 6.80 (s, 1H), 6.72 (dd, 1H), 4.24-4.10 (m, 6H), 3.60-3.48 (m, 1H), 2.98-2.90 (m, 2H), 2.72 (dd, 1H), 2.46-2.36 (m, 2H), 2.36-2.23 (m, 2H), 1.85-1.70 (m, 1H), 1.30 (t, 3H).

Example 96

Preparation of ((1S)-5-{3-[4-(3-thienyl)phenoxy]propoxy}-2,3-dihydro-1H-inden-1-yl)acetic acid

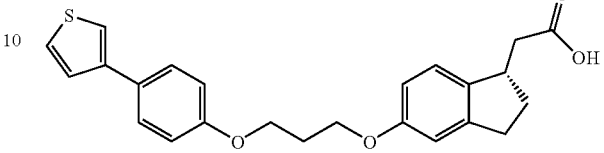

Using Example 95 as starting material, the title compound was prepared as described in Example 49. $^1$H NMR (400 MHz, CDCl$_3$): δ 7.42 (d, 2H), 7.32-7.20 (m, 3H), 7.05-6.96 (m, 1H), 6.82 (d, 2H), 6.72 (s, 1H), 6.72-6.60 (br, 1H), 4.14-4.0 (m, 4H), 3.52-3.40 (m, 1H), 2.90-2.62 (m, 3H), 2.43-2.22 (m, 2H), 2.22-2.10 (m, 2H), 1.76-1.60 (m, 1H); LC-MS: RT=3.71 min, (M+H)$^+$ 408.9.

Example 97

Preparation of ethyl {(1S)-5-[3-(4-bromo-2-methoxyphenoxy)propoxy]-2,3-dihydro-1H-inden-1-yl}acetate

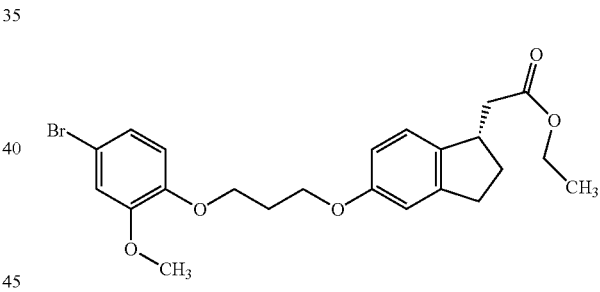

To a solution of ethyl [(1S)-5-(3-bromopropoxy)-2,3-dihydro-1H-inden-1-yl]acetate (1.4 g, 4.10 mmol) (Example 45) in DMF (130 mL, containing 1 vol % water) was added 4-bromo-2-methoxyphenol (832.9 mg, 4.10 mmol) followed by Cs$_2$CO$_3$ (2.66 g, 8.18 mmol). The reaction mixture was heated for 12 h at 80° C. Upon cooling to rt, the reaction mixture was diluted with water and extracted with EtOAc. The combined organic layers were dried over MgSO$_4$, filtered, and concentrated under reduced pressure. The crude material was purified by silica gel flash chromatography (gradient 1:4 to 1:1 (v/v) EtOAc/hexane) to give the product as a colorless oil. $^1$H NMR (400 MHz, acetone-d$_6$) δ 7.11-7.07 (m, 2H), 7.03-7.01 (m, 1H), 6.94-6.92 (m, 1H), 6.82-6.81 (m, 1H), 6.75-6.72 (m, 1H), 4.20-4.11 (m, 6H), 3.84 (s, 3H), 3.48-3.44 (m, 1H), 2.89-2.69 (m, 3H), 2.42-2.30 (m, 2H), 2.07 (q, 2H), 1.75-1.70 (m, 1H), 1.25 (t, 3H).

Example 98

Preparation of ethyl ((1S)-5-{3-[2-methoxy-4-(3-thienyl)phenoxy]propoxy}-2,3-dihydro-1H-inden-1-yl)acetate

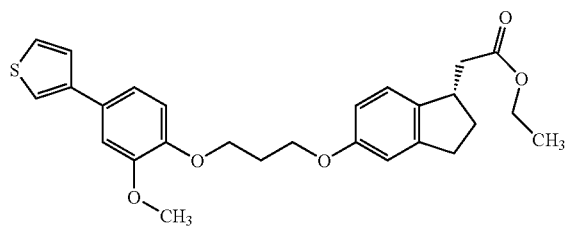

Ethyl {(1S)-5-[3-(4-bromo-2-methoxyphenoxy)propoxy]-2,3-dihydro-1H-inden-1-yl}acetate (140 mg, 0.3 mmol) (Example 97), 3-thiopheneboronic acid (81.2 mg, 0.63 mmol), PdCl$_2$(dppf).CH$_2$Cl$_2$ (90.5 mg, 0.07 mmol), and NaHCO$_3$ (76.1 mg, 0.91 mmol) were suspended in DME (10 mL) and water (1 mL). The reaction mixture was degassed under vacuum for 3 min, and then purged with argon, after which the reaction mixture was agitated by orbital shaker at 80° C. for 24 h, and then at rt for 24 h. The reaction mixture was filtered through a pad of silica gel, and the filtrate was concentrated under reduced pressure. The crude material was purified by silica gel flash chromatography (EtOAc/hexanes (v/v)=1:9 to 1:1 gradient) to give 83 mg (59%) of the title compound as a yellow oil. $^1$H NMR (400 MHz, acetone-d$_6$): δ 7.62-7.71 (m, 1H), 7.52-7.46 (m, 2H), 7.29 (d, 1H), 7.23-7.19 (m, 1H), 7.11-7.09 (m, 1H), 7.02-6.99 (m, 1H), 6.83-6.82 (m, 1H), 6.76-6.73 (m, 1H), 4.22-4.09 (m, 6H), 3.87 (s, 3H), 3.44 (m, 1H), 2.87-2.66 (m, 3H), 2.40-2.18 (m, 4H), 1.74-1.70 (m, 1H), 1.25 (t, 3H).

Example 99

Preparation of ((1S)-5-{3-[2-methoxy-4-(3-thienyl) phenoxy]propoxy}-2,3-dihydro-1H-inden-1-yl)acetic acid

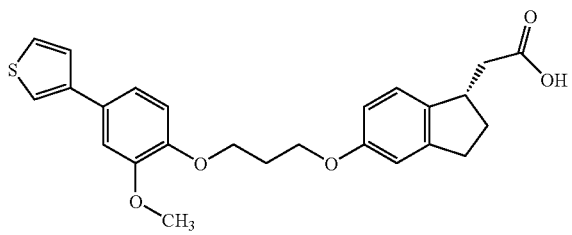

The ester prepared in Example 98 (83 mg 0.18 mmol) was dissolved in a mixture of EtOH (3 mL), THF (3 mL), and water (1 mL), LiOH (42.6 mg; 1.78 mmol) was added and the reaction mixture was heated at 50° C. for 3 h. The reaction mixture was concentrated under reduced pressure, diluted with water, and extracted with EtOAc. The combined organic phases were dried over MgSO$_4$, filtered, and concentrated under reduced pressure. The crude material was purified by preparative HPLC (CH$_3$CN, 0.01% TFA/Water, 0.01% TFA (v/v)=2:3 to 100% CH$_3$CN, 0.01% TFA) to give 60 mg (73%) of the title compound as a white solid. $^1$H NMR (400 MHz, acetone-d$_6$): δ 7.62-7.61 (m, 1H), 7.52-7.47 (m, 2H), 7.29 (d, 1H), 7.23-7.20 (m, 1H), 7.14 (d, 1H), 7.01 (d, 1H), 6.33-6.32 (m, 1H), 6.77-6.74 (m, 1H), 4.23-4.18 (m, 4H), 3.89 (s, 3H), 3.48-3.45 (m, 1H), 3.22-2.71 (b, 1H), 2.93-2.71 (m, 3H), 2.42-2.32 (m, 2H), 2.28-2.22 (q, 2H), 1.76-1.70 (m, 1H). LC-MS: RT=5.28 min, (M−H)437.3.

Example 100

Preparation of ethyl ((1S)-5-{3-[4-(6-methyl-2-pyridinyl)phenoxy]propoxy}-2,3-dihydro-1H-inden-1-yl)acetate

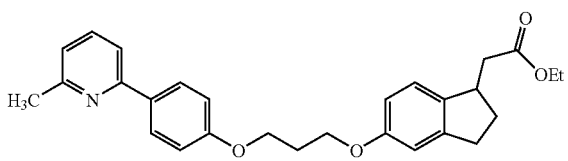

To a solution of ethyl {(1S)-5-[3-(4-iodophenoxy)propoxy]-2,3-dihydro-1H-inden-1H-inden-1-yl}acetate (70 mg, 0.15 mmol, Example 94) in DMF (1 mL), was added bis(pinacolato)diboron (41 mg, 0.16 mmol), PdCl$_2$(dppf).CH$_2$Cl$_2$ (11 mg, 0.01 mmol), and KOAc (43 mg, 0.44 mmol). Argon was passed through the solution, and the reaction mixture was heated at 80° C. for 2 h, and then cooled to rt. More PdCl$_2$(dppf).CH$_2$Cl$_2$ (5 mg, 0.005 mmol) was added, followed by the addition of 2-bromo-6-methylpyridine (50 mg, 0.29 mmol) and Na$_2$CO$_3$ (2 M aqueous solution, 0.37 mL). The reaction mixture was heated to 80° C. for 12 h, after which the reaction mixture was cooled to rt, diluted with HCl (1N aqueous solution) and extracted with EtOAc. The combined organic phases were dried, filtered, and concentrated under reduced pressure. Purification by a preparative thin layer chromatography (2:3 EtOAc/hexanes) gave 286 mg (40%) of the title compound. $^1$H NMR (400 MHz, CDCl$_3$): δ 8.00 (d, 2H), 7.73-7.62 (m, 1H), 7.62-7.52 (m, 1H), 7.16-6.96 (m, 4H), 6.83 (s, 1H), 6.52 (d, 1H), 4.28-4.04 (m, 6H), 3.52-3.38 (m, 1H), 2.96-2.63 (m, 3H), 2.54 (s, 3H), 2.48-2.12 (m, 4H), 1.82-1.62 (m, 1H), 1.23 (t, 3H).

Example 101

Preparation of ((1S)-5-{3-[4-(6-methyl-2-pyridinyl) phenoxy]propoxy}-2,3-dihydro-1H-inden-1-yl)acetic acid

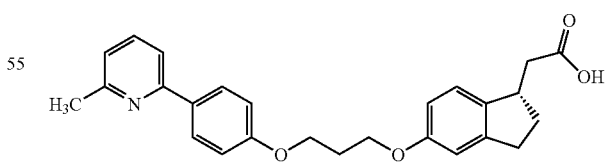

Using Example 100 as starting material, the title compound was prepared as described in Example 49. $^1$H NMR (400 MHz, CD$_3$OD): δ 8.30-8.22 (m, 1H), 7.90 (d, 1H), 7.75 (d, 2H), 7.60 (d, 1H), 7.08 (d, 2H), 6.95 (d, 1H), 6.68 (s, 1H), 6.60 (dd, 1H), 4.20 (t, 2H), 4.04 (t, 2H), 3.40-3.28 (m, 1H), 2.84-2.62 (m, 5H), 2.58 (dd, 1H), 2.32-2.13 (m, 4H), 1.68-1.58 (m, 1H); LC-MS: RT=2.38 min, (M+H)$^+$ 418.2.

Example 102

Preparation of ethyl [(1S)-5-(3-anilinopropoxy)-2,3-dihydro-1H-inden-1-yl]acetate

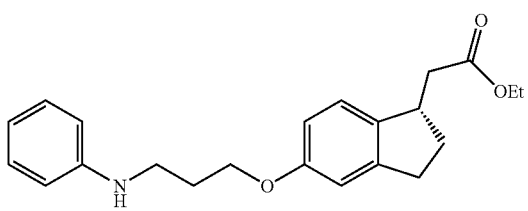

To a solution of aniline (273 mg, 2.93 mmol) in DMF (4 mL) under argon was added sodium hydride (117 mg, 2.93 mmol, 60% dispersion in mineral oil), and the mixture was stirred under argon for 20 min. A solution of ethyl [(1S)5-(3-bromopropoxy)-2,3-dihydro-1H-inden-1-yl]acetate (Example 45, 500 mg, 1.47 mmol) in DMF (4 mL) was added and the reaction mixture was stirred for 24 h at rt. A saturated aqueous NH$_4$Cl solution was added, and the solvents were evaporated under vacuum. The residue was suspended in EtOAc and filtered through a small silica gel plug. The filtrate was concentrated under reduced pressure and then purified by silica gel chromatography (5-10% EtOAc in hex) to give the title compound (44 mg, 9%) as an oil containing minor impurities. $^1$H NMR (400 MHz, CDCl$_3$): δ 7.11-6.92 (m, 3H), 6.68-6.48 (m, 5H), 4.12-3.93 (m, 4H), 3.50-3.37 (br, 1H), 3.22 (t, 2H), 2.85-2.68 (m, 2H), 2.62 (dd, 1H), 2.38-2.23 (m, 2H), 2.04-1.96 (m, 2H), 1.72-1.60 (m, 1H), 1.08 (t, 3H).

Example 103

Preparation of [(1S)-5-(3-anilinopropoxy)-2,3-dihydro-1H-inden-1-yl]acetic acid

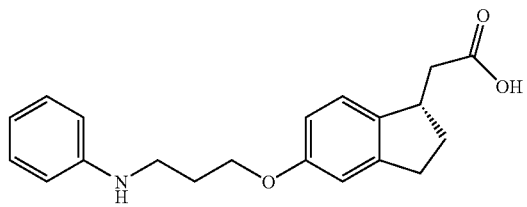

Using Example 102 as starting material, the product was prepared as described in Example 49. $^1$H NMR (400 MHz, CDCl$_3$): δ 7.48-7.20 (m, 5H), 7.04 (d, 1 H), 6.80 (s, 1H), 6.88 (d, 1H), 4.19-4.06 (m, 2H), 3.62-3.52 (m, 2H), 3.42-3.35 (m, 1H), 3.00-2.75 (m, 3H), 2.58-2.38 (m, 2H), 2.18-2.06 (m, 2H), 1.86-1.76 (m, 1H); LC-MS: RT=2.34 min, (M+H)$^+$ 326.1.

Using the methods described in Example 89-103 and the appropriate starting materials, the compounds of Formula (Inn) [Formula (I) where R$^1$ and R$^2$ are H, L is —Y—(CH$_2$)$_n$—, X and Y are O, Ar is substituted phenyl, and n is 3] appearing below in Table 3a, were similarly prepared.

TABLE 3a (Inn)

| Ex. No | R$^{3-1}$ | R$^{3-2}$ | HPLC RT (min) | LC-MS [M + H]$^+$ |
|---|---|---|---|---|
| 104 | H | H | 3.98 | * |
| 105 | n-Pr | H | 4.44 | * |
| 106 | H | Me | 4.14 | * |
| 107 | Me | Me | 3.80 | * |
| 108 | OMe | Me | 3.25 | 371.0 |
| 109 | OEt | Me | 3.42 | 385.0 |
| 110 | Br | Me | 4.29 | * |
| 111 | —NH(C(=O)C$_3$H$_7$) | Me | 3.35 | 426.2 |
| 112 | (5-isoxazolyl) | Me | 3.22 | 407.8 |
| 113 | H | Et | 4.26 | 355.0 |
| 114 | OMe | Et | 3.47 | 384.9 |
| 115 | H | i-Pr | 3.96 | 369.2 |
| 116 | H | CF$_3$ | 3.67 | * |
| 117 | H | CN | 3.31 | 351.8 |
| 118 | n-Pr | CN | 3.70 | 393.8 |
| 119 | OMe | CN | 3.06 | 381.8 |
| 120 | H | OMe | 3.18 | * |
| 121 | n-Pr | OPh | 4.21 | * |
| 122 | H | OEt | 3.47 | 370.9 |
| 123 | H | OCF$_3$ | 3.75 | * |
| 124 | OMe | Br | 5.00 | 435.2 (M − H)$^-$ |

TABLE 3a-continued
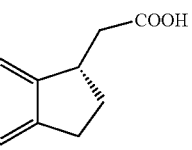
(Inn)
| Ex. No | R³⁻¹ | R³⁻² | HPLC RT (min) | LC-MS [M + H]⁺ |
|---|---|---|---|---|
| 125 | H | 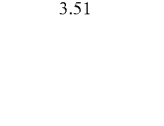 | 3.51 | 394.3 |
| 126 | —NH(C(=O)CH₃ | 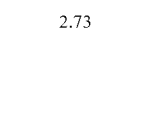 | 3.25 | 451.2 |
| 127 | Cl | 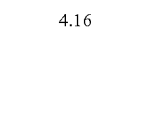 | 2.73 | 428.1 |
| 128 | Me | 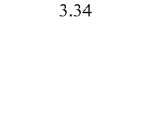 | 4.16 | 492.9** |
| 129 | H |  | 3.34 | 496.0 |
| 130 | H | 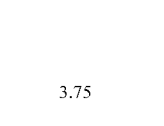 | 355 | 393.0 |
| 131 | OMe | 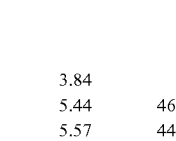 | 5.49 | 437.2 (M − H)⁻ |
| 132 | OMe |  | 3.75 | 453.0 |
| 133 | H | Ph | 3.84 | * |
| 134 | OMe | 4-MeO—Ph— | 5.44 | 461.3 (M − H)⁻ |
| 135 | OMe | 4-F—Ph— | 5.57 | 449.3 (M − H)⁻ |
| 136 | H |  | 2.42 | 404.2 |
| 137 | OMe |  | 2.36 | 434.0 |

TABLE 3a-continued

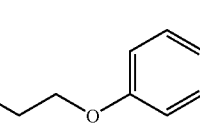

(Inn)

| Ex. No | R³⁻¹ | R³⁻² | HPLC RT (min) | LC-MS [M + H]⁺ |
|---|---|---|---|---|
| 138 | H | 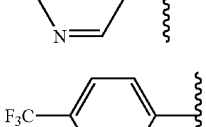 4-methoxypyridin-3-yl | 3.47 | 434.2 |
| 139 | H | 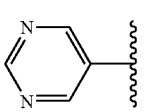 5-trifluoromethylpyridin-2-yl | 3.82 | 472.1 |
| 140 | H | 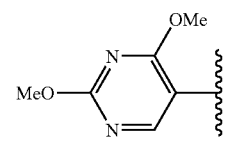 pyrimidin-5-yl | 2.95 | 405.1 |
| 141 | H | 2,4-dimethoxypyrimidin-5-yl | 3.31 | 465.2 |
| 142 | H | 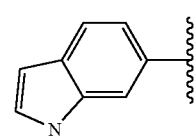 1H-indol-6-yl | 3.57 | 492.0 |

\* These compounds did not ionize under ESI-MS conditions.
\*\*The starting material was the same as that used for the synthesis of Example 235.

TABLE 3b

IUPAC Names for Compounds in Table 3a

| Ex. No. | IUPAC Name |
|---|---|
| 104 | 2-[(1S)-5-(3-phenoxypropoxy)indanyl]acetic acid |
| 105 | 2-{(1S)-5-[3-(2-propylphenoxy)propoxy]indanyl}acetic acid |
| 106 | 2-{(1S)-5-[3-(4-methylphenoxy)propoxy]indanyl}acetic acid |
| 107 | 2-{(1S)-5-[3-(2,4-dimethylphenoxy)propoxy]indanyl}acetic acid |
| 108 | 2-{(1S)-5-[3-(2-methoxy-4-methylphenoxy)propoxy]indanyl}-acetic acid |
| 109 | 2-{(1S)-5-[3-(2-ethoxy-4-methylphenoxy)propoxy]indanyl}-acetic acid |
| 110 | 2-{(1S)-5-[3-(2-bromo-4-methylphenoxy)propoxy]indanyl}-acetic acid |
| 111 | 2-((1S)-5-{3-[2-(butanoylamino)-4-methylphenoxy]propoxy}-indanyl)acetic acid |
| 112 | 2-{(1S)-5-[3-(2-isoxazol-5-yl-4-methylphenoxy)propoxy]-indanyl}acetic acid |
| 113 | 2-{(1S)-5-[3-(4-ethylphenoxy)propoxy]indanyl}acetic acid |
| 114 | 2-{(1S)-5-[3-(4-ethyl-2-methoxyphenoxy)propoxy]indanyl}-acetic acid |
| 115 | 2-((1S)-5-{3-[4-(methylethyl)phenoxy]propoxy}indanyl)-acetic acid |
| 116 | 2-((1S)-5-{3-[4-(trifluoromethyl)phenoxy]propoxy}indanyl)-acetic acid |
| 117 | 2-{(1S)-5-[3-(4-cyanophenoxy)propoxy]indanyl}acetic acid |
| 118 | 2-{(1S)-5-[3-(4-cyano-2-propylphenoxy)propoxy]indanyl}-acetic acid |
| 119 | 2-{(1S)-5-[3-(4-cyano-2-methoxyphenoxy)propoxy]indanyl}-acetic acid |
| 120 | 2-{(1S)-5-[3-(4-methoxyphenoxy)propoxy]indanyl}acetic acid |
| 121 | 2-{(1S)-5-[3-(4-phenoxy-2-propylphenoxy)propoxy]indanyl}-acetic acid |
| 122 | 2-{(1S)-5-[3-(4-ethoxyphenoxy)propoxy]indanyl}acetic acid |
| 123 | 2-((1S)-5-{3-[4-(trifluoromethoxy)phenoxy]propoxy}indanyl)-acetic acid |
| 124 | 2-{(1S)-5-[3-(4-bromo-2-methoxyphenoxy)propoxy]indanyl}-acetic acid |
| 125 | 2-{(1S)-5-[3-(4-(1,2,4-triazolyl)phenoxy)propoxy]indanyl}-acetic acid |
| 126 | 2-((1S)-5-{3-[2-(acetylamino)-4-(1,2,3-triazolyl)phenoxy]-propoxy}indanyl)acetic acid |
| 127 | 2-{(1S)-5-[3-(2-chloro-4-(1,2,4-triazol-4-yl)phenoxy)propoxy]-indanyl}acetic acid |
| 128 | 2-[(1S)-5-(3-{2-methyl-4-[3-(trifluoromethyl)(1,2,4-thiadiazol-5-yl)]phenoxy}propoxy)indanyl]acetic acid |
| 129 | 2-[(1S)-5-(3-{4-[4-hydroxy-4-(trifluoromethyl)(1,3-thiazolin-2-yl)]phenoxy}propoxy)indanyl]acetic acid |

TABLE 3b-continued

IUPAC Names for Compounds in Table 3a

| Ex. No. | IUPAC Name |
|---|---|
| 130 | 2-{(1S)-5-[3-(4-(3-furyl)phenoxy)propoxy]indanyl}acetic acid |
| 131 | 2-{(1S)-5-[3-(2-methoxy-4-(2-thienyl)phenoxy)propoxy]-indanyl}acetic acid |
| 132 | 2-((1S)-5-{3-[2-methoxy-4-(4-methyl(2-thienyl))phenoxy]-propoxy}indanyl)acetic acid |
| 133 | {(1S)-5-[3-(1,1'-biphenyl-4-yloxy)propoxy]-2,3-dihydro-1H-inden-1-yl}acetic acid |
| 134 | 2-((1S)-5-{3-[2-methoxy-4-(4-methoxyphenyl)phenoxy]-propoxy}indanyl)acetic acid |
| 135 | 2-((1S)-5-{3-[4-(4-fluorophenyl)-2-methoxyphenoxy]propoxy}-indanyl)acetic acid |
| 136 | 2-{(1S)-5-[3-(4-(3-pyridyl)phenoxy)propoxy]indanyl}acetic acid |
| 137 | 2-{(1S)-5-[3-(2-methoxy-4-(3-pyridyl)phenoxy)propoxy]-indanyl}acetic acid |
| 138 | 2-((1S)-5-{3-[4-(4-methoxy-(3-pyridyl))phenoxy]propoxy}-indanyl)acetic acid |
| 139 | 2-[(1S)-5-(3-{4-[5-(trifluoromethyl)(2-pyridyl)]phenoxy}-propoxy)indanyl]acetic acid |
| 140 | 2-{(1S)-5-[3-(4-pyrimidin-5-ylphenoxy)propoxy]indanyl}-acetic acid |
| 141 | 2-((1S)-5-{3-[4-(2,4-dimethoxypyrimidin-5-yl)phenoxy]-propoxy}indanyl)acetic acid |
| 142 | 2-{(1S)-5-[3-(4-indol-6-ylphenoxy)propoxy]indanyl}acetic acid |

Example 143

Preparation of ethyl {(1S)-5-[3-(4-cyano-2-propylphenoxy)propoxy]-2,3-dihydro-1H-inden-1-yl}acetate

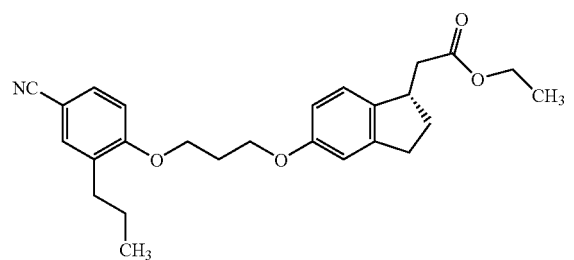

To a mixture of 4-hydroxy-3-propylbenzonitrile (Example 29, 0.5 g, 3.1 mmol), ethyl [(1S-5-(3-bromopropoxy)-2,3-dihydro-1H-inden-1-yl]acetate (Example 45, 1.1 g, 3.1 mmol) and $Cs_2CO_3$ (1.2 g, 3.7 mmol) in DMF (10 mL) was added water (6 drops). The reaction mixture was stirred at 40° C. for 16 h and then concentrated under reduced pressure. The residue was taken up in water and extracted with EtOAc (2×). The combined organic phases were dried over $MgSO_4$, filtered, and concentrated under reduced pressure. Purification by silica gel flash chromatography (EtOAc/Hexane (v/v) 1:20) gave 0.86 g (66%) of the title compound as a light yellow oil. LC-MS: RT=4.12 min; (M+H)$^+$ 422.0.

Example 144

Preparation of ethyl ((1S)-5-{3-[4-(aminocarbonothioyl)-2-propylphenoxy]propoxy}-2.3-dihydro-1H-inden-1-yl)acetate

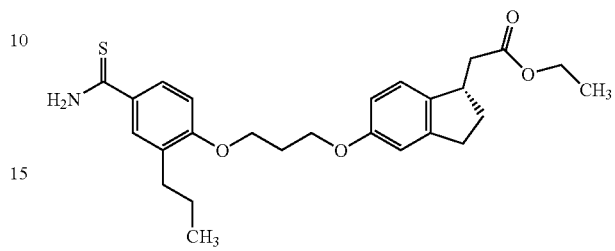

To a solution of ethyl {(1S-5-[3-(4-cyano-2-propylphenoxy)propoxy]-2,3-dihydro-1H-inden-1-yl}acetate (Example 143, 1.2 g, 2.9 mmol) in DMF (anhydrous, 15 mL) under argon at rt was passed $H_2S$ gas at a moderate rate for 20 min. Then, a solution of diethylamine (0.3 g, 4.3 mmol) in DMF (3 mL) was added in one portion, and the reaction mixture was stirred at 60° C. for 3 h. Upon completion, the reaction was cooled to rt and argon was passed through the reaction mixture for 1 h to remove residual $H_2S$. The reaction mixture was concentrated under reduced pressure and the residue purified by silica gel flash chromatography (EtOAc/Hexane (v/v)=1:1) to give 0.9 g (76%) of the title compound as a yellow solid. $^1$H NMR (300 MHz, $CD_3OD$): δ 0.94 (t, 3H), 1.31 (t, 3H), 1.52-1.64 (m, 2H), 1.65-1.80 (m, 1H), 2.20-2.44 (m, 4H), 2.58-2.95 (m, 5H), 3.38-3.61 (m, 1H), 4.16-4.21 (m, 4H), 4.26 (t, 2H), 6.69 (d, 1H), 6.80 (s, 1H), 6.95 (d, 1H), 7.09 (d, 1H), 7.79 (d, 1H), 7.84 (s, 1H).

Example 145

Preparation of ethyl {(1S)-5-[3-(4-cyano-2-methoxyphenoxy)propoxy]-2,3-dihydro-1H-inden-1-yl}acetate

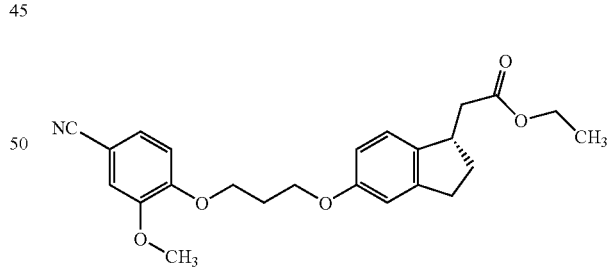

To a mixture of 4-hydroxy-3-methoxybenzonitrile (2.6 g, 17.6 mmol), ethyl [(1S)-5-(3-bromopropoxy)-2,3-dihydro-1H-inden-1-yl]acetate (Example 45) (6 g, 17.6 mmol), and $Cs_2CO_3$ (6.9 g, 21.1 mmol) in DMF (30 mL) was added water (15 drops). The reaction mixture was stirred at 40° C. for 16 h and concentrated under reduced pressure. The residue was diluted with water and extracted with EtOAc (2×). The combined organic phases were dried over $MgSO_4$, filtered, and concentrated under reduced pressure. Recrystallization from MeOH (5 mL) gave 4.9 g (68%) of the title compound as an off-white solid. LC-MS: RT=3.59 min; (M+H)$^+$ 410.0.

Example 146

Preparation of ethyl ((1S)-5-{3-[4-(aminocarbonothioyl)-2-methoxyphenoxy]propoxy}-2,3-dihydro-1H-inden-1-yl)acetate

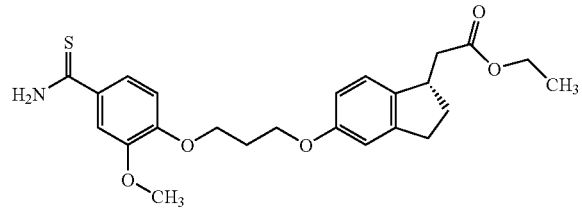

Into a solution of ethyl {(1S-5-[3-(4-cyano-2-methoxyphenoxy)propoxy]-2,3-dihydro-1H-inden-1-yl}acetate (2.2 g, 5.4 mmol) (Example 145) in DMF (anhydrous, 20 mL) under argon at rt was passed $H_2S$ gas at a moderate rate for 30 min. A solution of diethylamine (0.8 g, 8.1 mmol) in DMF (5 mL) was added in one portion, and the reaction was stirred at 60° C. for 3 h. Then the reaction was cooled to rt and argon was passed through the reaction mixture for 1 h to remove residual $H_2S$. The reaction mixture was then concentrated under reduced pressure and the residue purified by silica gel flash chromatography (EtOAc/Hexane (v/v)=1:1) to afford 1.9 g (81%) of the title compound as a yellow solid. $^1H$ NMR (400 MHz, DMSO-$d_6$): δ 1.21 (t, 3H), 1.60-1.68 (m, 1H), 2.15-2.22 (m, 2H), 2.23-2.34 (m, 1H), 2.38 (q, 1H), 2.70-2.86 (m, 3H), 3.38-3.44 (m, 1H), 3.80 (s, 3H), 4.05-4.16 (m, 4H), 4.19 (t, 2H), 6.70 (d, 1H), 6.80 (s, 1H), 6.97 (d, 1H), 7.06 (d, 1H), 7.56-7.64 (m, 2H), 9.33-9.40 (s, 1H), 9.65 (s, 1H).

Example 147

Preparation of ethyl ((1S)-5-{3-[4-(4-ethyl-1,3-thiazol-2-yl)-2-propylphenoxy]propoxy}-2,3-dihydro-1H-inden-1-yl)acetate

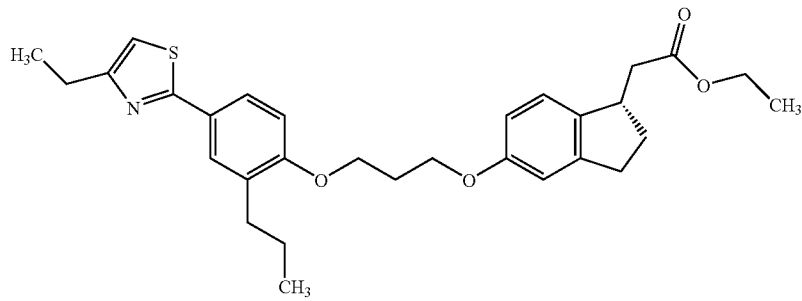

A solution of ethyl ((1S)-5-{3-[4-(aminocarbonothioyl)-2-propylphenoxy]propoxy}-2,3-dihydro-1H-inden-1-yl)acetate (90 mg, 0.2 mmol) (Example 144) and 1-bromo-2-butanone (35.8 mg, 0.24 mmol) in EtOH (anhydrous, 8 mL) was heated at 70° C. for 6 h. The reaction mixture was cooled to rt, and then concentrated under reduced pressure. Purification by silica gel flash chromatography (EtOAc/hexane (v/v) 1:2) gave 42 mg (42%) of the title compound as a clear oil. LC-MS: RT=4.85 min; (M+H)$^+$ 508.2.

Example 148

Preparation of ((1S)-5-{3-[4-(4-ethyl-1,3-thiazol-2-yl)-2-propylphenoxy]propoxy}-2,3-dihydro-1H-inden-1-yl)acetic acid

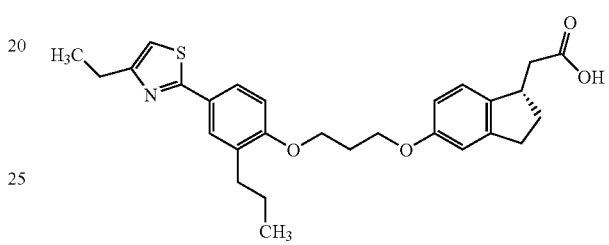

To a solution of ethyl ((1S-5-{3-[4-(4-ethyl-1,3-thiazol-2-yl)2-propylphenoxy]propoxy}-2,3-dihydro-1H-inden-1-yl)acetate (60 mg 0.12 mmol) (Example 147) in THF (3.0 mL) was added a solution of LiOH.$H_2O$ (20 mg, 0.48 mmol) in water (1.0 mL) and MeOH (1.0 mL), and the mixture was stirred for 12 h at rt. The reaction mixture was concentrated under reduced pressure, and the residue was diluted with water and extracted with $Et_2O$ (3×). The aqueous phase was brought to pH 3 using HCl (1N aqueous solution), and then the aqueous layer was extracted with EtOAc. The organic phase was dried over $MgSO_4$, filtered, and concentrated under reduced pressure to give 36 mg (63%) of the title compound as a white solid. $^1H$ NMR (300 MHz, $CD_3OD$): δ 0.96 (t, 3H), 1.34 (t, 3H), 1.59-1.71 (m, 2H), 1.73-1.81 (m, 1H), 2.25-2.38 (m, 2H), 2.39-2.47 (m, 2H), 2.62-2.98 (m, 7H), 3.44-3.57 (m, 1H), 4.20 (t, 2H), 4.26 (t, 2H), 6.75 (d, 1H), 6.84 (s, 1H), 7.02 (d, 1H), 7.07 (s, 1H), 7.14 (d, 1H), 7.71 (s, 1H), 7.78 (d, 1H); LC-MS: RT=4.04 min, (M+H)$^+$ 480.2.

Example 149

Preparation of ethyl((1S)-5-{3-[2-propyl-4-(4,5,6,7-tetrahydro-1,3-benzothiazol-2-yl)phenoxy]propoxy}-2,3-dihydro-1H-inden-1-yl)acetate

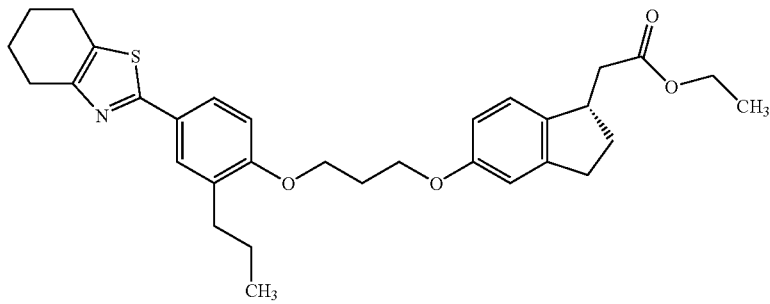

A solution of ethyl ((1S)-5-{3-[4-aminocarbonothioyl]-2-propylphenoxy]propoxy}-2,3-dihydro-1H-inden-1-yl)acetate (90 mg, 0.2 mmol) (Example 144) and 2-chlorocyclohexanone (239 mg 1.8 mmol) in EtOH (anhydrous, 8 mL) was stirred at 70° C. for 48 h. The reaction mixture was cooled to rt, and then concentrated under reduced pressure. Purification by silica gel flash chromatography (EtOAc/hexane (v/v) 1:2) gave 45 mg (43%) of the title compound as a clear oil. LC-MS: RT=4.69 min; (M+H)$^+$ 534.3.

Example 150

Preparation of ((1S)-5-{3-[2-propyl-4-(4,5,6,7-tetrahydro-1,3-benzothiazol-2-yl)phenoxy]propoxy}-2,3-dihydro-1H-inden-1-yl)acetic acid

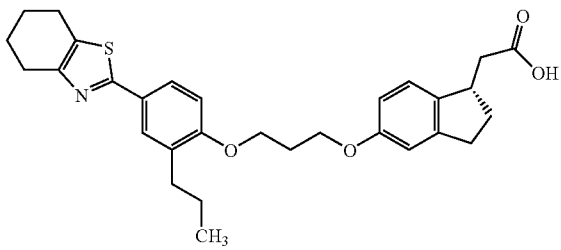

Using Example 149 as starting material, the title compound was prepared following similar procedures to those described for Example 148. $^1$H NMR (300 MHz, CD$_3$OD): δ 0.94 (t, 3H), 1.56-1.68 (m, 2H), 1.69-1.80 (m, 1H), 1.82-1.97 (m, 4H), 2.20-2.31 (m, 2H), 2.31-2.40 (m, 2H), 2.59-2.92 (m, 9H), 3.36-3.52 (m, 1H), 4.17 (t, 2H), 4.23 (t, 2H), 6.68 (d, 1H), 6.77 (s, 1H), 7.01 (d, 1H), 7.09 (d, 1H), 7.59-7.63 (s, 1H), 7.64-7.70 (d, 1H); LC-MS: RT=4.05 min, (M+H)$^+$ 506.3.

Example 151

Preparation of 3-bromotetrahydro-2H-pyran-2-one

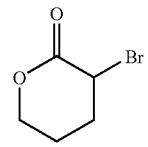

2-Trimethylsilyloxy-5,6-dihydropyran (1.00 g, 5.80 mmol) and Et$_3$N (0.93 mL, 6.67 mmol) were dissolved in CH$_2$Cl$_2$ (anhydrous, 15 mL) under an atmosphere of argon, and the mixture was cooled to −15° C. A solution of bromine (928 mg, 5.80 mmol) in CH$_2$Cl$_2$ (5 mL) was added dropwise over 15 min with vigorous stirring. The reaction mixture was allowed to warm to rt, and then was washed with NH$_4$Cl (saturated aqueous solution, 2×). The organic layer was dried over Na$_2$SO$_4$, filtered, and concentrated under reduced pressure to provide 1.28 g of the crude product contaminated with triethylammonium salt impurities. The material was used without further purification. $^1$H NMR (400 MHz, CDCl$_3$): δ 1.91 (m, 1H), 2.20-2.39 (m, 2H), 2.48 (m, 1H), 4.41 (m, 1H), 5.59 (m, 2H).

Example 152

Preparation of ethyl((1S)-5-{3-[4-(6,7-dihydro-5H-pyrano[2,3-d][1,3]thiazol-2-yl)-2-yl)-2-propylphenoxy]propoxy}-2,3-dihydro-1H-inden-1-yl)acetate

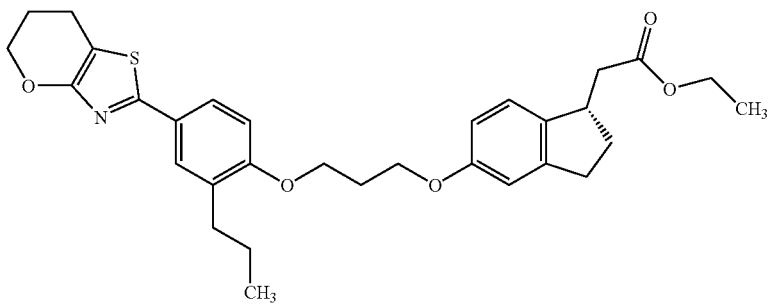

A solution of ethyl ((1S)-5-{3-[4-(aminocarbonothioyl)-2-propylphenoxy]propoxy}-2,3-dihydro-1H-inden-1-yl)acetate (0.5 g, 1.1 mmol) (Example 144) and 3-bromotetrahydro-2H-pyran-2-one (1.2 g, 6.6 mmol) (Example 151) in EtOH (anhydrous, 15 mL) was heated at 70° C. for 18 h. The reaction mixture was cooled to rt, and concentrated under reduced pressure. Purification by silica gel flash chromatography (EtOAc/hexane (v/v)=1:2) gave 0.17 g (29%) of the title compound as a light yellow oil. LC-MS: RT=4.52 min, (M+H)+: 536.4.

Example 153

Preparation of ((1S)-5-{3-[4-(6,7-dihydro-5H-pyrano[2,3-d][1,3]thiazol-2-yl)-2-propylphenoxy]propoxy}-2,3-dihydro-1H-inden-1-yl)acetic acid Ethyl ((1S)-5-{3-[4-(aminocarbonothioyl)-2-methoxyphenoxy]propoxy}-2,3-dihydro-1H-inden-1-yl)acetate (90 mg, 0.2 mmol) (Example 146) and 1-bromo-2-butanone (36.7 mg, 0.24 mmol) were dissolved in EtOH (anhydrous, 8 mL) and stirred at 70° C. for 6 h. The reaction was cooled to rt, and concentrated under reduced pressure. Purification by silica gel flash chromatography (EtOAc:hexane (v/v)=1:2) gave 50 mg (51%) of the title compound as a clear oil. LC-MS: RT=4.07 min; (M+H)+ 496.2.

Example 155

Preparation of ((1S)-5-{3-[4-(4-ethyl-1,3-thiazol-2-yl)-2-methoxyphenoxy]propoxy}-2,3-dihydro-1H-inden-1-yl)acetic acid

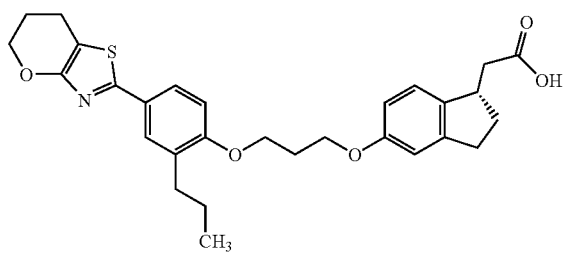

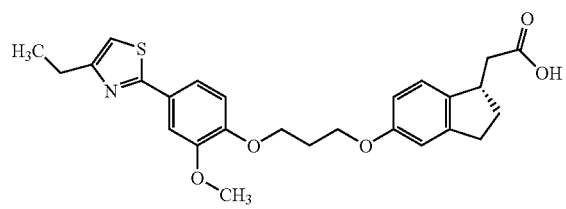

Using Example 152 as starting material, the title compound was prepared following similar procedures to those described for Example 148. ¹H NMR (300 MHz, CD₃OD): δ 0.92 (t, 3H), 1.51-1.65 (m, 2H), 1.66-1.77 (m, 1H), 2.02-2.17 (m, 2H), 2.20-2.42 (m, 4H), 2.55-2.93 (m, 7H), 3.36-3.50 (m, 1H), 4.18 (t, 2H), 4.22 (t, 2H), 4.32 (t, 2H), 6.70 (d, 1H), 6.79 (s, 1H), 6.98 (d, 1H), 7.08 (d, 1H), 7.59 (s, 1H), 7.65 (d, 1H); LG-MS: RT=4.02 min, (M+H)+ 508.2.

Example 154

Preparation of ethyl((1S)-5-{3-[4-(4-ethyl-1,3-thiazol-2-yl)-2-methoxyphenoxy]propoxyl}-2,3-dihydro-1H-inden-1-yl)acetate Using Example 154 as starting material, the title compound was prepared following similar procedures to those described for Example 148. ¹H NMR (300 MHz, CDCl₃): δ 1.36 (t, 3H), 1.76-1.82 (m, 1H), 2.23-2.38 (m, 2H), 2.39-2.54 (m, 2H), 2.68-2.96 (m, 5H), 3.43-3.6 (m, 1H), 3.93 (s, 3H), 4.17 (t, 2H), 4.26 (t, 2H), 6.73 (d, 1H), 6.80 (s, 1H), 6.82 (s, 1H), 6.90 (d, 1H), 7.06 (d, 1H), 7.41 (d, 1H), 7.48 (s, 1H); LC-MS: RT=3.42 min, (M+H)+ 468.2.

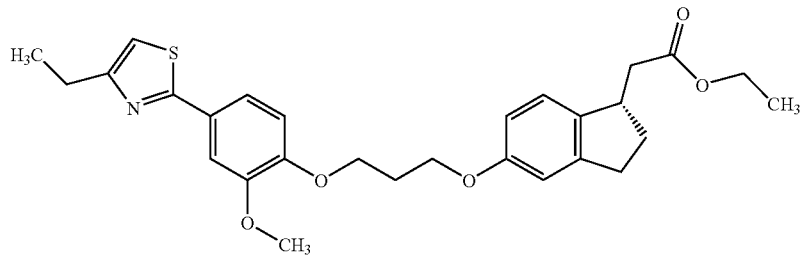

Example 156

Preparation of ethyl((1S)-5-{3-[4-(4-isopropoxy-1,3-thiazol-2-yl)-2-methoxyphenoxy]propoxy}-2,3-dihydro-1H-inden-1-yl)acetate

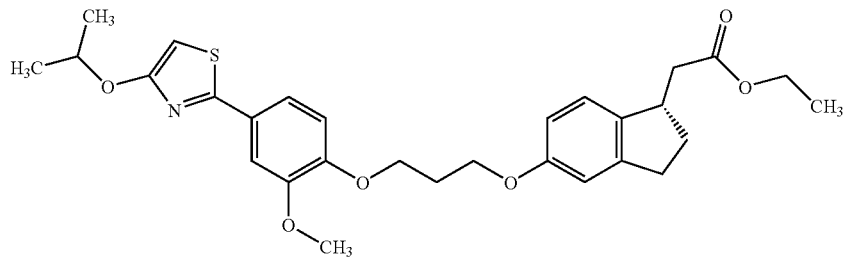

A solution of ethyl ((1S)-5-{3-[4-(aminocarbonothioyl)-2-methoxyphenoxy]propoxy}-2,3-dihydro-1H-inden-1-yl)acetate (500 mg, 1.1 mmol) (Example 146) and 2-chloro-N,N-dimethylacetamide (800 mg, 6.6 mmol) in i-PrOH (anhydrous, 15 mL) was stirred at 70° C. for 8 h. The reaction was cooled to rt, and concentrated under reduced pressure. Purification by silica gel flash chromatography (EtOAc:hexane (v/v)=1:2) gave 292 mg (49%) of the title compound as a yellow oil. LC-MS: RT=4.27 min; (M+H)$^+$: 526.1.

Example 157

Preparation of ((1S)-5-{3-[4-(4-isopropoxy-1,3-thiazol-2-yl)-2-methoxyphenoxy]propoxy}-2,3-dihydro-1H-inden-1-yl)acetic acid

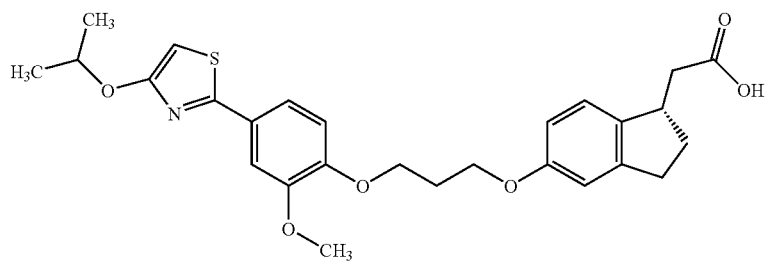

Using Example 156 as starting material, the title compound was prepared following similar procedures to those described for Example 148. $^1$H NMR (300 MHz, CDCl$_3$): δ 1.41 (d, 6H), 1.76-1.84 (m, 1H), 2.26-2.38 (m, 2H), 2.38-2.52 (m, 2H), 2.73-2.96 (m, 3H), 3.48-3.6 (m, 1H), 3.91 (s, 3H), 4.14 (t, 2H), 4.26 (t, 2H), 4.62-4.77 (m, 1H), 5.96 (s, 1H), 6.71 (d, 1H), 6.80 (s, 1H), 6.91 (d, 1H), 7.10 (d, 1H), 7.39 (d, 1H), 7.52 (s, 1H); LC-MS: RT=3.61 min, (M+H)$^+$ 498.2.

Example 158

Preparation of ethyl((1S)-5-{4-[2-methoxy-4-(1,3-thiazol-2-yl)phenoxy]propoxy}-2,3-dihydro-1H-inden-1-yl)acetate

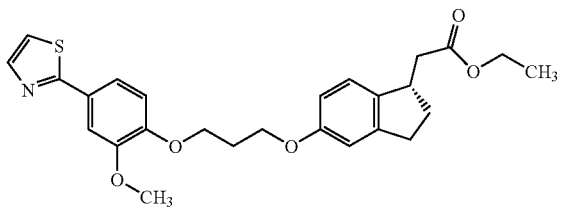

Ethyl ((1S)-5-{3-[4-(aminocarbonothioyl)-2-methoxyphenoxy]propoxy}-2,3-dihydro-1H-inden-1-yl)acetate (1.00 g, 2.3 mmol) (Example 146) and bromoacetaldehyde diethyl acetal (1.78 g, 9.2 mmol) were dissolved in EtOH (30 mL) and water (2 drops) was added. The mixture was heated at 70° C. for 18 h, and then the reaction mixture was cooled to rt, and concentrated under reduced pressure. Purification by silica gel flash chromatography (EtOAc:hexane (v/v)=1:1) gave 610 mg (58%) of the title compound as a clear oil. LC-MS: RT=3.81 min; (M+H)$^+$ 468.1.

Example 159

Preparation of ((1S)-5-{4-[2-methoxy-4-(1,3-thiazol-2-yl)phenoxy]propoxy}-2,3-dihydro-1H-inden-1-yl) acetic acid

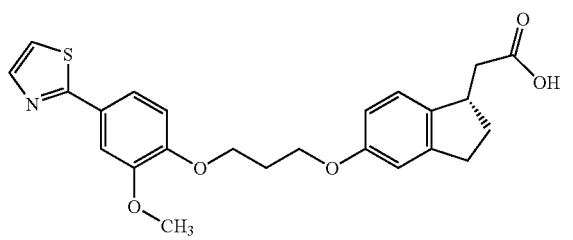

Using Example 158 as starting material, the title compound was prepared following similar procedures to those described for Example 148. $^1$H NMR (300 MHz, CDCl$_3$): δ 1.72-1.83 (m, 1H), 2.24-2.39 (m, 2H), 2.40-2.57 (m, 2H), 2.68-2.97 (m, 3H), 3.53 (s, 1H), 3.96 (s, 3H), 4.15 (t, 2H), 4.30 (t, 2H), 6.73 (d, 1H), 6.80 (s, 1H), 6.87 (d, 1H), 7.11 (d, 1H), 7.26 (s, 1H), 7.45 (d, 1H), 7.56 (s, 1H), 7.85 (s, 1H); LC-MS: RT=3.17 min, (M+H)$^+$ 440.1.

Example 160

Preparation of ethyl 2-[4-(3-{[(1S)-1-(2-ethoxy-2-oxoethyl)-2,3-dihydro-1H-inden-5-yl]oxy}propoxy)-3-propylphenyl]-4-(hydroxymethyl)-1,3-thiazole-5-carboxylate Ethyl ((1S)-5-{3-[4-aminocarbonothioyl)-2-propylphenoxy]propoxy}2,3-dihydro-1H-inden-1-yl)acetate (90 mg, 0.2 mmol) (Example 144) and 3-chloro-2,4(3H, 5H)-furandione (106 mg, 0.8 mmol) were dissolved in EtOH (anhydrous, 8 mL), and the mixture was heated at 70° C. for 18 h. The reaction was cooled to rt, and then concentrated under reduced pressure. Purification by silica gel flash chromatography (EtOAc:hexane (v/v)=1:1) gave 38 mg (33%) of the btle compound as a clear oil. LC-MS: RT=4.38 min; (M+H)$^+$ 582.3.

Example 161

Preparation of 2-[4-(3-{[(1S)-1-(carboxymethyl)-2,3-dihydro-1H-inden-5-yl]oxy}propoxy)-3-propylphenyl]-4-(hydroxymethyl)-1,3-thiazole-5-carboxylic acid

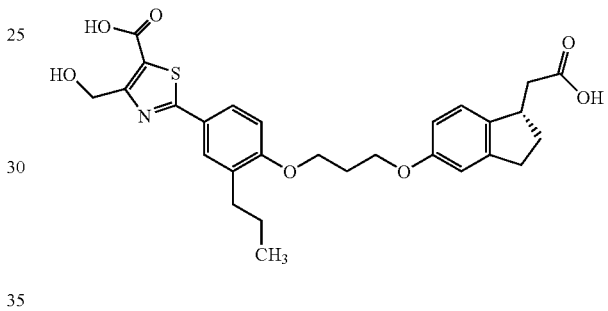

Using Example 160 as starting material, the title compound was prepared following similar procedures to those described for Example 148. $^1$H NMR (300 MHz, acetone-d$_6$): δ 0.93 (t, 3H), 1.56-1.67 (m, 2H), 1.68-1.80 (m, 1H) 2.21-2.42 (m, 4H), 2.58-2.95 (m, 7H), 3.37-3.52 (m, 1H), 4.22 (t, 2H), 4.30 (t, 2H), 6.72 (d, 1H), 6.83 (s, 1H), 7.07 (d, 1H), 7.14 (d, 1H), 7.80 (s, 1H), 7.89 (d, 1H); LC-MS: RT=3.20 min, (M+H)$^+$ 526.1.

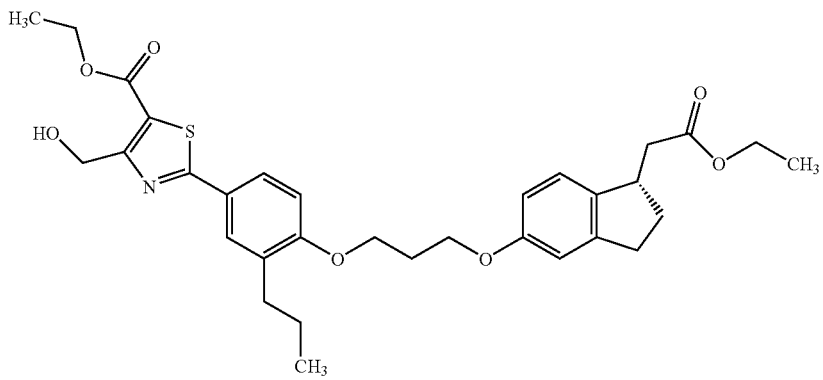

Example 162

Preparation of methyl 2-[4-(3-{[(1S)-1-(2-ethoxy-2-oxoethyl)-2,3-dihydro-1H-inden-5-yl]oxy}propoxy)-3-methoxyphenyl]-1,3-thiazole-5-carboxylate

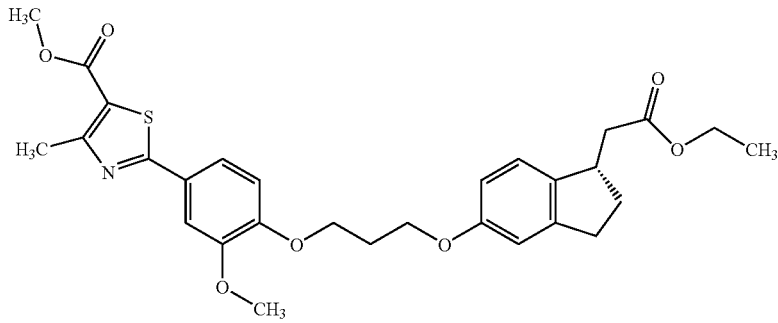

Ethyl ((1S)-5-{3-[4-(aminocarbonothioyl2-methoxyphenoxy]propoxy}-2,3-dihydro-1H-inden-1-yl)acetate (90 mg, 0.2 mmol) (Example 146) and methyl 2-chloroacetoacetate (37 mg, 0.24 mmol) were dissolved in EtOH (8 mL), and the mixture was heated at 70° C. for 6 h. The reaction was cooled to rt, and then concentrated under reduced pressure. Purification by silica gel flash chromatography (EtOAc:hexane (v/v) =1:2) provided 52 mg (48%) of the title compound as a clear oil. LC-MS: RT=4.18 min, (M+H)+ 540.1.

Example 163

Preparation of 2-[4-(3-{[(1S)-1-(carboxymethyl)-2,3-dihydro-1H-inden-5-yl]oxy}propoxy)-3-methoxyphenyl]-4-methyl-1,3-thiazole-5-carboxylic acid

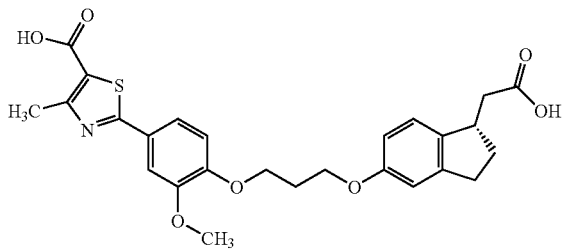

Using Example 162 as starting material, the title compound was prepared following similar procedures to those described for Example 148. ¹H NMR (300 MHz, CD₃OD): δ 1.65-1.82 (m, 1H), 2.20-2.38 (m, 4H), 2.47-2.59 (m, 1H), 2.62 (s, 3H), 2.65-2.94 (m, 2H), 3.46 (s, 1H), 3.86 (s, 3H), 4.11 (t, 2H), 4.20 (t, 2H), 6.71 (d, 1H), 6.78 (s, 1H), 7.03 (dd, 2H), 7.49 (d, 1H), 7.57 (s, 1H); LC-MS: RT=3.04 min, (M+H)+ 498.1.

Example 164

Preparation of ethyl ((1S)-5-{3-[2-methoxy-4-(4,5,6,7-tetrahydro-1,3-benzothiazol-2-yl)phenoxy]propoxy}-2,3-dihydro-1H-inden-1-yl)acetate

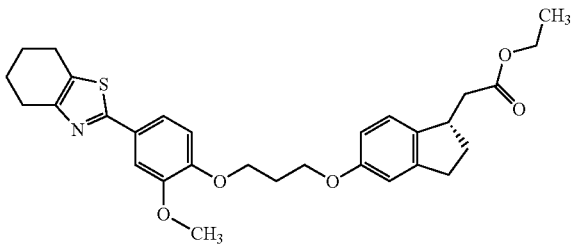

A solution of ethyl ((1S)-5-{3-[4-(aminocarbonothioyl)-2-methoxyphenoxy]propoxy}-2,3-dihydro-1H-inden-1-yl)acetate (Example 146, 90 mg, 0.2 mmol) and 2-chlorocyclohexanone (215 mg 1.6 mmol) in anhydrous EtOH (8 mL) was stirred at 70° C. for 48 h. The reaction was cooled, and the solvent was removed under reduced pressure. The residue was purified by silica gel flash chromatography (2:1 hexanes/ethyl acetate) to provide the title compound (62 mg, 58%) as clear oil. LC-MS: RT=4.08 min, (M+H)+ 522.5.

Example 165

Preparation of ethyl ((1S)-5-{3-[2-hydroxy-4-(4,5,6,7-tetrahydro-1,3-benzothiazol-2yl)phenoxy]propoxy}-2,3-dihydro-1H-inden-1-yl)acetate

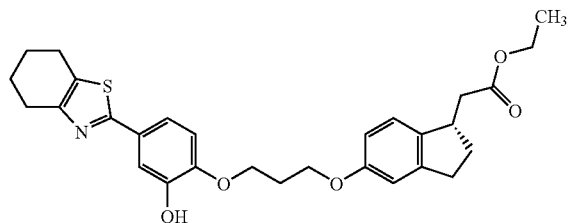

To a solution of ethyl ((1S)-5-{3-[2-methoxy-4-(4,5,6,7-tetrahydro-1,3-benzothiazol-2-yl)phenoxy]propoxy}-2,3- dihydro-1H-inden-1-yl)acetate (Example 164, 400 mg, 0.787 mmol) dissolved in CH₂Cl₂ (10 mL) was added AlCl₃ (511.2 mg, 3.834 mmol), and then the solution was cooled to 0° C. Ethanethiol (0.284 mL, 3.834 mmol) was added dropwise to the solution which was stirred at 0° C. for 3 h. The reaction mixture was poured onto ice-water (20 mL) with vigorous stirring. The organic layer was separated and the aqueous layer was extracted with CH₂Cl₂. The combined organic layers were dried (MgSO₄), filtered, and concentrated under reduced pressure. The crude material was purified by preparative HPLC, giving the desired product as a white solid (180.0 mg, 46%). ¹H NMR (400 MHz, DMSO-d₆): δ 9.27 (s, 1H), 7.28 (d, 1H), 7.20 (dd, 1H), 7.05 (d, 1H), 6.96 (d, 1H), 6.79 (s, 1H), 6.69 (dd, 1H), 4.07-4.18 (m, 6H), 3.39 (m, 1H), 2.72 (dd, 6H), 2.09-2.20 (m, 5H), 1.80-1.59 (m, 5H), 1.18 (t, 3H).

Example 166

Preparation of ethyl ((1S)-5-{3-[2-propoxy-4-(4,5,6,7-tetrahydro-1,3-benzothiazol-2-yl)phenoxy]propoxy}-2,3-dihydro-1H-inden-1-yl)acetate

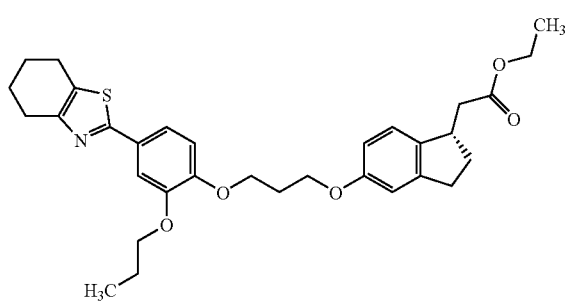

Ethyl ((1S)-5-{3-[2-hydroxy-4-(4,5,6,7-tetrahydro-1,3-benzothiazol-2-yl)-phenoxy]-propoxy}-2,3-dihydro-1H-inden-1-yl)acetate (Example 165, 90 mg, 0.177 mmol) was dissolved in DMF (3 mL) after which Cs₂CO₃ (69.3 mg, 0.213 mmol) and water (3 drops) were added. Iodopropane (0.02 mL, 0.213 mmol) was added to the flask, and the reaction mixture was stirred at room temperature for 18 h. The mixture was then filtered and the filtrate purified by preparative HPLC giving the desired ester as a white solid (88.7 mg, 91%). ¹H NMR (400 MHz, CD₂Cl₂): δ 7.47 (s, 1H), 7.37 (dd, 1H), 7.05 (d, 1H), 6.93 (d, 1H), 6.79 (s, 1H), 6.71 (dd, 1H), 4.23 (t, 2H), 4.19-4.13 (m, 4H), 4.03 (t, 2H), 3.50 (m, 1H), 2.94-2.78 (m, 6H), 2.70 (dd, 1H), 2.44-2.25 (m, 4H), 1.92-1.70 (m, 7H), 1.28 (t, 3H), 1.07 (t, 3H).

Example 167

Preparation of ((1S)-5-{3-[2-propoxy-4-(4,5,6,7-tetrahydro-1,3-benzoxazol-2-yl)phenoxy]propoxy}-2,3-dihydro-1H-inden-1-yl)acetic acid

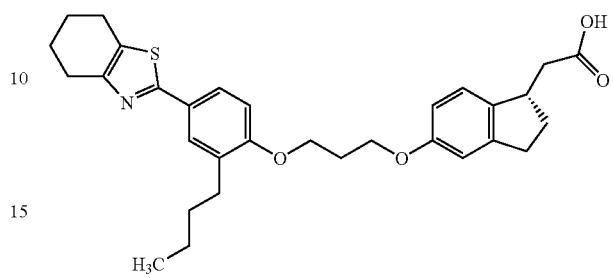

To a solution of ethyl ((1S)-5-{3-[2-propoxy-4-(4,5,6,7-tetrahydro-1,3-benzthiazol-2-yl)phenoxy]propoxy}-2,3-dihydro-1H-inden-1-yl)acetate (Example 166, 88.0 mg, 0.160 mmol) in THF/Water/Methanol (1:2:1) was added solid lithium hydroxide (38.4 mg, 1.60 mmol). The solution was stirred at rt for 3 h, and the solvent was then removed under reduced pressure. The residue was diluted with water and acidified using HCl (2 N aqueous solution) upon which a white precipitate formed. The solid was isolated by filtration to provide the title compound (43.5 mg, 52%) that did not require further purification. ¹H NMR (400 MHz, DMSO-d₆) δ 7.37 (d, 1H), 7.32 (dd, 1H), 7.07 (d, 1H), 7.04 (d, 1H), 6.78 (s, 1H), 6.69 (dd, 1H), 4.15 (t, 2H), 4.11 (t, 2H), 3.96 (t, 2H), 3.33 (m, 1H), 2.61-2.85 (m, 7H), 2.2-2.30 (m, 3H), 2.11-2.19 (m, 2H), 1.58-1.84 (m, 7H), 0.98 (t, 3H); LC-MS: RT 3.80 min, (M+H)⁺ 22.3.

Example 168

Preparation of 4-(1,3-benzothiazol-2-yl)-2-methoxyphenol

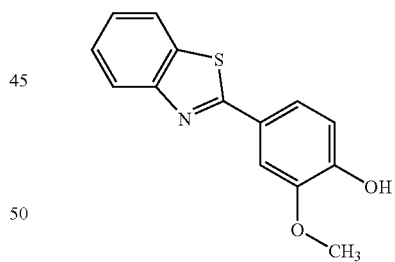

A slurry of 2-aminothiophenol (357 mg, 2.85 mmol) in polyphosphoric acid (14.0 g) was heated to 110° C. and 4-hydroxy-3-methoxybenzoic acid (480 mg, 2.85 mmol) was added. After 2 h, the reaction mixture was cooled to rt. The mixture was poured carefully into ice cold water, and the solution was neutralized with KOH (3 M aqueous solution). The aqueous phase was extracted with EtOAc (2×). The combined organic layers were washed with Na₂CO₃ (1 M aqueous solution), HCl (1 M aqueous solution) and water, dried, and concentrated under reduced pressure. Purification by silica gel chromatography gave 22 mg (3%) of the title compound as an oil. ¹H NMR (400 MHz, CDCl₃): δ 8.02 (d, 1H), 7.88 (d, 1H), 7.72 (s, 1H), 7.55 (d, 1H), 7.48 (m, 1H), 7.36 (m, 1H), 7.00 (d, 1H), 5.92 (s, 1H), 4.03 (s, 3H).

Example 169

Preparation of ethyl ((1S)-5-{3-[4-(1,3-benzothiazol-2-yl)-2-methoxyphenoxy]propoxy}-2,3-dihydro-1H-inden-1-yl)acetate

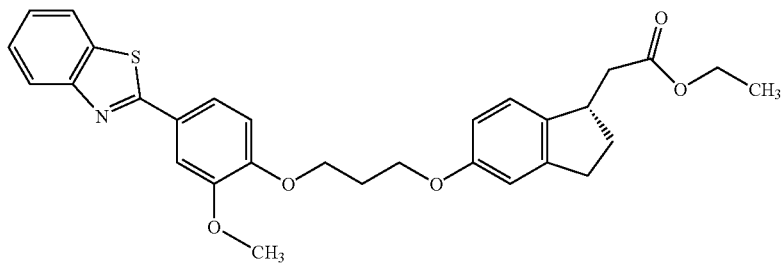

Using Examples 168 and 45 as starting materials, the title compound was prepared as described in Example 48. ¹H NMR (400 MHz, CDCl₃): δ 8.03 (d, 1H), 7.86 (d, 1 H), 7.70 (s, 1H), 7.58 (m, 1H), 7.48 (m, 1H), 7.37 (m, 1H), 7.06 (d, 1H), 6.96 (d, 1H), 6.81 (s, 1H), 6.72 (d, 1H), 4.34-4.24 (m, 2H), 4.24-4.12 (m, 4H), 4.00 (s, 3H), 3.58-3.48 (m, 1H), 2.95-2.80 (m, 2H), 2.72 (dd, 1H), 2.44-2.28 (m, 4H), 1.84-1.68 (m, 1H), 1.28 (t, 3H).

Example 170

Preparation of ((1S)-5-{3-[4-(1,3-benzothiazol-2-yl)-2-methoxyphenoxy]propoxy}-2,3-dihydro-1H-inden-1-yl)acetic acid

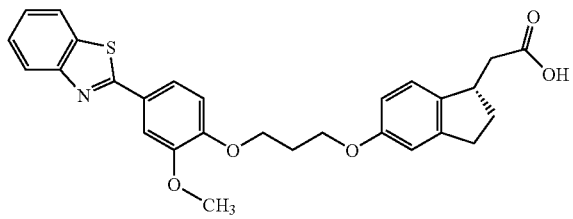

Using Example 169 as starting material, the product was prepared as described in Example 49. ¹H NMR (400 MHz, CDCl₃): δ 7.94 (d, 1H), 7.78 (d, 1H), 7.60 (d, 1H), 7.46 (d, 1H), 7.38 (m, 1H), 7.28 (m, 1H), 7.00 (d, 1H), 6.86 (d, 1H), 6.71 (s, 1H), 6.63 (d, 1H), 4.28-4.17 (m, 2H), 4.17-4.04 (m, 2H), 3.92 (s, 3H), 3.52-3.38 (m, 1H), 2.90-2.63 (m, 3H), 2.42-2.20 (m, 4H), 1.78-1.66 (m, 1H); LC-MS: RT=3.63 min, (M+H)⁺ 490.2.

Example 171

Preparation of 4-hydroxy-3-methoxybenzamide

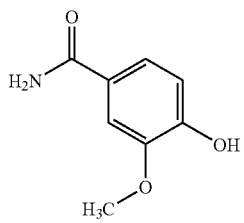

Hydrogen peroxide (3% aqueous solution, 155 mL, 0.151 mol) was added to 4-hydroxy-3-methoxybenzonitrile (5.00 g, 33.52 mmol) at rt. KOH (9.78 g, 148 mmol, 85% purity, reagent grade) was added, resulting in strong gas evolution [exotherm!. The solution stirred at rt for 16 h at which time sodium sulfite (5 equiv.) were added. The reaction mixture was filtered and acidified to pH 2 with HCl (2 N aqueous solution). The aqueous phase was extracted with CH₂Cl₂ (10×50 mL) until no product was detected by TLC in the organic extract. The combined organic phases were dried over MgSO₄, filtered, and concentrated under reduced pressure to give 4.27 g (76%) of the title compound as a pale yellow solid, which was used without further purification. ¹H NMR (400 MHz, DMSO-d₆): δ 9.52 (s, 1H), 7.75 (s, 1H), 7.42 (d, 1H), 7.34 (dd, 1H), 7.10 (s, 1H), 6.76 (d, 1H), 3.78 (s, 3H).

Example 172

Preparation of 4-(4-ethyl-1,3-oxazol-2-yl)-2-methoxyphenol

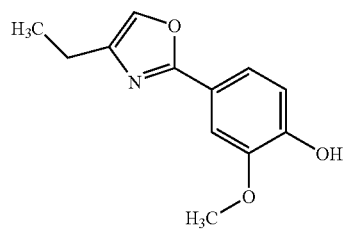

To a solution of the amide prepared in Example 171 (460 mg, 2.75 mmol) in toluene (3 mL) and 1,4-dioxane (3 mL) was added 1-bromo-2-butanone (623 mg, 4.13 mmol), and the solution was heated to 125° C. for 18 h. The reaction mixture was cooled to rt, and then concentrated under reduced pressure. Purification by silica gel chromatography (EtOAc:hexane (v/v)=4:1) gave 382 mg (73%) of the title compound as a yellow oil. ¹H NMR (400 MHz, DMSO-d₆): δ 9.60 (s, 1H), 7.78 (s, 1H), 7.39 (d, 1H), 7.36 (dd, 1H), 6.83 (d, 1H), 3.79 (s, 3H), 2.45 (m, 2H), 1.18 (t, 3H).

Example 173

Preparation of ethyl ((1S)-5-{3-[4-(4-ethyl-1,3-oxazol-2-yl)-2-methoxy-phenoxy]propoxy}-2,3-dihydro-1H-inden-1-yl)acetate

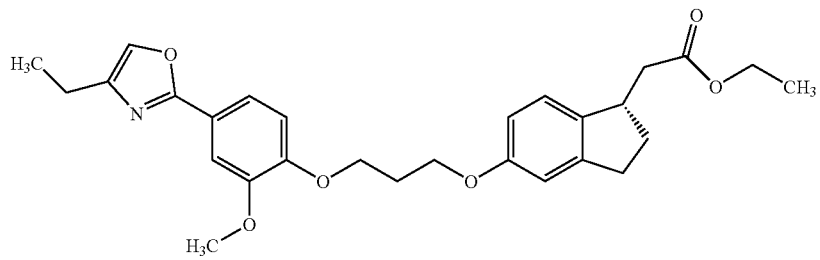

To a solution of [(1S-5-(3-bromopropoxy)-2,3-dihydro-1H-inden-1-yl]acetate (Example 45) (93.4mg, 0.274 mmol) and 4-(4-ethyl-1,3-oxazol-2-yl)-2-methoxyphenol (40.0 mg, 0.182 mmol) (Example 172) in DMF (4 mL) was added $Cs_2CO_3$ (118.9 mg, 0.365 mmol) and water (4 drops). The reaction mixture was stirred at rt for 16 h, then filtered, and the filtrate concentrated under reduced pressure. Purification by preparative HPLC (acetonitrile/water (v/v)=1:1 to 9:1 gradient) gave 73.6 mg (84%) of the title compound as an off-white solid. $^1$H NMR (400 MHz, $CD_2Cl_2$) δ 7.57 (d, 2H), 7.41 (s, 1H), 7.05 (d, 1H), 6.98 (d, 1H), 6.80 (s, 1H), 6.72 (d, 1H), 4.25 (t, 2H), 4.17 (m, 4H), 3.93 (s, 3H), 3.51 (m, 1H), 2.85 (m, 2H), 2.71 (dd, 1H), 2.62 (q, 2H), 2.40 (m, 2H), 2.31 (t, 2H), 1.76 (m, 1H), 1.29 (m, 6H).

Example 174

Preparation of ((1S)-5-{3-[4-(ethyl-1,3-oxazol-2-yl)-2-methoxyphenoxy]propoxy}-2,3-dihydro-1H-inden-1-yl)acetic acid

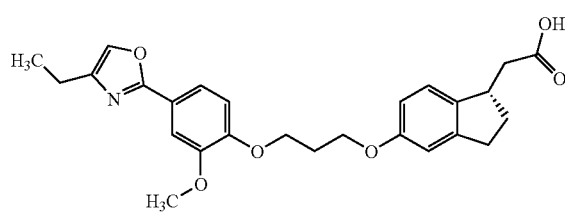

To a solution of ethyl ((1S)-5-{3-[4-(4-ethyl-1,3-oxazol-2-yl)-2-methoxyphenoxy]propoxy}-2,3-dihydro-1H-inden-1-yl)acetate (52.2 mg, 0.109 mmol) (Example 173) in THF/water/EtOH (1:2:1, 4 mL) was added LiOH (5.2 mg, 0.218 mmol). The solution was stirred at rt for 3 h and concentrated under reduced pressure. The residue was diluted with water and acidified using HCl (2 N aqueous solution), resulting in precipitation of a white solid. The solid was collected by filtration and dried to give 38.0 mg (77%) of the title compound. $^1$H NMR (400 MHz, $CD_2Cl_2$): δ 7.82 (s, 1H), 7.66 (d, 1H), 7.47 (s, 1H), 7.07 (d, 1H), 6.98 (d, 1H), 6.79 (s, 1H), 6.70 (d, 1H), 4.28 (t, 2H), 4.19 (t, 2H), 3.94 (s, 3H), 3.51 (m, 1H), 2.91 (m, 2H), 2.75 (m, 3H), 2.50 (m, 1H), 2.40 (m, 1H), 2.30 (m, 2H), 1.79 (m, 1H), 1.34 (t, 3H); LC-MS: RT=3.31 min, (M+H)$^+$ 452.1.

Using the above methods described for Example 143-174, and the appropriate starting materials, compounds of Formula (Ioo)) [Formula (I), where $R^1$ and $R^2$ are H, L is —Y—$(CH_2)_n$—X—, X and Y are O, Ar is heterocyclyl substituted phenyl, and n is 3], and (Ipp) [Formula (I), where $R^1$ and $R^2$ are H, L is —Y—$(CH_2)_n$—X—, X and Y are O, Ar is substituted phenyl, and n is 3], were similarly prepared and are listed in Table 4a and Table 5a, respectively, below.

TABLE 4a (Ioo)

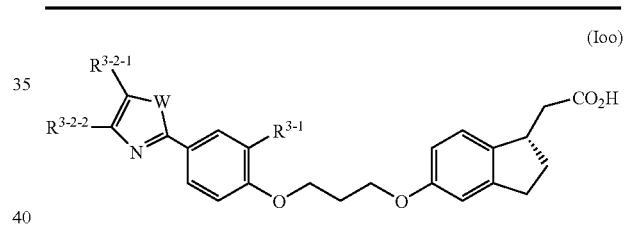

| Ex. No | W | $R^{3-2-1}$ | $R^{3-2-2}$ | $R^{3-1}$ | HPLC RT (min) | LC-MS [M + H]$^+$ |
|---|---|---|---|---|---|---|
| 175 | S | H | H | n-Pr | 3.73 | 452.1 |
| 176 | S | H | Me | OMe | 3.18 | 454.3 |
| 177 | S | H | Et | H | 3.56 | 438.3 |
| 178 | O | H | Et | H | 3.35 | 422.3 |
| 179 | O | H | Et | n-Pr | 3.82 | 464.2 |
| 180 | S | H | t-Bu | n-Pr | 4.64 | 508.3 |
| 181 | S | H | t-Bu | H | 3.77 | 450.2 |
| 182 | O | H | t-Bu | OMe | 3.69 | 480.2 |
| 183 | S | H | $CF_3$ | n-Pr | 4.18 | 520.2 |
| 184 | S | H | $CF_3$ | OMe | 3.63 | 507.9 |
| 185 | O | H | $CF_3$ | H | 3.58 | 462.1 |
| 186 | O | H | $CF_3$ | OMe | 3.52 | 491.9 |
| 187 | S | Me | Me | H | 3.31 | 438.3 |
| 188 | S | Me | Me | OMe | 3.19 | 468.3 |
| 189 | S | 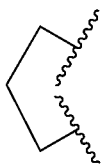 | | H | 3.66 | 450.3 |
| 190 | S | | | n-Pr | 4.12 | 492.4 |
| 191 | S | | | OMe | 3.51 | 480.4 |

TABLE 4a-continued (Ioo)

| Ex. No | W | R³⁻²⁻¹ R³⁻²⁻² | R³⁻¹ | HPLC RT (min) | LC-MS [M + H]⁺ |
|---|---|---|---|---|---|
| 192 | S | (cyclohexyl) | H | 3.61 | 464.4 |
| 193 | S | (cyclohexyl) | OMe | 3.49 | 494.2 |
| 194 | O | (cyclohexyl) | H | 3.47 | 448.4 |
| 195 | O | (cyclohexyl) | n-Pr | 3.98 | 490.3 |
| 196 | S | (cyclohexyl) | OEt | 3.59 | 508.3 |
| 197 | S | (cyclohexyl) | O—Pr | 3.80 | 522.3 |
| 198 | O | (cyclohexyl) | OMe | 3.39 | 478.2 |
| 199 | S | (tetrahydropyranyl) | OMe | 3.41 | 496.4 |
| 200 | S | (4,4-dimethyl-cyclohexanone) | n-Pr | 4.12 | 548.3 |

TABLE 4a-continued (Ioo)

| Ex. No | W | R³⁻²⁻¹ | R³⁻²⁻² | R³⁻¹ | HPLC RT (min) | LC-MS [M + H]⁺ |
|---|---|---|---|---|---|---|
| 201 | S | H | OMe | H | 3.41 | 440.2 |
| 202 | S | H | OMe | OMe | 3.27 | 470.3 |
| 203 | S | H | OEt | H | 3.60 | 454.2 |
| 204 | S | H | OEt | n-Pr | 4.10 | 496.2 |
| 205 | S | H | OEt | OMe | 3.46 | 484.3 |
| 206 | S | H | O-i-Pr | n-Pr | 4.24 | 510.1 |
| 207 | S | Me | OEt | n-Pr | 4.51 | 510.2 |
| 208 | S | Me | OEt | OMe | 3.90 | 498.2 |
| 209 | S | Et | OEt | OMe | 4.07 | 512.1 |
| 210 | S | C(=O)CH₃ | Me | H | 3.50 | 466.1 |
| 211 | S | C(=O)CH₃ | Me | n-Pr | 3.99 | 508.2 |
| 212 | S | C(=O)CH₃ | Me | OMe | 3.30 | 496.3 |
| 213 | O | C(=O)CH₃ | Me | H | 3.21 | 450.3 |
| 214 | O | C(=O)CH₃ | Me | n-Pr | 3.74 | 492.1 |
| 215 | O | C(=O)CH₃ | Me | OMe | 3.08 | 480.3 |
| 216 | S | C(=O)NMe₂ | Me | n-Pr | 3.42 | 537.5 |
| 217 | S | C(=O)NMe₂ | Me | OMe | 2.96 | 525.1 |
| 218 | S | C(=O)OH | Me | H | 3.13 | 468.3 |
| 219 | S | C(=O)OH | Me | n-Pr | 3.58 | 510.2 |

TABLE 4b

IUPAC Names for Compounds in Table 4a

| Ex. No. | IUPAC Name |
|---|---|
| 175 | 2-{(1S)-5-[3-(2-propyl-4-(1,3-thiazol-2-yl)phenoxy)propoxy]indanyl}acetic acid |
| 176 | 2-((1S)-5-{3-[2-methoxy-4-(4-methyl(1,3-thiazol-2-yl))phenoxy]propoxy}indanyl)acetic acid |
| 177 | 2-((1S)-5-{3-[4-(4-ethyl(1,3-thiazol-2-yl))phenoxy]propoxy}indanyl)acetic acid |
| 178 | 2-((1S)-5-{3-[4-(4-ethyl(1,3-oxazol-2-yl))phenoxy]propoxy}indanyl)acetic acid |
| 179 | 2-((1S)-5-{3-[4-(4-ethyl(1,3-oxazol-2-yl))-2-propylphenoxy]propoxy}indanyl)acetic acid |
| 180 | 2-[(1S)-5-(3-{4-[4-(tert-butyl)(1,3-thiazol-2-yl)]-2-propylphenoxy}propoxy)indanyl]acetic acid |
| 181 | 2-[(1S)-5-(3-{4-[4-(tert-butyl)(1,3-oxazol-2-yl)]phenoxy}propoxy)indanyl]acetic acid |
| 182 | 2-[(1S)-5-(3-{4-[4-(tert-butyl)(1,3-oxazol-2-yl)]-2-methoxyphenoxy}propoxy)indanyl]acetic acid |
| 183 | 2-[(1S)-5-(3-{2-propyl-4-[4-(trifluoromethyl)(1,3-thiazol-2-yl]phenoxy}propoxy)indanyl]acetic acid |
| 184 | 2-[(1S)-5-(3-{2-methoxy-4-[4-(trifluoromethyl)(1,3-thiazol-2-yl)]phenoxy}propoxy)indanyl]acetic acid |
| 185 | 2-[(1S)-5-(3-{4-[4-(trifluoromethyl)(1,3-oxazol-2-yl)]phenoxy}propoxy)indanyl]acetic acid |
| 186 | 2-[(1S)-5-(3-{2-methoxy-4-[4-(trifluoromethyl)(1,3-oxazol-2-yl)]phenoxy}propoxy)indanyl]acetic acid |
| 187 | 2-((1S)-5-{3-[4-(4,5-dimethyl(1,3-thiazol-2-yl))phenoxy]propoxy}indanyl)acetic acid |
| 188 | 2-((1S)-5-{3-[4-(4,5-dimethyl(1,3-thiazol-2-yl))-2-methoxyphenoxy]propoxy}indanyl)acetic acid |

TABLE 4b-continued

IUPAC Names for Compounds in Table 4a

| Ex. No. | IUPAC Name |
|---|---|
| 189 | 2-{(1S)-5-[3-(4-(4,5,6-trihydrocyclopenta[1,2-d]1,3-thiazol-2-yl)phenoxy)propoxy]indanyl}acetic acid |
| 190 | 2-{(1S)-5-[3-(2-propyl-4-(4,5,6-trihydrocyclopenta[1,2-d]1,3-thiazol-2-yl)phenoxy)propoxy]indanyl}acetic acid |
| 191 | 2-{(1S)-5-[3-(2-methoxy-4-(4,5,6-trihydrocyclopenta[1,2-d]1,3-thiazol-2-yl)phenoxy)propoxy]indanyl}acetic acid |
| 192 | 2-{(1S)-5-[3-(4-(4,5,6,7-tetrahydrobenzothiazol-2-yl)phenoxy)propoxy]indanyl}acetic acid |
| 193 | 2-{(1S)-5-[3-(2-methoxy-4-(4,5,6,7-tetrahydrobenzothiazol-2-yl)phenoxy)propoxy]indanyl}acetic acid |
| 194 | 2-{(1S)-5-[3-(4-(4,5,6,7-tetrahydrobenzoxazol-2-yl)phenoxy)propoxy]indanyl}acetic acid |
| 195 | 2-{(1S)-5-[3-(2-propyl-4-(4,5,6,7-tetrahydrobenzoxazol-2-yl)phenoxy)propoxy]indanyl}acetic acid |
| 196 | 2-{(1S)-5-[3-(2-ethoxy-4-(4,5,6,7-tetrahydrobenzothiazol-2-yl)phenoxy)propoxy]indanyl}acetic acid |
| 197 | 2-{(1S)-5-[3-(2-propoxy-4-(4,5,6,7-tetrahydrobenzothiazol-2-yl)phenoxy)propoxy]indanyl}acetic acid |
| 198 | 2-{(1S)-5-[3-(2-methoxy-4-(4,5,6,7-tetrahydrobenzoxazol-2-yl)phenoxy)propoxy]indanyl}acetic acid |
| 199 | 2-{(1S)-5-[3-(2-methoxy-4-(5,6,7-trihydro-2H-pyrano[2,3-d]1,3-thiazol-2-yl)phenoxy)propoxy]indanyl}acetic acid |
| 200 | 2-((1S)-5-{3-[4-(5,5-dimethyl-7-oxo(4,5,6-trihydrobenzothiazol-2-yl))-2-propylphenoxy]propoxy}indanyl)acetic acid |
| 201 | 2-((1S)-5-{3-[4-(4-methoxy(1,3-thiazol-2-yl))phenoxy]propoxy}indanyl)acetic acid |
| 202 | 2-((1S)-5-{3-[2-methoxy-4-(4-methoxy(1,3-thiazol-2-yl))phenoxy]propoxy}indanyl)acetic acid |
| 203 | 2-((1S)-5-{3-[4-(4-ethoxy(1,3-thiazol-2-yl))phenoxy]propoxy}indanyl)acetic acid |
| 204 | 2-((1S)-5-{3-[4-(4-ethoxy(1,3-thiazol-2-yl))-2-propylphenoxy]propoxy}indanyl)acetic acid |
| 205 | 2-((1S)-5-{3-[4-(4-ethoxy(1,3-thiazol-2-yl))-2-methoxyphenoxy]propoxy}indanyl)acetic acid |
| 206 | 2-[(1S)-5-(3-{4-[4-(methylethoxy)(1,3-thiazol-2-yl)]-2-propylphenoxy}propoxy)indanyl]acetic acid |
| 207 | 2-((1S)-5-{3-[4-(4-ethoxy-5-methyl(1,3-thiazol-2-yl))-2-propylphenoxy]propoxy}indanyl)acetic acid |
| 208 | 2-((1S)-5-{3-[4-(4-ethoxy-5-methyl(1,3-thiazol-2-yl))-2-methoxyphenoxy]propoxy}indanyl)acetic acid |
| 209 | 2-((1S)-5-{3-[4-(4-ethoxy-5-ethyl(1,3-thiazol-2-yl))-2-methoxyphenoxy]propoxy}indanyl)acetic acid |
| 210 | 2-((1S)-5-{3-[4-(5-acetyl-4-methyl(1,3-thiazol-2-yl))phenoxy]propoxy}indanyl)acetic acid |
| 211 | 2-((1S)-5-{3-[4-(5-acetyl-4-methyl(1,3-thiazol-2-yl))-2-propylphenoxy]propoxy}indanyl)acetic acid |
| 212 | 2-((1S)-5-{3-[4-(5-acetyl-4-methyl(1,3-thiazol-2-yl))-2-methoxyphenoxy]propoxy}indanyl)acetic acid |
| 213 | 2-((1S)-5-{3-[4-(5-acetyl-4-methyl(1,3-oxazol-2-yl))phenoxy]propoxy}indanyl)acetic acid |
| 214 | 2-((1S)-5-{3-[4-(5-acetyl-4-methyl(1,3-oxazol-2-yl))-2-propylphenoxy]propoxy}indanyl)acetic acid |
| 215 | 2-((1S)-5-{3-[4-(5-acetyl-4-methyl(1,3-oxazol-2-yl))-2-methoxyphenoxy]propoxy}indanyl)acetic acid |
| 216 | 2-[(1S)-5-(3-{4-[5-(N,N-dimethylcarbamoyl)-4-methyl(1,3-thiazol-2-yl)]-2-propylphenoxy}propoxy)indanyl]acetic acid |
| 217 | 2-[(1S)-5-(3-{4-[5-(N,N-dimethylcarbamoyl)-4-methyl(1,3-thiazol-2-yl)]-2-methoxyphenoxy}propoxy)indanyl]acetic acid |
| 218 | 2-(4-{3-[(1S)-1-(carboxymethyl)indan-5-yloxy]propoxy}phenyl)-4-methyl-1,3-thiazole-5-carboxylic acid |
| 219 | 2-(4-{3-[(1S)-1-(carboxymethyl)indan-5-yloxy]propoxy}-3-propylphenyl)-4-methyl-1,3-thiazole-5-carboxylic acid |

TABLE 5a (Ipp)

[Structure: R³-phenyl-O-(CH₂)₃-O-indanyl-CH₂-CO₂H]

| Ex. No | R³ | HPLC RT (min) | LC-MS [M + H]⁺ |
|---|---|---|---|
| 220 | [4,5,6,7-tetrahydro-1,3-benzothiazol-2-yl] | 3.79 | 464.3 |
| 221 | [4-ethyl-1,3-oxazol-2-yl with H₃C] | 3.49 | 422.2 |
| 222 | [4,5,6,7-tetrahydro-1,3-benzoxazol-2-yl] | 3.64 | 448.3 |
| 223 | [4-hydroxy-5-methyl-4,5-dihydro-1,3-oxazol-2-yl with HO and F₃C] | 3.17 | 480.1* |

*Elimination of water did not occur in this case.

TABLE 5b

IUPAC Names for Compounds in Table 5a

| Ex. No | IUPAC Name |
|---|---|
| 220 | ((1S)-5-{3-[3-(4,5,6,7-tetrahydro-1,3-benzothiazol-2-yl)phenoxy]propoxy}-2,3-dihydro-1H-inden-1-yl)acetic acid |
| 221 | ((1S)-5-{3-[3-(4-ethyl-1,3-oxazol-2-yl)phenoxy]propoxy}-2,3-dihydro-1H-inden-1-yl)acetic acid |
| 222 | ((1S)-5-{3-[3-(4,5,6,7-tetrahydro-1,3-benzoxazol-2-yl)phenoxy]propoxy}-2,3-dihydro-1H-inden-1-yl)acetic acid |
| 223 | ((1S)-5-{3-[3-(4-hydroxy-5-methyl-4,5-dihydro-1,3-oxazol-2-yl)phenoxy]propoxy}-2,3-dihydro-1H-inden-1-yl)acetic acid |

Example 224

Preparation of 3-methoxy-2-propylphenol

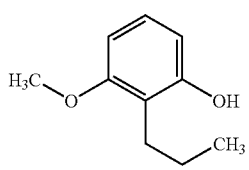

2-Propyl resorcinol (1.50 g, 9.86 mmol) was dissolved in DMF (anhydrous, 20 mL) and K₂CO₃ (681 mg, 4.93 mmol) was added. After stirring for 10 min at rt, iodomethane (0.92 mL, 14.8 mmol) was added and the reaction mixture was stirred for 6 h at 60° C. After cooling to rt, the reaction mixture was acidified with HCl (1 N aqueous solution) and concentrated under reduced pressure. Water was added and the aqueous phase was extracted with EtOAc (2×). The combined organic phases were dried over Na₂SO₄, filtered, and concentrated under reduced pressure. Purification by silica gel flash chromatography (EtOAc/hexane (v/v) 1:15) gave 33 mg (24%) of the title compound as an oil. ¹H NMR (400 MHz, CDCl₃): δ 0.97 (t, 3H), 1.54 (m, 2H), 2.61 (t, 2H), 3.81 (s, 3H), 4.68 (br, 1H), 6.47 (m, 2H), 7.03 (t, 1H).

Example 225

Preparation of ethyl {(1S)-5-[3-(3-methoxy-2-propylphenoxy)propoxy]-2,3-dihydro-1H-inden-1-yl}acetate

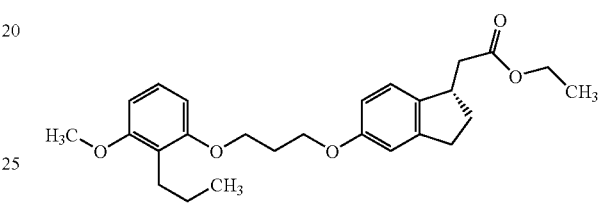

Using Example 224 and Example 45 as starting materials, the title compound was prepared as described in Example 48. ¹H NMR (400 MHz, CDCl₃): δ 7.18-7.0 (m, 2H), 6.90 (s, 1H), 6.82 (d, 1H), 6.60-6.41 (m, 2H), 4.28-4.02 (m, 6H), 3.91 (s, 3H), 3.62-3.44 (m, 1H), 3.0-2.54 (m, 5H), 2.48-2.18 (m, 4H), 1.84-1.62 (m, 1H), 1.60-1.40 (m, 2H), 1.36-1.22 (m, 3H), 1.10-0.82 (m, 3H).

Example 226

Preparation of {(1S)-5-[3-(3-methoxy-2-propylphenoxy)propoxy]-2,3-dihydro-1H-inden-1-yl}acetic acid

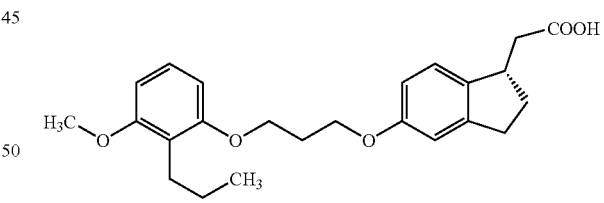

Using Example 225 as starting material, the title compound was prepared as described in Example 49. ¹H NMR (400 MHz, CDCl₃): δ 7.12-7.05 (m, 2H), 6.90 (s, 1H), 6.84 (dd, 1H), 6.58-6.50 (m, 2H), 4.22-4.10 (m, 4H), 3.82 (s, 3H), 3.60-3.48 (m, 1H), 2.98-2.78 (m, 3H), 2.68-2.58 (m, 2H), 2.51-2.39 (m, 2H), 2.30-2.20 (m, 2H), 1.84-1.72 (m, 1H), 1.58-1.42 (m, 2H), 0.92 (t, 3H); LC-MS: RT=3.78 min, (M+H)⁺ 399.1.

Using the methods described above for Example 224-226 and the appropriate starting materials, compounds of Formula (Iqq) [Formula (I), where R¹ and R² are H, L is —Y—(CH₂)ₙ—X—, X and Y are O, Ar is substituted phenyl, and n is 3], were similarly prepared ear in Table 6a below.

TABLE 6a (Iqq)

R3-2, R3-3, R3-1, R3-4 — substituents on phenyl-O-(CH2)3-O-indanyl-CH2-COOH

| Ex. No | R3-1 | R3-2 | R3-3 | R3-4 | HPLC RT (min) | LC-MS [M + H]+ |
|---|---|---|---|---|---|---|
| 227 | H | Me | H | H | 3.45 | * |
| 228 | H | OMe | H | H | 3.23 | 357.0 |
| 229 | H | Ph | H | H | 3.53 | * |
| 230 | OMe | OMe | H | H | 3.07 | 387.0 |
| 231 | H | H | NHC(=O)CH3 | OMe | 3.38 | 414.1 |
| 232 | H | H | Me | Me | 4.24 | * |
| 233 | H | OMe | OMe | OMe | 3.73 | 417.2 |

*These compounds did not ionize under ESI-MS conditions.

TABLE 6b

IUPAC Names for Compounds in Table 6a

| Ex. No. | IUPAC Name |
|---|---|
| 227 | 2-{(1S)-5-[3-(3-methylphenoxy)propoxy]indanyl}acetic acid |
| 228 | 2-{(1S)-5-[3-(3-methoxyphenoxy)propoxy]indanyl}acetic acid |
| 229 | 2-{(1S)-5-[3-(3-phenylphenoxy)propoxy]indanyl}acetic acid |
| 230 | 2-{(1S)-5-[3-(2,3-dimethoxyphenoxy)propoxy]indanyl}acetic acid |
| 231 | 2-((1S)-5-{3-[4-(acetylamino)-3-methoxyphenoxy]propoxy}indanyl)acetic acid |
| 232 | 2-{(1S)-5-[3-(3,4-dimethylphenoxy)propoxy]indanyl}acetic acid |
| 233 | 2-{(1S)-5-[3-(3,4,5-trimethoxyphenoxy)propoxy]indanyl}acetic acid |

Example 234

Preparation of methyl (2S)-2-[(1S)-5-(3-bromopropoxy)-2,3-dihydro-1H-inden-1-yl]propanoate

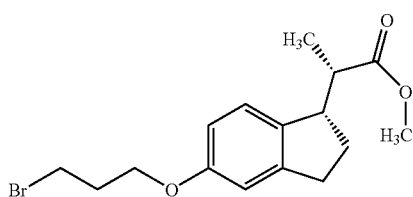

Methyl (2S)-2-[(1S)-5-hydroxy-2,3-dihydro-1H-inden-1-yl]propanoate (Example 14) (500 mg, 2.27 mmol), dibromopropane (4.308 g, 21.34 mmol), Cs2CO3 (834 mg, 2.56 mmol), and water (5 drops) were combined in DMF (20 mL) and stirred for 7 h at rt. The reaction mixture was concentrated under reduced pressure, water was added and the aqueous solution was extracted with EtOAc (2×). The combined organic phases were dried over Na2SO4, filtered, and concentrated under reduced pressure. Purification by silica gel flash chromatography (EtOAc/hexane (v/v)=1:25) gave 263 mg (34%) of the title compound as a colorless oil. 1H NMR (400 MHz, CDCl3): δ 1.08 (d, 3H), 1.91 (m, 1H), 2.17 (m, 1H), 2.32 (m, 2H), 2.80 (m, 1H), 2.88 (m, 2H), 3.51 (m, 1H), 3.61 (t, 2H), 3.72 (s, 3H), 4.08 (t, 2H), 6.69 (d, 1H), 6.76 (s, 1H), 6.98 (d, 1H).

Example 235

Preparation of methyl (2S)-2-[(1S)-5-(3-{2-methyl-4-[3-(trifluoromethyl)-1,2,4-thiadiazol-5-yl]phenoxy}propoxy)-2,3-dihydro-1H-inden-1-yl]propanoate

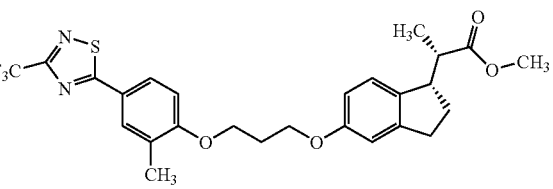

Step 1: Preparation of 2-methyl-4-[3-(trifluoromethyl)-1,2,4-thiadiazol-5-yl]phenol

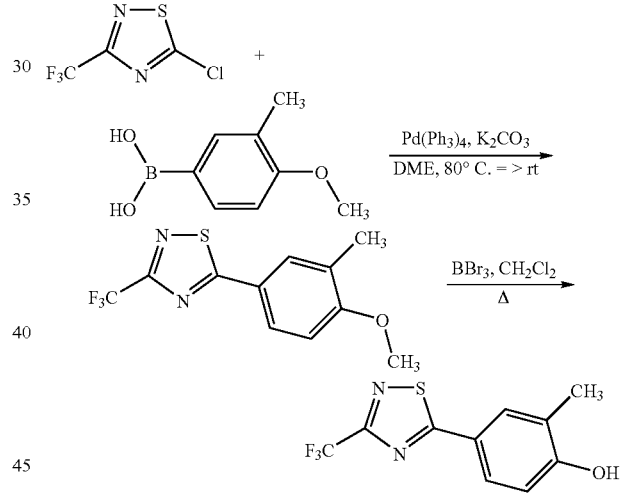

Step 1a: 5-(4-Methoxy-3-methylphenyl)-3-(trifluoromethyl)-1,2,4-thiadiazole

5-Chloro-3-(trifluoromethyl)-1,2,4-thiadiazole (2.26 g, 12.0 mmol) (synthesis described in DE 3228147) was dissolved in 1,2-dimethoxyethane (50 mL) and 4-methoxy-3-methylphenylboronic acid (2.4 g, 14.4 mmol) and tetrakis(triphenylphosphine)palladium (0.1 g, 0.09 mmol) were added. After 1.5 h at rt, Na2CO3 (19.2 mL, 2M aqueous solution) was added and the mixture was stirred for 4 h at 80° C. and for 14h at rt. Water was added and the mixture was extracted with ethyl acetate. The organic phase was dried over MgSO4, filtered, and concentrated under reduced pressure. Due to low conversion the crude product was again reacted with 5-chloro-3-(trifluoromethyl)-1,2,4-thiadiazole (2.4 g, 14.4 mmol), tetrakis(triphenylphosphine)palladium (0.1 g, 0.09 mmol) in DME (50 mL) and Na2CO3 (19.2 mL, 2M aqueous solution). After stirring at 80° C. for 16 h, the reaction mixture was cooled and water was added. The mixture was extracted with ethyl acetate, the organic phase dried over MgSO$_4$, filtered and concentrated under reduced pressure. The crude product (3.2 g) had a purity of ~90% and was used in the next step without further purification.

Step 1b: 2-Methyl-4-[3-(trifluoromethyl)-1,2,4-thiadiazol-5-yl]phenol 5-(4-Methoxy-3-methylphenyl)-3-(trifluoromethyl)-1,2,4-thiadiazole (3.2 g, 11.7 mmol) as obtained from the previous step was dissolved in CH$_2$Cl$_2$ (80 mL), and BBr$_3$ (1.7 mL, 17.5 mmol, 1.5 eq.) was added at rt. After stirring at reflux for 1 h, more BBr$_3$ (1 mL) was added. The reaction mixture was stirred at reflux for 14 h. The solvent was removed under reduced pressure and the residue was carefully treated with a NaHCO$_3$ aquoeus solution. The mixture was filtered and the filter cake was dried under reduced pressure to obtain 2-methyl-4-[3-(trifluoromethyl)-1,2,4-thiadiazol-5-yl]phenol (3.6 g, 100%) as a solid, which was sufficiently pure for use in the next step. $^1$H NMR (400 MHz, DMSO-d$_6$): δ 2.19 (s, 3H), 6.93 (d, 1H), 7.78 (d, 1H), 7.84 (s, 1H), 10.52 (s, 1H); LC-MS RT=3.12 min; (M+H)$^+$=261

Step 2: Preparation of methyl (2S)-2-[(1S)-5-(3-{2-methyl-4-[3-(trifluoromethyl)-1,2,4-thiadiazol-5-yl]phenoxy}propoxy)-2,3-dihydro-1H-inden-1-yl]propanoate 2-Methyl-4-[3-(trifluoromethyl)-1,2,4-thiadiazol-5-yl]phenol (57.7 mg, 0.22 mmol), methyl (2S)-2-[(1S)-5-(3-bromopropoxy)-2,3-dihydro-1H-inden-1-yl]propanoate (Example 234) (72.0 mg, 0.21 mmol), Cs$_2$CO$_3$ (82.5 mg, 0.25 mmol), and water (3 drops) were combined in DMF (4 mL) and stirred at 40° C. for 16 h. The reaction mixture was concentrated under reduced pressure, water was added and the aqueous phase was extracted with EtOAc (2×). The combined organic phases were dried over Na$_2$SO$_4$, filtered, and concentrated under reduced pressure. Purification by silica gel flash chromatography (EtOAc/hexane (v/v)=1:20) gave 70 mg (64%) of the title compound as a colorless oil. $^1$H NMR (400 MHz, CDCl$_3$): δ 1.07 (d, 3H), 1.90 (m, 1H), 2.17 (m, 1H), 2.29 (s, 3H), 2.34 (m, 2H), 2.77-2.91 (m, 3H), 3.50 (m, 1H), 3.71 (s, 3H), 4.17 (t, 2H), 4.25 (t, 2H), 6.70 (d, 1H), 6.78 (s, 1H), 6.92 (d, 1H), 6.99 (d, 1H), 7.79 (m, 2H).

Example 236

Preparation of (2S)-2-[(1S)-5-(3-{2-methyl-4-[3-(trifluoromethyl)-1,2,4-thiadiazol-5-yl]phenoxy}propoxy)-2,3-dihydro-1H-inden-1-yl]propanoic acid

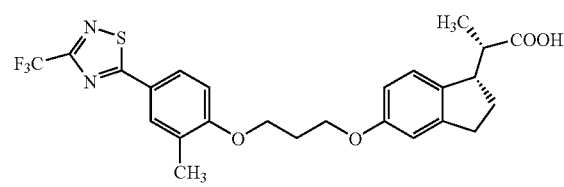

The title compound was prepared following similar procedures to those described for Example 49. $^1$H NMR (400 MHz, CDCl$_3$): δ 7.88-7.76 (m, 2H), 7.08 (d, 1H), 6.91 (d, 1H), 6.83-6.66 (m, 2H), 4.32-4.08 (m, 4H), 3.68-3.49 (m, 1H), 3.00-2.76 (m, 3H), 2.44-2.12 (m, 6H), 2.00-1.82 (m, 1H), 1.08 (d, 3H); LC-MS: RT=4.15 min, (M+H)$^+$ 506.9.

Using the methods described above for Example 234-236 and the appropriate starting materials, compounds of Formula (Irr)) [Formula (I), where R$^1$ is H, R$^2$ is methyl, L is —Y—(CH$_2$)$_n$—X—, X and Y are O, and n is 3], were similarly prepared and appear in Table 7a below.

TABLE 7a (Irr)

| Ex. No | Ar | HPLC RT (min) | LC-MS [M + H]$^+$ |
|---|---|---|---|
| 237 | F$_3$C-, N-O, H$_3$C- (benzisoxazole) | 4.21 | * |
| 238 | H$_3$C-, O (benzofuran) | 3.79 | 395.0 |
| 239 | H$_3$C-phenyl | 3.70 | * |
| 240 | H$_3$C-CH$_2$-phenyl | 3.87 | 369.1 |
| 241 | F$_3$C-, H$_3$C-CH$_2$-phenyl | 4.06 | * |

Note:
* These compounds did not ionize under ESI conditions.

TABLE 7b

IUPAC Names for Compounds in Table 7a

| Ex. No. | IUPAC Name |
|---|---|
| 237 | (2S)-2-((1S)-5-{3-[7-propyl-3-(trifluoromethyl)benzo[d]isoxazol-6-yloxy]propoxy}indanyl)propanoic acid |
| 238 | (2S)-2-{(1S)-5-[3-(3-methylbenzo[3,4-b]furan-6-yloxy)propoxy]indanyl}propanoic acid |
| 239 | (2S)-2-{(1S)-5-[3-(4-methylphenoxy)propoxy]indanyl}propanoic acid |
| 240 | (2S)-2-{(1S)-5-[3-(4-ethylphenoxy)propoxy]indanyl}propanoic acid |
| 241 | (2S)-2-((1S)-5-{3-[2-propyl-4-(trifluoromethyl)phenoxy]propoxy}indanyl) propanoic acid |

Example 242

Preparation of methyl (2S)-2-[(1S)-5-(3-{[7-propyl-3-(trifluoromethyl)-1,2-benzisoxazol-6-yl]oxy}propoxy)-2,3-dihydro-1H-inden-1-yl]propanoate and methyl (2R)-2-[(1R)-5-(3-{[7-propyl-3-(trifluoromethyl)-1,2-benzisoxazol-6-yl]oxy}propoxy)-2,3-dihydro-1H-inden-1-yl]propanoate

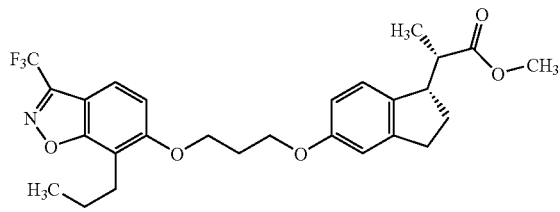

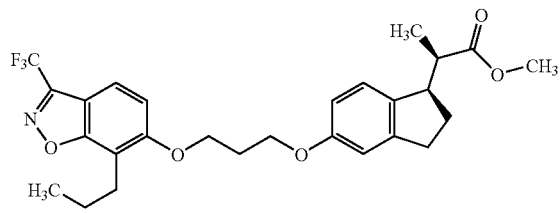

A mixture of 6-3-bromopropoxy)-7-propyl-3-(trifluoromethyl)-1,2-benzo[d]isoxazole (137.1 mg, 0.37 mmol) (Example 86), methyl (2S-2-[(1S)-5-hydroxy-2,3-dihydro-1H-inden-1-yl)propanoate/methyl (2R)-2-[(1R)-5-hydroxy-2,3-dihydro-1H-inden-1-yl)propanoate (rac. mixture) (93.0 mg, 0.42 mmol) (Example 17), Cs₂CO₃ (137.6 mg, 0.42), water (4 drops), and DMF (4.2 mL) was stirred under argon at rt for 44 h. Water (25 mL) was added and the aqueous phase was extracted with EtOAc (2×25 mL). The combined organic phases were dried over Na₂SO₄, filtered, and concentrated under reduced pressure. Purification by preparative HPLC (acetonitrile/water (v/v)=4:1 to 19:1 gradient) gave 104.9 mg (55%) of the title compound as a thick colorless oil. ¹H NMR (400 MHz, CDCl₃) δ 7.54 (d, 1H), 7.08 (d, 1H), 6.98 (d, 1H), 6.77 (s, 1H), 6.69-6.72 (m, 1H), 4.30 (t, 2H), 4.18 (t, 2H), 3.71 (s, 3H), 3.52 (q, 1H), 2.74-2.93 (m, 5), 2.30-2.36 (m, 2H), 2.13-2.22 (m, 1H), 1.87-1.94 (m, 1H), 1.65-1.74 (m, 2H), 1.08 (d, 3H), 0.96 (t, 3H), LC-MS: RT=4.71, (M+H)⁺ 506.0.

Example 243

(2S)-2-[(1S)-5-(3-{[7-propyl-3-(trifluoromethyl)-1,2-benzisoxazol-6-yl]oxy}propoxy)-2,3-dihydro-1H-inden-1-yl]propanoic acid and (2R)-2-[(1R)-5-(3-{[7-propyl-3-(trifluoromethyl)-1,2-benzisoxazol-6-yl]oxy}propoxy)-2,3-dihydro-1H-inden-1-yl]propanoic acid

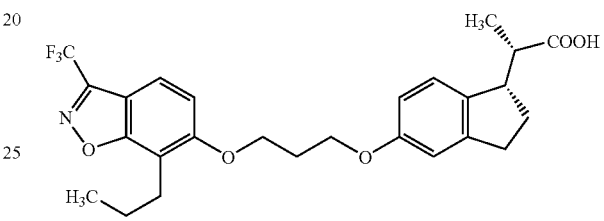

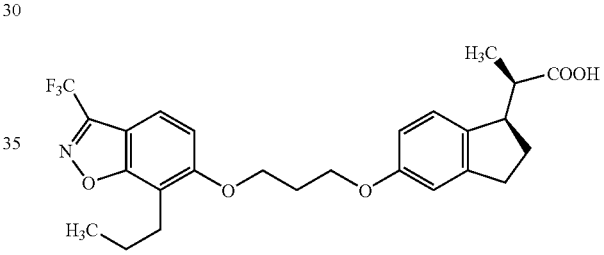

A mixture of methyl (2S)-2-[(1S)-5-(3-{[7-propyl-3-(trifluoromethyl)-1,2-benzisoxazol-6-yl]oxy}propoxy)-2,3-dihydro-1H-inden-1-yl]propanoate/methyl (2R)-2-[(1R)-5-(3-{[7-propyl-3-trifluoromethyl)-1,2-benzisoxazol-6-yl]oxy}propoxy)-2,3-dihydro-1H-inden-1-yl]propanoate (racemic mixture) (Example 242) (95.0 mg, 0.19 mmol) and KOH (112.6 mg, 2.01 mmol) in MeOH (2 mL) and water (0.2 mL) was heated at 60° C. under argon for 2.5 h. The reaction mixture was concentrated under reduced pressure, dissolved in water (20 mL), and acidified with HCl (concentrated aqueous solution, 5 mL). The aqueous phase was extracted with CH₂Cl₂ (2×). The combined organic phases were dried over MgSO₄, filtered, and concentrated under reduced pressure to give 76.5 mg (83%) of the title compound as a colorless solid: ¹H NMR (CDCl₃) δ 6.71-7.55 (m, 5H), 4.29 (t, 2H), 4.18 (t, 2H), 3.59 (q, 1H), 2.80-2.93 (m, 5H), 2.30-2.39 (m, 2H), 2.17-2.25 (m, 1H), 1.88-1.97 (m, 1H), 1.65-1.74 (m, 2H), 1.08 (d, 3H), 0.96 (t, 3H); LC-MS: RT=4.26, (M+H)⁺ 491.7.

Using the methods described above for Example 242 and Example 243, and the appropriate starting materials, the compounds appearing in Table 8a below were similarly prepared.

TABLE 8a

| Ex. No | Structure | HPLC RT (min) | LC-MS [M + H]+ |
|---|---|---|---|
| 244 | 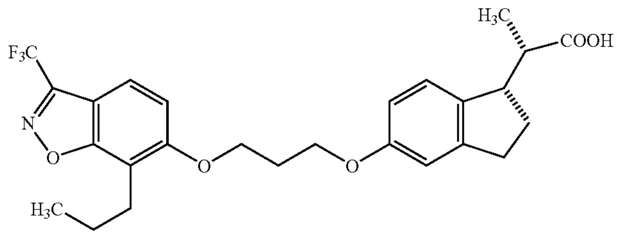 | 4.21 | * |
| 245 | 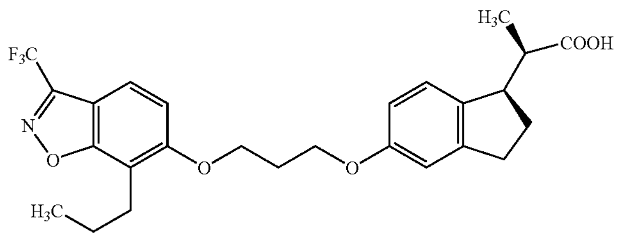 | 4.20 | * |

Note:
* These compounds did not ionize under ESI conditions.

TABLE 8b

IUPAC Names for Compounds in Table 8a

| Ex. No. | IUPAC Name |
|---|---|
| 244 | (2S)-2-[(1S)-5-(3-{[7-propyl-3-(trifluoromethyl)-1,2-benzisoxazol-6-yl]oxy}propoxy)-2,3-dihydro-1H-inden-1-yl]propanoic acid |
| 245 | (2R)-2-[(1R)-5-(3-{[7-propyl-3-(trifluoromethyl)-1,2-benzisoxazol-6-yl]oxy}propoxy)-2,3-dihydro-1H-inden-1-yl]propanoic acid |

Example 246

Preparation of methyl ((1S)-5-{3-[(6-ethyl-2-methyl-3-pyridinyl)oxy]propoxy}-2,3-dihydro-1H-inden-1-yl)acetate

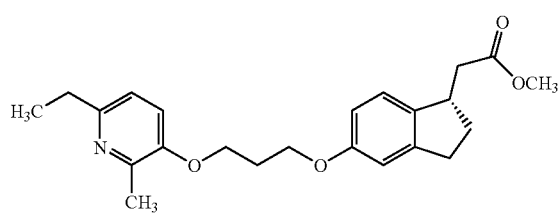

6-Ethyl-2-methyl-3-pyridinol (40.6 mg, 0.30 mmol) and [(1S)-5-(3-bromopropoxy)-2,3-dihydro-1H-inden-1-yl]acetate (101.0 mg, 0.30 mmol) (Example 45) were dissolved in DMF (4 mL) and cesium carbonate (193 mg, 0.59 mmol) and 4 drops of water were added. The mixture was stirred at rt for 16 h. The DMF was removed in vacuo and the residue was suspended in EtOAc and filtered. This filtrate was concentrated to give the pure title compound as a yellow oil (73 mg, 62%) which was used in the next step without further purification. $^1$H NMR (400 MHz, CDCl$_3$): δ 7.08-6.99 (m, 2H), 6.90 (d, 1H), 6.78 (s, 1H), 6.62 (dd, 1H), 4.20-4.08 (m, 4H), 3.72 (s, 3H), 3.58-3.48 (m, 1H), 2.96-2.70 (m, 6H), 2.51-2.34 (m, 4H), 2.30-2.23 (m, 2H), 1.80-1.68 (m, 1H), 1.21 (t, 3H).

Example 247

Preparation of ((1S)-{3-[(6-ethyl-2-methyl-3-pyridinyl)oxy]propoxy}-2,3-dihydro-1H-inden-1-yl)acetic acid

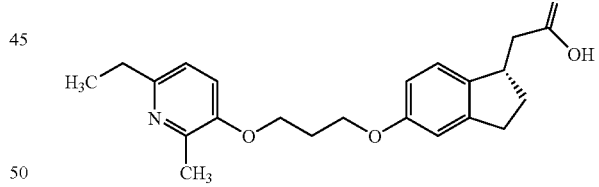

To a solution of methyl ((1S)-5-{3-[(6-ethyl-2-methyl-3-pyridinyl)oxy]propoxy}-2,3-dihydro-1H-inden-1-yl)acetate (Example 246) in a mixture of THF (3 mL) and MeOH (~0.2 mL), was added LiOH.H$_2$O (15 mg, 0.36 mmol) in water (1 mL). The mixture was stirred for 12 h at rt, the solvents were evaporated, and the residue was suspended in a small volume of water. The aqueous solution was acidified to pH<3 using HCl (1 N aqueous solution), and then it was extracted with excess EtOAc. The organic layer was dried, concentrated and purified by preparative HPLC to give 18 mg (16%) of the product as a solid. $^1$H NMR (400 MHz, CDCl$_3$): δ 7.16-6.88 (m, 3H), 6.71 (s, 1H), 6.62 (dd, 1H), 4.12-4.0 (m, 4H), 3.52-3.40 (m, 1H), 2.90-2.62 (m, 6H), 2.52-2.26 (m, 4H), 2.23-2.12 (m, 2H), 1.78-1.64 (m, 1H), 1.08 (t, 3H).

Example 248

Preparation of ethyl [(1S)-5-(2,2-diethoxyethoxy)-2,3-dihydro-1H-inden-1-yl]acetate

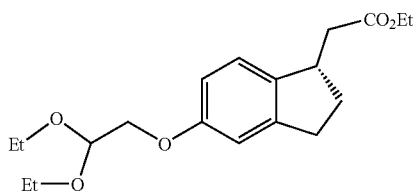

To a solution of ethyl [(1S)-5-hydroxy-2,3-dihydro-1H-inden-1-yl]acetate (Example 6, 1.55 g, 7.04 mmol) and bromoacetaldehyde diethyl acetal (4.85 g, 24.6 mmol) in DMF (10 mL) was added $Cs_2CO_3$ (2.75 g, 8.44 mmol) followed by water (5 mL). The reaction mixture was heated to reflux for 5 h, cooled to rt, and stirred for 18 h. The solvents were then evaporated under reduced pressure and the residue was dissolved in EtOAc. The organic solution was washed with water, dried ($Na_2SO_4$), filtered, and concentrated under reduced pressure. The residue was purified by silica gel flash chromatography to afford the product (1.62 g, 68%) containing minor impurites. $^1$H NMR (400 MHz, $CDCl_3$) δ 1.21-1.29 (m, 9H) 1.72-1.78 (m, 1H), 2.35-2.48 (m, 2H), 2.74-2.89 (m, 3H), 3.53-3.78 (m, 7H), 4.16 (d, 2H), 4.69 (t, 1H), 6.71 (d, 1H), 6.78 (s, 1H) 7.05 (d, 1H).

Example 249

Preparation of ethyl [(1S)-5-(2-hydroxyethoxy)-2,3-dihydro-1H-inden-1-yl]acetate

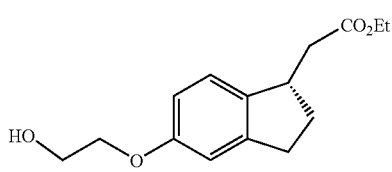

Ethyl [(1S)-5-(2,2-diethoxyethoxy)-2,3-dihydro-1H-inden-1-yl]acetate (Example 248, 849 mg, 2.52 mmol) was dissolved in a mixture of acetone (60 mL) and HCl (30 mL of a 2N aqueous solution). The reaction mixture was stirred at rt for 18 h, then neutralized (pH 7) by addition of a saturated solution of $NaHCO_3$. The aqueous phase was extracted with $CH_2Cl_2$, and the combined organic phases were dried ($Na_2SO_4$), filtered, and concentrated under reduced pressure. To a solution of the crude aldehyde in $CH_2Cl_2$ (30 mL) were then added $NaBH_4$ (69 mg, 1.82 mmol) and MeOH (5 mL) were added. After stirring for 5 h at rt, the reaction mixture was washed with a saturated solution of $NaHCO_3$, the organic phase was dried ($Na_2SO_4$), filtered, and concentrated under reduced pressure. The residue was purified by a plug of silica gel (eluent: EtOAc) to provide the product (264 mg, 38%). $^1$H NMR (400 MHz, $CDCl_3$) δ 1.21 (t, 3H) 1.65-1.71 (m, 1H), 2.29-2.36 (m, 2H), 2.63 (dd, 1H) 2.75-2.83 (m, 2H), 3.43-3.45 (m, 1H), 3.86 (t, 2H), 3.98 (t, 2H), 4.09 (q, 2H), 6.63 (d, 1H), 6.69 (s, 1H) 6.99 (d, 1).

Example 250

Preparation of ethyl ((1S)-5-{2-[(2,6-dimethyl-3-pyridinyl)oxy]ethoxy}-2,3-dihydro-1H-inden-1-yl)acetate

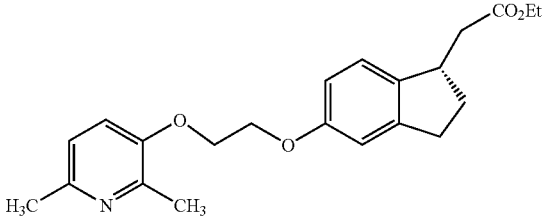

To a solution of ethyl [(1S)-5-(2-hydroxyethoxy)2,3-dihydro-1H-inden-1-yl]acetate (Example 249, 50.0 mg, 0.19 mmol) and 2,6-dimethylpyridin-3-ol (46.6 mg, 0.38 mmol) in THF (1.5 mL) were added $PPh_3$ (99.2 mg, 0.38 mmol) and ADDP (95.5 mg, 0.38 mmol). The reaction mixture was vigorously stirred at rt for 24 h, and then directly applied to a silica gel column for purification (1:1 hexanes/EtOAc) to give the product (58.9 mg, 84%) as a colorless oil. $^1$H NMR (400 MHz, $CDCl_3$) δ 1.29 (t, 3H) 1.72-1.81 (m, 1H), 2.36-2.2.44 (m, 2H), 2.45 (s, 3H), 2.47 (s, 3H), 2.73 (dd, 1H) 2.82-2.92 (m, 2H), 3.52-3.56 (m, 1H) 4.19 (q, 2H), 4.26-4.33 (m, 4H), 6.75 (d, 1H), 6.82 (s, 1H) 6.92 (d, 1H), 7.05 (d, 1H), 7.08 (d, 1H).

Example 251

Preparation of ((1S)-5-{2-[(2,6-Dimethyl-3-pyridinyl)oxy]ethoxy}-2,3-dihydro-1H-inden-1-yl)acetic acid

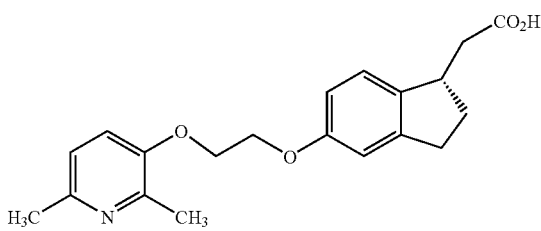

To a solution of ethyl ((1S)-5-{2-[(2,6-dimethyl-3-pyridinyl)oxy]ethoxy}-2,3-dihydro-1H-inden-1-yl)acetate (Example 250, 43.1 mg, 0.12 mmol) in a mixture of THF (2 mL), water (2 mL), and EtOH (1 mL), was added LiOH (11.5 mg, 0.48 mmol). The reaction mixture was vigorously stirred for 24 h, acidified to pH ~5 with HCl (1N aqueous solution), and then extracted with $CH_2Cl_2$. The combined organic layers were dried ($Na_2SO_4$), filtered, and concentrated under reduced pressure to give the title compound as a white solid (36.2 mg, 91%). $^1$H NMR (400 MHz, $CDCl_3$) δ 1.72-1.75 (m, 1H), 2.33-2.44 (m, 2H), 2.37 (s, 3H), 2.41 (s, 3H), 2.68-2.85 (m, 3H), 3.52-3.55 (m, 1H), 4.19-4.25 (m, 4H), 6.67 (d, 1H), 6.74 (s, 1H) 6.85 (d, 1H), 6.99 (d, 1H), 7.01 (d, 1H); LCMS: RT=2.41 min, $(M+H)^+$ 342.3.

By using the methods described above for Example 246-251 and by substituting the appropriate starting materials, compounds of Formula (Iss) listed in Table 9a below, were similarly prepared.

TABLE 9a

Preparative Examples of Compounds of Formula

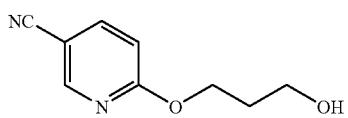
(Iss)

| Ex. No. | $R^{3-1}$ | $R^{3-2}$ | $R^{3-3}$ | LC-MS RT (min) | LC-MS $[M + H]^+$ |
|---|---|---|---|---|---|
| 252 | H | H | H | 1.66 | 314.3 |
| 253 | H | CH₃ | H | 1.73 | 328.2 |
| 254 | CH₃ | H | H | 2.15 | 328.3 |
| 255 | H | H | Cl | 3.46 | 348.2 |
| 256 | H | H | C(=O)OH | 2.79 | 358.2 |

TABLE 9b

IUPAC Names for Compounds in Table 9a

| Ex. No. | IUPAC Name |
|---|---|
| 252 | 2-[(1S)-5-(2-(3-pyridyloxy)ethoxy)indanyl]acetic acid |
| 253 | 2-{(1S)-5-[2-(6-methyl(3-pyridyloxy))ethoxy]indanyl}acetic acid |
| 254 | 2-{(1S)-5-[2-(2-methyl(3-pyridyloxy))ethoxy]indanyl}acetic acid |
| 255 | 2-{(1S)-5-[2-(5-chloro(3-pyridyloxy))ethoxy]indanyl}acetic acid |
| 256 | 5-{2-[(1S)-1-(carboxymethyl)indan-5-yloxy]ethoxy}pyridine-3-carboxylic acid |

Example 257

Preparation of 6-(3-hydroxypropoxy)nicotinonitrile

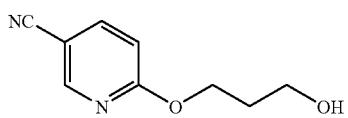

Sodium hydride (0.42 g, 10.61 mmol) was added to a solution of 1,3-propanediol (2.30 mL, 31.83 mmol) in DMF (22 mL) at 0° C. and the mixture was stirred at rt for 20 min. To the resultant heterogeneous mixture was added 6-chloronicotinonitrile (1.50 g, 10.6 mmol) in one portion. The mixture was stirred at rt for 18 h, poured into water, and filtered. The filtrate was extracted with EtOAc. The combined organic layers were washed with brine, dried (Na₂SO₄), and concentrated under reduced pressure to give the product (1.56 g, 83%) as a white solid. ¹H NMR (CD₂Cl₂) δ 8.47 (d, 1 H), 7.82-7.79 (m, 1H), 6.84-6.82 (m, 1H), 4.53 (t, 2H), 3.75 (t, 2H), 2.06-1.99 (m, 2H).

Example 258

Preparation of ethyl ((1S)-5-{3-[(5-cyano-2-pyridinyl)oxy]propoxy}-2,3-dihydro-1H-inden-1-yl)acetate

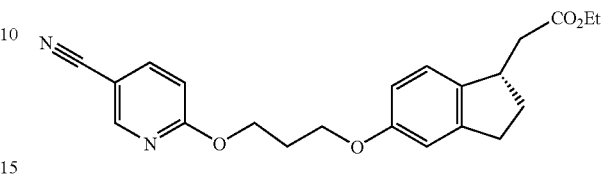

To a solution of 6-(3-hydroxypropoxy)nicotinonitrile (Example 257) (0.86 g, 4.83 mmol) and ethyl [(1S)-5-hydroxy-2,3-dihydro-1H-inden-1-yl]acetate (Example 6, 0.89 g, 4.02 mmol) in THF (20 mL) was added triphenylphosphine (1.49 g, 5.63 mmol) and 1,1'-(azodicarbonyl)-dipiperidine (1.44 g, 5.63 mmol) under argon. The golden yellow mixture was stirred at rt for 18 h and concentrated under reduced pressure. The product (1.22 g, 80%) was isolated after purification by silica gel flash chromatography (2:1 hexanes/EtOAc). ¹H NMR (400 MHz, CD₂Cl₂) δ 8.47 (dd, 1H), 7.79 (dd, 1H), 7.05 (d, 1H), 6.82 (d, 1H), 6.77 (d, 1H), 6.69 (dd, 1H), 4.56 (t, 2H), 4.16 (q, 2H), 4.11 (t, 2H), 3.51 (qt, 1H), 2.95-2.78 (m, 2H), 2.70 (dd, 1H), 2.44-2.32 (m, 2H), 2.30-2.20 (m, 2H), 1.80-1.70 (m, 1H), 1.28 (t, 3H).

Example 259

Preparation of ethyl [(1S)-5-(3-{[5-(aminocarbonothioyl)-2-pyridinyl]oxy}propoxy)-2,3-dihydro-1H-inden-1-yl]acetate

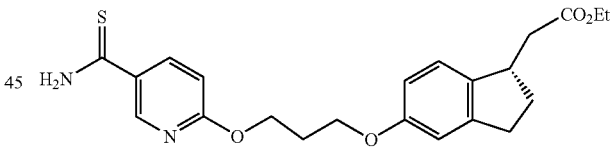

Through a solution of ethyl ((1S)-5-{3-[(5-cyano-2-pyridinyl)oxy]propoxy}2,3-dihydro-1H-inden-1-yl)acetate (Example 258) (600 mg, 1.58 mmol) in DMF (8 mL) was passed H₂S, gently at rt for 20 min. Diethylamine (0.24 mL, 2.37 mmol) was added in one portion and the resultant light-green solution was heated at 60° C. for 3 h (TLC in 2:1 hexanes/EtOAc indicated that the reaction was complete). The dark-green solution was purged with a strong flow of argon, and then concentrated under reduced pressure. The product (0.56 g, 86%) was isolated by column chromatography (1:1 hexanes/EtOAc) as a bright yellow solid. ¹H NMR (400 MHz, CD₂Cl₂) δ 8.65 (dd, 1H), 8.16 (dd, 1H), 7.56 (b, 1H), 7.19 (b, 1H), 7.04 (d, 1H), 6.80-6.72 (m, 2H), 6.69 (dd, 1H), 4.56 (t, 2H), 4.16 (q, 2H), 4.12 (t, 2H), 3.50 (qt, 1H), 2.90-2.78 (m, 2H), 2.70 (dd, 1H), 2.45-2.32 (m, 2H), 2.30-2.22 (m, 2H), 1.80-1.70 (m, 1H), 1.28 (t, 3H).

Example 260

Preparation of ethyl [(1S)-5-(3-{[5-(4,5-dimethyl-1,3-thiazol-2-yl)-2-pyridinyl]oxy}propoxy)-2,3-dihydro-1H-inden-1-yl]acetate

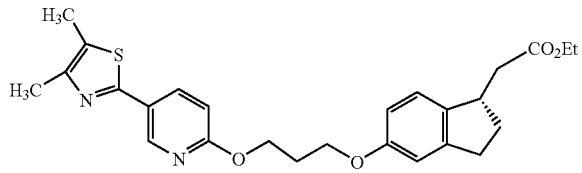

A mixture of ethyl [(1 S)-5-(3-{[5-(aminocarbonothioyl)2-pyridinyl]oxy}propoxy)-2,3-dihydro-1H-inden-1-yl]acetate (Example 259, 90 mg, 0.22 mmol) and 3-bromo-2-butanone (40 mg, 0.26 mmol) in ethanol (9 mL) was heated under argon at 80° C. for 18 h, and then concentrated under reduced pressure. The product (85 mg, 84%) was isolated after purification by silica gel chromatography (2:1 hexanes/EtOAc). $^1$H NMR (400 MHz, CD$_2$Cl$_2$) δ 8.54 (dd, 1H), 8.05 (dd, 1H), 7.02 (d, 1H), 6.83 (d, 1H), 6.78 (d, 1H), 6.69 (dd, 1H), 4.51 (t, 2H), 4.18-4.10 (m, 4H), 3.48 (qt, 1H), 2.92-2.75 (m, 2H), 2.69 (dd, 1H), 2.42-2.30 (m, 8H), 2.29-2.20 (m, 2H), 1.80-1.68 (m, 1H), 1.27 (t, 3H).

Example 261

Preparation of [(1S)-5-(3-{[5-(4,5-dimethyl-1,3-thiazol-2-yl)-2-pyridinyl]oxy}propoxy)-2,3-dihydro-1H-inden-1-yl]acetic acid

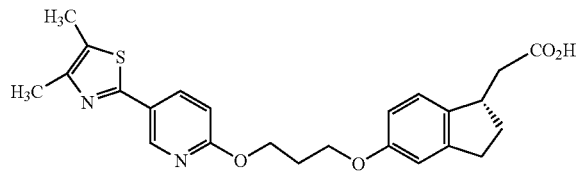

To a solution of ethyl [(1S)-5-(3-{[5-(4,5-dimethyl-1,3-thiazol-2-yl)-2-pyridinyl]oxy}propoxy)-2,3-dihydro-1H-inden-1-yl]acetate (Example 260) (80 mg, 0.17 mmol) in THF (2 mL), methanol (2 mL) and water (1 mL) was added LiOH (40 mg, 1.74 mmol). The reaction mixture was stirred at rt for 18 h, and then concentrated under reduced pressure. The residue was taken up in water and acidified with a 5% aqueous solution of H$_3$PO$_4$, and extracted with EtOAc. The combined organic layers were dried (Na$_2$SO$_4$) and concentrated under reduced pressure to give the product (67 mg, 89%). $^1$H NMR (400 MHz, CD$_2$Cl$_2$) δ 8.57 (d, 1H), 8.06 (dd, 1H), 7.09 (d, 1H), 6.85 (d, 1H), 6.80 (d, 1H), 6.71 (dd, 1H), 4.53 (t, 2H), 4.15 (t, 2H), 3.49 (qt, 1H), 2.92-2.75 (m, 2H), 2.71 (dd, 1H), 2.45-2.28 (m, 8H), 2.32-2.22 (m, 2H), 1.82-1.70 (m, 1H); LC-MS: RT=3.41 min, (M+H)$^+$ 439.0.

Example 262

Preparation of ethyl ((1S)-5-{3-[(tert-butoxycarbonyl)amino]propoxy}-2,3-dihydro-1H-inden-1-yl)acetate

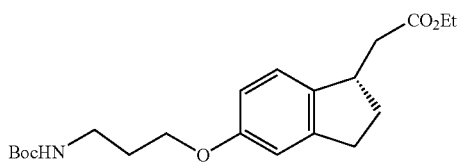

To a solution of ethyl [(1S-5-hydroxy-2,3-dihydro-1H-inden-1-yl]acetate (Example 6, 1 g, 4.54 mmol) and (3-Boc-amino)propyl bromide (1.51 g, 6.36 mmol) in DMF (40 mL) was added Cs$_2$CO$_3$ (2.96 g, 9.08 mmol). The mixture was stirred at rt for 18 h, and diluted with a saturated solution of NH$_4$Cl. The mixture was extracted with Et$_2$O and the combined ether extracts were dried (MgSO$_4$), filtered, and concentrated under reduced pressure. The product (2.15 g, 94%) was isolated by silica gel column chromatography (2:1 hexanes/EtOAc). $^1$H NMR (400 MHz, CD$_2$Cl$_2$) δ 7.05 (d, 1H), 6.77 (s, 1H), 6.69 (dd, 1H), 4.16 (q, 2H), 3.99 (t, 2H), 3.48 (qt, 1H), 3.34-3.25 (m, 2H), 2.95-2.78 (m, 2H), 2.71 (dd, 1H), 2.45-2.33 (m, 2H), 1.95 (qt, 2H), 1.80-1.72 (m, 1H), 1.44 (s, 9H), 1.28 (t, 3H).

Example 263

Preparation of ethyl [(1S)-5-(3-aminopropoxy)-2,3-dihydro-1H-inden-1-yl]acetate trifluoroacetate

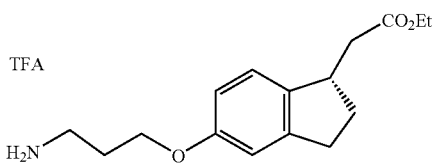

Trifluoroacetic acid (4.03 mL, 51.9 mmol) was added to a solution of ethyl ((1S)-5-{3-[(tert-butoxycarbonyl)amino]propoxy}-2,3-dihydro-1H-inden-1-yl)acetate (Example 262, 2.47 g, 6.54 mmol) in CH$_2$Cl$_2$ (32 mL). The mixture was stirred at rt for 18 h, and then concentrated under reduced pressure to give the product as a viscous oil (2.74 g, 94%). $^1$H NMR (400 MHz, CD$_2$Cl$_2$) δ 7.86 (b, 3H), 7.05 (d, 1H), 6.76 (d, 1H), 6.68 (dd, 1H), 4.15 (q, 2H), 4.08 (t, 2H), 3.49 (qt, 1H), 3.32-3.20 (m, 2H), 2.92-2.78 (m, 2H), 2.67 (dd, 1H), 2.45-2.32 (m, 2H), 2.16 (qt, 2H), 1.80-1.70 (m, 1H), 1.28 (t, 3H).

Example 264

Preparation of ethyl ((1S)-5-{3-[(5-cyano-2-pyridinyl)amino]propoxy}-2,3-dihydro-1H-inden-1-yl)acetate

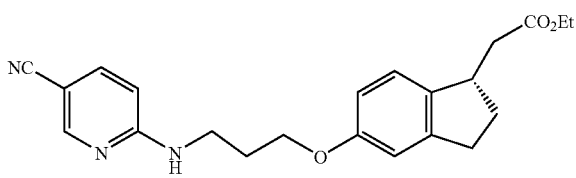

A mixture of 6-chloronicotinonitrile (0.78 9, 5.54 mmol) and ethyl [(1S)-5-(3-aminopropoxy)-2,3-dihydro-1H-inden-1-yl]acetate trifluoroacetate (Example 263, 2.17 g, 5.54 mmol) in CH$_3$CN (14 mL) and 1,4-dioxane (14 mL) was heated to reflux for 8 h, cooled to rt, and then concentrated under reduced pressure. The product (1.14 g, 54%) was isolated after column chromatography (2:1 hexanes/EtOAc). $^1$H NMR (400 MHz, CD$_2$Cl$_2$) δ 8.20 (s, 1H), 7.45 (dd, 1H), 6.94 (d, 1H), 6.67 (s, 1H), 6.58 (dd, 1H), 6.32 (d, 1H), 5.42 (b, 1H), 4.02 (q, 2H), 3.95 (t, 2H), 3.50-3.35 (m, 3H), 2.85-2.68 (m, 2H), 2.59 (dd, 1H), 2.32-2.20 (m, 2H), 2.00 (qt, 2H), 1.70-1.60 (m, 1H), 1.17 (t, 3H).

Example 265

Preparation of ethyl ((1S)-5-{3-[(5-cyano-2-pyridinyl)(propyl)amino]propoxy}-2,3-dihydro-1H-inden-1-yl)acetate

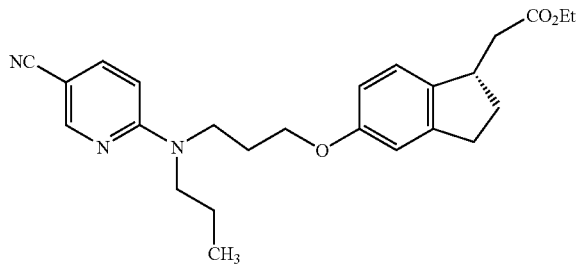

Sodium hydride (0.08 9, 3.16 mmol) was added to a solution of ethyl ((1S)-5-{3-[(5-cyano-2-pyridinyl)amino]propoxy}-2,3-dihydro-1H-inden-1-yl)acetate (Example 264) (0.6 g, 1.58 mmol) in DMF (15 mL). The heterogeneous mixture was stirred at rt for 30 min. Propyl iodide (0.62 mL, 6.32 mmol) was added, and the mixture was stirred at rt for 18 h. The excess NaH was quenched by the addition of water (5 mL) and the aqueous phase extracted with $Et_2O$. The combined $Et_2O$ extracts were washed with water and brine, then dried ($MgSO_4$), filtered, and concentrated under reduced pressure. The product (0.63 g, 99%) was isolated after column chromatography (2:1 hexanes/EtOAc). $^1$H NMR (400 MHz, $CD_2Cl_2$) δ 8.35 (dd, 1H), 7.54 (dd, 1H), 7.06 (d, 1H), 6.78 (d, 1H), 6.69 (d, 1H), 6.52 (dd, 1H), 4.17 (q, 2H), 3.99 (t, 2H), 3.72 (t, 2H), 3.56-3.44 (m, 3H), 2.95-2.78 (m, 2H), 2.71 (dd, 1H), 2.46-2.35 (m, 2H), 2.12-2.05 (m, 2H), 1.72-1.58 (m, 3H), 1.28 (t, 3H), 0.96 (t, 3H).

Example 266

Preparation of ethyl ((1S)-5-{3-[[5-(aminocarbonothioyl)-2-pyridinyl](propyl) amino]propoxy}-2,3-dihydro-1H-inden-1-yl)acetate

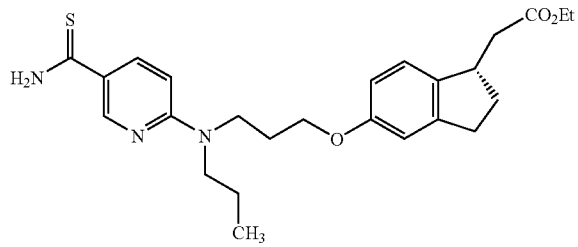

Through a solution of ethyl ((1S-5-{3-[(5-cyano-2-yridinyl)(propyl)amino]propoxy}-2,3-dihydro-1H-inden-1-yl)acetate (Example 265) (0.62 g, 1.47 mmol) in DMF (7 mL) at rt for 20 min was gently passed $H_2S$. Diethylamine (0.23 mL, 2.21 mmol) was added in one portion, and the resultant light green solution was heated at 60° C. for 3 h. Upon completion of the reaction, the dark green solution was purged with a strong flow of argon, and then concentrated under reduced pressure. The product (0.63 g, 95%) was isolated after silica gel column chromatography (1:1 hexanes/EtOAc) as a yellow solid. $^1$H NMR (400 MHz, $CD_2Cl_2$) δ 8.68 (d, 1H), 8.02 (dd, 1H), 7.30 (b, 1H), 7.15-7.02 (m, 2H), 6.79 (d, 1H), 6.71 (dd, 1H), 6.49 (d, 1H), 4.16 (q, 2H), 4.00 (t, 2H), 3.75 (t, 2H), 3.56-3.45 (m, 3H), 2.96-2.78 (m, 2H), 2.75-2.68 (m, 1H), 2.48-2.34 (m, 2H), 2.11 (qt, 2H), 1.82-1.60 (m, 3H), 1.28 (t, 3H), 0.97 (t, 3H).

Example 267

Preparation of ethyl ((1S)-5-{3-[[5-(4,5-dimethyl-1,3-thiazol-2-yl)-2-pyridinyl](propyl)amino]propoxy}-2,3-dihydro-1H-inden-1-yl)acetate

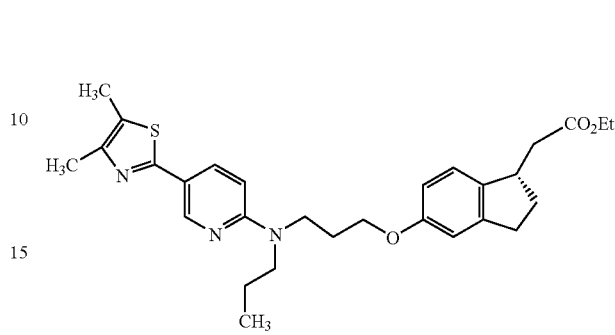

A mixture of ethyl ((1S-5-{3-[[5-(aminocarbonothioyl)-2-pyridinyl]-(propyl)-amino]-propoxy}-2,3-dihydro-1H-inden-1-yl)acetate (Example 266) (90 mg, 0.20 mmol) and 3-bromo-2-butanone (40 mg, 0.26 mmol) in ethanol (9 mL) was heated under argon at 80° C. for 18 h. The solution was then concentrated and the residue purified by column chromatography (2:1 hexanes/EtOAc) to provide the title compound (0.1 g, 100%). $^1$H NMR (400 MHz, $CD_2Cl_2$) δ 8.54 (d, 1H), 7.89 (d, 1H), 7.06 (d, 1H), 6.79 (d, 1H), 6.71 (dd, 1H), 6.56 (d, 1H), 4.16 (q, 2H), 4.01 (t, 2H), 3.74 (t, 2H), 3.55-3.45 (m, 3H), 2.95-2.78 (m, 2H), 2.76-2.68 (m, 1H), 2.46-2.30 (m, 8H), 2.11 (qt, 2H), 1.72-1.62 (m, 3H), 1.28 (t, 3H), 0.97 (t, 3H).

Example 268

Preparation of ((1S)-5-{3-[[5-(4,5-dimethyl-1,3-thiazol-2-yl)-2-pyridinyl](propyl)amino]propoxy}-2,3-dihydro-1H-inden-1-yl)acetic acid

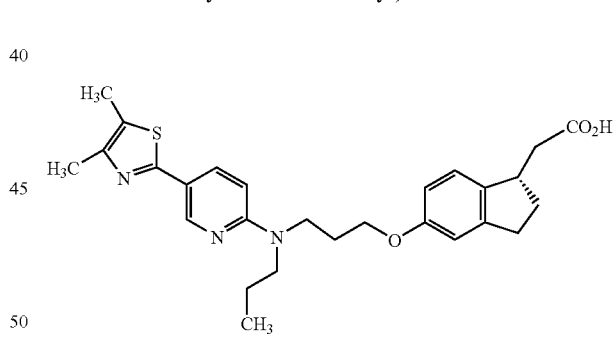

To a solution of ethyl ((1S)-5-{3-[[5-(4,5-dimethyl-1,3-thiazol-2-yl)-2-pyridinyl]propyl)amino]-propoxy}-2,3-dihydro-1H-inden-1-yl)acetate (Example 267) (70 mg, 0.15 mmol) in a mixture of THF (2 mL), methanol (2 mL), and water (1 mL) was added LiOH (40 mg, 1.74 mmol). The mixture was stirred at rt for 18 h and then concentrated under reduced pressure. The residue was taken up in water and acidified using $H_3PO_4$ (5% solution in water). The aqueous phase was extracted with ethyl acetate, and the combined organic layers were dried ($Na_2SO_4$), filtered, and concentrated under reduced pressure to provide the product (56 mg, 86%). $^1$H NMR (400 MHz, DMSO-$d_6$) δ 8.44 (d, 1H), 7.80 (d, 1H), 7.06 (d, 1H), 6.79 (d, 1H), 6.71 (dd, 1H), 6.56 (d, 1H), 3.95 (t, 2H), 3.62 (t, 2H), 3.44-3.25 (m, 3H), 2.81-2.62 (m, 2H), 2.30-2.23 (m, 8H), 1.99-1.96 (m, 2H), 1.65-1.53 (m, 3H), 0.87 (t, 3H); LC-MS: RT=2.73 min, (M+H)$^+$ 480.2.

By using the methods described above for Examples 262-268 and by substituting the appropriate starting materials, compounds of Formula (Itt) listed in Table 10 below, were similarly prepared.

TABLE 10a

Preparative Examples of Compounds of Formula (Ii)

(Itt)

| Ex. No. | $R^{3\text{-}1\text{-}1}$ | $R^{3\text{-}1\text{-}2}$ | Y | LC-MS RT (min) | LC-MS [M + H]$^+$ |
| --- | --- | --- | --- | --- | --- |
| 269 | H | Et | O | 3.55 | 439.1 |
| 270 | $CH_3C(=O)$ | $CH_3$ | O | 3.30 | 467.1 |
| 271 | —$CH_2CH_2CH_2CH_2$— | | O | 3.67 | 465.1 |
| 272 | H | EtO | O | 3.40 | 455.1 |
| 273 | H | Et | NH | 2.31 | 438.2 |
| 274 | $CH_3C(=O)$ | $CH_3$ | NH | 2.35 | 466.2 |
| 275 | $CH_3$ | $CH_3$ | NH | 2.27 | 438.2 |
| 276 | H | Et | $NCH_3$ | 2.40 | 452.4 |
| 277 | $CH_3C(=O)$ | $CH_3$ | $NCH_3$ | 2.52 | 480.4 |
| 278 | $CH_3$ | $CH_3$ | $NCH_3$ | 2.32 | 452.4 |
| 279 | H | Et | N-n-Pr | 2.84 | 480.2 |
| 280 | $CH_3C(=O)$ | $CH_3$ | N-n-Pr | 3.03 | 508.2 |

TABLE 10b

IUPAC Names for Compounds in Table 10a

| Ex. No. | IUPAC Name |
| --- | --- |
| 269 | 2-((1S)-5-{3-[5-(4-ethyl(1,3-thiazol-2-yl))(2-pyridyloxy)]propoxy}indanyl)acetic acid |
| 270 | 2-((1S)-5-{3-[5-(5-acetyl-4-methyl(1,3-thiazol-2-yl))(2-pyridyloxy)]propoxy}indanyl)acetic acid |
| 271 | 2-{(1S)-5-[3-(5-(4,5,6,7-tetrahydrobenzothiazol-2-yl)(2-pyridyloxy))propoxy]indanyl}acetic acid |
| 272 | 2-((1S)-5-{3-[5-(4-ethoxy(1,3-thiazol-2-yl))(2-pyridyloxy)]propoxy}indanyl)acetic acid |
| 273 | 2-[(1S)-5-(3-{[5-(4-ethyl(1,3-thiazol-2-yl))(2-pyridyl)]amino}propoxy)indanyl]acetic acid |
| 274 | 2-[(1S)-5-(3-{[5-(5-acetyl-4-methyl(1,3-thiazol-2-yl))(2-pyridyl)]amino}propoxy)indanyl]acetic acid |
| 275 | 2-[(1S)-5-(3-{[5-(4,5-dimethyl(1,3-thiazol-2-yl))(2-pyridyl)]amino}propoxy)indanyl]acetic acid |
| 276 | 2-[(1S)-5-(3-{[5-(4-ethyl(1,3-thiazol-2-yl))(2-pyridyl)]methylamino}propoxy)indanyl]acetic acid |
| 277 | 2-[(1S)-5-(3-{[5-(5-acetyl-4-methyl(1,3-thiazol-2-yl))(2-pyridyl)]methylamino}propoxy)indanyl]acetic acid |
| 278 | 2-[(1S)-5-(3-{[5-(4,5-dimethyl(1,3-thiazol-2-yl))(2-pyridyl)]methylamino}propoxy)indanyl]acetic acid |
| 279 | 2-[(1S)-5-(3-{[5-(4-ethyl(1,3-thiazol-2-yl))(2-pyridyl)]propylamino}propoxy)indanyl]acetic acid |
| 280 | 2-[(1S)-5-(3-{[5-(5-acetyl-4-methyl(1,3-thiazol-2-yl))(2-pyridyl)]propylamino}propoxy)indanyl]acetic acid |

Example 281

Preparation of ethyl ((1S)-5-{3-[(5-bromo-2-pyrimidinyl)amino]propoxy}-2,3-dihydro-1H-inden-1-yl)acetate

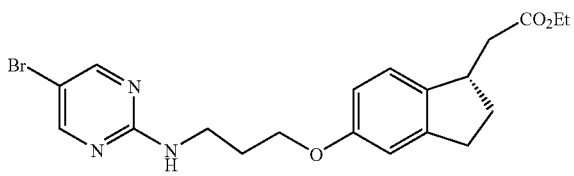

To a solution of 5-bromo-2-aminopyrimidine (2.35 g, 13.5 mmol) in DMF (50 mL) was added NaH (539 mg, 13.5 mmol of a 60% dispersion in mineral oil) [$H_2$ evolution]. Then, ethyl [(1S)-5-(3-bromopropoxy)-2,3-dihydro-1H-inden-1-yl]acetate (Example 45, 2.3 g, 6.74 mmol) was added over 5 min, and the reaction mixture was stirred at rt for 4 h, after which $NH_4Cl$ (10% aqueous solution) was added, and the mixture was concentrated under reduced pressure. The residue was taken up in EtOAc and washed with water and brine successively. The organic phase was dried ($Na_2SO_4$), filtered, and concentrated under reduced pressure. The residue was purified by silica gel chromatography to provide the product (600 mg, 21%) as a colorless oil. $^1$H NMR (400 MHz, $CDCl_3$) δ 1.27 (t, 3H), 1.70-1.81 (m, 1H), 2.02-2.12 (m, 2H), 2.34-2.43 (m, 1H), 2.41 (dd, 1H), 2.73 (dd, 1H), 2.77-2.94 (m, 2H), 3.48-3.56 (m, 1H), 3.58 (q, 2H), 4.03 (t, 2H), 4.18 (q, 2H), 5.95 (b t, 1H), 6.69 (dd, 1H), 6.75 (d, 1H), 7.04 (d, 1 H), 8.22 (s, 2H).

Example 282

Preparation of ethyl ((1S)-5-{3-[(5-bromo-2-pyrimidinyl)(methyl)amino]propoxy}-2,3-dihydro-1H-inden-1-yl)acetate

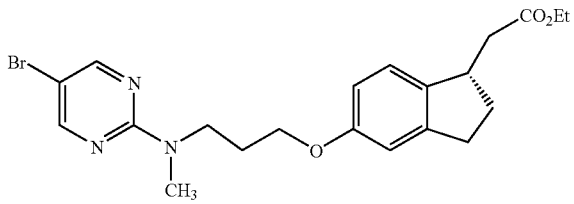

To a solution of ethyl ((1S)-5-{3-[(5-bromo-2-pyrimidinyl)amino]propoxy}2,3-dihydro-1H-inden-1-yl)acetate (Example 281, 500 mg, 1.15 mmol) in DMF (10 mL) was added NaH [$H_2$ evolution], followed by MeI (180 mg, 1.27 mmol) added over 5 min. The reaction mixture was stirred at rt for 4 h, $NH_4Cl$ (10% aqueous solution) was added, after which the mixture was concentrated under reduced pressure. The residue was taken up in EtOAc, then washed with water and brine successively. The organic phase was dried ($Na_2SO_4$), filtered, and concentrated under reduced pressure. The residue was purified by silica gel chromatography to provide the product (600 mg, 21%) as a colorless oil. $^1$H NMR (300 MHz, $CDCl_3$) δ 1.29 (t, 3H), 1.71-1.81 (m, 1H), 2.05-2.13 (m, 2H), 2.34-2.45 (m, 2H), 2.73 (dd, 1H), 2.73-2.94 (m, 2H), 3.14 (s, 3H), 3.49-3.56 (m, 1H), 3.77 (t, 2H), 3.97 (t, 2H), 4.18 (q, 2H), 6.74 (dd, 1H), 6.75 (d, 1H), 7.05 (d, 1H), 8.24 (s, 2H).

Example 283

Preparation of ((1S)-5-{3-[[5-(4-ethylphenyl)-2-pyrimidinyl](methyl)amino]propoxy)}-2,3-dihydro-1H-inden-1-yl)acetic acid

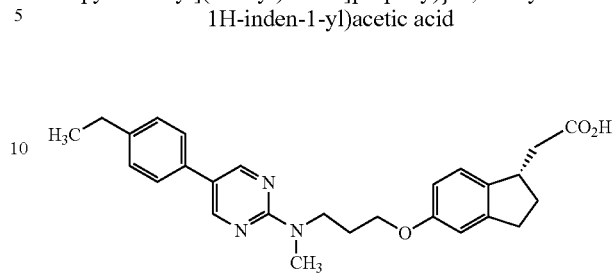

To a round-bottom flask charged with ethyl ((1S)-5-{3-[(5-bromo-2-pyrimidinyl) amino]propoxy}-2,3-dihydro-1H-inden-1-yl)acetate (Example 282, 100 mg, 0.220 mmol), 4-ethylphenyl boronic acid (134 mg, 0.090 mmol) and $PdCl_2$ (dppf).$CH_2Cl_2$ (16.4 mg, 0.020 mmol) were added toluene (6 mL) and 1,4-dioxane (1.12 mL). A flow of argon was passed through the mixture for 30 min. Then a 2 N aqueous solution of $Na_2CO_3$ (1.12 mL, 2.24 mmol, 2 N aqueous solution) was added, and the reaction was heated to 75° C. for 18 h. The reaction mixture was cooled to rt. Filtration through a short plug of silica gel gave the crude ester, which was dissolved in a mixture of THF (3 mL), water (3 mL), and EtOH (1.5 mL). Subsequently, LiOH (57 mg, 2.39 mmol) was added, and the reaction was stirred at rt for 18 h. The reaction mixture was concentrated under reduced pressure, and then purified by preparative HPLC. The desired fractions were concentrated under reduced pressure. The residue was dissolved in $CH_2Cl_2$, and treated for 15 min with Dowex® 66 weakly basic resin. The mixture was then filtered and the filtrate concentrated under reduced pressure to give the product (65 mg, 61%). $^1$H NMR (400 MHz, $CDCl_3$) δ 1.29 (t, 3H), 1.73-1.84 (m, 1H), 2.16 (qt, 2H), 2.33-2.51 (m, 2H), 2.70 (q, 2H), 2.77-2.96 (m, 3H), 3.24 (s, 3H), 3.49-3.56 (m, 1H), 3.87 (t, 2H), 4.03 (t, 2H), 6.72 (dd, 1H), 6.78 (d, 1H), 7.08 (d, 1H), 7.27 (d, 2H), 7.39 (d, 2H), 8.24 (s, 2H); LCMS: RT=3.39 min, (M+H)$^+$ 446.3.

By using the methods described above for Examples 281-283 and by substituting the appropriate starting materials, compounds of Formula (Iuu), listed in Table 11 below, were similarly prepared.

TABLE 11a (Iuu)

| Example | R$^3$ | LCMS (M + H) | RT (min) |
|---|---|---|---|
| 284 | 3,4-dioxolane-Ph | 462.2 | 3.02 |
| 285 | 4-F—Ph | 436.2 | 3.18 |
| 286 | 4-MeO—Ph | 448.3 | 3.01 |
| 287 | 4-t-Bu | 474.2 | 3.70 |
| 288 | 3-thienyl | 424.1 | 3.07 |
| 289 | 2-benzothienyl | 474.2 | 3.72 |

TABLE 11b

IUPAC Names for Compounds in Table 11a

| Ex. No. | IUPAC Name |
|---|---|
| 284 | ((1S)-5-{3-[[5-(1,3-benzodioxol-5-yl)-2-pyrimidinyl](methyl)amino]propoxy}-2,3-dihydro-1H-inden-1-yl)acetic acid |
| 285 | 2-[(1S)-5-(3-{[5-(4-fluorophenyl)pyrimidin-2yl]methylamino}propoxy)indanyl]acetic acid |
| 286 | 2-[(1S)-5-(3-{[5-(4-methoxyphenyl)pyrimidin-2-yl]methylamino}propoxy)indanyl]acetic acid |
| 287 | 2-{(1S)-5-[3-({5-[4-(tert-butyl)phenyl]pyrimidin-2-yl}methylamino)propoxy]indanyl}acetic acid |
| 288 | 2-((1S)-5-{3-[methyl(5-(3-thienyl)pyrimidin-2-yl)amino]propoxy}indanyl)acetic acid |
| 289 | 2-((1S)-5-{3-[(5-benzo[b]thiophen-2-ylpyrimidin-2-yl)methylamino]propoxy}indanyl)acetic acid |

Example 290

Preparation of 4-(1,3-benzodioxol-5-yl)-2-chloropyrimidine

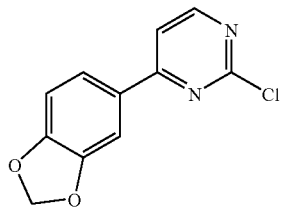

To a mixture of 3,4-dioxolanephenylboronic acid (0.938 g, 5.54 mmol) and 2,4-dichloropyrimidine (1 g, 6.65 mmol) in toluene (112 mL) were added 1,4-dioxane (14 mL) and PdCl$_2$(dppf).CH$_2$Cl$_2$ (0.452 g, 0.554 mmol). The mixture was purged with argon for 15 min after which a 2M aqueous solution of Na$_2$SO$_4$ (28 mL, 56 mmol) was added. The reaction mixture was stirred at 75° C. for 24 h, cooled to rt, and then washed with saturated solution of NaHCO$_3$. The organic layer was separated from the mixture, and the aqueous phase extracted with EtOAc. The combined organic phases were dried (Na$_2$SO$_4$), filtered, and concentrated under reduced pressure. The residue was then purified by silica gel flash chromatography (1:5 EtOAc/Hexanes) to give the product (324 mg, 25%) as crystalline white needles. $^1$H NMR (400 MHz, acetone-d$_6$): δ 6.15 (s, 2H), 7.18 (d, 1H), 7.70 (d, 1H), 7.84 (d, 1H), 7.96 (d, 1H), 8.71 (d, 1H); LC-MS: RT=2.65 min, (M+H)$^+$ 235.2.

Example 291

Preparation of ethyl [(1S)-5-(3-{[4-(1,3-benzodioxol-5-yl)-2-pyrimidinyl]amino}propoxy)-2,3-dihydro-1H-inden-1-yl]acetate

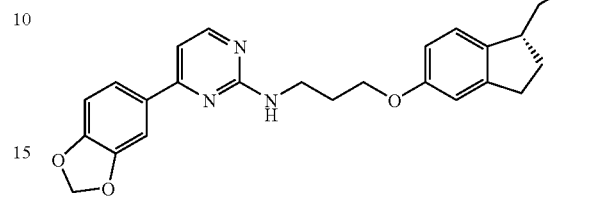

4-(1,3-Benzodioxol-5-yl)-2-chloropyrimidine (Example 290, 108 mg, 0.46 mmol) and ethyl [(1S)-5-3-aminopropoxy)-2,3-dihydro-1H-inden-1-yl]acetate trifluoroacetate (Example 263, 277 mg, 0.418 mmol) were dissolved in MeCN (2.6 mL) and 1,4-dioxane (2.6 mL), afterwhich triethylamine (0.175 mL) was added. The reaction mixture was stirred at 90° C. for 18 h, and then cooled to rt. The solvents removed under reduced pressure, and the residue was purified by silica gel flash chromatography (1:2 EtOAc/Hexanes) to give the title compound (136 mg, 69%). $^1$H NMR (400 MHz, CDCl$_3$): δ 1.32 (t, 3H), 1.70-1.79 (m, 1H), 2.15-2.20 (m, 2H), 2.30-2.51 (m, 2H), 2.73 (dd, 1H), 2.80-2.95 (m, 2H), 3.55-3.64 (m, 1H), 3.74 (q, 2H), 4.14 (t, 2H), 4.22 (q, 2H), 5.42 (s, 1H), 6.01 (s, 1H), 6.65 (d, 1H), 6.75 (s, 1H), 6.90 (d, 2H), 7.05 (d, 1H), 7.20 (d, 2H), 8.15 (s, 1H), 8.25 (d, 1H); LC-MS: RT=2.80 min, (M+H)$^+$ 506.3.

Example 292

Preparation of ethyl ((1S)-5-{3-[[4-(1,3-benzodioxol-5-yl)-2-pyrimidinyl](methyl)amino]-propoxy}-2,3-dihydro-1H-inden-1-yl)acetate

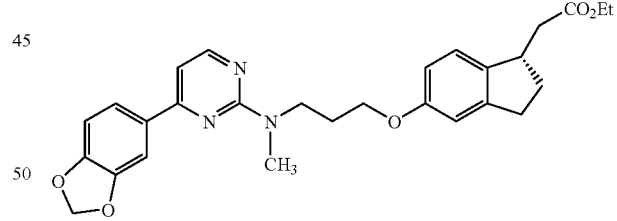

To a suspension of sodium hydride (8.4 mg of a 60% dispersion, 0.210 mmol) in DMF (4 mL) cooled in an ice-bath, was added ethyl [(1S)5-(3-{[4-(1,3-benzodioxol-5-yl)-2-pyrimidinyl]amino}propoxy)2,3-dihydro-1H-inden-1-yl]acetate (Example 291, 50 mg, 0.105 mmol). The mixture was stirred for 15 min after which iodomethane (61 mg, 0.421 mmol) was added dropwise. The mixture was then stirred at rt for 16 h. A solution of ammonium chloride (10% in water) was added to the reaction mixture after which the mixture was concentrated under reduced pressure and brought to basic pH using a saturated solution of NaHCO$_3$. The mixture was extracted with EtOAc (2×). The combined organic layers were washed with water and brine, dried, filtered, and then concentrated under reduced pressure. The residue was purified by silica gel flash column chromatography (1:2 EtOAc/hexanes) to give the product (136 mg, 69%) as a yellow oil. $^1$H NMR (400 MHz, CDCl$_3$): δ 1.33 (t, 3H), 1.70-1.79 (m, 1H), 2.15-2.20 (m, 2H), 2.33-2.51 (m, 2H), 2.70 (dd, 1H), 2.82-2.95 (m, 2H), 3.30 (s, 3H), 3.53-3.64 (m, 1H), 3.71 (q, 2H), 4.13 (t, 2H), 4.22 (q, 2H), 6.01 (s, 2H), 6.65 (d, 1H), 6.75 (s, 1H), 6.90 (d, 2H), 7.05 (d, 1H), 7.62 (d, 1H), 7.15 (s, 1H), 8.30 (d, 1H); LC-MS: RT=3.01 min, (M+H)$^+$ 490.2.

Example 293

Preparation of ((1S)-5-{3-[[4-(1,3-benzodioxol-yl)-2-pyrimidinyl](methyl)amino]propoxy}-2,3-dihydro-1H-inden-1-yl)acetic acid

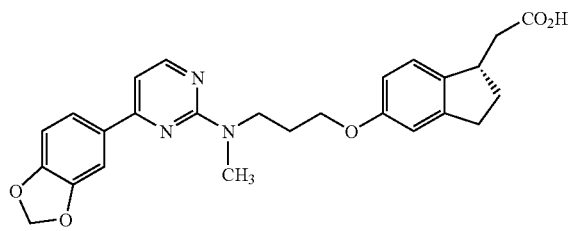

To a solution of ethyl ((1S)-5-{3-[[4-(1,3-benzodioxol-5-yl)-2-pyrimidinyl](methyl)amino]propoxy}2,3-dihydro-1H-inden-1-yl)acetate (Example 292, 35 mg, 0.071 mmol) in THF (2 mL), ethanol (1 mL), and water (2 mL) was added LiOH.H$_2$O (7 mg, 0.29 mmol), and the mixture was stirred at rt for 16 h. The reaction mixture was then extracted with Et$_2$O (2×), organic layers discarded, and the remaining aqueous solution was acidified to pH ~5 using HCl (1 M aqueous solution). The aqueous solution was then extracted with EtOAc. The organic layer was dried (Na$_2$SO$_4$), filtered, and concentrated under reduced pressure to give 9 mg (27%) of the product. $^1$H NMR (400 MHz, CDCl$_3$): δ 1.70-1.80 (m, 1H), 2.15-2.20 (m, 2H), 2.32-2.50 (m, 2H), 2.71 (dd, 1H), 2.83-2.95 (m, 2H), 3.30 (s, 3H), 3.51-3.64 (m, 1H), 3.72 (q, 2H), 3.99 (t, 2H), 6.00 (s, 2H), 6.62 (d, 1H), 6.54 (s, 1H), 6.80 (d, 2H), 7.05 (d, 1H), 7.61 (s, 2H), 8.30 (d, 1H); LC-MS: RT=2.50 min, (M+H)$^+$ 462.3.

By using the methods described above for Examples 290-293 and by substituting the appropriate starting materials, compounds of Formula (Ivv), listed in Table 12 below, were similarly prepared.

TABLE 12a (Ivv)

| Ex. No. | R$^{3-1}$ | R$^5$ | R$^{3-2-1}$ | R$^{3-2-2}$ | LCMS (M + H) | RT (min) |
|---|---|---|---|---|---|---|
| 294 | H | Me | H | CF$_3$ | 3.28 | 486.4 |
| 295 | H | n-Pr | H | CF$_3$ | 3.73 | 514.4 |
| 296 | H | n-Pr | —O—CH$_2$—O— | | 2.94 | 490.2 |
| 297$^1$ | CF$_3$ | Me | H | Et | 4.04 | 514.3 |

TABLE 12a-continued (Ivv)

| Ex. No. | R$^{3-1}$ | R$^5$ | R$^{3-2-1}$ | R$^{3-2-2}$ | LCMS (M + H) | RT (min) |
|---|---|---|---|---|---|---|
| 298$^1$ | CF$_3$ | Me | H | MeO | 3.73 | 516.3 |
| 299$^1$ | CF$_3$ | Me | H | Cl | 3.96 | 520.3 |
| 300$^1$ | CF$_3$ | Me | —O—CH$_2$—O— | | 3.68 | 530.3 |

Note
$^1$These compounds were prepared following the procedure described for Examples 408-410. The appropriate starting material (3-[(4-chloro-5-trifluoromethyl-2-pyrimidinyl)amino]-1-propanol) was obtained through the condensation of 1-amino-3-propanol with 2,4-dichloro-5-trifluoromethylpyrimidine to yield a 1:1 mixture of the two possible regioisomers (See Reaction Scheme 14). The 2-chloro- and 4-chloro- substituted pyrimidines were separated by column chromatography.

TABLE 12b

IUPAC Names for Compounds in Table 12a

| Ex. No. | IUPAC Name |
|---|---|
| 294 | 2-{(1S)-5-[3-(methyl{4-[4-(trifluoromethyl)phenyl]pyrimidin-2-yl}amino)propoxy]indanyl}acetic acid |
| 295 | 2-{(1S)-5-[3-(propyl{4-[4-(trifluoromethyl)phenyl]pyrimidin-2-yl}amino)propoxy]indanyl}acetic acid |
| 296 | ((1S)-5-{3-[[4-(1,3-benzodioxol-5-yl)-2-pyrimidinyl](propyl)amino]propoxy}-2,3-dihydro-1H-inden-1-yl)acetic acid |
| 297 | 2-[(1S)-5-(3-{[4-(4-ethylphenyl)-5-(trifluoromethyl)pyrimidin-2-yl]methylamino}propoxy)indanyl]acetic acid |
| 298 | 2-[(1S)-5-(3-{[4-(4-methoxyphenyl)-5-(trifluoromethyl)pyrimidin-2-yl]methylamino}propoxy)indanyl]acetic acid |
| 299 | 2-[(1S)-5-(3-{[4-(4-chlorophenyl)-5-(trifluoromethyl)pyrimidin-2-yl]methylamino}propoxy)indanyl]acetic acid |
| 300 | 2-[(1S)-5-(3-{[4-(2H-benzo[3,4-d]1,3-dioxolan-5-yl)-5-(trifluoromethyl)pyrimidin-2-yl]methylamino}propoxy)indanyl]acetic acid |

Example 301 and Example 302

Preparation of 3-{[6-chloro-5-(trifluoromethyl)-2-pyridinyl]amino-}1-propanol and 3-{[6-chloro-3-(trifluoromethyl)-2-pyridinyl]amino}-1-propanol

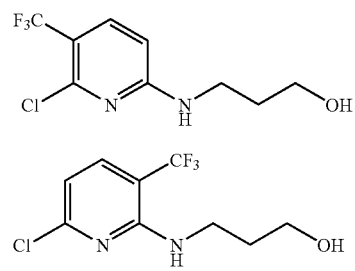

A solution of 2,6-dichloro-3-trifluoromethyl pyridine (2 g, 9.26 mmol) and 3-amino-1-propanol in CH₃CN (46 mL) was heated to reflux for 18 h, and then concentrated under reduced pressure. The reaction produced two regioisomers that were separated by silica gel flash chromatography (2:1 hexanes /EtOAc). Example 301 (1.45 g, 62%). ¹H NMR (400 MHz, CD₂Cl₂) δ 7.66 (d, 1H), 6.60 (d, 1H), 6.53 (b, 1H), 3.67 (t, 2H), 3.56 (q, 2H), 1.83 (t, 2H). Example 302: (0.66 g, 28%). ¹H NMR (400 MHz, CD₂Cl₂) δ 7.60 (d, 1H), 6.43 (d, 1H), 3.64 (t, 2H), 3.44 (t, 2H), 1.82 (dt, 2H).

Example 303

Preparation of ethyl [(1S)-5-(3-{[6-chloro-5-(trifluoromethyl)-2-pyridinyl]amino}propoxy)-2,3-dihydro-1H-inden-1-yl]acetate

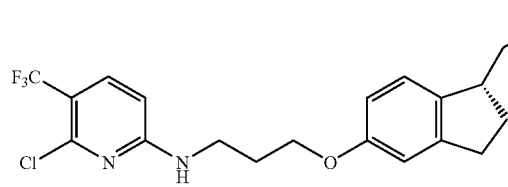

To a solution of 3-{[6-chloro-5-trifluoromethyl)-2-pyridinyl]amino}-1-propanol (Example 301) (2.0 g, 7.85 mmol) and ethyl [(1S)-5-hydroxy-2,3-dihydro-1H-inden-1-yl]acetate (Example 6, 0.87 g, 3.93 mmol) in THF (20 mL) were added triphenylphosphine (1.35 g, 5.11 mmol) and 1,1'-(azodicarbonyl)dipiperidine (1.30 g, 5.11 mmol) under argon. The golden yellow mixture was stirred at rt for 18 h, and then concentrated under reduced pressure. The product (1.15 g, 64%) was isolated after column chromatography (2:1 hexanes /EtOAc). ¹H NMR (400 MHz, CD₃OD) δ 7.58 (d, 1H), 6.94 (d, 1H), 6.77 (d, 1H), 6.61 (dd, 1H), 6.42 (d, 1H), 4.16 (q, 2H), 4.01 (t, 2H), 3.55 (q, 2H), 3.55-3.420 (m, 1H), 2.92-2.68 (m, 3H), 2.42-2.30 (m, 2H), 2.08 (qt, 2H), 1.78-1.68 (m, 1H), 1.27 (t, 3H).

Example 304

Preparation of ethyl [(1S)-5-(3-{[6-(4-methoxyphenyl)-5-(trifluoromethyl)-2-pyridinyl]amino}propoxy)-2,3-dihydro-1H-inden-1-yl]acetate

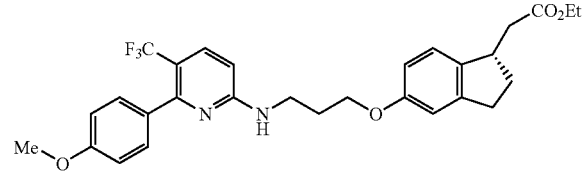

To a solution of ethyl [(1S-5-(3-{[6-chloro-5-(trifluoromethyl)-2-pyridinyl]amino}propoxy)-2,3-dihydro-1H-inden-1-yl]acetate (Example 303, 0.06 9, 0.14 mmol) in a mixture of toluene (3.75 mL), 1,4-dioxane (0.75 mL), and water (0.88 mL) were added Na₂CO₃ (0.15 g, 1.38 mmol), 4-methoxyphenyl boronic acid (0.08 g, 0.55 mmol), and PdCl₂(dppf) CH₂Cl₂ (0.02 g, 0.03 mmol). The mixture was heated at 80° C. for 4 h, and then concentrated under reduced pressure. The product (0.11 g, 94%) was purified by silica gel flash chromatography (2:1 hexanes /EtOAc). ¹H NMR (400 MHz, DMSO-d₆) δ 7.66 (d, 1H), 7.39 (t, 1H), 7.33 (d, 2H), 7.04 (d, 1H), 6.94 (dd, 2H), 6.74 (d, 1H), 6.65 (dd, 1H), 6.50 (d, 1H), 4.08 (q, 2H), 3.97 (t, 2H), 3.79 (s, 3H), 3.45-3.30 (m, 3H), 2.76-2.68 (m, 3H), 2.35 (dd, 1H), 2.30-2.20 (m, 1H), 1.95 (qt, 2H), 1.70-1.58 (m, 1H), 1.19 (t, 3H).

Example 305

Preparation of [(1S)-5-(3-{[6-(4-methoxyphenyl)-5-(trifluoromethyl)-2-pyridinyl]amino}propoxy)-2,3-dihydro-1H-inden-1-yl]acetic acid

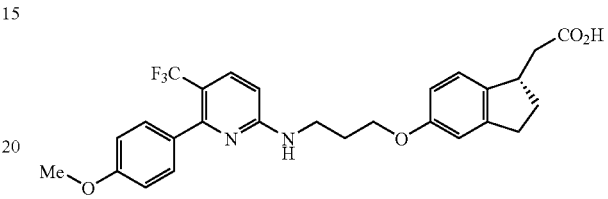

To a solution of ethyl [(1S)-5-(3-{[6-(4-methoxyphenyl)-5-(trifluoromethyl)-2-pyridinyl]amino}propoxy)2,3-dihydro-1H-inden-1-yl]acetate (Example 304, 0.05 g, 0.09 mmol) in a mixture of THF (1 mL), methanol (1 mL), and water (0.5 mL) was added LiOH (0.02 g, 0.85 mmol). The mixture was stirred at rt for 18 h, and then concentrated under reduced pressure. The residue was taken up in water and acidified with 5% H₃PO₄. The aqueous solution was extracted with ethyl acetate. The combined organic phases dried (Na₂SO₄), filtered, and concentrated under reduced pressure to give the product (0.038 g, 88%). ¹H NMR (400 MHz, CD₂Cl₂) δ 7.65 (d, 1H), 7.35 (d, 2H), 7.05 (d, 1H), 6.92 (d, 2H), 6.73 (s, 1H), 6.66 (dd, 1H), 6.49 (d, 1H), 4.02 (t, 2H), 3.84 (s, 3H), 3.55 (t, 3H), 3.45 (qt, 1H), 2.92-2.65 (m, 3H), 2.40-2.30 (m, 2H), 2.10-2.02 (m, 2H), 1.80-1.68 (m, 1H); LC-MS: RT=3.02 min, (M+H)⁺ 531.1.

Example 306

Preparation of ethyl [(1S)-5-(3-{[6-chloro-3-(trifluoromethyl)-2-pyridinyl]amino}propoxy)-2.3-dihydro-1H-inden-1-yl]acetate

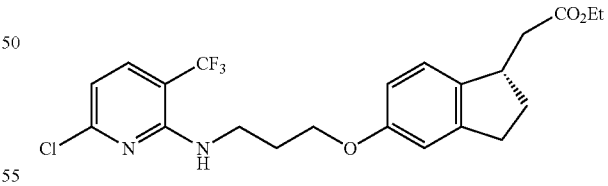

To a solution of 3-{[6-chloro-3-(trifluoromethyl)-2-pyridinyl]amino}-1-propanol (Example 302) (0.63 g, 2.45 mmol) and ethyl [(1S)-5-hydroxy-2,3-dihydro-1H-inden-1-yl]acetate (Example 6, 0.45 g, 2.05 mmol) in THF (6.80 mL) was added triphenylphosphine (0.70 g, 2.66 mmol) and 1,1'-azodicarbonyl)-dipiperidine (0.68 g, 2.66 mmol) under argon. The golden yellow mixture was stirred at rt for 18 h, and then concentrated under reduced pressure. The product (0.58 g, 62%) was isolated after column chromatography (2:1 hexanes/EtOAc). ¹H NMR (400 MHz, CD₃OD) δ 7.65 (d, 1H), 7.02 (d, 1H), 6.76 (d, 1H), 6.69 (dd, 1H), 6.60 (d, 1H), 6.48 (b, 1H), 4.15 (q, 2H), 4.04 (t, 2H), 3.65 (q, 2H), 3.46 (qt. 1H), 2.92-2.68 (m, 3H), 2.42-2.30 (m, 2H), 1.78-1.68 (m, 1H), 1.27 (t, 3H).

Example 307

Preparation of ethyl [(1S)-5-(3-{[6-(4-methoxyphenyl)-3-(trifluoromethyl)-2-pyridinyl]amino}propoxy)-2,3-dihydro-1H-inden-1-yl]acetate

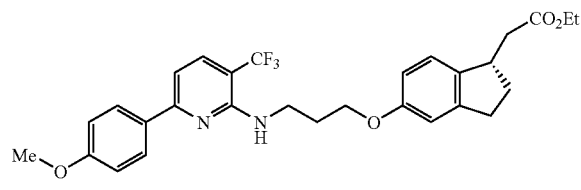

To a solution of ethyl [(1S-5-(3-{[6-chloro-3-(trifluoromethyl)-2-pyridinyl]amino}propoxy)-2,3-dihydro-1H-inden-1-yl]acetate (Example 306) (0.08 g, 0.18 mmol) in a mixture of toluene (3.75 mL), 1,4-dioxane (0.75 mL), and water (0.88 mL) were added sodium carbonate (0.15 g, 1.38 mmol), 4-methoxyphenyl boronic acid (0.11 g, 0.70 mmol), and $PdCl_2(dppf) \cdot CH_2Cl_2$ (0.03 g, 0.04 mmol). The mixture was stirred at 80° C. for 4 h, and then concentrated under reduced pressure. The product (0.065 g, 70%) was isolated after by silica gel flash chromatography (2:1 hexanes/EtOAc). $^1$H NMR (400 MHz, $CD_3OD$) δ $^1$H NMR (400 MHz, $CD_2Cl_2$) δ 8.03 (d, 2H), 7.68 (d, 1H), 7.05 (dd, 2H), 6.97 (d, 2H), 6.77 (s, 1H), 6.71 (dd, 1H), 5.39 (b, 1H), 4.15 (q, 2H), 4.09 (t, 2H), 3.90-3.80 (m, 5H), 3.51 (qt, 1H), 2.95-2.78 (m, 2H), 2.71 (dd, 1H), 2.45-2.33 (m, 2H), 2.22-2.10 (m, 2H), 1.80-1.70 (m, 1H), 1.28 (t, 3H).

Example 308

Preparation of [(1S)-5-(3-{[6-(4-methoxyphenyl)-3-(trifluoromethyl)-2-pyridinyl]amino}propoxy)-2,3-dihydro-1H-inden-1-yl]acetic acid

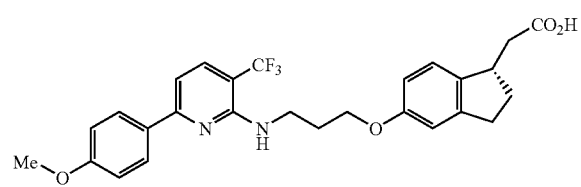

To a solution of ethyl [(1S)-5-(3-{[6-(4-methoxyphenyl)-3-(trifluoromethyl)-2-pyridinyl]amino}propoxy)2,3-dihydro-1H-inden-1-yl]acetate (Example 307) (0.05 g, 0.09 mmol) in THF (1 mL), methanol (1 mL), and water (0.5 mL) was added LiOH (0.02 g, 0.85 mmol). The mixture was stirred at rt for 18 h, and then concentrated under reduced pressure. The residue was taken up in water and acidified to pH ~5 using $H_3PO_4$ (5% aqueous solution). The aqueous solution was then extracted with EtOAc. The combined organic phases were dried ($Na_2SO_4$), filtered, and then concentrated under reduced pressure to give the product (0.034 g, 80%). $^1$H NMR (400 MHz, $CD_2Cl_2$) δ 8.03 (d, 2H), 7.68 (d, 1H), 7.07 (dd, 2H), 6.97 (d, 2H), 6.80 (s, 1H), 6.72 (dd, 1H), 5.37 (b, 1H), 4.11 (t, 2H), 3.91-3.81 (m, 5H), 3.56-3.48 (m, 1H), 2.95-2.77 (m, 3H), 2.15-2.37 (m, 2H), 2.23-2.18 (m, 2H), 1.65-1.55 (m, 1H).

Example 309

Preparation of 6-[(3-{[tert-butyl(dimethyl)silyl]oxy}propyl)amino]-2-chloro-5-fluoronicotinonitrile

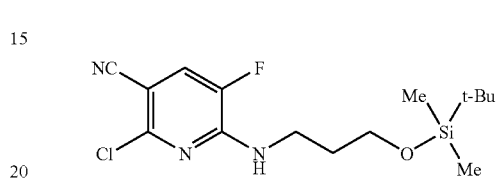

To a solution of t-butyidimethylsilyl chloride (0.73 9, 4.79 mmol) in $CH_2Cl_2$ (21 mL) was added 2-chloro-5fluoro-6-[(3-hydroxypropyl)amino]nicotinonitrile [prepared as in Example 302] and starting from 2,6dichloro-5fluoronicotinonitrile] (1.0 g, 4.35 mmol), followed by $Et_3N$ (0.48 9, 4.79 mmol) and DMAP (0.01 g, 0.09 mmol). The resulting cloudy mixture was stirred at rt for 18 h, and then diluted with $CH_2Cl_2$. The organic layer was washed with water, dried ($MgSO_4$), filtered, and then concentrated under reduced pressure. The product (1.47 g, 98%) was isolated after silica gel flash chromatography (2:1 hexanes/EtOAc) as a white solid. $^1$H NMR (400 MHz, $CD_3OD$) δ 7.46 (d, 1H), 3.67 (t, 2H), 3.49 (t, 2H), 1.77 (qt, 2H), 0.84 (s, 9H), 0.00 (s, 6H).

Example 310

Preparation of 6-[(3-{[tert-butyl(dimethyl)silyl]oxy}propyl)(methyl)amino]-2-chloro-5-fluoronicotinonitrile

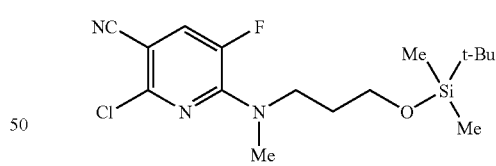

Sodium hydride (0.11 g, 4.65 mmol) was added to a solution of 6-[(3-{[tert-butyl(dimethyl)-14-silyl]oxy}propyl)amino]-2-chloro-5-fluoronicotinonitrile (Example 309, 0.80 9, 2.33 mmol) in DMF (23.26 mL). The mixture was stirred at rt for 30 min, and then MeI (0.58 mL, 9.30 mmol) added. The reaction mixture was stirred at rt for 18 h, quenched with water, and the aqueous phase was extracted with ether. The combined ether extracts were washed with water, brine, and then dried ($MgSO_4$), filtered, and concentrated under reduced pressure. The product (0.88 g, 99%) was isolated after silica gel flash chromatography (2:1 hexanes/EtOAc). $^1$H NMR (400 MHz, $CD_3OD$) δ 7.53 (d, 1H), 3.70-3.60 (m, 4H), 3.17 (d, 3H), 1.84-1.76 (m, 2H), 0.84 (s, 9H), 0.00 (s, 6H).

Example 311

Preparation of 2-chloro-5-fluoro-6-[(3-hydroxypropyl)(methyl)amino]nicotinonitrile

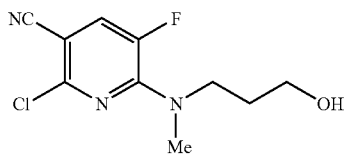

A mixture of 6-[(3-{[tert-butyl(dimethyl)silyl]oxy}propyl)(methyl)amino]-2-chloro-5-fluoronicotinonitrile (Example 310, 0.73 g, 2.04 mmol) in ethanol/HCl/water (95:1:4) (50 mL) was stirred at rt for 18 h, and then concentrated under reduced pressure. The residue was passed through a plug of silica gel with ethyl acetate as the eluent to give the product (0.5 g, 100%) as a waxy yellow solid. $^1$H NMR (400 MHz, CD$_3$OD) δ 7.54 (d, 1H), 3.65 (dt, 2H), 3.54 (t, 2H), 3.18 (d, 3H), 1.85-1.77 (m, 2H).

Example 312

Preparation of ethyl ((1S)-5-{3-[(6-chloro-5-cyano-3-fluoro-2-pyridinyl)(methyl)amino]propoxy}-2,3-dihydro-1H-inden-1-yl)acetate

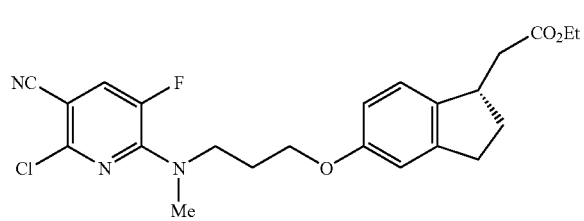

To a solution of 2-chloro-5-fluoro-6-[(3-ydroxypropyl)(methyl)amino]nicotinonitrile (Example 311) (0.50 g, 2.05 mmol) and ethyl [(1S)-5-hydroxy-2,3-dihydro-1H-inden-1-yl]acetate (Example 6, 0.25 9, 1.14 mmol) in THF (9 mL) were added PPh$_3$ (0.54 g, 2.05 mmol) and ADDP (0.52 g, 2.05 mmol) under argon. The golden yellow mixture was stirred at rt for 18 h, and then concentrated under reduced pressure. The product (0.41 g, 81%) was isolated after silica gel flash chromatography (2:1 hexanes/EtOAc). $^1$H NMR (400 MHz, CD$_2$Cl$_2$) δ 7.29 (d, 1H), 7.04 (d, 1H), 6.73 (d, 1H), 6.66 (dd, 1H), 4.16 (q, 2H), 3.99 (t, 2H), 3.82 (t, 2H), 3.51 (qt, 1H), 3.25 (d, 3H), 2.95-2.78 (m, 2H), 2.70 (dd, 1H), 2.45-2.32 (m, 2H), 2.12 (qt, 2H), 1.82-1.72 (m, 1H), 1.29 (t, 3H).

Example 313

Preparation of ethyl ((1S)-5-{3-[[5-cyano-3-fluoro-6-(4-methoxyphenyl)-2-pyridinyl](methyl)amino]propoxy}-2,3-dihydro-1H-inden-1-yl)acetate

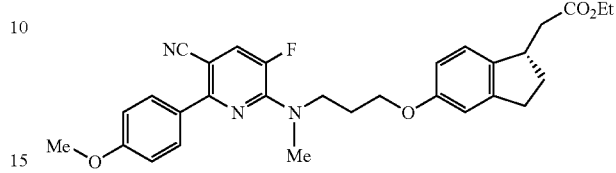

To a solution of ethyl ((1S)-5-{3-[(6-chloro-5-cyano-3-fluoro-2-pyridinyl)(methyl)amino]propoxy}-2,3-dihydro-1H-inden-1-yl)acetate (Example 312, 0.10 g, 0.22 mmol) in a mixture of toluene (1.5 mL), 1,4-dioxane (0.5 mL), and water (0.6 mL) were added sodium carbonate (0.24 g, 2.24 mmol), 4-methoxyphenyl boronic acid (0.14 g, 0.90 mmol) and PdCl$_2$(dppf).CH$_2$Cl$_2$ (0.04 g, 0.04 mmol). The mixture was heated at 80° C. for 4 h, and then concentrated under reduced pressure. The product (0.10 g, 88%) was isolated after silica gel flash chromatography (2:1 hexanes/EtOAc). $^1$H NMR (400 MHz, CD$_2$Cl$_2$) δ 7.87 (d, 2H), 7.37 (d, 1H), 7.04 (d, 1H), 6.98 (d, 2H), 6.72 (d, 1H), 6.65 (dd, 1H), 4.16 (q, 2H), 4.00 (t, 2H), 3.90-3.85 (m, 5H), 3.49 (qt, 1 H), 3.30 (d, 3H), 2.94-2.76 (m, 2H), 2.70 (dd, 1H), 2.45-2.32 (m, 2H), 2.16 (qt, 2H), 1.80-1.70 (m, 1H), 1.29 (t, 3H).

Example 314

Preparation of ((1S)-5-{3-[[5-cyano-3-fluoro-6-(4-methoxyphenyl)-2-pyridinyl](methyl)amino]propoxy}-2,3-dihydro-1H-inden-1-yl)acetic acid

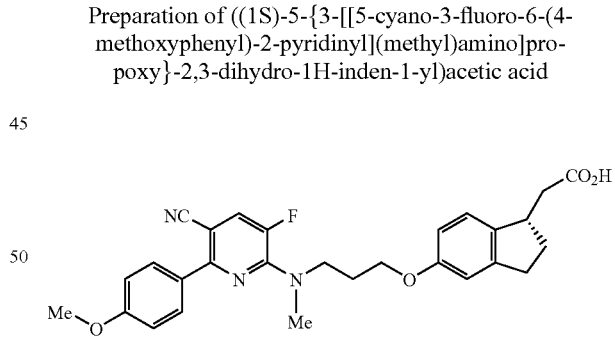

The title compound was prepared as described for Example 308 and starting with ethyl ((1S)-5-{3-[[5-cyano-3-fluoro-6-(4-methoxyphenyl)-2-pyridinyl](methyl)amino]propoxy}-2,3-dihydro-1H-inden-1-yl)acetate (Example 313). $^1$H NMR (400 MHz, CD$_2$Cl$_2$) δ 7.88 (d, 2H), 7.37 (d, 1H), 7.08 (d, 1H), 6.99 (d, 2H), 6.73 (d, 1H), 6.66 (dd, 1H), 4.00 (t, 2H), 3.92-3.85 (m, 5H), 3.53 (qt, 1H), 3.30 (d, 3H), 2.96-2.76 (m, 3H), 2.55-2.38 (m, 2H), 2.16 (qt, 2H), 1.85-1.74 (m, 1H); LC-MS: RT=3.61 min, (M+H)$^+$ 490.3.

Example 315

Preparation of 2-chloro-6-(4-ethylphenyl)-3-(trifluoromethyl)pyridine

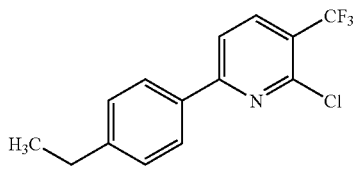

To a solution of 2,6-dichloro-3-trifluoromethyl pyridine (1 g, 4.54 mmol) in a mixture of toluene (11 mL), 1,4-dioxane (5.88 mL), and water (5.88 mL) were added sodium carbonate (0.96 g, 9.07 mmol), 4-ethylphenyl boronic acid (0.61 g, 4.08 mmol), and PdCl$_2$(dppf)CH$_2$Cl$_2$ (0.75 g, 0.92 mmol). The mixture was stirred at 80° C. for 4 h, and then concentrated under reduced pressure. The product (0.69 g, 53%) was isolated after silica gel flash chromatography (2:1 hexanes/EtOAc). $^1$H NMR (400 MHz, CD$_3$OD) δ 8.15 (d, 1H), 8.01 (d, 2H), 7.95 (d, 1H), 7.33 (d, 2H), 2.71 (q, 2H), 1.27 (t, 3H).

Example 316

Preparation of 3-{[6-(4-ethylphenyl)-3-(trifluoromethyl)-2-pyridinyl]amino}-1-propanol

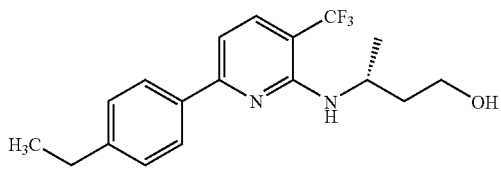

To a solution of 2-chloro-6-(4-ethylphenyl)-3-(trifluoromethyl)pyridine (Example 315, 0.36 g, 1.25 mmol) and 3-amino-1-propanol (0.38 g, 5.00 mmol) in CH$_3$CN (2 mL), TFA (0.5 mL) was added. The mixture was stirred at reflux for 18 h, and then concentrated under reduced pressure. The product (0.21 g, 52%) was isolated after silica gel flash chromatography (2:1 hexanes/EtOAc). $^1$H NMR (400 MHz, CD$_3$OD) δ 7.95 (d, 2H), 7.72 (d, 1H), 7.27 (d, 2H), 7.10 (d, 1H), 3.72 (t, 2H), 3.66 (t, 2H), 2.69 (q, 2H), 1.90 (q, 2H), 1.27 (t, 3H).

Example 317

Preparation of ethyl [(1S)-5-(3-{[6-(4-ethylphenyl)-3-(trifluoromethyl)-2-pyridinyl]amino}propoxy)-2,3-dihydro-1H-inden-1-yl]acetate To a solution of 3-{[6-(4-ethylphenyl)-3-(trifluoromethyl)-2-pyridinyl]amino}-1-propanol (Example 316) (0.34 g, 1.05 mmol) and ethyl [(1S)-5-hydroxy-2,3-dihydro-1H-inden-1-yl]acetate (Example 6, 0.18 g, 0.84 mmol) in THF (8.50 mL) was added PPh$_3$ (0.29 g, 1.09 mmol) and ADDP (0.28 g, 1.09 mmol) under argon. The golden yellow mixture was stirred at rt for 18 h, and then concentrated under reduced pressure. The product (0.33 g, 74%) was isolated after silica gel flash chromatography (2:1 hexanes/EtOAc). $^1$H NMR (400 MHz, CD$_2$Cl$_2$) δ 7.99 (d, 2H), 7.72 (d, 1H), 7.25 (d, 2H), 7.12 (d, 1H), 7.01 (d, 1H), 6.76 (d, 1H), 6.68 (dd, 1H), 4.15 (q, 2H), 4.08 (t, 2H), 3.82 (t, 2H), 3.45 (qt, 1H), 2.90-2.68 (m, 5H), 2.42-2.28 (m, 2H), 2.16 (qt, 2H), 1.78-1.68 (m, 1H), 1.30-1.24 (m, 6H).

Example 318

Preparation of [(1S)-5-(3-{[6-(4-ethylphenyl)-3-(trifluoromethyl)-2-pyridinyl]amino}propoxy)-2,3-dihydro-1H-inden-1-yl]acetic acid To a solution of ethyl [(1S)-5-(3-{[6-(4-ethylphenyl)-3-(trifluoromethyl)-2-pyridinyl]amino}propoxy)-2,3-dihydro-1H-inden-1-yl]acetate (Example 317, 0.07 9, 0.09 mmol) in THF (2 mL), methanol (1 mL), and water (1 mL) was added LiOH (0.03 9, 1.37 mmol). The mixture was stirred at rt for 18 h, and then concentrated under reduced pressure. The residue was taken up in water and acidified to pH ~5 using H$_3$PO$_4$ (a 5% aqueous solution). The aqueous solution was then extracted with EtOAc. The combined organic phases were dried (Na$_2$SO$_4$), filtered, and concentrated under reduced pressure to give the product (0.048 g, 71%). $^1$H NMR (400 MHz, CD$_2$Cl$_2$) δ 7.99 (d, 2H), 7.71 (d, 1H), 7.29 (d, 2H), 7.09 (dd, 2H), 6.81 (d, 1H), 6.73 (dd, 1H), 5.41 (b, 1H), 4.11 (t, 2H), 3.84 (q, 2H), 3.53 (qt, 1H), 2.95-2.70 (m, 5H), 2.52-2.38 (m, 2H), 2.20 (qt, 2H), 1.82-1.75 (m, 1H), 1.29 (m, 3H); LC-MS: RT=4.10 min, (M+H)$^+$ 499.3.

Example 319

Preparation of ethyl ((1S)-5-{3-[[6-(4-ethylphenyl)-3-(trifluoromethyl)-2-pyridinyl](methyl)amino]propoxy}-2,3-dihydro-1H-inden-1-yl)acetate

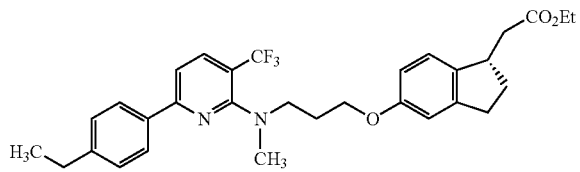

Sodium hydride (0.02 g, 0.86 mmol) was added to a solution of ethyl [(1 S)-5-(3-{[6-(4-ethylphenyl)-3-(trifluoromethyl)-2-pyridinyl]amino}propoxy)-2,3-dihydro-1H-inden-1-yl]acetate (Example 318) (0.21 g, 0.39 mmol) in DMF (2 mL). After stirring at rt for 30 min, MeI (0.05 mL, 6.32 mmol) was added. The mixture was stirred at rt for 18 h, quenched with water (5 mL), and extracted with ether (3×). The combined ether extracts were washed with water and brine, dried (MgSO$_4$), filtered, and concentrated under reduced pressure. The product (0.017 g, 8%) was isolated after silica gel flash chromatography (2:1 hexanes/EtOAc). $^1$H NMR (400 MHz, CD$_2$Cl$_2$) δ 7.99 (d, 2H), 7.85 (d, 1H), 7.35-7.25 (m, 3H), 7.01 (d, 1H), 6.72 (d, 1H), 6.65 (dd, 1H), 4.15 (q, 2H), 4.00 (t, 2H), 3.73 (t, 2H), 3.47 (qt, 1H), 3.08 (s, 3H), 2.90-2.68 (m, 5H), 2.42-2.30 (m, 2H), 2.15 (qt, 2H), 1.78-1.68 (m, 1H), 1.32-1.26 (m, 6H).

Example 320

Preparation of ethyl ((1S)-5-{3-[[6-(4-ethylphenyl)-3-(trifluoromethyl)-2-pyridinyl](methyl)amino]propoxy}-2,3-dihydro-1H-inden-1-yl)acetic acid

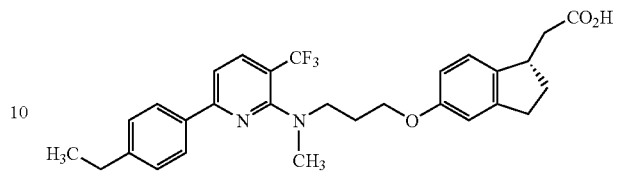

Following the procedure described in Example 308 and starting with ethyl ((1S)-5-{3-[[6-(4-ethylphenyl)-3-trifluoromethyl)-2-pyridinyl](methyl)amino]propoxy}-2,3-dihydro-1H-inden-1-yl)acetate (Example 319, 10 mg, 0.018 mmol), LiOH (0.1 mg, 0.004 mmol) in THF (1 mL), MeOH (1 mL), and water (0.5 mL), the title compound was obtained (0.0024 g, 51%). $^1$H NMR (400 MHz, CD$_2$Cl$_2$) δ 7.98 (d, 2H), 7.85 (d, 1H), 7.35-7.25 (m, 3H), 7.01 (d, 1H), 6.72 (d, 1H), 6.65 (dd, 1H), 4.02 (t, 2H), 3.83 (t, 2H), 3.47 (qt, 1H), 3.08 (s, 3H), 2.90-2.68 (m, 5H), 2.42-2.30 (m, 2H), 2.15 (qt, 2H), 1.78-1.68 (m, 1H), 1.33 (m, 3H); LC-MS: RT=4.50 min, (M+H)$^+$ 513.2.

By using the methods described above for Examples 315-320 and by substituting the appropriate starting materials, the compounds of Formula (Iww) appearing in Table 13 below were similarly prepared.

TABLE 13a

Preparative Examples of Compounds of Formula (In)

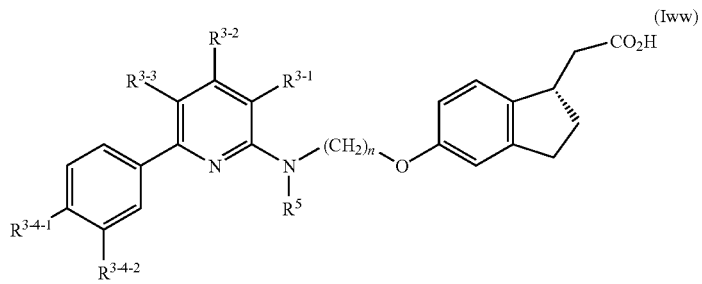

| Ex. No. | R$^{3-1}$ | R$^{3-2}$ | R$^{3-3}$ | R$^{3-4-1}$ | R$^{3-4-2}$ | R$^5$ | n | LC-MS RT (min) | LC-MS [M + H]$^+$ |
|---|---|---|---|---|---|---|---|---|---|
| 321 | CF$_3$ | H | H | CH$_3$O | F | H | 3 | 3.80 | 519.3 |
| 322 | CF$_3$ | H | H | CH$_3$O | CH$_3$O | H | 3 | 3.61 | 531.3 |
| 323 | CF$_3$ | H | H | —OCH$_2$O— | | H | 3 | 3.76 | 515.3 |
| 324 | CF$_3$ | H | H | F | H | H | 3 | 4.02 | 489.1 |
| 325 | CF$_3$ | H | H | CH$_3$ | H | H | 3 | 4.69 | 485.3 |
| 326 | CF$_3$ | H | H | H | H | H | 3 | 4.00 | 471.1 |
| 327 | CF$_3$ | H | H | Et | H | H | 2 | 4.04 | 485.3 |
| 328 | CF$_3$ | H | H | Et | H | CH$_3$ | 3 | 4.50 | 513.2 |
| 329 | CF$_3$ | H | H | Et | H | CH$_3$ | 2 | 4.44 | 499.1 |
| 330 | H | H | CF$_3$ | CH$_3$O | F | H | 3 | 3.38 | 519.1 |
| 331 | H | H | CF$_3$ | CH$_3$O | CH$_3$O | H | 3 | 3.02 | 531.1 |
| 332 | H | H | CF$_3$ | —OCH$_2$O— | | H | 3 | 3.23 | 515.1 |
| 333 | H | H | CF$_3$ | F | H | H | 3 | 3.46 | 489.1 |
| 334 | H | H | CF$_3$ | CH$_3$ | H | H | 3 | 3.37 | 485.2 |
| 335 | H | H | CF$_3$ | H | H | H | 3 | 3.31 | 471.2 |
| 336 | F | H | CN | Et | H | CH$_3$ | 3 | 3.86 | 488.3 |
| 337 | H | CH$_3$ | CN | Et | H | CH$_3$ | 3 | 3.78 | 484.4 |
| 338 | H | CH$_3$ | CN | CH$_3$O | H | CH$_3$ | 3 | 3.54 | 486.4 |

TABLE 13b

IUPAC Names for Compounds in Table 13a

| Ex. No. | IUPAC Name |
|---|---|
| 321 | 2-[(1S)-5-(3-{[6-(3-fluoro-4-methoxyphenyl)-3-(trifluoromethyl)(2-pyridyl)]amino}propoxy)indanyl]acetic acid |
| 322 | 2-[(1S)-5-(3-{[6-(3,4-dimethoxyphenyl)-3-(trifluoromethyl)(2-pyridyl)]amino}propoxy)indanyl]acetic acid |
| 323 | 2-[(1S)-5-(3-{[6-(2H-benzo[3,4-d]1,3-dioxolan-5-yl)-3-(trifluoromethyl)(2-pyridyl)]amino}propoxy)indanyl]acetic acid |
| 324 | 2-[(1S)-5-(3-{[6-(4-fluorophenyl)-3-(trifluoromethyl)(2-pyridyl)]amino}propoxy)indanyl]acetic acid |
| 325 | 2-[(1S)-5-(3-{[6-(4-methylphenyl)-3-(trifluoromethyl)(2-pyridyl)]amino}propoxy)indanyl]acetic acid |
| 326 | 2-[(1S)-5-(3-{[6-phenyl-3-(trifluoromethyl)(2-pyridyl)]amino}propoxy)indanyl]acetic acid |
| 327 | 2-[(1S)-5-(2-{[6-(4-ethylphenyl)-3-(trifluoromethyl)(2-pyridyl)]amino}ethoxy)indanyl]acetic acid |
| 328 | 2-[(1S)-5-(3-{[6-(4-ethylphenyl)-3-(trifluoromethyl)(2-pyridyl)]methylamino}propoxy)indanyl]acetic acid |
| 329 | 2-[(1S)-5-(2-{[6-(4-ethylphenyl)-3-(trifluoromethyl)(2-pyridyl)]methylamino}ethoxy)indanyl]acetic acid |
| 330 | 2-[(1S)-5-(3-{[6-(3-fluoro-4-methoxyphenyl)-5-(trifluoromethyl)(2-pyridyl)]amino}propoxy)indanyl]acetic acid |
| 331 | 2-[(1S)-5-(3-{[6-(3,4-dimethoxyphenyl)-5-(trifluoromethyl)(2-pyridyl)]amino}propoxy)indanyl]acetic acid |
| 332 | 2-[(1S)-5-(3-{[6-(2H-benzo[3,4-d]1,3-dioxolan-5-yl)-5-(trifluoromethyl)(2-pyridyl)]amino}propoxy)indanyl]acetic acid |
| 333 | 2-[(1S)-5-(3-{[6-(4-fluorophenyl)-5-(trifluoromethyl)(2-pyridyl)]amino}propoxy)indanyl]acetic acid |
| 334 | 2-[(1S)-5-(3-{[6-(4-methylphenyl)-5-(trifluoromethyl)(2-pyridyl)]amino}propoxy)indanyl]acetic acid |
| 335 | 2-[(1S)-5-(3-{[6-phenyl-5-(trifluoromethyl)(2-pyridyl)]amino}propoxy)indanyl]acetic acid |
| 336 | 2-[(1S)-5-(3-{[5-cyano-6-(4-ethylphenyl)-3-fluoro(2-pyridyl)]methylamino}propoxy)indanyl]acetic acid |
| 337 | 2-[(1S)-5-(3-{[5-cyano-6-(4-ethylphenyl)-4-methyl(2-pyridyl)]methylamino}propoxy)indanyl]acetic acid |
| 338 | 2-[(1S)-5-(3-{[5-cyano-6-(4-methoxyphenyl)-4-methyl(2-pyridyl)]methylamino}propoxy)indanyl]acetic acid |

Example 339

Preparation of 3-[(2-chloro-5-methyl-4-pyrimidinyl)amino]-1-propanol

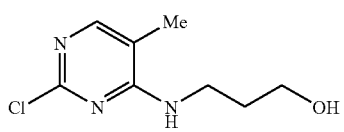

To a solution of 2,4-dichloro-5-methylpyrimidine (8.00 g, 49.1 mmol) and 3-amino-1-propanol (4.50 mL, 58.9 mmol) in ethanol (200 mL) was added sodium carbonate (26.0 g, 245 mmol). The solution was vigorously stirred at rt for 24 h. The mixture was filtered over Celite® and the filtrate concentrated under reduced pressure. The resulting solid was triturated with Et$_2$O to give the product as a white solid (9.80 g, 99%). $^1$H NMR (400 MHz, CDCl$_3$) δ 1.86 (qt, 2H), 2.00 (s, 3H), 3.55 (t, 2H), 3.64 (t, 2H), 4.92 (broad, 2H), 7.68 (s, 1H).

Example 340

Preparation of N-(3-{[tert-butyl(dimethyl)silyl]oxy}propyl)-2-chloro-5-methyl-4-pyrimidinamine

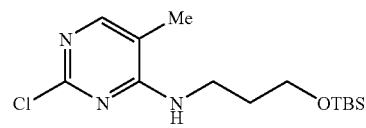

To a solution of 3-[(2-chloro-5-methyl-4-pyrimidinyl)amino]-1-propanol (Example 339, 5.00 g, 24.8 mmol) in CH$_2$Cl$_2$ (90 mL) was added Et$_3$N (3.80 mL, 27.3 mmol), followed by tert-butylsilylchloride (4.11 g, 27.3 mmol) and DMAP (60.0 mg, 0.50 mmol). The solution was stirred for 18 h at rt, and then diluted with brine. The aqueous phase was extracted with CH$_2$Cl$_2$. The combined organic layers were dried (Na$_2$SO$_4$), filtered, and then concentrated under reduced pressure to yield the product (6.85 g, 87%) as a colorless oil that solidified upon standing. $^1$H NMR (400 MHz, CDCl$_3$) δ 0.00 (s, 6H), 0.81 (s, 9H), 1.75 (qt, 2H), 1.85 (s, 3H), 3.52 (q, 2H), 3.72 (t, 2H), 5.74 (broad, 1H), 7.64 (s, 1H).

Example 341

Preparation of 3-[(2-chloro-5-methyl-4-pyrimidinyl)(methyl)amino]-1-propanol

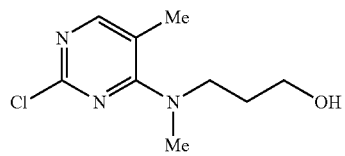

To a solution of N-(3-{[tert-butyl(dimethyl)silyl]oxy}propyl)-2-chloro-5-methyl-4-pyrimidinamine (Example 340, 5.00 g, 15.8 mmol) in DMF (60 mL) was added portionwise NaH (0.95 g, 60% dispersion in mineral oil, 23.7 mmol) [$H_2$ evolution]. The heterogeneous mixture was stirred for 30 min, then iodomethane (1.97 mL, 31.7 mmol) was added. After 3 h of stirring at rt, the excess NaH was quenched by the slow addition of a saturated solution of $NH_4Cl$ [$H_2$ evolution]. The product was extracted with $Et_2O$. The combined organic layers were then dried ($Na_2SO_4$), filtered, and concentrated under reduced pressure. The residue was purified using a pad of silica gel (3:1 hexanes/EtOAc) and the desired fractions were concentrated under reduced pressure. The resulting silyl derivative was dissolved in a mixture of ethanol (46 mL) and HCl (4.2 mL of a 2 N aqueous solution), and stirred at rt until the reaction was complete (6-10 h). The reaction mixture was then concentrated under reduced pressure, diluted with EtOAc, and washed with a saturated solution of $NaHCO_3$ and brine. The organic layer was dried ($MgSO_4$), filtered, and concentrated under reduced pressure. The residue was purified by silica gel chromatography (3:1 hexanes/EtOAc) to yield the title compound (1.22 g, 62%). $^1$H NMR (400 MHz, $CDCl_3$) δ 1.83 (qt, 2H), 2.32 (s, 3H), 3.19 (s, 3H), 3.56 (t, 2H), 3.69 (t, 2H), 7.70 (s, 1H).

Example 342

Preparation of ethyl ((1S)-5-{3-[(2-chloro-5-methyl-4-pyrimidinyl)(methyl)amino]propoxy}-2,3-dihydro-1H-inden-1-yl)acetate

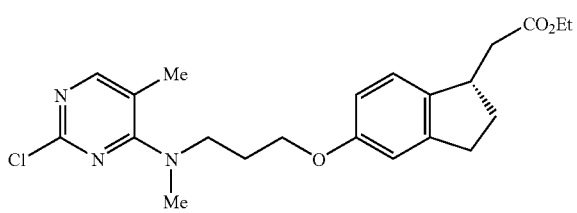

To a solution of 3-[(2-chloro-5-methyl-4-pyrimidinyl)(methyl)amino]-1-propanol (Example 341, 785 mg, 3.64 mmol) and ethyl [(1S)-5-hydroxy-2,3-dihydro-1H-inden-1-yl]acetate (Example 6, 401 mg, 1.82 mmol) in THF (17 mL) were added $PPh_3$ (954 mg, 3.64 mmol) and ADDP (918 mg, 3.64 mmol). The reaction mixture was vigorously stirred at rt for 24 h after which additional $PPh_3$ (954 mg, 3.64 mmol) and ADDP (918 mg, 3.64 mmol) were added. After an additional 24 h, the reaction mixture was concentrated under reduced pressure and the residue was purified by silica gel chromatography (3:1 hexanes/EtOAc) to give the product (586 mg, 77%) as a colorless oil. $^1$H NMR (400 MHz, $CDCl_3$) δ 1.26 (t, 3H), 1.71-1.76 (m, 1H), 2.06-2.11 (m, 2H), 2.26 (s, 3H), 2.34-2.42 (m, 2H), 2.67-2.88 (m, 3H), 3.15 (s, 3H), 3.49-3.50 (m, 1H), 3.70 (t, 2H), 3.94 (t, 2H), 4.13 (q, 2H), 6.64 (d, 1H), 6.70 (s, 1H), 7.02 (d, 1H), 7.75 (s, 1H).

Example 343

Preparation of ethyl ((1S)-5-{3-[[2-(4-ethylphenyl)-5-methyl-4-pyrimidinyl](methyl)amino]propoxy}-2,3-dihydro-1H-inden-1-yl)acetate

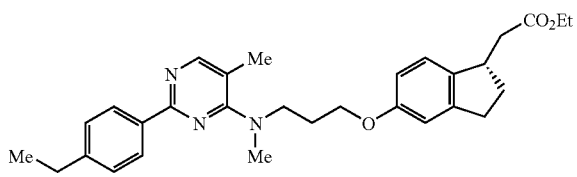

To a mixture of toluene (12 mL) and 1,4-dioxane (2.5 mL) were added ethyl ((1S)-5-{3-[(2chloro-5-methyl-4-pyrimidinyl)(methyl)amino]propoxy}-2,3-dihydro-1H-inden-1-yl)acetate (Example 342, 205 mg, 0.49 mmol), 4-ethylphenyl boronic acid (294 mg, 1.96 mmol), and $PdCl_2(dppf).CH_2Cl_2$ (35.9 mg, 0.05 mmol). A flow of argon was passed through the reaction mixture for 30 min, then $Na_2CO_3$ (2.45 mL, 4.91 mmol, 2 M aqueous solution) was added, and the reaction was stirred at 75° C. for 18 h. After cooling to rt, the reaction mixture was diluted with EtOAc, and washed with a saturated aqueous solution of $NaHCO_3$. The organic layer was then dried ($Na_2SO_4$), filtered, and then concentrated under reduced pressure. The residue was purified by silica gel flash chromatography (4:1 hexanes/EtOAc) to provide the product (140 mg, 59%) as a colorless oil. $^1$H NMR (400 MHz, $CDCl_3$) δ 1.26-1.32 (m, 6H), 1.73-1.80 (m, 1H), 2.16-2.19 (m, 2H), 2.33 (s, 3H), 2.35-2.42 (m, 2H), 2.67-2.88 (m, 5H), 3.22 (s, 3H), 3.51-3.55 (m, 1H), 3.79 (t, 2H), 4.00 (t, 2H), 4.19 (q, 2H), 6.69 (d, 1H), 6.75 (s, 1H), 7.04 (d, 1H), 7.26 (d, 2H), 8.08 (s, 1H), 8.30 (d, 2H).

Example 344

Preparation of ((1S)-5-{3-[[2-(4-ethylphenyl)-5-methyl-4-pyrimidinyl](methyl)amino]propoxy}-2,3-dihydro-1H-inden-1-yl)acetic acid

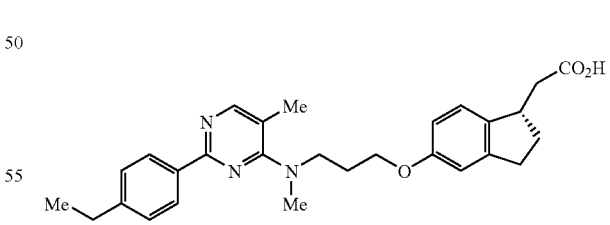

To a solution of ethyl ((1S)-5-{3-[[2-(4-ethylphenyl)-5-methyl-4-pyrimidinyl](methyl)amino]propoxy}-2,3-dihydro-1H-inden-1-yl)acetate (Example 343,140 mg, 0.290 mmol) in a mixture of THF (5 mL), water (5 mL), and EtOH (2.5 mL) was added LiOH (27.5 mg, 1.15 mmol). After vigorously stirring for 24 h, the reaction mixture was acidified to pH ~5 using HCl (1 N aqueous solution) and extracted with $CH_2Cl_2$. The combined organic layers were dried ($Na_2SO_4$), filtered, and then concentrated under reduced pressure to give the product (118 mg, 89%) as a white foam. $^1$H NMR (400 MHz, acetone-$d_6$) δ 1.26 (t, 3H), 1.70-1.76 (m, 1H), 2.18-2.21 (m, 2H), 2.37 (s, 3H), 2.33-2.42 (m, 2H), 2.67-2.85 (m, 5H), 3.28 (s, 3H), 3.44-3.45 (m, 1H), 3.86 (t, 2H), 4.07 (t, 2H), 6.71 (d, 1H), 6.78 (s, 1H), 7.12 (d, 1H), 7.27 (d, 2H), 8.08 (s, 1H), 8.35 (d, 2H); LC-MS: RT=2.53 min, (M+H)$^+$ 460.4.

Example 345

Preparation of ethyl((1S)-5-{3-[[2-(3-methoxyphenoxy)-5-methyl-4-pyrimidinyl](methyl)amino]propoxy}-2,3-dihydro-1H-inden-1-yl)acetate

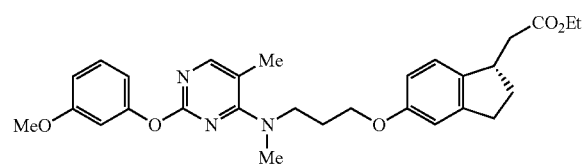

To a suspension of K$_2$CO$_3$ (132 mg, 0.96 mmol) in DMF (5 mL) was added 3-methoxyphenol (36 mg, 0.290 mmol), followed by the portionwise addition of ethyl((1S)-5-{3-[(2-chloro-5-methyl-4-pyrimidinyl)(methyl)amino]propoxy}-2,3-dihydro-1H-inden-1-yl)acetate prepared in Example 342. The reaction mixture was stirred at 80° C. for 48 h, and then concentrated under reduced pressure. The residue was purified by silica gel flash chromatography to yield the title compound (56.5 mg, 47%) as a yellow oil. $^1$H NMR (400 MHz, CDCl$_3$) δ 1.29 (t, 3H), 1.71-1.83 (m, 1H), 2.02 (m, 2H), 2.28 (s, 3H), 2.35-2.47 (m, 2H), 2.75 (dd, 1H), 2.79-2.96 (m, 2H), 3.15 (s, 3H), 3.49-3.57 (m, 1H), 3.56-3.61 (m, 2H), 3.78 (s, 3H), 3.81 (t, 2H), 4.19 (q, 2H), 6.64 (dd, 1H), 6.69-6.78 (m, 3H), 7.05 (d, 1H), 7.21-7.27 (m, 2H), 7.80 (s, 1H); LC-MS: RT=2.85 min, (M+H)+506.3.

Example 346

((1S)-5-{3-[[2-(3-methoxyphenoxy)-5-methyl-4-yrimidinyl](methyl)amino]propoxy}-2,3-dihydro-1H-inden-1-yl)acetic acid

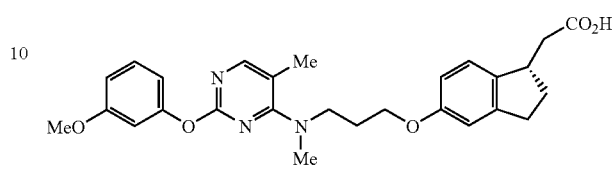

To a solution of ethyl((1S)-5-{3-[[2-(3-methoxyphenoxy)-5-methyl-4-pyrimidinyl](methyl)amino]propoxy}-2,3-dihydro-1H-inden-1-yl)acetate (Example 345, 29 mg, 0.057 mmol) in a mixture of THF (2 mL), water (2 mL), and ethanol (2 mL) was added LiOH (5.7 mg, 0.23 mmol), and the mixture was agitated in an orbital shaker for 16 h. The reaction mixture was washed with Et$_2$O, then acidified to pH 5 using HCl (1 N aqueous solution). The aqueous phases was extracted with EtOAc, and the combined organic phases were dried (Na$_2$SO$_4$), filtered, and concentrated under reduced pressure. The residue was purified by silica gel flash chromatography (1:1 hexanes/EtOAc) to provide the title compound (20.5 mg, 74%) as a white solid). 1H NMR (400 MHz, CDCl$_3$) δ 1.75-1.86 (m, 1H), 1.93-2.01 (m, 2H), 2.29 (s, 3H), 2.38-2.62 (m, 2H), 2.79 (dd, 1H), 2.81-2.98 (m, 2H), 3.15 (s, 3H), 3.50-3.60 (m, 3H), 3.77 (s, 3H), 3.78 (q, 2H), 6.62 (dd, 1H), 6.67-6.76 (m, 4H), 7.09 (d, 1H), 7.21-7.28 (m, 2H), 7.82 (s, 1H); LC-MS: RT=2.39 min, (M+H)$^+$ 478.5.

By using the methods described above for Examples 339-346 and by substituting the appropriate starting materials, compounds of Formula (Ixx) and (Iyy), listed in Table 14a and Table 15a below, were similarly prepared.

TABLE 14a (Ixx)

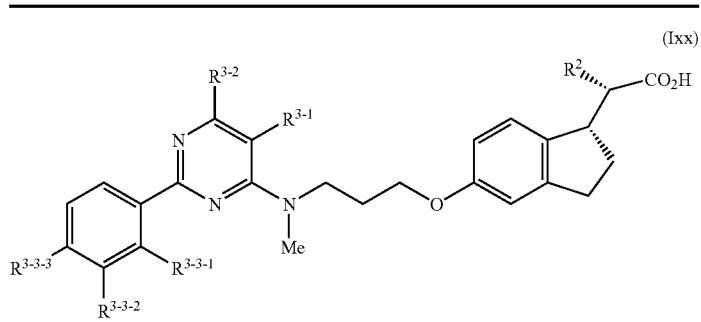

| Ex. No. | $R^2$ | $R^{3-1}$ | $R^{3-2}$ | $R^{3-3-1}$ | $R^{3-3-2}$ | $R^{3-3-3}$ | LCMS (M + H) | RT (min) |
|---|---|---|---|---|---|---|---|---|
| 347 | H | H | H | H | H | Me | 432.2 | 2.41 |
| 348 | H | H | H | H | H | Et | 446.4 | 2.27 |
| 349 | H | H | H | H | H | F | 436.3 | 2.27 |
| 350 | H | H | H | H | —O—CH$_2$—O— | | 462.3 | 2.25 |
| 351 | H | H | H | H | H | EtO | 462.3 | 2.50 |
| 352 | H | H | H | H | H | MeO | 448.4 | 2.30 |
| 353 | H | H | H | H | MeO | MeO | 478.4 | 2.20 |
| 354 | H | H | H | H | H | Ac | 460.3 | 2.31 |

TABLE 14a-continued (Ixx)

| Ex. No. | $R^2$ | $R^{3-1}$ | $R^{3-2}$ | $R^{3-3-1}$ | $R^{3-3-2}$ | $R^{3-3-3}$ | LCMS (M + H) | RT (min) |
|---|---|---|---|---|---|---|---|---|
| 355 | H | Me | H | H | H | F | 450.2 | 2.44 |
| 356 | H | Me | H | H | —O—CH$_2$—O— | | 476.3 | 2.43 |
| 357 | H | Me | H | H | H | MeO | 462.3 | 2.44 |
| 358 | H | Me | H | H | H | Me | 446.4 | 2.38 |
| 359 | H | Me | H | H | H | t-Bu | 488.5 | 2.64 |
| 360 | H | Me | H | H | F | Me | 464.4 | 2.43 |
| 361 | H | Me | H | H | EtO | H | 476.4 | 2.41 |
| 362 | H | Me | H | H | MeO | MeO | 492.4 | 2.27 |
| 363 | H | Me | H | H | Me | Me | 460.3 | 2.46 |
| 364 | H | Me | H | H | H | i-Pr | 474.5 | 2.56 |
| 365 | H | Me | H | H | H | EtO | 476.4 | 2.43 |
| 366 | H | Me | H | H | H | Ac | 474.3 | 2.25 |
| 367 | H | Me | H | H | H | H | 432.4 | 2.27 |
| 368 | H | Me | H | H | Me | H | 446.3 | 2.38 |
| 369 | H | Me | H | H | Cl | H | 466.4 | 3.18 |
| 370 | H | Me | H | H | H | Cl | 466.3 | 2.43 |
| 371 | Me | Me | H | H | H | Et | 474.5 | 2.59 |
| 372 | Me | Me | H | H | H | MeO | 476.5 | 2.44 |
| 373 | Me | Me | H | H | H | Cl | 480.4 | 2.55 |
| 374 | Me | Me | H | H | —O—CH$_2$—O— | | 490.5 | 2.40 |
| 375 | H | F | H | H | H | MeO | 466.4 | 2.57 |
| 376 | H | F | H | H | H | CF$_3$ | 504.4 | 3.58 |
| 377 | H | F | H | H | H | i-Pr | 478.4 | 3.01 |
| 378 | H | F | H | H | H | Ac | 478.4 | 3.00 |
| 379 | H | F | H | H | H | Cl | 470.3 | 3.28 |
| 380 | H | F | H | H | H | H | 436.2 | 2.88 |
| 381 | H | F | H | H | H | CF$_3$O | 520.2 | 3.64 |
| 382 | H | F | H | H | H | EtO | 480.3 | 2.83 |
| 383 | H | F | H | H | H | Me | 450.2 | 2.93 |
| 384 | H | F | H | H | H | F | 454.2 | 3.20 |
| 385 | H | F | H | H | H | Et | 464.3 | 3.06 |
| 386 | H | F | H | H | —O—CH$_2$—O— | | 480.4 | 2.66 |
| 387 | H | Et | H | H | H | F | 464.3 | 2.49 |
| 388 | H | Et | H | H | H | Et | 474.5 | 2.61 |
| 389 | H | Et | H | H | —O—CH$_2$—O— | | 490.4 | 2.43 |
| 390 | H | H | Me | H | H | Et | 460.3 | 2.56 |
| 391 | H | H | Me | H | H | i-Pr | 474.3 | 2.62 |
| 392 | H | H | Me | H | H | EtO | 476.3 | 2.53 |
| 393 | H | H | Me | H | H | Cyclohexyl | 514.4 | 2.97 |
| 394 | H | H | Me | H | H | n-butyl | 488.6 | 2.69 |
| 395 | H | H | Me | H | H | Me | 448.3 | 2.46 |
| 396 | H | H | Me | H | H | t-Bu | 448.3 | 2.30 |
| 397 | H | H | Me | H | H | Ac | 474.3 | 2.30 |
| 398 | H | H | Me | H | —O—CH$_2$—O— | | 476.3 | 2.36 |
| 399 | H | H | Me | H | H | F | 450.4 | 2.29 |
| 400 | H | H | Me | F | H | H | 450.4 | 2.22 |

TABLE 14b

IUPAC Names for Compounds in Table 14a

| Ex. No. | IUPAC Name |
|---|---|
| 347 | 2-[(1S)-5-(3-{[2-(4-methylphenyl)pyrimidin-4-yl]methylamino}propoxy)indanyl]acetic acid |
| 348 | 2-[(1S)-5-(3-{[2-(4-ethylphenyl)pyrimidin-4-yl]methylamino}propoxy)indanyl]acetic acid |
| 349 | 2-[(1S)-5-(3-{[2-(4-fluorophenyl)pyrimidin-4-yl]methylamino}propoxy)indanyl]acetic acid |

TABLE 14b-continued

IUPAC Names for Compounds in Table 14a

| Ex. No. | IUPAC Name |
|---|---|
| 350 | 2-((1S)-5-{3-[(2-(2H-benzo[3,4-d]1,3-dioxolan-5-yl)pyrimidin-4-yl)methyl amino]propoxy}indanyl)acetic acid |
| 351 | 2-[(1S)-5-(3-{[2-(4-ethoxyphenyl)pyrimidin-4-yl]methylamino}propoxy) indanyl]acetic acid |
| 352 | 2-[(1S)-5-(3-{[2-(4-methoxyphenyl)pyrimidin-4-yl]methylamino}propoxy) indanyl]acetic acid |
| 353 | 2-[(1S)-5-(3-{[2-(3,4-dimethoxyphenyl)pyrimidin-4-yl]methylamino}propoxy) indanyl]acetic acid |
| 354 | 2-[(1S)-5-(3-{[2-(4-acetylphenyl)pyrimidin-4-yl]methylamino}propoxy) indanyl]acetic acid |
| 355 | 2-[(1S)-5-(3-{[2-(4-fluorophenyl)-5-methylpyrimidin-4-yl]methylamino}propoxy) indanyl]acetic acid |
| 356 | 2-((1S)-5-{3-[(2-(2H-benzo[3,4-d]1,3-dioxolan-5-yl)-5-methylpyrimidin-4-yl) methylamino]propoxy}indanyl)acetic acid |
| 357 | 2-[(1S)-5-(3-{[2-(4-methoxyphenyl)-5-methylpyrimidin-4-yl]methylamino} propoxy)indanyl]acetic acid |
| 358 | 2-[(1S)-5-(3-{methyl[5-methyl-2-(4-methylphenyl)pyrimidin-4-yl]amino} propoxy)indanyl]acetic acid |
| 359 | 2-{(1S)-5-[3-({2-[4-(tert-butyl)phenyl]-5-methylpyrimidin-4-yl}methylamino) propoxy]indanyl}acetic acid |
| 360 | 2-[(1S)-5-(3-{[2-(3-fluoro-4-methylphenyl)-5-methylpyrimidin-4-yl]methylamino} propoxy)indanyl]acetic acid |
| 361 | 2-[(1S)-5-(3-{[2-(3-ethoxyphenyl)-5-methylpyrimidin-4-yl]methylamino} propoxy)indanyl]acetic acid |
| 362 | 2-[(1S)-5-(3-{[2-(3,4-dimethoxyphenyl)-5-methylpyrimidin-4-yl]methylamino} propoxy)indanyl]acetic acid |
| 363 | 2-[(1S)-5-(3-{[2-(3,4-dimethylphenyl)-5-methylpyrimidin-4-yl]methylamino} propoxy)indanyl]acetic acid |
| 364 | 2-{(1S)-5-[3-(methyl{5-methyl-2-[4-(methylethyl)phenyl]pyrimidin-4-yl}amino) propoxy]indanyl}acetic acid |
| 365 | 2-[(1S)-5-(3-{[2-(4-ethoxyphenyl)-5-methylpyrimidin-4-yl]methylamino} propoxy)indanyl]acetic acid |
| 366 | 2-[(1S)-5-(3-{[2-(4-acetylphenyl)-5-methylpyrimidin-4-yl]methylamino} propoxy)indanyl]acetic acid |
| 367 | 2-((1S)-5-{3-[methyl(5-methyl-2-phenylpyrimidin-4-yl)amino]propoxy}indanyl) acetic acid |
| 368 | 2-[(1S)-5-(3-{methyl[5-methyl-2-(3-methylphenyl)pyrimidin-4-yl]amino} propoxy)indanyl]acetic acid |
| 369 | 2-[(1S)-5-(3-{[2-(3-chlorophenyl)-5-methylpyrimidin-4-yl]methylamino} propoxy)indanyl]acetic acid |
| 370 | 2-[(1S)-5-(3-{[2-(4-chlorophenyl)-5-methylpyrimidin-4-yl]methylamino} propoxy)indanyl]acetic acid |
| 371 | (2S)-2-[(1S)-5-(3-{[2-(4-ethylphenyl)-5-methylpyrimidin-4-yl]methylamino} propoxy)indanyl]propanoic acid |
| 372 | (2S)-2-[(1S)-5-(3-{[2-(4-methoxyphenyl)-5-methylpyrimidin-4-yl]methylamino} propoxy)indanyl]propanoic acid |
| 373 | (2S)-2-[(1S)-5-(3-{[2-(4-chlorophenyl)-5-methylpyrimidin-4-yl]methylamino} propoxy)indanyl]propanoic acid |
| 374 | (2S)-2-((1S)-5-{3-[(2-(2H-benzo[3,4-d]1,3-dioxolan-5-yl)-5-methylpyrimidin-4-yl)methylamino]propoxy}indanyl)propanoic acid |
| 375 | 2-[(1S)-5-(3-{[5-fluoro-2-(4-methoxyphenyl)pyrimidin-4-yl]methylamino} propoxy)indanyl]acetic acid |
| 376 | 2-{(1S)-5-[3-({5-fluoro-2-[4-(trifluoromethyl)phenyl]pyrimidin-4-yl}methyl amino)propoxy]indanyl}acetic acid |
| 377 | 2-{(1S)-5-[3-({5-fluoro-2-[4-(methylethyl)phenyl]pyrimidin-4-yl}methylamino) propoxy]indanyl}acetic acid |
| 378 | 2-[(1S)-5-(3-{[2-(4-acetylphenyl)-5-fluoropyrimidin-4-yl]methylamino}propoxy) indanyl]acetic acid |
| 379 | 2-[(1S)-5-(3-{[2-(4-chlorophenyl)-5-fluoropyrimidin-4-yl]methylamino} propoxy)indanyl]acetic acid |
| 380 | ((1S)-5-{3-[(5-fluoro-2-phenyl-4-pyrimidinyl)(methyl)amino]propoxy}-2,3-dihydro-1H-inden-1-yl)acetic acid |
| 381 | 2-{(1S)-5-[3-({5-fluoro-2-[4-(trifluoromethoxy)phenyl]pyrimidin-4-yl}methyl amino)propoxy]indanyl}acetic acid |
| 382 | 2-[(1S)-5-(3-{[2-(4-ethoxyphenyl)-5-fluoropyrimidin-4-yl]methylamino} propoxy)indanyl]acetic acid |
| 383 | 2-[(1S)-5-(3-{[5-fluoro-2-(4-methylphenyl)pyrimidin-4-yl]methylamino} propoxy)indanyl]acetic acid |
| 384 | 2-[(1S)-5-(3-{[5-fluoro-2-(4-fluorophenyl)pyrimidin-4-yl]methylamino} propoxy)indanyl]acetic acid |
| 385 | 2-[(1S)-5-(3-{[2-(4-ethylphenyl)-5-fluoropyrimidin-4-yl]methylamino} propoxy)indanyl]acetic acid |
| 386 | 2-((1S)-5-{3-[(2-(2H-benzo[3,4-d]1,3-dioxolan-5-yl)-5-fluoropyrimidin-4-yl) methylamino]propoxy}indanyl)acetic acid |

TABLE 14b-continued

IUPAC Names for Compounds in Table 14a

| Ex. No. | IUPAC Name |
|---|---|
| 387 | ((1S)-5-{3-[[5-ethyl-2-(4-fluorophenyl)-4-pyrimidinyl](methyl)amino]propoxy}-2,3-dihydro-1H-inden-1-yl)acetic acid |
| 388 | 2-[(1S)-5-(3-{[5-ethyl-2-(4-ethylphenyl)pyrimidin-4-yl]methylamino}propoxy)indanyl]acetic acid |
| 389 | 2-((1S)-5-{3-[(2-(2H-benzo[3,4-d]1,3-dioxolan-5-yl)-5-ethylpyrimidin-4-yl)methylamino]propoxy}indanyl)acetic acid |
| 390 | ((1S)-5-{3-[[2-(4-ethylphenyl)-6-methyl-4-pyrimidinyl](methyl)amino]propoxy}-2,3-dihydro-1H-inden-1-yl)acetic acid |
| 391 | 2-{(1S)-5-[3-(methyl{6-methyl-2-[4-(methylethyl)phenyl]pyrimidin-4-yl}amino)propoxy]indanyl}acetic acid |
| 392 | 2-[(1S)-5-(3-{[2-(4-ethoxyphenyl)-6-methylpyrimidin-4-yl]methylamino}propoxy)indanyl]acetic acid |
| 393 | 2-[(1S)-5-(3-{[2-(4-cyclohexylphenyl)-6-methylpyrimidin-4-yl]methylamino}propoxy)indanyl]acetic acid |
| 394 | 2-[(1S)-5-(3-{[2-(4-butylphenyl)-6-methylpyrimidin-4-yl]methylamino}propoxy)indanyl]acetic acid |
| 395 | 2-[(1S)-5-(3-{methyl[6-methyl-2-(4-methylphenyl)pyrimidin-4-yl]amino}propoxy)indanyl]acetic acid |
| 396 | 2-{(1S)-5-[3-({2-[4-(tert-butyl)phenyl]-6-methylpyrimidin-4-yl}methylamino)propoxy]indanyl}acetic acid |
| 397 | 2-[(1S)-5-(3-{[2-(4-acetylphenyl)-6-methylpyrimidin-4-yl]methylamino}propoxy)indanyl]acetic acid |
| 398 | 2-((1S)-5-{3-[(2-(2H-benzo[3,4-d]1,3-dioxolan-5-yl)-6-methylpyrimidin-4-yl)methylamino]propoxy}indanyl)acetic acid |
| 399 | 2-[(1S)-5-(3-{[2-(4-fluorophenyl)-6-methylpyrimidin-4-yl]methylamino}propoxy)indanyl]acetic acid |
| 400 | 2-[(1S)-5-(3-{[2-(2-fluorophenyl)-6-methylpyrimidin-4-yl]methylamino}propoxy)indanyl]acetic acid |

TABLE 15a (Iyy)

| Ex. No. | $R^{3-1}$ | $R^{3-3}$ | LCMS (M + H) | RT (min) |
|---|---|---|---|---|
| 401 | H | Cl | 390.3 | 3.46 |
| 402 | Me | 3-thienyl | 438.3 | 2.25 |
| 403 | Me | 4-MeO—Ph—O | 478.5 | 2.35 |
| 404 | Me | 4-F—Ph—O | 466.4 | 2.41 |
| 405 | Me | 3-F—Ph—O | 478.5 | 2.39 |
| 406 | H | 2-benzofuryl | 458.3 | 2.45 |
| 407 | F | 2-benzofuryl | 476.4 | 3.10 |

TABLE 15b

IUPAC Names for Compounds in Table 15a

| Ex. No. | IUPAC Name |
|---|---|
| 401 | ((1S)-5-{3-[(2-chloro-4-pyrimidinyl)(methyl)amino]propoxy}-2,3-dihydro-1H-inden-1-yl)acetic acid |
| 402 | 2-((1S)-5-{3-[methyl(5-methyl-2-(3-thienyl)pyrimidin-4-yl)amino]propoxy}indanyl)acetic acid |
| 403 | ((1S)-5-{3-[[2-(4-methoxyphenoxy)-5-methyl-4-pyrimidinyl](methyl)amino]propoxy}-2,3-dihydro-1H-inden-1-yl)acetic acid |
| 404 | ((1S)-5-{3-[[2-(4-fluorophenoxy)-5-methyl-4-pyrimidinyl](methyl)amino]propoxy}-2,3-dihydro-1H-inden-1-yl)acetic acid |
| 405 | ((1S)-5-{3-[[2-(3-methoxyphenoxy)-5-methyl-4-pyrimidinyl](methyl)amino]propoxy}-2,3-dihydro-1H-inden-1-yl)acetic acid |
| 406 | 2-((1S)-5-{3-[(2-benzo[d]furan-2-ylpyrimidin-4-yl)methylamino]propoxy}indanyl)acetic acid |
| 407 | 2-((1S)-5-{3-[(2-benzo[d]furan-2-yl-5-fluoropyrimidin-4-yl)methylamino]propoxy}indanyl)acetic acid |

Example 408

Preparation of ethyl((1S)-5-{3-[(2-chloro-5-methyl-4-pyrimidinyl)amino]propoxy}-2,3-dihydro-1H-inden-1-yl)acetate

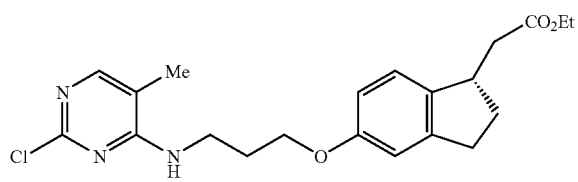

To a solution of 3-[(2-chloro-5-methyl-4-pyrimidinyl)amino]-1-propanol (Example 339, 1.77 g, 8.81 mmol) and ethyl[(1S)-5-hydroxy-2,3-dihydro-1H-inden-1-yl]acetate Example 6, 970 mg, 8.81 mmol) in THF (33 mL) were added PPh$_3$ (2.31 g, 8.81 mmol) and ADDP (2.22 g, 8.81 mmol). The reaction mixture was vigorously stirred at rt for 24 h, after which additional amounts of PPh$_3$ (2.31 g, 8.81 mmol) and ADDP (2.22 g, 8.81 mmol) were added. After an additional 24 h, the reaction mixture was diluted with hexanes, filtered through Celite®, and the filtrate concentrated under reduced pressure. The residue was then purified by silica gel chromatography (2:1 to 1:1 hexanes/EtOAc) to give the product (1.70 g, 99%). $^1$H NMR (400 MHz, CDCl$_3$) δ 1.29 (t, 3H), 1.75-1.80 (m, 1H), 2.02 (s, 3H), 2.12-2.18 (m, 2H), 2.38-2.46 (m, 2H), 2.72 (dd, 1H), 2.84-2.2.92 (m, 2H), 3.52-3.55 (m, 1H), 3.73 (q, 2H), 4.13 (t, 2H), 4.18 (q, 2H), 6.70 (d, 1H), 6.77 (s, 1H), 7.08 (d, 1H), 7.78 (s, 1H).

Example 409

Preparation of ethyl((1S)-5-{3-[(2-chloro-5-methyl-4-pyrimidinyl)(propyl)amino]propoxy}-2,3-dihydro-1H-inden-1-yl)acetate

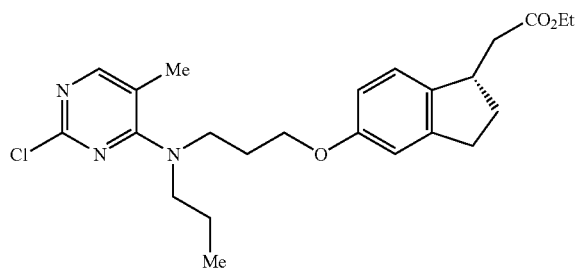

To a solution of ethyl((1S)-5-{3-[(2-chloro-5-methyl-4-pyrimidinyl)amino]propoxy}-2,3-dihydro-1H-inden-1-yl)acetate (Example 408, 800 mg, 0.25 mmol) in DMF (20 mL) was added portion wise NaH (118 mg, 2.97 mmol, 60% dispersion in mineral oil) [H$_2$ evolution]. The heterogeneous mixture was stirred for 30 min, then iodopropane (0.39 mL, 3.96 mmol) was added. After 18 h of stirring at rt, the excess NaH was quenched by the slow addition of brine (40 mL) [H$_2$ evolution]. The product was then extracted with Et$_2$O. The combined organic layers were dried (Na$_2$SO$_4$), filtered, and then concentrated under reduced pressure. The residue was purified by silica gel chromatography (4:1 hexanes/EtOAc) to yield the product (403 mg, 46%). $^1$H NMR (400 MHz, CDCl$_3$) δ 0.93 (t, 3H), 1.30 (t, 3H), 1.65 (t, 2H), 1.74-1.79 (m, 1H), 2.06-2.11 (m, 2H) 2.27 (s, 3H), 2.37-2.45 (m, 2H), 2.70-2.74 (dd, 1H), 2.84-2.91 (m, 2H), 3.45-3.55 (m, 3H), 3.73 (t, 2H), 3.97 (t, 2H), 4.16 (q, 2H), 6.68 (d, 1H), 6.6.74 (s, 1H), 7.05 (d, 1H), 7.79 (s, 1H).

Example 410

Preparation of ((1S)-5-{3-[[2(4-ethylphenyl)-5-methyl-4-pyrimidinyl](propyl)amino]propoxy}-2,3-dihydro-1H-inden-1-yl)acetic acid

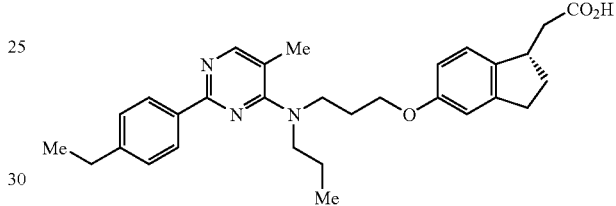

To a mixture of toluene (2.8 mL) and 1,4dioxane (0.56 mL) were added ethyl ((1S)-5-{3-[(2-chloro-5-methyl-4-pyrimidinyl)(propyl)amino]propoxy}-2,3-dihydro-1-H-inden-1-yl)acetate (Example 409, 50 mg, 0.11 mmol), 4-ethylphenyl boronic acid (67.3 mg, 0.45 mmol), and PdCl$_2$(dppf).CH$_2$Cl$_2$ (8.2 mg, 0.01 mmol). A flow of argon was passed through the reaction mixture for 30 min, then Na$_2$CO$_3$ (0.56 mL, 1.12 mmol, 2 M aqueous solution) was added, and the reaction was stirred at 75° C. for 18 h. The reaction mixture was cooled to rt, and then concentrated under reduced pressure. The residue was partly purified by preparative HPLC. The resulting crude ester was dissolved in a mixture of THF (2 mL), water (2 mL), and EtOH (1.0 mL), and then LiOH (24.2 mg, 1.01 mmol) was added. The reaction mixture was vigorously stirred for 18 h, acidified to pH ~5 using HCl (1N aqueous solution), and the aqueous phase was extracted with CH$_2$Cl$_2$. The combined organic phases were dried (Na$_2$SO$_4$), filtered, and concentrated under reduced pressure to give the product (11.5 mg, 21%). $^1$H NMR (400 MHz, CDCl$_3$) δ 0.93 (t, 3H), 1.27 (t, 3H), 1.69 (q, 2H), 1.76-1.81 (m, 1H), 2.13-2.16 (m, 2H) 2.30 (s, 3H), 2.40-2.51 (m, 2H), 2.68-2.85 (m, 5H), 3.47-3.55 (m, 3H), 3.80 (t, 2H), 3.98 (t, 2H), 6.66 (d, 1H), 6.71 (s, 1H), 7.07 (d, 1H), 7.267 (d, 2H), 8.05 (s, 1H), 8.22 (d, 2H); LC-MS: RT=3.38 min, (M+H)$^+$ 488.4.

By using the methods described above for Examples 408-410 and by substituting the appropriate starting materials, compounds of Formula (Izz), listed in Table 16a below, were similarly prepared.

TABLE 16a

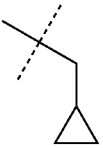

(Izz)

| Ex. No. | R[5] | R[3-1] | R[3-2] | R[3-3] | LCMS (M + H) | RT (min) |
|---|---|---|---|---|---|---|
| 411 | H | H | Ph | H | 404.3 | 2.11 |
| 412 | H | H | H | 4-MePh | 418.4 | 3.02 |
| 413 | H | Me | H | 4-Et—Ph | 446.3 | 2.46 |
| 414 | H | Me | H | 4-MePh | 432.3 | 2.46 |
| 415 | H | Me | H | 4-MeOPh | 448.4 | 2.30 |
| 416 | H | Me | H | 3,4-dioxolane-Ph | 462.3 | 2.25 |
| 417 | H | Me | H | 3-thienyl | 424.3 | 2.20 |
| 418 | H | Me | H | 4-F—Ph | 436.3 | 2.28 |
| 419 | H | Me | H | 3-MePh | 432.3 | 2.34 |
| 420 | H | Me | H | 3-MeO—Ph | 448.3 | 2.29 |
| 421 | H | Me | H | 4-CF$_3$—Ph | 486.3 | 2.48 |
| 422 | n-Pr | Me | H | 4-Me—Ph | 474.4 | 3.29 |
| 423 | n-Pr | Me | H | 4-MeO—Ph | 490.4 | 3.24 |
| 424 | n-Pr | Me | H | 3,4-dioxolane-Ph | 504.4 | 3.20 |
| 425 | n-Pr | Me | H | 3-thienyl | 466.3 | 3.17 |
| 426 | n-Pr | Me | H | 4-F—Ph | 478.4 | 3.24 |
| 427 | n-Pr | Me | H | 3-Me—Ph | 474.4 | 3.29 |
| 428 | n-Pr | H | H | 4-Me—Ph | 460.3 | 2.65 |
| 429 | n-Pr | H | H | 4-Et—Ph | 474.3 | 2.77 |
| 430 | n-Pr | H | H | 3,4-dioxolane-Ph | 490.3 | 2.53 |
| 431 | n-Pr | H | H | 4-MeO—Ph | 476.5 | 2.46 |
| 432 | CH$_2$-cyclopropyl | H | H | 4-Et | 500.5 | 2.74 |
| 433 | Et | Me | H | 4-Et—Ph | 474.5 | 2.61 |
| 434 | Et | Me | H | 4-Me—Ph | 460.4 | 2.52 |
| 435 | Et | Me | H | 3,4-dioxolane-Ph | 490.4 | 2.42 |
| 436 | Ac | Me | H | 4-Et—Ph | 488.1 | 3.35 |
| 437 | Ac | Me | H | 3,4-dioxolane-Ph | 504.2 | 2.92 |

TABLE 16b

IUPAC Names for Compounds in Table 16a

| Ex. No. | IUPAC Name |
|---|---|
| 411 | ((1S)-5-{3-[(6-phenyl-4-pyrimidinyl)amino]propoxy}-2,3-dihydro-1H-inden-1-yl)acetic acid |
| 412 | 2-[(1S)-5-(3-{[2-(4-methylphenyl)pyrimidin-4-yl]amino}propoxy)indanyl]acetic acid |
| 413 | 2-[(1S)-5-(3-{[2-(4-ethylphenyl)-5-methylpyrimidin-4-yl]amino}propoxy)indanyl]acetic acid |
| 414 | 2-[(1S)-5-(3-{[5-methyl-2-(4-methylphenyl)pyrimidin-4-yl]amino}propoxy)indanyl]acetic acid |
| 415 | 2-[(1S)-5-(3-{[2-(4-methoxyphenyl)-5-methylpyrimidin-4-yl]amino}propoxy)indanyl]acetic acid |
| 416 | 2-((1S)-5-{3-[(2-(2H-benzo[3,4-d]1,3-dioxolan-5-yl)-5-methylpyrimidin-4-yl)amino]propoxy}indanyl)acetic acid |
| 417 | 2-((1S)-5-{3-[(5-methyl-2-(3-thienyl)pyrimidin-4-yl)amino]propoxy}indanyl)acetic acid |
| 418 | 2-[(1S)-5-(3-{[2-(4-fluorophenyl)-5-methylpyrimidin-4-yl]amino}propoxy)indanyl]acetic acid |
| 419 | 2-[(1S)-5-(3-{[5-methyl-2-(3-methylphenyl)pyrimidin-4-yl]amino}propoxy)indanyl]acetic acid |
| 420 | 2-[(1S)-5-(3-{[2-(3-methoxyphenyl)-5-methylpyrimidin-4-yl]amino}propoxy)indanyl]acetic acid |

TABLE 16b-continued

IUPAC Names for Compounds in Table 16a

| Ex. No. | IUPAC Name |
|---|---|
| 421 | 2-{(1S)-5-[3-({5-methyl-2-[4-(trifluoromethyl)phenyl]pyrimidin-4-yl}amino)propoxy]indanyl}acetic acid |
| 422 | 2-[(1S)-5-(3-{[5-methyl-2-(4-methylphenyl)pyrimidin-4-yl]propylamino}propoxy)indanyl]acetic acid |
| 423 | ((1S)-5-{3-[[2-(4-methoxyphenyl)-5-methyl-4-pyrimidinyl](propyl)amino]propoxy}-2,3-dihydro-1H-inden-1-yl)acetic acid |
| 424 | 2-((1S)-5-{3-[(2-(2H-benzo[3,4-d]1,3-dioxolan-5-yl)-5-methylpyrimidin-4-yl)propylamino]propoxy}indanyl)acetic acid |
| 425 | 2-((1S)-5-{3-[(5-methyl-2-(3-thienyl)pyrimidin-4-yl)propylamino]propoxy}indanyl)acetic acid |
| 426 | 2-[(1S)-5-(3-{[2-(4-fluorophenyl)-5-methylpyrimidin-4-yl]propylamino}propoxy)indanyl]acetic acid |
| 427 | 2-[(1S)-5-(3-{[5-methyl-2-(3-methylphenyl)pyrimidin-4-yl]propylamino}propoxy)indanyl]acetic acid |
| 428 | 2-[(1S)-5-(3-{[2-(4-methylphenyl)pyrimidin-4-yl]propylamino}propoxy)indanyl]acetic acid |
| 429 | 2-[(1S)-5-(3-{[2-(4-ethylphenyl)pyrimidin-4-yl]propylamino}propoxy)indanyl]acetic acid |
| 430 | 2-((1S)-5-{3-[(2-(2H-benzo[3,4-d]1,3-dioxolan-5-yl)pyrimidin-4-yl)propylamino]propoxy}indanyl)acetic acid |
| 431 | 2-[(1S)-5-(3-{[2-(4-methoxyphenyl)pyrimidin-4-yl]propylamino}propoxy)indanyl]acetic acid |
| 432 | 2-[(1S)-5-(3-{(cyclopropylmethyl)[2-(4-ethylphenyl)-5-methylpyrimidin-4-yl]amino}propoxy)indanyl]acetic acid |
| 433 | 2-[(1S)-5-(3-{ethyl[2-(4-ethylphenyl)-5-methylpyrimidin-4-yl]amino}propoxy)indanyl]acetic acid |
| 434 | [(1S)-5-(3-{ethyl[5-methyl-2-(4-methylphenyl)-4-pyrimidinyl]amino}propoxy)-2,3-dihydro-1H-inden-1-yl]acetic acid |
| 435 | 2-((1S)-5-{3-[(2-(2H-benzo[3,4-d]1,3-dioxolan-5-yl)-5-methylpyrimidin-4-yl)ethylamino]propoxy}indanyl)acetic acid |
| 436 | 2-[(1S)-5-(3-{N-[2-(4-ethylphenyl)-5-methylpyrimidin-4-yl]acetylamino}propoxy)indanyl]acetic acid |
| 437 | [(1S)-5-(3-{acetyl[2-(1,3-benzodioxol-5-yl)-5-methyl-4-pyrimidinyl]amino}propoxy)-2,3-dihydro-1H-inden-1-yl]acetic acid |

Example 438

Preparation of 3-[(2-chloro-4-pyrimidinyl)oxy]-1-propanol

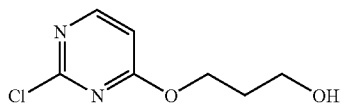

To a round-bottom flask charged with NaH (336 mg, 8.29 mmol, 60% dispersion in mineral oil) and THF (100 mL), 1,3-propanediol (0.91 mL, 12.6 mmol) was added dropwise [$H_2$ evolution] at rt. The reaction mixture was stirred for 30 min, then 2,4-dichloropyrimidine (5.0 g, 33.6 mmol) was added, and the reaction mixture was stirred for an additional 72 h. Brine was slowly added and the aqueous phase was extracted with EtOAc. The combined organic phases were dried ($MgSO_4$), filtered, and concentrated under reduced pressure. The residue was purified by silica gel flash chromatography to provide the product (350 mg, 22%) as a colorless oil. $^1$H NMR (400 MHz, $CDCl_3$): δ 2.01 (qt, 2H), 2.43-2.52 (b, 1H), 3.76 (t, 2H), 4.51 (t, 2H), 6.63 (d, 1H), 8.25 (d, 1H) LC-MS: RT=1.05 min, (M+H)$^+$ 189.1.

Example 439

Preparation of [(1S)-5-(3-{[2-(4-ethylphenyl)-4-pyrimidinyl]oxy}propoxy)-2,3-dihydro-1H-inden-1-yl]acetic acid

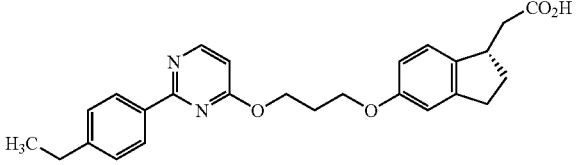

To a solution of 3-[(2-chloro-4-pyrimidinyl)oxy]-1-propanol (Example 438, 87 mg, 0.46 mmol) and ethyl[(1S)-5-hydroxy-2,3-dihydro-1H-inden-1-yl]acetate (Example 6, 112 mg, 0.51 mmol) in THF (4 mL) were added $PPh_3$ (181 mg, 0.59 mmol) and ADDP (175 mg, 0.59 mmol). The reaction mixture was vigorously stirred at rt for 72 h, after which additional $PPh_3$ (181 mg, 0.59 mmol) and ADDP (175 mg, 0.59 mmol) were added. After stirring for an additional 24 h, the solvent was evaporated under reduced pressure. The residue was purified by silica gel chromatography (3:1 hexanes/EtOAc) to afford the desired compound contaminated with residual ethyl[(1S)-5-hydroxy-2,3-dihydro-1H-inden-1-yl]

acetate. The crude adduct was dissolved in a mixture of toluene (12 mL) and 1,4-dioxane (2.45 mL), and then 4-ethylphenyl boronic acid (82.8 mg, 0.55 mmol) and PdCl$_2$(dppf).CH$_2$Cl$_2$ (10.1 mg, 0.0.01 mmol) were added. A flow of argon was passed through the mixture for 30 min, then Na$_2$CO$_3$ (0.69 mL, 1.38 mmol, 2 M aqueous solution) was added, and the reaction was stirred at 75° C. for 18 h. The reaction mixture was then cooled to rt, diluted with EtOAc, and washed with a saturated aqueous solution of NaHCO$_3$. The organic layer was dried (Na$_2$SO$_4$), filtered, and the filtrate concentrated under reduced pressure. The residue was purified by silica gel flash chromatography (4:1 hexanes/EtOAc), to provide the desired product containing minor impurities. Thus, to a solution of the crude ester in a mixture of THF (5 mL), water (5 mL) and EtOH (2.0 mL) was added LiOH (15.0 mg, 0.63 mmol). The reaction mixture was vigorously stirred for 18 h, concentrated under reduced pressure, and purified by preparative HPLC. The fractions containing the desired product were concentrated under reduced pressure. The residue dissolved in CH$_2$Cl$_2$, treated with Dowex 66® resin, filtered, and the concentrated under reduced pressure to give the product (29.3 mg, 43%) as a white foam. $^1$H NMR (400 MHz, CDCl$_3$): δ 1.34 (t, 3H), 1.75-1.85 (m, 1H), 2.32 (qt, 2H), 2.39-2.53 (m, 2H), 2.74 (q, 2H), 2.77-2.98 (m, 3H), 3.51-3.61 (m, 1H), 4.15 (t, 2H), 4.71 (t, 2H), 6.60 (d, 1H), 6.75 (dd, 1H), 6.81 (d, 1H), 7.10 (d, 1H), 7.31 (d, 2H), 8.32 (d, 2H), 8.53 (d, 1H); LC-MS: RT=3.44 min, (M+H)$^+$ 433.2.

Example 440

Preparation of 3-[(2,5-dichloro-4-pyrimidinyl)amino]-1-propanol

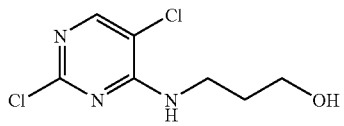

Using 2,4,5-trichloropyrimidine as starting material, the title compound was prepared following a similar procedure as the one described for the preparation of Example 339. $^1$H NMR (400 MHz, CDCl$_3$): δ 1.85 (qt, 2H), 3.58 (t, 2H), 3.67 (t, 2H), 4.89 (s, 2H), 7.99 (s, 1H).

Example 441

Preparation of ethyl((1S)-5-{3-[(2,5-dichloro-4-pyrimidinyl)amino]propoxy}-2,3-dihydro-1H-inden-1-yl)acetate

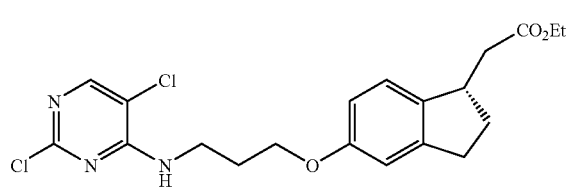

To a solution of 3-[(2-chloro-5-chloro-4-pyrimidinyl)amino]-1-propanol (Example 440, 1.08 g, 4.90 mmol) and ethyl[(1S)-5-hydroxy-2,3-dihydro-1H-inden-1-yl]acetate (Example 6, 539 mg, 2.45 mmol) in THF (40 mL) were added PPh$_3$ (1.29 g, 4.90 mmol) and ADDP (1.26 g, 4.90 mmol). The reaction mixture was vigorously stirred at rt for 72 h, after which additional amounts of PPh$_3$ (1.29 g, 4.90 mmol) and ADDP (1.26 g, 4.90 mmol) were added. After stirring for an additional 24 h, the reaction mixture was diluted with hexanes, filtered through Celite® and the filtrate concentrated under reduced pressure. The residue was then purified by silica gel chromatography (1:1 hexanes/EtOAc) to give the product (920 mg, 89%). $^1$H NMR (400 MHz, CDCl$_3$): δ 1.29 (t, 3H), 1.71-1.82 (m, 1H), 2.15 (qt, 2H), 2.35-2.47 (m, 2H), 2.72 (dd, 1H), 2.79-2.98 (m, 2H), 3.48-3.58 (m, 1H), 3.74 (q, 2H), 4.12 (t, 2H), 4.18 (q, 2H), 6.22-6.31 (b, 1H), 6.73 (dd, 1H), 6.79 (d, 1H), 7.08 (d, 1H), 7.25 (s, 1H).

Example 442

Preparation of ethyl((1S)-5-{3-[(2,5-dichloro-4-pyrimidinyl)(methyl)amino]propoxy}-2,3-dihydro-1H-inden-1-yl)acetate

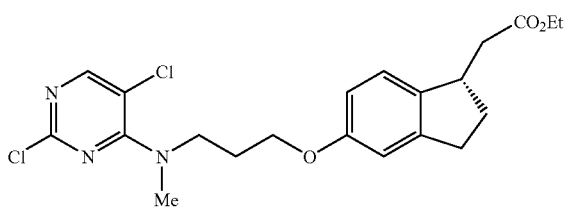

To a solution of Example 441 (520 mg, 1.23 mmol) in DMF (15 mL) at 0° C. was added portionwise NaH (95 mg, 2.45 mmol, 60% dispersion in mineral oil) [H$_2$ evolution]. The heterogeneous mixture was stirred for 30 min, then iodomethane (0.31 mL, 4.90 mmol) was added. After 18 h of agitation at rt, the excess NaH was quenched by the slow addition of NH$_4$Cl (10% solution in water) [H$_2$ evolution]. The resulting mixture was concentrated under reduced pressure, brought to basic pH using a saturated solution of NaHCO$_3$, and the product was extracted with EtOAc. The combined organic layers were washed with water and brine, after which they were dried (Na$_2$SO$_4$), filtered, and then concentrated under reduced pressure. The residue was purified by silica gel chromatography (4:1 hexanes/EtOAc) to yield the product (442 mg, 82%). $^1$H NMR (400 MHz, CDCl$_3$): δ 1.30 (t, 3H), 1.75-1.82 (m, 1H), 2.12-2.20 (m, 2H), 2.30-2.45 (m, 2H), 2.70 (dd, 1H), 2.72-2.90 (m, 2H), 3.30 (s, 3H), 3.44-3.54 (m, 1H), 3.84 (t, 2H), 3.95 (t, 2H), 4.16 (q, 2H), 6.65 (d, 1H), 6.75 (s, 1H), 7.05 (d, 1H), 8.15 (s, 1H).

Example 443

Preparation of ethyl((1S)-5-{3-[[2-chloro-5-(4-methoxyphenyl)-4-pyrimidinyl](methyl)amino]propoxy}-2,3-dihydro-1H-inden-1-yl)acetate

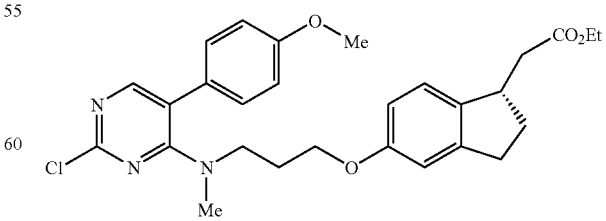

To mixture of 4-methoxyphenylboronic acid (28.5 mg, 0.183 mmol) and ethyl((1S)-5-{3-[(2,5-dichloro-4-pyrimidinyl)(methyl)amino]propoxy}-2,3-dihydro-1H-inden-1-yl)

acetate (Example 442, 80 mg, 0.183 mmol) in toluene (6.72 mL) and 1,4-dioxane (1.68 mL) was added PdCl$_2$(dppf).CH$_2$Cl$_2$ (15 mg, 0.018 mmol). The mixture was purged with argon for 15 min after which a 2 M Na$_2$CO$_3$ aqueous solution (1.68 mL, 1.83 mmol) was added. The mixture was stirred and heated at 75° C. for 2 h, the reaction mixture was allowed cool to rt, and then washed with a saturated aqueous solution of NaHCO$_3$. The organic layer was separated and the aqueous phase extracted with EtOAc (2×). The combined organic phases were dried, filtered, and then concentrated under reduced pressure. The residue was purified by silica gel flash column chromatography (1:3 EtOAc/Hexanes) to give the product (74 mg, 79%). $^1$H NMR (400 MHz, CDCl$_3$): δ 1.25 (t, 3H), 1.70-1.79 (m, 1H), 2.15-2.20 (m, 2H), 2.28-2.42 (m, 2H), 2.66 (dd, 1H), 2.72-2.90 (m, 2H), 3.31 (s, 3H), 3.44-3.54 (m, 1H), 3.82 (s, 3H), 3.84 (t, 2H), 3.95 (t, 2H), 4.16 (q, 2H), 6.65 (d, 1H), 6.72 (s, 1H), 6.91 (d, 2H), 7.05 (s, 1H), 8.15 (s, 1H), 8.25 (d, 2H); LC-MS: RT=3.51 min, (M+H)$^+$ 510.5.

Example 444

Preparation of ethyl((1S)-5-{3-[[2,5-bis(4-methoxyphenyl)-4-pyrimidinyl](methyl)amino]propoxy}-2,3-dihydro-1H-inden-1-yl)acetate

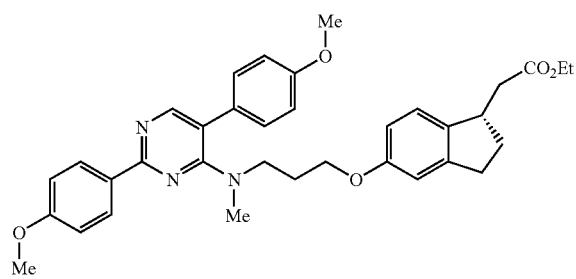

To a mixture of 4-methoxyphenylboronic acid (142 mg, 0.913 mmol) and ethyl((1S)-5-{3-[(2,5-dichloro-4-pyrimidinyl)(methyl)amino]propoxy}-2,3-dihydro-1H-inden-1-yl)acetate (Example 442, 100 mg, 0.228 mmol) in toluene (5 mL) and 1,4-dioxane (1.25 mL) was added PdCl$_2$(dppf).CH$_2$Cl$_2$(19 mg, 0.023 mmol). The mixture was purged with argon for 15 min after which sodium carbonate (1.2 mL, 2.40 mmol, 2 M aqueous solution) was added. The mixture was stirred at 75° C. for 18 h, cooled to rt, and then washed with a saturated sodium bicarbonate solution. The organic layer was separated from the mixture and the aqueous phase extracted with EtOAc. The combined organic phases were dried (Na$_2$SO$_4$), filtered, and concentrated under reduced pressure. The residue was purified by flash column chromatography (1:4 EtOAc/Hexanes) to give (86 mg, 64%) of the desired product. $^1$H NMR (400 MHz, CDCl$_3$): δ 1.30 (t, 3H), 1.70-1.80 (m, 1H), 2.15-2.20 (m, 2H), 2.28-2.45 (m, 2H), 2.70 (dd, 1H), 2.72-2.90 (m, 2H), 2.80 (s, 3H), 3.45-3.55 (m, 1H), 3.75 (t, 2H), 3.85 (s, 3H), 3.92 (s, 3H), 3.95 (t, 2H), 4.20 (q, 2H), 6.65 (d, 1H), 6.7 (s, 1H), 6.9 (d, 2H), 6.95 (d, 2H), 7.05 (s, 1H), 7.32 (d, 2H), 8.15 (s, 1H), 8.40 (d, 2H).

Example 445

Preparation of ((1S)-5-{3-[[2-chloro-5-(4-methoxyphenyl)-4-pyrimidinyl](methyl)amino]propoxy}-2,3-dihydro-1H-inden-1-yl)acetic acid

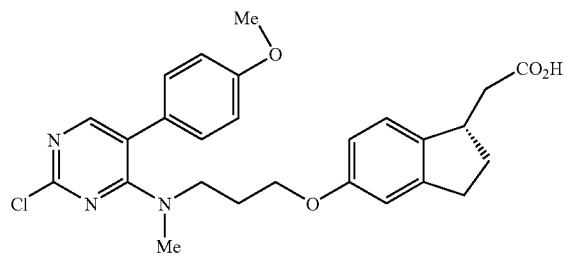

To a solution of ethyl((1S)-5-{3-[[2-chloro-5-(4-methoxyphenyl)-4-pyrimidinyl](methyl)amino]propoxy}2,3-dihydro-1H-inden-1-yl)acetate (Example 443, 70 mg, 0.137 mmol) in a mixture of THF (2 mL), ethanol (1 mL), and water (2 mL) was added LiOH.H$_2$O (13 mg, 0.55 mmol). The mixture was maintained at rt in an orbital shaker for 16 h after which the reaction mixture was washed with Et$_2$O. To the remaining aqueous solution was added HCl (1 N aqueous solution) dropwise until pH 5 was reached. The aqueous solution was then extracted with EtOAc, the combined organic layers dried (Na$_2$SO$_4$), filtered, and concentrated under reduced pressure to give 20 mg (30%) of the product as a white solid. $^1$H NMR (400 MHz, CDCl$_3$): δ 1.75-1.79 (m, 1H), 2.18-2.21 (m, 2H), 2.24-2.49 (m, 2H), 2.77-2.90 (m, 3H), 3.31 (s, 3H), 3.52-3.74 (m, 1H), 3.92 (s, 3H), 3.99 (t, 2H), 4.05 (t, 2H), 6.67 (d, 1H), 6.75 (s, 1H), 6.94 (d, 2H), 7.08 (s, 1H), 8.15 (s, 1H), 8.27 (d, 2H); LC-MS: RT=2.91 min, (M+H)$^+$ 482.2.

Example 446

Preparation of ((1S)-5-{3-[[2,5-bis(4-methoxyphenyl)-4-pyrimidinyl](methyl)amino]propoxy}-2,3-dihydro-1H-inden-1-yl)acetic acid

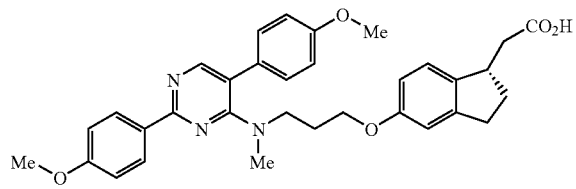

Using Example 444 as starting material, the title compound was prepared following the hydrolysis procedure described for Example 445. $^1$H NMR (400 MHz, CDCl$_3$): δ 1.65-1.78 (m, 1H), 1.98-2.17 (m, 2H), 2.42-2.53 (m, 2H), 2.65-2.80 (m, 3H), 2.91 (s, 3H), 3.45-3.60 (m, 1H), 3.70 (t, 2H), 3.89 (t, 2H), 3.91 (s, 3H), 3.95 (s, 3H), 6.62 (d, 2H), 6.80-6.91 (m, 4H), 6.95 (d, 1H), 7.18 (d, 2H), 8.02 (s, 1H). 8.32 (d, 2H); LC-MS: RT=2.65 min, (M+H)$^+$ 554.4.

By using the methods described above for Examples 440-446 and by substituting the appropriate starting materials, compounds of Formula (Iaaa) listed in Table 17a below, were similarly prepared.

TABLE 17a (Iaaa)

| Ex. No. | R³⁻¹ | R³⁻² | LCMS (M + H) | RT (min) |
|---|---|---|---|---|
| 447 | 4-Ac—Ph | 4-Ac—Ph | 578.2 | 2.75 |
| 448 | 4-CF₃—Ph | 4-CF₃—Ph | 630.5 | 3.61 |
| 449 | 4-F—Ph | 4-F—Ph | 530.3 | 2.78 |
| 450 | 4-Et—Ph | Cl | 480.6 | 3.34 |
| 451 | 4—CF₃O—Ph | Cl | 536.5 | 3.90 |
| 452 | 4-Ac—Ph | Cl | 494.5 | 3.37 |
| 453 | 4—CF₃—Ph | Cl | 520.5 | 3.96 |
| 454 | 3,4-dioxolane-Ph | Cl | 496.3 | 3.06 |
| 455 | 4-F—Ph | Cl | 470.5 | 3.41 |
| 456 | 4-Me—Ph | Cl | 466.2 | 3.16 |
| 457 | 3,4-diF—Ph | Cl | 488.2 | 3.81 |

TABLE 17b

IUPAC Names for Compounds in Table 17a

| Ex. No. | IUPAC Name |
|---|---|
| 447 | 2-[(1S)-5-(3-{[2,5-bis(4-acetylphenyl)pyrimidin-4-yl]methylamino}propoxy)indanyl]acetic acid |
| 448 | 2-{(1S)-5-[3-({2,5-bis[4-(trifluoromethyl)phenyl]pyrimidin-4-yl}methylamino)propoxy]indanyl}acetic acid |
| 449 | 2-[(1S)-5-(3-{[2,5-bis(4-fluorophenyl)pyrimidin-4-yl]methylamino}propoxy)indanyl]acetic acid |
| 450 | 2-[(1S)-5-(3-{[2-chloro-5-(4-ethylphenyl)pyrimidin-4-yl]methylamino}propoxy)indanyl]acetic acid |
| 451 | 2-{(1S)-5-[3-({2-chloro-5-[4-(trifluoromethoxy)phenyl]pyrimidin-4-yl}methylamino)propoxy]indanyl}acetic acid |
| 452 | 2-[(1S)-5-(3-{[5-(4-acetylphenyl)-2-chloropyrimidin-4-yl]methylamino}propoxy)indanyl]acetic acid |
| 453 | 2-{(1S)-5-[3-({2-chloro-5-[4-(trifluoromethyl)phenyl]pyrimidin-4-yl}methylamino)propoxy]indanyl}acetic acid |
| 454 | 2-((1S)-5-{3-[(5-(2H-benzo[3,4-d]1,3-dioxolan-5-yl)-2-chloropyrimidin-4-yl)methylamino]propoxy}indanyl)acetic acid |
| 455 | 2-[(1S)-5-(3-{[2-chloro-5-(4-fluorophenyl)pyrimidin-4-yl]methylamino}propoxy)indanyl]acetic acid |
| 456 | ((1S)-5-{3-[[(2-chloro-5-(4-methylphenyl)-4-pyrimidinyl](methyl)amino]propoxy}-2,3-dihydro-1H-inden-1-yl)acetic acid |
| 457 | ((1S)-5-{3-[[2-chloro-5-(3,4-difluorophenyl)-4-pyrimidinyl](methyl)amino]propoxy}-2,3-dihydro-1H-inden-1-yl)acetic acid |

Example 458
Preparation of 1-(2-chloro-5-methyl-4-pyrimidinyl)-4-piperidinol

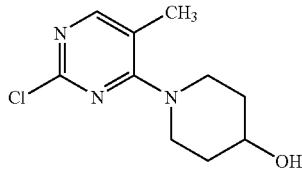

To a solution of 2,4-dichloro-5-methylpyrimidine (5.0 g, 30.7 mmol) in EtOH (100 mL) were added 4-piperidinol (3.1 g, 30.7 mmol) and Na₂CO₃ (16.3 g, 153.4 mmol). The reaction mixture was stirred at rt for 72 h, after which the reaction mixture was filtered through Celite®. The filtrate was then concentrated under reduced pressure, the residue dissolved in EtOAc, and the organic solution washed with water and brine after which it was dried (Na₂SO₄), filtered, and concentrated under reduced pressure. The residue was then purified by silica gel flash chromatography (1:1 EtOAc/hexanes to 100% EtOAc) to give the product (4.8 g, 90%) as a white waxy solid. ¹H NMR (400 MHz, CDCl₃) δ 1.62-1.70 (m, 2H), 1.70 (d, 1H), 1.98-2.03 (m, 2H), 2.21 (s, 3H), 3.22-3.28 (m, 2H), 3.87-3.92 (m, 2H), 3.97-3.98 (m, 1H), 7.92 (s, 1H).

Example 459
Preparation of ethyl((1S)-5-{[1-(2-chloro-5-methyl-4-pyrimidinyl)-4-piperidinyl]oxy}-2,3-dihydro-1H-inden-1-yl)acetate

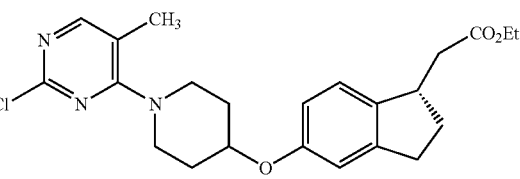

To a solution of 1-(2-chloro-5-methyl-4-pyrimidinyl)-4-piperidinol (Example 458, 2.01 g, 8.81 mmol) and ethyl[(1S)-5-hydroxy-2,3-dihydro-1H-inden-1-yl]acetate (Example 6, 970 mg, 4.40 mmol) in THF (35 mL) were added PPh₃ (2.31 g, 8.81 mmol) and ADDP (2.22 g, 8.81 mmol). The reaction mixture was vigorously stirred at rt for 24 h. The precipitate was filtered off, and the filtrate was concentrated under reduced pressure. The residue was then purified by silica gel chromatography (9:1 to 3:1 hexanes/EtOAc) to give the title product (1.54 g, 81%). ¹H NMR (400 MHz, CDCl₃) δ 1.28 (t, 3H), 1.74-1.80 (m, 1H), 1.91-1.95 (m, 2H), 2.02-2.07 (m, 2H), 2.22 (s, 3H), 2.38-2.46 (m, 2H), 2.71-2.88 (m, 3H), 3.50-3.55 (m, 3H), 3.75-3.81 (m, 2H), 4.18 (q, 2H), 4.52-4.54 (m, 1H), 6.73 (d, 1H), 6.80 (s, 1H), 7.07 (d, 1H), 7.93 (s, 1H).

Example 460

Preparation of [(1S)-5-({1-[2-(4-ethylphenyl)-5-methyl-4-pyrimidinyl]-4-piperidinyl}methyl)-2,3-dihydro-1H-inden-1yl]acetic acid

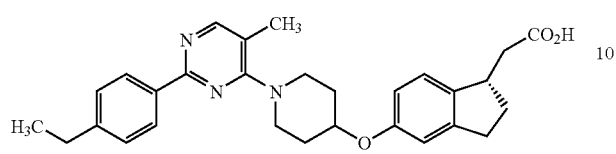

To a mixture of toluene (5.8 mL) and 1,4-dioxane (1.16 mL) were added ethyl ((1S)-5-{[1-(2-chloro-5-methyl-4-pyrimidinyl)-4-piperidinyl]oxy}-2,3-dihydro-1H-inden-1-yl)acetate (Example 459, 100 mg, 0.23 mmol), 4-ethylphenyl boronic acid (139.5 mg, 0.93 mmol), and $PdCl_2(dppf)$·$CH_2Cl_2$ (17 mg, 0.02 mmol). A flow of argon was passed through the mixture for 30 min, then $Na_2CO_3$ (1.16 mL, 2.33 mmol, 2 M aqueous solution) was added, and the reaction was stirred at 75° C. for 4 h. The reaction mixture was cooled to rt and filtered through a plug of silica gel. Then the desired fractions were concentrated under reduced pressure. The crude ester was dissolved in a mixture of THF (3 mL), water (3 mL), and EtOH (1.5 mL) was added LiOH (55.8 mg, 2.33 mmol). The reaction mixture was vigorously stirred for 24 h and then concentrated under reduced pressure. The residue was purified by preparative HPLC and the fractions containing the desired product were concentrated under reduced pressure. The residue was dissolved in $CH_2Cl_2$, treated with to Dowex 66® resin, filtered, and then concentrated under reduced pressure to give the product (50 mg, 43%). $^1H$ NMR (400 MHz, $CDCl_3$) δ 1.27 (t, 3H), 1.73-1.78 (m, 1H), 1.90-1.96 (m, 2H), 2.18-2.22 (m, 2H), 2.40 (s, 3H), 2.35-2.44 (m, 2H), 2.69-2.91 (m, 4H), 3.46-3.49 (m, 1H), 3.67-3.72 (m, 2H), 4.00-4.06 (m, 2H), 4.70-4.72 (m, 1H), 6.81 (d, 1H), 6.90 (d, 1H), 7.16 (s, 1H), 7.34 (d, 2H), 8.29 (s, 1H), 8.35 (d,2H); LC-MS: MS: RT=2.66 min, (M+H)⁺ 472.4.

Using the methods described for (Examples 458-460) above using the appropriate starting materials, compounds of Formula (Ibbb), Examples 461-466 were similarly prepared and are shown in Table 18a below.

TABLE 18b

IUPAC Names for Compounds in Table 18a

| Ex. No. | IUPAC Name |
|---|---|
| 461 | [(1S)-5-({(2S)-1-[2-(4-ethylphenyl)-5-methyl-4-pyrimidinyl]-2-pyrrolidinyl}methoxy)-2,3-dihydro-1H-inden-1-yl]acetic acid |
| 462 | [(1S)-5-({1-[2-(4-fluorophenyl)-5-methyl-4-pyrimidinyl]-4-piperidinyl}oxy)-2,3-dihydro-1H-inden-1-yl]acetic acid |
| 463 | [(1S)-5-({1-[2-(4-i-propylphenyl)-5-methyl-4-pyrimidinyl]-4-piperidinyl}oxy)-2,3-dihydro-1H-inden-1-yl]acetic acid |
| 464 | [(1S)-5-({1-[2-(4-methoxyphenyl)-5-methyl-4-pyrimidinyl]-4-piperidinyl}oxy)-2,3-dihydro-1H-inden-1-yl]acetic acid |
| 465 | [(1S)-5-({1-[2-(4-chlorophenyl)-5-methyl-4-pyrimidinyl]-4-piperidinyl}oxy)-2,3-dihydro-1H-inden-1-yl]acetic acid |
| 466 | [(1S)-5-({1-[2-(1,3-benzodioxol-5-yl)-5-methyl-4-pyrimidinyl]-4-piperidinyl}oxy)-2,3-dihydro-1H-inden-1-yl]acetic acid |

Example 467

Preparation of ethyl(4-{[1-(2-chloro-5-methyl-4-pyrimidinyl)-4-piperidinyl]oxy}-2,3-dihydro-1H-inden-1-yl)acetate

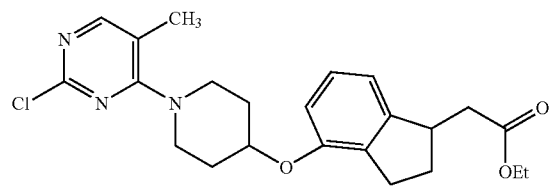

Using Examples 9 and 458 as starting material, the title compound was prepared following the procedure described for Example 459 and was used for the next step without further purification. LC-MS: RT=2.81 min, (M+H)⁺ 430.4.

TABLE 18a (Ibbb)

| Ex. No. | $R^{3\text{-}3\text{-}2}$ | $R^{3\text{-}3\text{-}1}$ | p | q | t | LCMS (M + H) | RT (min) |
|---|---|---|---|---|---|---|---|
| 461[1] | Et | H | 0 | 3 | 1 | 472.5 | 2.57 |
| 462 | F | H | 2 | 2 | 0 | 462.3 | 2.52 |
| 463 | i-Pr | H | 2 | 2 | 0 | 486.4 | 2.76 |
| 464 | MeO | H | 2 | 2 | 0 | 474.3 | 2.47 |
| 465 | Cl | H | 2 | 2 | 0 | 478.3 | 2.70 |
| 466 | —O—$CH_2$—O— | | 2 | 2 | 0 | 488.3 | 2.45 |

[1] The absolute configuration at carbon * is S.

Example 468

Preparation of (4-{[1-(2-chloro-5-methyl-4-pyrimidinyl)-4-piperidinyl]oxy}-2,3-dihydro-1H-inden-1-yl)acetic acid

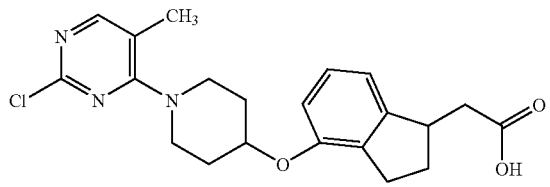

Using Example 467 as starting material, the title compound was prepared following the procedure described for Example 460. $^1$H NMR (400 MHz, acetone-$d_6$) δ 7.99 (1H, s), 7.12 (1H, t), 6.86 (2H, t), 4.75-4.72 (1H, m), 3.87-3.81 (2H, m), 3.60-3.52 (3H, m), 2.98-2.91 (1H, m), 2.82-2.74 (2H, m), 2.54-2.34 (2H, m), 2.28 (3H, s), 2.15-2.08 (2H, m), 1.91-1.79 (2H, br), 1.78-1.71 (1H, s). LC-MS: RT=3.12 min, (M+H)$^+$ 402.3.

Example 469

Preparation of ethyl(6-chloro-2-pyridinyl)acetate

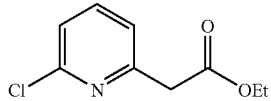

To a solution of n-BuLi (100 mL, 250 mmol of a 2.5 M solution in hexanes) in THF (200 mL) was added DIA (36 mL, 255 mmol) at 0° C. After stirring for 45 min, 6-methyl-2-chloropyridine (14.2 g, 111 mmol) was added slowly, maintaining the temperature <5° C. After 30 min, diethyl carbonate (30 mL, 250 mmol) was added dropwise maintaining the temperature below 10° C. The solution was stirred at 0° C. for 1 h, then water was slowly added, followed by the addition of a saturated solution of NH$_4$Cl. The organic phase was dried (Na$_2$SO$_4$), filtered, and then concentrated under reduced pressure. The residue was purified through a pad of silica gel to give the product (13.3 g, 66.6 mmol) as a yellow oil. $^1$H NMR (400 MHz, CDCl$_3$) δ 1.27 (t, 3H), 2.04 (s, 2H), 4.19 (q, 2H), 7.23 (dd, 2H), 7.62 (t, 1H).

Example 470

Preparation of 2-(6-chloro-2-pyridinyl)ethanol

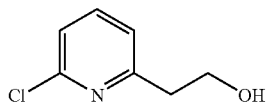

To a solution of ethyl(6-chloro-2-pyridinyl)acetate (Example 469, 5.00 g, 25 mmol) in THF (50 mL) was added LiBH$_4$ (13.0 mL, 25.0 mmol, 2M solution in THF) at 0° C. The mixture was stirred at rt for 18 h, then water was slowly added [strong gaseous evolution] followed by HCl (10 mL, 1N aqueous solution). The mixture was extracted with CH$_2$Cl$_2$. The combined organic phases were dried (Na$_2$SO$_4$), filtered and then concentrated under reduced pressure. The residue was purified using a short pad of silica gel (4:1 hexanes/EtOAc) to give the product (3.00 g, 76%) as a light-yellow oil which solidified upon standing. $^1$H NMR (400 MHz, CDCl$_3$) δ 2.97 (t, 2H), 3.98 (t, 2H), 7.10 (dd, 2H), 7.54 (t, 1H).

Example 471

Preparation of ethyl{(1S)-5-[2-(6-chloro-2-pyridinyl)ethoxy]-2,3-dihydro-1H-inden-1-yl}acetate

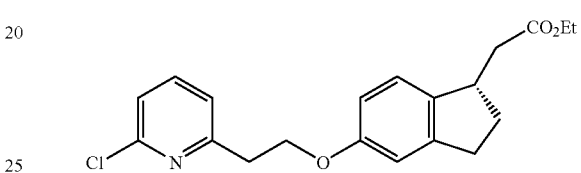

To a solution of 2-6-chloro-2-pyridinyl)ethanol (Example 470, 250 mg, 1.59 mmol) and ethyl[(1S)-5-hydroxy-2,3-dihydro-1H-inden-1-yl]acetate (Example 6, 698 mg, 3.17 mmol) in THF (4 mL) were added PPh$_3$ (832 mg, 3.17 mmol) and DIAD (641 mg, 3.17 mmol). The reaction mixture was vigorously stirred at rt for 24 h, concentrated under reduced pressure, and the residue was purified by silica gel chromatography (6:1 hexanes/EtOAc) to give the product (170 mg, 30%). $^1$H NMR (400 MHz, CDCl$_3$) δ 1.28 (t, 3H), 1.72-1.77 (m, 1H), 2.34-2.43 (m, 2H), 2.71 (dd, 1H), 2.81-2.89 (m, 2H), 3.21 (t, 2H), 3.51-3.52 (m, 1H), 4.17 (q, 2H), 4.31 (t, 2H), 6.69 (d, 1H), 6.76 (s, 1H), 7.04 (d, 1H), 7.19 (dd, 2H), 7.57 (t, 1H).

Example 472

Preparation of ((1S)-5-{2-[6-(4-ethylphenyl)-2-pyridinyl]ethoxy}-2,3-dihydro-1H-inden-1-yl)acetic acid

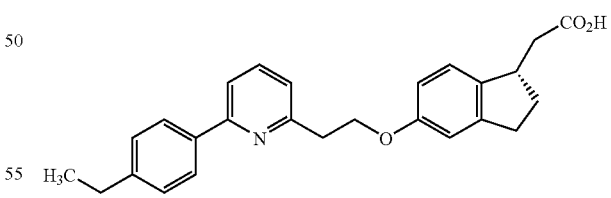

Step 1. To a mixture of toluene (4.2 mL) and 1,4-dioxane (0.84 mL) were added ethyl{(1S)-5-[2-(6-chloro-2-pyridinyl)ethoxy]-2,3-dihydro-1H-inden-1-yl}acetate (Example 471, 60 mg, 0.17 mmol), 4-ethylphenyl boronic acid (100 mg, 0.67 mmol), and PdCl$_2$(dppf) δ CH$_2$Cl$_2$ (12.2 mg, 0.02 mmol). A flow of argon was passed through the mixture for 30 min, then Na$_2$CO$_3$ (0.83 mL, 1.67 mmol, 2 M aqueous solution) was added, and the reaction was stirred at 75° C. for 18 h. The reaction mixture was then cooled to rt, diluted with EtOAc, and washed with a saturated solution of NaHCO$_3$.

The organic layer was dried (Na₂SO₄), filtered, and concentrated under reduced pressure. The residue was purified by a short pad of silica gel (2:1 to 1:1 hexanes/EtOAc).

Step 2. To the crude ester dissolved in a mixture a THF (2 mL), water (2 mL), and EtOH (1 mL) was added LiOH (32.6 mg, 1.36 mmol). The reaction mixture was vigorously stirred for 24 h, concentrated under reduced pressure, and the residue purified by preparative HPLC. The desired fractions were then concentrated, the residue dissolved in CH₂Cl₂, treated with to Dowex 66® resin, filtered, and concentrated under reduced pressure to give the product (24 mg, 35%). ¹H NMR (400 MHz, CDCl₃) δ 1.27 (t, 3H), 1.73-1.80 (m, 1H), 2.37-2.50 (m, 2H), 2.67-2.90 (m, 3H), 3.22 (t, 2H), 3.46-3.58 (m, 1H), 4.17 (q, 2H), 4.42 (t, 2H), 6.74 (d, 1H), 6.82 (s, 1H), 7.08 (d, 1H), 7.19 (d, 1H), 7.29 (d, 2H), 7.55 (d, 1H), 7.67 (t, 1H), 7.90 (d, 2H); LC-MS: RT=3.50 min, (M+H)⁺ 402.3.

Example 473

Preparation of [(1S)-5-(2-{6-[methyl(phenyl)amino]-2-pyridinyl}ethoxy)-2,3-dihydro-1H-inden-1-yl] acetic acid

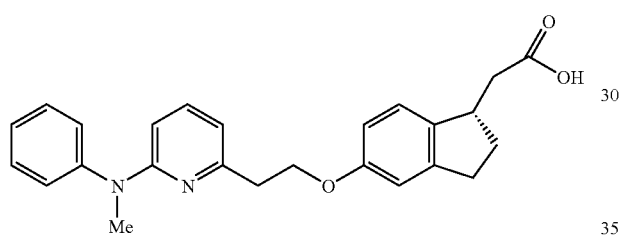

An oven-dried flask charged with ethyl{(1S)-5-[2-6-chloro-2-pyridinyl)ethoxy]-2,3-dihydro-1H-inden-1-yl}acetate (Example 471, 100 mg, 0.277 mmol), Pd(OAc)₂ (1.3 mg, 0.01 mmol), 2-di-t-butylphosphino)biphenyl (3.3 mg, 0.02 mmol), and sodium tert-butoxide (37.4 mg, 0.39 mmol) was purged with argon. Toluene (1 mL) and N-methyl aniline (59.6 mg, 0.56 mmol) were added, and the mixture was stirred at 100° C. for 18 h. The reaction mixture was then cooled to rt, loaded on an ion-exchange resin column (SCX sorbent, Varian, strong cation exchange), and eluted with MeOH followed with NH₃ (1N solution in MeOH). The fractions containing the desired product were combined and then concentrated under reduced pressure. The crude ester was then dissolved in a mixture of THF (2 mL), H₂O (2 mL), and EtOH (1 mL), to which LiOH (26.8 mg, 1.12 mmol) was added. The reaction mixture was stirred at rt for 18 h, concentrated under reduced pressure, and then purified by preparative HPLC. The fractions containing the desired fractions were concentrated under reduced pressure, and then dissolved in a mixture of CH₂Cl₂ and a saturated aqueous solution of NaHCO₃. The aqueous phase was brought to pH 4 using HCl (1N aqueous solution), the organic layer separated, dried, and then concentrated to give the product (51.4 mg, 46%). ¹H NMR (400 MHz, CDCl₃) δ 1.70-1.75 (m, 1H), 2.34-2.43 (m, 2H), 2.70-2.87 (m, 3H), 3.43-3.50 (m, 3H), 3.71 (s, 3H), 4.32 (t, 2H), 6.41 (d, 1H), 6.66 (d, 1H) 6.75 (s, 1H), 6.79 (d, 1H), 7.03 (d, 1H), 7.25 (d, 1H), 7.27 (d, 1H), 7.43 (t, 1H), 7.49-7.53 (m, 3H); LC-MS: RT=2.32 min, (M+H)⁺ 403.3.

Example 474

Preparation of sodium 2-methyl-3-oxo-1-buten-1-olate

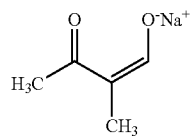

A mixture of 2-butanone (6.36 g, 88.1 mmol) and ethyl formate (6.86 g, 92.6 mmol) was added dropwise at 0° C. to a suspension of sodium methoxide (5.00 g, 92.6 mmol) in a mixture of Et₂O (75 mL) and EtOH (12 mL), resulting in formation of a white precipitate. Upon complete addition, the reaction mixture was allowed to warm to rt. After 2 h, the precipitate was collected by filtration, washed with Et₂O (2×), and dried under vacuum overnight in a dessicator over Drierite, yielding 8.01 g (74%) of the title compound as a white solid. This was used in the following step without further characterization.

Example 475

Preparation of 5,6-dimethyl-2-oxo-1,2-dihydro-3-pyridinecarbonitrile

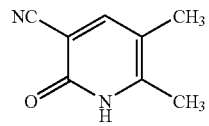

2-Cyanoacetamide (Example 474, 6.01 g, 71.51 mmol) and sodium 2-methyl-3-oxo-1-buten-1-olate (8.01 g, 65.6 mmol) were added to a solution of piperidine (0.950 g, 11.2 mmol) in water (35 mL) and acetic acid (0.64 mL, 11 mmol). The mixture was heated to reflux for 3 h, cooled to rt, and then more acetic acid (25 mL) was added, resulting in the precipitation of a white solid. The solid was collected by filtration, washed with water (3×), and dried under vacuum, yielding the title compound (3.23 g, 33%) as an off-white solid. ¹H NMR (400 MHz, DMSO-d₆) δ 12.40 (bs, 1H), 7.92 (s, 1H), 2.22 (s, 3H), 1.96 (s, 3H).

Example 476

Preparation of 5,6-dimethyl-2(1H)-pyridinone

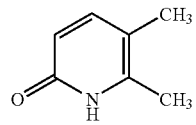

A 100 mL Parr reactor was charged with 5,6-dimethyl-2-oxo-1,2-dihydro-3-pyridinecarbonitrile (Example 475, 3.00 g, 20.3 mmol), concentrated hydrochloric acid (18 mL), and water (18 mL). The reactor was slowly heated to 175° C. for 9 h and then cooled to rt. The solution was basified with 1N NaOH in water and was extracted with EtOAc. The combined organic phases were dried (MgSO$_4$), filtered, and concentrated in vacuo, yielding the title compound (1.21 g, 48%) as an off-white solid. $^1$H NMR (400 MHz, DMSO-d$_6$) δ 11.36 (bs, 1H), 7.18 (d, 1H), 6.04 (d, 1H), 2.10 (s, 3H), 1.93 (s, 3H).

Example 477

Preparation of 6-chloro-2,3-dimethylpyridine

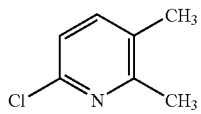

5,6-dimethyl-2(1H)pyridinone (Example 476, 0.39 g, 3.2 mmol) was suspended in phosphorous oxychloride (5.00 mL, 53.6 mmol) and heated to 100° C. Then, phosphorous pentachloride (4.00 g, 19.2 mmol) was added, and the mixture was heated to 140° C. After 16 h, the mixture was cooled to rt, diluted with CH$_2$Cl$_2$ (5 mL), and slowly poured into a 0° C. solution of potassium hydroxide (5 g) and potassium carbonate (5 g) in water (100 mL). Upon complete addition, the mixture was allowed to warm to rt and stirred for 1 h. The aqueous solution was extracted with CH$_2$Cl$_2$, and the combined organics layers were dried (MgSO$_4$), filtered, and concentrated in vacuo to provide the title compound (0.35 g, 77%) as a brown oil. The material was used in the next step without further purification. $^1$H NMR (400 MHz, CDCl$_3$) δ 7.36 (d, 1H), 7.07 (d, 1H), 2.49 (s, 3H), 2.27 (s, 3H).

Example 478

Preparation of ethyl(6chloro-3-methyl-2-pyridinyl)acetate

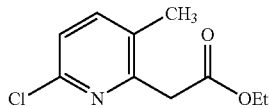

Following the same procedure described for the preparation of ethyl(6-chloro-2-pyridinyl)acetate (Example 469) and starting from 6-chloro-2,3dimethylpyridine (0.35 g, 2.5 mmol), LDA (5.17 mmol), and diethyl carbonate (0.75 mL, 6.2 mmol) in THF (10 mL), the title compound was obtained (0.15 g, 29%) as a yellow oil. $^1$H NMR (400 MHz, CDCl$_3$): δ 7.42 (d, 1H), 7.15 (d, 1H), 4.18 (q, 2H), 3.84 (s, 2H), 2.29 (s, 3H), 1.27 (t, 3H); LC-MS: RT=2.30 min, (M+H)$^+$ 214.2.

Example 479

Preparation of ethyl[6-(4-methoxyphenyl)-3-methyl-2-pyridinyl]acetate

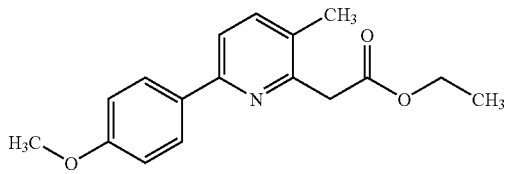

Following the same procedure described for Example 472 (Step 1) and starting from ethyl(6-chloro-3-methyl-2-pyridinyl)acetate (Example 478, 0.20 g, 0.94 mmol), Na$_2$CO$_3$ (0.24 g, 2.24 mmol), 4-methoxyphenyl boronic acid (0.57 g, 3.74 mmol), and PdCl$_2$(dppf)CH$_2$Cl$_2$ (0.15 g, 0.19 mmol) in a mixture of toluene (1.50 mL), 1,4dioxane (0.50 mL) and water (0.60 mL), the title compound was obtained (0.25 g, 94%). $^1$H NMR (400 MHz, CD$_2$Cl$_2$) δ 7.95 (d, 2H), 7.53 (s, 2H), 6.98 (d, 2H), 4.20 (q, 2H), 3.92 (s, 2H), 3.86 (s, 3H), 2.33 (s, 3H), 1.29 (t, 3H).

Example 480

Preparation of 2-[6-(4-methoxyphenyl)-3-methyl-2-pyridinyl]ethanol

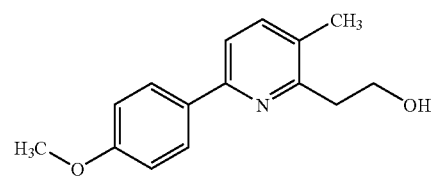

Following the same procedure described for the preparation of Example 470 and starting from [6-4-methoxyphenyl)-3-methyl-2-pyridinyl]acetate (Example 479, 0.25 g, 0.88 mmol), LiBH$_4$(0.88 mL, 2 M in THF, 1.75 mmol) in THF (4.4 mL), the title compound was obtained (0.18 g, 84%). $^1$H NMR (400 MHz, CD$_2$Cl$_2$) δ 7.87 (d, 2H), 7.55-7.45 (m, 2H), 6.98 (d, 2H), 4.18-4.08 (m, 2H), 3.85 (s, 3H), 3.06-2.95 (m, 2H), 2.29 (s, 3H).

Example 481

Preparation of ethyl((1S)-5-{2-[6-4-methoxyphenyl)-3-methyl-2-pyridinyl]ethoxy}-2,3-dihydro-1H-inden-1-yl)acetate

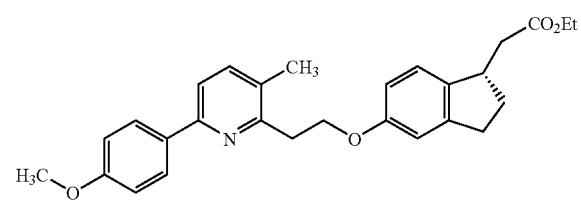

To a solution of 2-[6-(4-methoxyphenyl)-3-methyl-2-pyridinyl]ethanol (Example 480, 0.15 g, 0.62 mmol) and ethyl [(1S-5-hydroxy-2,3-dihydro-1H-inden-1-yl]acetate (Example 6, 0.11 g, 51 mmol) in THF (2.50 mL) were added triphenylphosphine (0.17 g, 0.67 mmol) and 1,1'-azodicarbonyl)-dipiperidine (0.18 g, 67 mmol) under argon. The golden yellow mixture was stirred at rt for 18 h, and concentrated under reduced pressure. The title compound (0.094 g, 41%) was isolated after silica gel chromatography (2:1 hexanes/ EtOAc). $^1$H NMR (400 MHz, CD$_2$Cl$_2$) δ 7.96 (d, 2H), 7.53-7.45 (m, 2H), 7.05 (d, 1H), 6.96 (d, 2H), 6.85-6.80 (m, 1H), 6.73 (dd, 1H), 4.48 (t, 2H), 4.14 (q, 2H), 3.86 (s, 3H), 3.51 (qt, 1H), 3.30 (t, 2H), 2.95-2.78 (m, 2H), 2.71 (dd, 1H) 2.45-2.33 (m, 5H), 1.80-1.70 (m, 1H), 1.28 (t, 3H).

Example 482

Preparation of ((1S)-5-{2-[6-(4-methoxyphenyl)-3-methyl-2-pyridinyl]ethoxy}-2,3-dihydro-1H-inden-1-yl)acetic acid

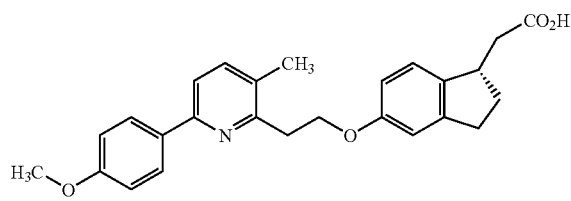

Following the procedure described above (Example 472, step 2) and starting with ethyl((1S)-5-{2-[6-(4-methoxyphenyl)-3-methyl-2-pyridinyl]ethoxy}-2,3-dihydro-1H-inden-1-yl)acetate (Example 481, 90 mg, 0.190 mmol) and LiOH (50 mg, 1.91 mmol) in a mixture of THF (4 mL), MeOH (5 mL), and water (2 mL), the title compound was obtained (0.052 g, 65%). $^1$H NMR (400 MHz, CD$_2$Cl$_2$) δ 7.96 (d, 2H), 7.52-7.45 (m, 2H), 7.09 (d, 1H), 6.96 (d, 2H), 6.83 (d, 1H), 6.74 (dd, 1H), 4.49 (t, 2H), 3.86 (s, 3H), 3.50 (qt, 1H), 3.31 (t, 2H), 2.96-2.75 (m, 3H), 2.52-2.35 (m, 5H), 1.82-1.73 (m, 1H); LC-MS: RT=2.48 min, (M+H)$^+$ 418.2.

By using the methods described above for Examples 474-482 and by substituting the appropriate starting materials, compounds of Formula (Iccc), listed in Table 19 below, were similarly prepared.

TABLE 19a

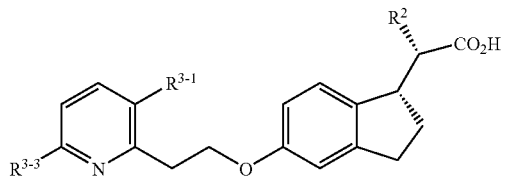
(Iccc)

| Ex. No. | R$^2$ | R$^{3-1}$ | R$^{3-3}$ | LCMS (M + H) | RT (min) |
|---|---|---|---|---|---|
| 483 | H | Me | H | 312.2 | 1.75 |
| 484 | H | H | 4-Me—Ph | 388.2 | 2.64 |
| 485 | H | H | 4-Ac—Ph | 416.2 | 2.94 |
| 486 | H | H | 4-MeO—Ph | 404.1 | 2.55 |
| 487 | H | H | 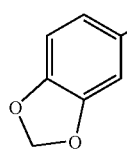 | 418.1 | 2.67 |

TABLE 19a-continued (Iccc)

| Ex. No. | R$^2$ | R$^{3-1}$ | R$^{3-3}$ | LCMS (M + H) | RT (min) |
|---|---|---|---|---|---|
| 488 | H | H | 4-Cl—Ph | 408.1 | 3.24 |
| 489 | H | H | 4-F—Ph | 392.1 | 2.93 |
| 490 | H | H | H | 374.2 | 2.69 |
| 491 | H | H | 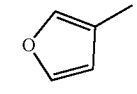 | 364.1 | 2.43 |
| 492 | H | H | 4-CF$_3$—Ph | 442.2 | 4.13 |
| 493 | H | H |  | 380.3 | 3.19 |
| 494 | H | H | 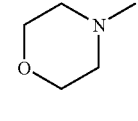 | 383.3 | 2.68 |
| 495 | H | H | 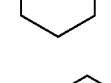 | 381.3 | 2.10 |
| 496 | H | H | 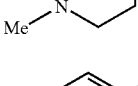 | 396.3 | 1.91 |
| 497 | Et | H | 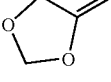 | 446.3 | 3.74 |
| 498 | Et | H | 4-Et—Ph | 430.4 | 3.74 |
| 499 | Et | H | 4-CF$_3$—Ph | 470.4 | 4.35 |
| 500 | H | Me | 4-Et-Ph | 416.2 | 2.85 |
| 501 | H | Me | 4-CF$_3$—Ph | 456.2 | 3.57 |
| 502 | Me | H | Et | 340.2 | 2.07 |
| 503 | H | H | Et | 326.2 | 1.94 |

TABLE 19b

IUPAC Names for Compounds in Table 19a

| Ex. No. | IUPAC Name |
|---|---|
| 483 | 2-{(1S)-5-[2-(3-methyl(2-pyridyl))ethoxy]indanyl}acetic acid, trifluoromethanane acetic acid salt |
| 484 | 2-(5-{2-[6-(4-methylphenyl)-2-pyridyl]ethoxy}indanyl)acetic acid |
| 485 | 2-((1S)-5-{2-[6-(4-acetylphenyl)(2-pyridyl)]ethoxy}indanyl)acetic acid |

TABLE 19b-continued

IUPAC Names for Compounds in Table 19a

| Ex. No. | IUPAC Name |
|---|---|
| 486 | 2-((1S)-5-{2-[6-(4-methoxyphenyl)(2-pyridyl)]ethoxy}indanyl)acetic acid |
| 487 | 2-{5-[2-(6-(2H-benzo[3,4-d]1,3-dioxolan-5-yl)(2-pyridyl))ethoxy](1S)indanyl}acetic acid |
| 488 | 2-((1S)-5-{2-[6-(4-chlorophenyl)(2-pyridyl)]ethoxy}indanyl)acetic acid |
| 489 | 2-((1S)-5-{2-[6-(4-fluorophenyl)(2-pyridyl)]ethoxy}indanyl)acetic acid |
| 490 | 2-{(1S)-5-[2-(6-phenyl(2-pyridyl))ethoxy]indanyl}acetic acid |
| 491 | 2-{(1S)-5-[2-(6-(3-furyl)(2-pyridyl))ethoxy]indanyl}acetic acid |
| 492 | 2-((1S)-5-{2-[6-(4-trifluoromethylphenyl)(2-pyridyl)]ethoxy}indanyl)acetic acid |
| 493 | 2-{(1S)-5-[2-(6-(3-thienyl)(2-pyridyl))ethoxy]indanyl}acetic acid |
| 494 | 2-{(1S)-5-[2-(6-morpholin-4-yl(2-pyridyl))ethoxy]indanyl}acetic acid |
| 495 | ((1S)-5-{2-[6-(1-piperidinyl)-2-pyridinyl]ethoxy}-2,3-dihydro-1H-inden-1-yl)acetic acid |
| 496 | 2-((1S)-5-{2-[6-(4-methylpiperazinyl)(2-pyridyl)]ethoxy}indanyl)acetic acid |
| 497 | 2-{5-[2-(6-(2H-benzo[3,4-d]1,3-dioxolan-5-yl)(2-pyridyl))ethoxy](1S)indanyl}(2S)butanoic acid |
| 498 | (2S)-2-((1S)-5-{2-[6-(4-ethylphenyl)(2-pyridyl)]ethoxy}indanyl)butanoic acid |
| 499 | (2S)-2-[(1S)-5-(2-{6-[4-(trifluoromethyl)phenyl](2-pyridyl)}ethoxy)indanyl]butanoic acid |
| 500 | 2-((1S)-5-{2-[6-(4-ethylphenyl)-3-methyl(2-pyridyl)]ethoxy}indanyl)acetic acid, chloride |
| 501 | 2-[(1S)-5-(2-{3-methyl-6-[4-(trifluoromethyl)phenyl](2-pyridyl)}ethoxy)indanyl]acetic acid |
| 502 | (2S)-2-{(1S)-5-[2-(5-ethyl(2-pyridyl))ethoxy]indanyl}propanoic acid |
| 503 | 2-{(1S)-5-[2-(5-ethyl(2-pyridyl))ethoxy]indanyl}acetic acid |

Example 504

Preparation of 4-hydroxy-3-propylbenzenecarbothioamide

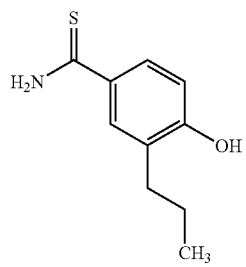

A solution of 4-hydroxy-3-propylbenzonitrile (35.63 g, 0.221 mol) (Example 29 in DMF (300 mL) was saturated with hydrogen sulfide at rt (moderate flow over 45 min). Temperature was monitored (increase of about 7° C.). Diethylamine (45.73 mL, 0.442 mol) was added to the solution. The temperature rose to 10° C. and the already green reaction mixture became darker green. Hydrogen sulfide was passed through the solution for another 30 min (at this point the reaction temperature was 40° C.). The reaction mixture was warmed to 60° C. (gaseous evolution noted). Hydrogen sulfide was again passed through the solution at 60° C. over 2 h. The reaction mixture was cooled and stirred at rt for 54 h, and most of the solvent removed under reduced pressure. The resultant residue was partitioned between ethyl acetate (300 mL) and water (200 mL). The organic layer was washed with water (4×100 mL), then brine, and dried over sodium sulfate, filtered, and concentrated. The resultant orange oil was triturated in hexanes (300 mL) and ether (25 mL) to give a yellow solid (39.97 g, 93%) after drying for 1 h under suction. LC/MS m/z 196.1 (M+H)$^+$, RT 2.16 min. $^1$H NMR (400 MHz, DMSO-d$_6$) δ 9.94 (s, 1H), 9.44 (s, 1H), 9.14 (s, 1H), 7.73-7.65 (m, 2H), 6.73 (d, 1H), 2.51-2.47 (m, 2H), 1.59-1.50 (m, 2H), 0.90 (t, 3H).

Example 505

Preparation of 4-(6,7-dihydro-5H-pyrano[2,3-d][1,3]thiazol-2-yl)-2-propylphenol

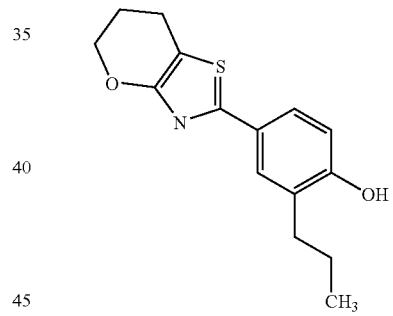

A stirred mixture of α-bromo-δ-valerolactone (77% pure; 300 g, 1.3 mol), 4-hydroxy-3-propylbenzenecarbothioamide (229.09 g; 1.2 mol) (Example 504), and absolute ethanol (2.5 L) was gradually heated under nitrogen. A significant gas evolution occurred. When the latter had slowed, the mixture was brought to reflux. After 16 h at reflux, the mixture was cooled to rt, and then concentrated in vacuo. The residue was taken-up in 50% dichloromethane/hexanes, filtered, and the solid triturated and washed with more of the solvent mixture (700 mL total). After washing with hexanes and drying in vacuo, 207.1 g (58%) of the title compound were obtained as a yellow solid. The filtrate was concentrated in vacuo, and the residue chromatographed on silica gel to afford a thick oil containing impure product in which crystals formed. Filtration, trituration, and washing of the solid with ethanol afforded 27.6 g (234.7g total; 66.1% yield) of opaque, pastel orange crystals, mp 152-154° C.; $^1$H NMR (DMSO-d$_6$): δ 9.8δ (broad exchangeable s, 1H), 7.5 (d, 1H), 7.4 (dd, 1H), 6.8 (d, 1H), 4.2 (t, 2H), 2.7 (t, 2H), 2.5 (t, 2H), 2.0 (m, 2H), 1.5 (m, 2H), 0.9 (t, 3H); LCMS: RT=3.0 min, (M+H)$^+$ 276.

Example 506

Preparation of 2[4-(3-bromopropyl)-3-propylphenyl]-6,7-dihydro-5H-pyrano{2,3-d}thiazole

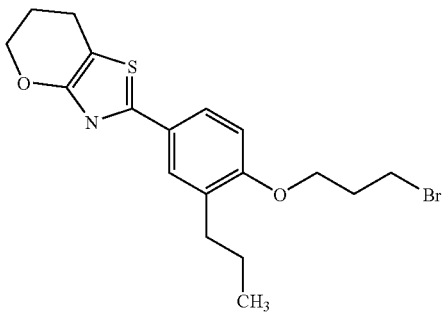

To a solution of 4-6,7-dihydro-5H-pyrano[2,3-d][1,3]thiazol-2-yl)-2-propylphenol (560 mg, 2.02 mmol) (Example 505) in DMF (5 mL) were added $Cs_2CO_3$ (0.99 g, 3.03 mmol) and 1,3-dibromopropane (0.72 mL, 7.07 mmol). The reaction mixture was stirred at rt for 18 h. Water was added, and the aqueous phase was extracted with $Et_2O$. The combined organic phases were dried ($Na_2SO_4$), filtered, and concentrated under reduced pressure. The residue was purified by silica gel flash chromatography (9:1 hexanes/EtOAc) to give the title compound was a white solid (121 mg, 15%). $^1$H NMR (400 MHz, $CDCl_3$) 7.68 (d, 1H), 7.65 (dd, 1H), 6.82 (d, 1H), 4.30 (t, 2H), 4.12 (t, 2H), 3.62 (t, 2H), 2.78 (t, 2H), 2.61 (t, 2H), 2.34 (quintet, 2H), 2.11-2.03 (m, 2H), 1.63 (hex, 2H), 0.96 (t, 3H); LC-MS: RT=4.05 min, $(M+H)^+$ 396.3.

Example 507

Preparation of ethyl((1S)-5-{[(dimethylamino)carbonothioyl]oxy}-2,3-dihydro-1H-inden-1-yl)acetate

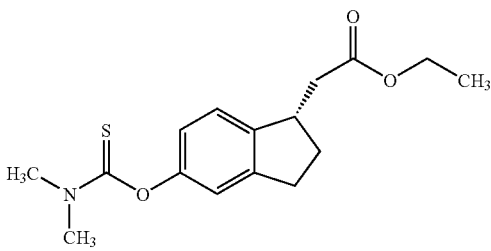

To a solution of ethyl[(1S)-5-hydroxy-2,3-dihydro-1H-inden-1-yl]acetate (620 mg, 2.81 mmol) (Example 6) in DMF (20 mL) was added NaH (124 mg, 3.10 mmol, 60% dispersion in mineral oil). Once the gaseous evolution had subsided (~10 min), dimethylthiocarbamoyl chloride (382 mg, 3.10 mmol) was added. The solution was stirred at rt for 16 h, then at 60° C. for an additional 8 h. The reaction mixture was cooled to rt, a saturated solution of $NH_4Cl$ added, and the aqueous phase was extracted with ether. The combined organic phases were dried ($Na_2SO_4$), filtered, and concentrated under reduced pressure. The residue was purified by silica gel flash chromatography (8:1 hexanes/EtOAc) to give the title compound as a yellowish oil (590 mg, 68%). $^1$H NMR (400 MHz, $CDCl_3$) 7.16 (d, 1H), 6.90 (s, 1H), 6.84 (dd, 1H), 4.18 (q, 2H), 3.63-3.51 (m, 1H), 3.46 (s, 3H), 3.30 (s, 3H), 2.98-2.84 (m, 2H), 2.78 (dd, 1H), 2.49-2.37 (m, 2H), 1.85-1.75 (m, 1H), 1.29 (t, 3H); LC-MS: RT=3.18 min, $(M+H)^+$ 308.1.

Example 508

Preparation of ethyl((1S)-5-{[(dimethylamino)carbonyl]sulfanyl}-2,3-dihydro-1H-inden-1-yl)acetate

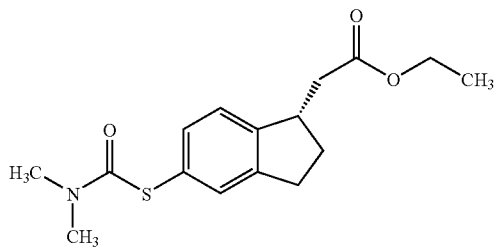

Ethyl((1S)-5-{([(dimethylamino)carbonothioyl]oxy}2,3-dihydro-1H-inden-1-yl)acetate (300 mg, 0.98 mmol) (Example 507) was placed in a round-bottom flask under a nitrogen atmosphere. The flask was fitted with a condenser and then heated to 280° C. [external temperature] for 8 h with gentle stirring. The flask was then cooled to rt, and the oil purified by silica gel flash chromatography (4:1 hexanes/EtOAc) to give the title compound as a yellow oil (101 mg, 34%). $^1$H NMR (400 MHz, $CDCl_3$) 7.33 (s, 1H), 7.26 (d, 1H), 7.18 (d, 1H), 4.17 (q, 2H), 3.63-3.53 (m, 1H), 3.12-2.98 (broad, 6H), 2.96-2.82 (m, 2H), 2.77 (dd, 1H), 2.47-2.34 (m, 2H), 1.81-1.71 (m, 1H), 1.29 (t, 3H); LC-MS: RT=3.13 min, $(M+H)^+$ 308.2.

Example 509

Preparation of ethyl[(1S)-5-({3-[4-(6,7-dihydro-5H-pyrano[2,3-d][1,3]thiazol-2-yl)-2-propylphenoxy]propyl}thio)-2,3-dihydro-1H-inden-1-yl]acetate

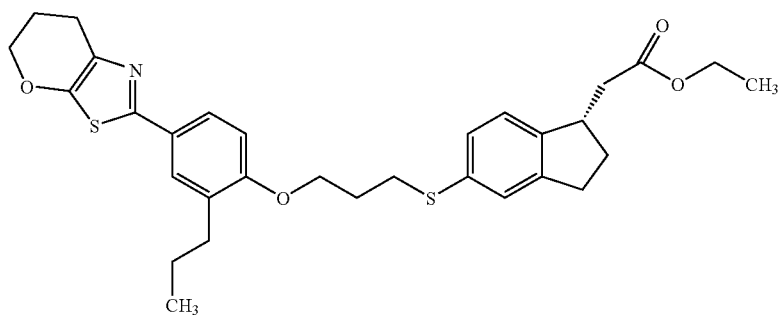

To a solution of ethyl((1S)-5-{[(dimethylamino)carbonyl]sulfanyl}-2,3-dihydro-1H-inden-1-yl)acetate (130 mg, 0.42 mmol) (Example 508) in DMF (5 mL) was added sodium ethoxide (0.63 mL, 1.69 mmol, 21% solution in EtOH), and the reaction mixture was stirred at rt. The solution turned purple, and after 2 h, the starting material had been consumed. A solution preparation of 2[4-(3-bromopropyl)-3-propylphenyl]-6,7-dihydro-5H-pyrano{2,3-d]thiazole (119 mg, 0.30 mmol) (Example 506) in DMF (1.5 mL) was added. After an additional 2 h of stirring at rt, HCl (4 mL, 1N aqueous solution) was added, followed by brine. The aqueous phase was extracted with ether, and the combined organic phases were dried (Na$_2$SO$_4$), filtered, and concentrated under reduced pressure. The residue was purified by silica gel flash chromatography (8:1 hexanes/EtOAc) to give the title compound (55 mg, 33%). $^1$H NMR (400 MHz, CDCl$_3$) 7.67 (d, 1H), 7.62 (dd, 1H), 7.21 (s, 1H), 7.15 (d, 1H), 7.07 (d, 1H), 6.77 (d, 1H), 4.30 (t, 2H), 4.17 (q, 2H), 4.08 (t, 2H), 3.58-3.48 (m, 1H), 3.11 (t, 2H), 2.92-2.73 (m, 2H), 2.77 (t, 2H), 2.72 (dd, 1H), 2.60 (t, 2H), 2.44-2.32 (m, 2H), 2.16-2.03 (m, 4H), 1.79-1.68 (m, 1H), 1.67-1.57 (m, 2H), 1.28 (t, 3H), 0.94 (t, 3H); LC-MS: RT=4.85 min, (M+H)$^+$ 552.2.

Example 510

Preparation of [(1S)-5-({3-[4-(6,7-dihydro-5H-pyrano[2,3d][1,3thiazol-2-yl)-2-propylphenoxy]propyl}sulfanyl)-2,3-dihydro-1H-inden-1-yl]acetic acid

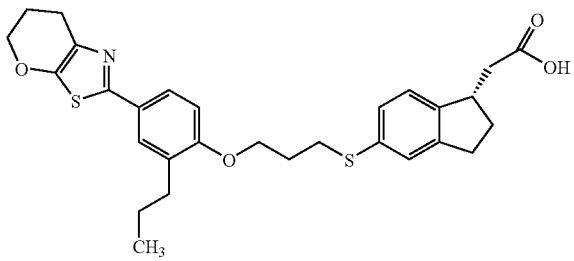

To a solution of ethyl[(1S)-5-({3-[4-(6,7-dihydro-5H-pyrano[2,3-d][1,3]thiazol-2-yl)-2-propylphenoxy]propyl}sulfanyl)-2,3-dihydro-1-H-inden-1-yl]acetate (50 mg, 0.09 mmol) (Example 509) in a mixture of THF (2 mL), ethanol (1 mL), and water (2 mL) was added LiOH (8.7 mg, 0.36 mmol). The reaction mixture was stirred vigorously at rt for 18 h, and then it was acidified to pH ~2 using HCl (1M aqueous solution). The aqueous phase was extracted with CH$_2$Cl$_2$, and the combined organic phases were dried (Na$_2$SO$_4$), filtered, and concentrated under reduced pressure. The residue was purified by silica gel flash chromatography (4:1 hexanes/EtOAc) to give the title compound (18 mg, 38%) as a white solid. $^1$H NMR (400 MHz, CDCl$_3$) 7.64 (d, 1H), 7.62 (dd, 1H), 7.22 (s, 1H), 7.15 (d, 1H), 7.08 (d, 1H), 6.75 (d, 1H), 4.31 (t, 2H), 4.15-4.05 (m, 2H), 3.58-3.50 (m, 1H), 3.12 (t, 2H), 2.93-2.80 (m, 2H), 2.78 (t, 2H), 2.78-2.73 (m, 1H), 2.60 (t, 2H), 2.49 (dd, 1H), 2.45-2.36 (m, 1H), 2.17-2.06 (m, 4H), 1.81-1.73 (m, 1H), 1.68-1.58 (m, 2H), 0.95 (t, 3H); LC-MS: RT=4.54 min, (M+H)$^+$ 524.2.

The compounds of the present invention may be employed in the treatment of diabetes, including both type 1 and type 2 diabetes (non-insulin dependent diabetes mellitus). Such treatment may also delay the onset of diabetes and diabetic complications. The compounds may be used to prevent subjects with impaired glucose tolerance from proceeding to develop type 2 diabetes. Other diseases and conditions that may be treated or prevented using compounds of the invention in methods of the invention include: Maturity-Onset Diabetes of the Young (MODY) (Herman, et al., Diabetes 43:40, 1994); Latent Autoimmune Diabetes Adult (LADA) (Zimmet, et al., Diabetes Med. 11:299, 1994); impaired glucose tolerance (IGT) (Expert Committee on Classification of Diabetes Mellitus, Diabetes Care 22 (Supp. 1):S5, 1999); impaired fasting glucose (IFG) (Charles, et al., Diabetes 40:796, 1991); gestational diabetes (Metzger, Diabetes, 40:197, 1991); and metabolic syndrome X.

The compounds of the present invention may also be effective in such disorders as obesity, and in the treatment of atherosclerotic disease, hyperlipidemia, hypercholesteremia, low HDL levels, hypertension, cardiovascular disease (including atherosclerosis, coronary heart disease, coronary artery disease, and hypertension), cerebrovascular disease and peripheral vessel disease.

The compounds of the present invention may also be useful for treating physiological disorders related to, for example, cell differentiation to produce lipid accumulating cells, regulation of insulin sensitivity and blood glucose levels, which are involved in, for example, abnormal pancreatic β-cell function, insulin secreting tumors and/or autoimmune hypoglycemia due to autoantibodies to insulin, autoantibodies to the insulin receptor, or autoantibodies that are stimulatory to pancreatic β-cells), macrophage differentiation which leads to the formation of atherosclerotic plaques, inflammatory response, carcinogenesis, hyperplasia, adipocyte gene expression, adipocyte differentiation, reduction in the pancreatic β-cell mass, insulin secretion, tissue sensitivity to insulin, liposarcoma cell growth, polycystic ovarian disease, chronic anovulation, hyperandrogenism, progesterone production, steroidogenesis, redox potential and oxidative stress in cells, nitric oxide synthase (NOS) production, increased gamma glutamyl transpeptidase, catalase, plasma triglycerides, HDL, and LDL cholesterol levels, and the like.

Compounds of the invention may also be used in methods of the invention to treat secondary causes of diabetes (Expert Committee on Classification of Diabetes Mellitus, Diabetes Care 22 (Supp. 1):S5, 1999). Such secondary causes include glucocorticoid excess, growth hormone excess, pheochromocytoma, and drug-induced diabetes. Drugs that may induce diabetes include, but are not limited to, pyriminil, nicotinic acid, glucocorticoids, phenytoin, thyroid hormone, β-adrenergic agents, α-interferon and drugs used to treat HIV infection.

The compounds of the present invention may be used alone or in combination with additional therapies and/or compounds known to those skilled in the art in the treatment of diabetes and related disorders. Alternatively, the methods and compounds described herein may be used, partially or completely, in combination therapy.

The compounds of the invention may also be administered in combination with other known therapies for the treatment of diabetes, including PPAR agonists, sulfonylurea drugs, non-sulfonylurea secretagogues, α-glucosidase inhibitors, insulin sensitizers, insulin secretagogues, hepatic glucose output lowering compounds, insulin and anti-obesity drugs. Such therapies may be administered prior to, concurrently with or following administration of the compounds of the invention. Insulin includes both long and short acting forms and formulations of insulin. PPAR agonist may include agonists of any of the PPAR subunits or combinations thereof. For example, PPAR agonist may include agonists of PPAR-α, PPAR-γ, PPAR-δ or any combination of two or three of the subunits of PPAR. PPAR agonists include, for example, rosiglitazone and pioglitazone. Sulfonylurea drugs include, for example, glyburide, glimepiride, chlorpropamide, and glipizide. α-glucosidase inhibitors that may be useful in treating diabetes when administered with a compound of the invention include acarbose, miglitol and voglibose. Insulin sensitizers that may be useful in treating diabetes include thiazolidinediones and non-thiazolidinediones. Hepatic glucose output lowering compounds that may be useful in treating diabetes when administered with a compound of the invention include metformin, such as Glucophage and Glucophage XR. Insulin secretagogues that may be useful in treating diabetes when administered with a compound of the invention include sulfonylurea and non-sulfonylurea drugs: GLP-1, GIP, secretin, nateglinide, meglitinide, repaglinide, glibenclamide, glimepiride, chlorpropamide, glipizide. GLP-1 includes derivatives of GLP-1 with longer half-lives than native GLP-1, such as, for example, fatty-acid derivatized GLP-1 and exendin. In one embodiment of the invention, compounds of the invention are used in combination with insulin secretagogues to increase the sensitivity of pancreatic β-cells to the insulin secretagogue.

Compounds of the invention may also be used in methods of the invention in combination with anti-obesity drugs. Anti-obesity drugs include β-3 agonists, CB-1 antagonists, appetite suppressants, such as, for example, sibutramine (Meridia), and lipase inhibitors, such as, for example, orlistat (Xenical).

Compounds of the invention may also be used in methods of the invention in combination with drugs commonly used to treat lipid disorders in diabetic patients. Such drugs include, but are not limited to, HMG-CoA reductase inhibitors, nicotinic acid, bile acid sequestrants, and fibric acid derivatives. Compounds of the invention may also be used in combination with anti-hypertensive drugs, such as, for example, β-blockers and ACE inhibitors.

Such co-therapies may be administered in any combination of two or more drugs (e.g., a compound of the invention in combination with an insulin sensitizer and an anti-obesity drug). Such co-therapies may be administered in the form of pharmaceutical compositions, as described above.

As used herein, various terms are defined below.

When introducing elements of the present invention or the preferred embodiment(s) thereof, the articles "a," "an," "the," and "said" are intended to mean that there are one or more of the elements. The terms "comprising," "including," and "having" are intended to be inclusive and mean that there may be additional elements other than the listed elements.

The term "subject" as used herein includes mammals (e.g., humans and animals).

The term "treatment" includes any process, action, application, therapy, or the like, wherein a subject, including a human being, is provided medical aid with the object of improving the subject's condition, directly or indirectly, or slowing the progression of a condition or disorder in the subject.

The term "combination therapy" or "co-therapy" means the administration of two or more therapeutic agents to treat a diabetic condition and/or disorder. Such administration encompasses co-administration of two or more therapeutic agents in a substantially simultaneous manner, such as in a single capsule having a fixed ratio of active ingredients or in multiple, separate capsules for each inhibitor agent. In addition, such administration encompasses use of each type of therapeutic agent in a sequential manner.

The phrase "therapeutically effective" means the amount of each agent administered that will achieve the goal of improvement in a diabetic condition or disorder severity, while avoiding or minimizing adverse side effects associated with the given therapeutic treatment.

The term "pharmaceutically acceptable" means that the subject item is appropriate for use in a pharmaceutical product.

Based on well known assays used to determine the efficacy for treatment of conditions identified above in mammals, and by comparison of these results with the results of known medicaments that are used to treat these conditions, the effective dosage of the compounds of this invention can readily be determined for treatment of each desired indication. The amount of the active ingredient (e.g., compounds) to be administered in the treatment of one of these conditions can vary widely according to such considerations as the particular compound and dosage unit employed, the mode of administration, the period of treatment, the age and sex of the patient treated, and the nature and extent of the condition treated.

The total amount of the active ingredient to be administered may generally range from about 0.0001 mg/kg to about 200 mg/kg, and preferably from about 0.01 mg/kg to about 200 mg/kg body weight per day. A unit dosage may contain from about 0.05 mg to about 1500 mg of active ingredient, and may be administered one or more times per day. The daily dosage for administration by injection, including intravenous, intramuscular, subcutaneous, and parenteral injections, and use of infusion techniques may be from about 0.01 to about 200 mg/kg. The daily rectal dosage regimen may be from 0.01 to 200 mg/kg of total body weight. The transdermal concentration may be that required to maintain a daily dose of from 0.01 to 200 mg/kg.

Of course, the specific initial and continuing dosage regimen for each patent will vary according to the nature and severity of the condition as determined by the attending diagnostician, the activity of the specific compound employed, the age of the patient, the diet of the patient, time of administration, route of administration, rate of excretion of the drug, drug combinations, and the like. The desired mode of treatment and number of doses of a compound of the present invention may be ascertained by those skilled in the art using conventional treatment tests.

The compounds of this invention may be utilized to achieve the desired pharmacological effect by administration to a patient in need thereof in an appropriately formulated pharmaceutical composition. A patient, for the purpose of this invention, is a mammal, including a human, in need of treatment for a particular condition or disease. Therefore, the present invention includes pharmaceutical compositions which are comprised of a pharmaceutically acceptable carrier and a therapeutically effective amount of a compound. A pharmaceutically acceptable carrier is any carrier which is relatively non-toxic and innocuous to a patient at concentrations consistent with effective activity of the active ingredient so that any side effects ascribable to the carrier do not vitiate the beneficial effects of the active ingredient. A therapeutically effective amount of a compound is that amount which produces a result or exerts an influence on the particular condition being treated. The compounds described herein may be administered with a pharmaceutically-acceptable carrier using any effective conventional dosage unit forms, including, for example, immediate and timed release preparations, orally, parenterally, topically, or the like.

For oral administration, the compounds may be formulated into solid or liquid preparations such as, for example, capsules, pills, tablets, troches, lozenges, melts, powders, solutions, suspensions, or emulsions, and may be prepared according to methods known to the art for the manufacture of pharmaceutical compositions. The solid unit dosage forms may be a capsule which can be of the ordinary hard- or soft-shelled gelatin type containing, for example, surfactants, lubricants, and inert fillers such as lactose, sucrose, calcium phosphate, and corn starch.

In another embodiment, the compounds of this invention may be tableted with conventional tablet bases such as lactose, sucrose, and cornstarch in combination with binders such as acacia, cornstarch, or gelatin; disintegrating agents intended to assist the break-up and dissolution of the tablet following administration such as potato starch, alginic acid, corn starch, and guar gum; lubricants intended to improve the flow of tablet granulation and to prevent the adhesion of tablet material to the surfaces of the tablet dies and punches, for example, talc, stearic acid, or magnesium, calcium or zinc stearate; dyes; coloring agents; and flavoring agents intended to enhance the aesthetic qualities of the tablets and make them more acceptable to the patient. Suitable excipients for use in oral liquid dosage forms include diluents such as water and alcohols, for example, ethanol, benzyl alcohol, and polyethylene alcohols, either with or without the addition of a pharmaceutically acceptable surfactant, suspending agent, or emulsifying agent. Various other materials may be present as coatings or to otherwise modify the physical form of the dosage unit. For instance tablets, pills or capsules may be coated with shellac, sugar or both.

Dispersible powders and granules are suitable for the preparation of an aqueous suspension. They provide the active ingredient in admixture with a dispersing or wetting agent, a suspending agent, and one or more preservatives. Suitable dispersing or wetting agents and suspending agents are exemplified by those already mentioned above. Additional excipients, for example, those sweetening, flavoring and coloring agents described above, may also be present.

The pharmaceutical compositions of this invention may also be in the form of oil-in-water emulsions. The oily phase may be a vegetable oil such as liquid paraffin or a mixture of vegetable oils. Suitable emulsifying agents may be (1) naturally occurring gums such as gum acacia and gum tragacanth, (2) naturally occurring phosphatides such as soy bean and lecithin, (3) esters or partial esters derived from fatty acids and hexitol anhydrides, for example, sorbitan monooleate, and (4) condensation products of said partial esters with ethylene oxide, for example, polyoxyethylene sorbitan monooleate. The emulsions may also contain sweetening and flavoring agents.

Oily suspensions may be formulated by suspending the active ingredient in a vegetable oil such as, for example, arachis oil, olive oil, sesame oil, or coconut oil; or in a mineral oil such as liquid paraffin. The oily suspensions may contain a thickening agent such as, for example, beeswax, hard paraffin, or cetyl alcohol. The suspensions may also contain one or more preservatives, for example, ethyl or n-propyl p-hydroxybenzoate; one or more coloring agents; one or more flavoring agents; and one or more sweetening agents such as sucrose or saccharin.

Syrups and elixirs may be formulated with sweetening agents such as, for example, glycerol, propylene glycol, sorbitol, or sucrose. Such formulations may also contain a demulcent, and preservative, flavoring and coloring agents.

The compounds of this invention may also be administered parenterally, that is, subcutaneously, intravenously, intramuscularly, or interperitoneally, as injectable dosages of the compound in a physiologically acceptable diluent with a pharmaceutical carrier which may be a sterile liquid or mixture of liquids such as water, saline, aqueous dextrose and related sugar solutions; an alcohol such as ethanol, isopropanol, or hexadecyl alcohol; glycols such as propylene glycol or polyethylene glycol; glycerol ketals such as 2,2-dimethyl-1,1-dioxolane-4-methanol, ethers such as poly(ethyleneglycol) 400; an oil; a fatty acid; a fatty acid ester or glyceride; or an acetylated fatty acid glyceride with or without the addition of a pharmaceutically acceptable surfactant such as a soap or a detergent, suspending agent such as pectin, carbomers, methylcellulose, hydroxypropylmethylcellulose, or carboxymethylcellulose, or emulsifying agent and other pharmaceutical adjuvants.

Illustrative of oils which can be used in the parenteral formulations of this invention are those of petroleum, animal, vegetable, or synthetic origin, for example, peanut oil, soybean oil, sesame oil, cottonseed oil, corn oil, olive oil, petrolatum, and mineral oil. Suitable fatty acids include oleic acid, stearic acid, and isostearic acid. Suitable fatty acid esters are, for example, ethyl oleate and isopropyl myristate. Suitable soaps include fatty alkali metal, ammonium, and triethanolamine salts and suitable detergents include cationic detergents, for example, dimethyl dialkyl ammonium halides, alkyl pyridinium halides, and alkylamine acetates; anionic detergents, for example, alkyl, aryl, and olefin sulfonates, alkyl, olefin, ether, and monoglyceride sulfates, and sulfosuccinates; nonionic detergents, for example, fatty amine oxides, fatty acid alkanolamides, and polyoxyethylenepolypropylene copolymers; and amphoteric detergents, for example, alkyl-beta-aminopropionates, and 2-alkylimidazoline quarternary ammonium salts, as well as mixtures.

The parenteral compositions of this invention may typically contain from about 0.5% to about 25% by weight of the active ingredient in solution. Preservatives and buffers may also be used advantageously. In order to minimize or eliminate irritation at the site of injection, such compositions may contain a non-ionic surfactant having a hydrophile-lipophile balance (HLB) of from about 12 to about 17. The quantity of surfactant in such formulation ranges from about 5% to about 15% by weight. The surfactant can be a single component having the above HLB or can be a mixture of two or more components having the desired HLB.

Illustrative of surfactants used in parenteral formulations are the class of polyethylene sorbitan fatty acid esters, for example, sorbitan monooleate and the high molecular weight adducts of ethylene oxide with a hydrophobic base, formed by the condensation of propylene oxide with propylene glycol.

The pharmaceutical compositions may be in the form of sterile injectable aqueous suspensions. Such suspensions may be formulated according to known methods using suitable dispersing or wetting agents and suspending agents such as, for example, sodium carboxymethylcellulose, methylcellulose, hydroxypropylmethyl-cellulose, sodium alginate, polyvinylpyrrolidone, gum tragacanth and gum acacia; dispersing or wetting agents which may be a naturally occurring phosphatide such as lecithin, a condensation product of an alkylene oxide with a fatty acid, for example, polyoxyethylene stearate, a condensation product of ethylene oxide with a long chain aliphatic alcohol, for example, heptadecaethyleneoxycetanol, a condensation product of ethylene oxide with a partial ester derived form a fatty acid and a hexitol such as polyoxyethylene sorbitol monooleate, or a condensation product of an ethylene oxide with a partial ester derived from a fatty acid and a hexitol an hydride, for example polyoxyethylene sorbitan monooleate.

The sterile injectable preparation may also be a sterile injectable solution or suspension in a non-toxic parenterally acceptable diluent or solvent. Diluents and solvents that may be employed are, for example, water, Ringer's solution, and isotonic sodium chloride solution. In addition, sterile fixed oils are conventionally employed as solvents or suspending media. For this purpose, any bland, fixed oil may be employed including synthetic mono or diglycerides. In addition, fatty acids such as oleic acid may be used in the preparation of injectables.

A composition of the invention may also be administered in the form of suppositories for rectal administration of the drug. These compositions may be prepared by mixing the drug (e.g., compound) with a suitable non-irritation excipient which is solid at ordinary temperatures but liquid at the rectal temperature and will therefore melt in the rectum to release the drug. Such material are, for example, cocoa butter and polyethylene glycol.

Another formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art (see, e.g., U.S. Pat. No. 5,023,252, incorporated herein by reference). Such patches may be constructed for continuous, pulsatile, or on demand delivery of pharmaceutical agents.

It may be desirable or necessary to introduce the pharmaceutical composition to the patient via a mechanical delivery device. The construction and use of mechanical delivery devices for the delivery of pharmaceutical agents is well known in the art. For example, direct techniques for administering a drug directly to the brain usually involve placement of a drug delivery catheter into the patient's ventricular system to bypass the blood-brain barrier. One such implantable delivery system, used for the transport of agents to specific anatomical regions of the body, is described in U.S. Pat. No. 5,011,472, incorporated herein by reference.

The compositions of the invention may also contain other conventional pharmaceutically acceptable compounding ingredients, generally referred to as carriers or diluents, as necessary or desired. Any of the compositions of this invention may be preserved by the addition of an antioxidant such as ascorbic acid or by other suitable preservatives. Conventional procedures for preparing such compositions in appropriate dosage forms can be utilized.

Commonly used pharmaceutical ingredients which may be used as appropriate to formulate the composition for its intended route of administration include: acidifying agents, for example, but are not limited to, acetic acid, citric acid, fumaric acid, hydrochloric acid, nitric acid; and alkalinizing agents such as, but are not limited to, ammonia solution, ammonium carbonate, diethanolamine, monoethanolamine, potassium hydroxide, sodium borate, sodium carbonate, sodium hydroxide, triethanolamine, trolamine.

Other pharmaceutical ingredients include, for example, but are not limited to, adsorbents (e.g., powdered cellulose and activated charcoal); aerosol propellants (e.g., carbon dioxide, $CCl_2F_2$, $F_2ClC$—$CClF_2$ and $CClF_3$); air displacement agents (e.g., nitrogen and argon); antifungal preservatives (e.g., benzoic acid, butylparaben, ethylparaben, methylparaben, propylparaben, sodium benzoate); antimicrobial preservatives (e.g., benzalkonium chloride, benzethonium chloride, benzyl alcohol, cetylpyridinium chloride, chlorobutanol, phenol, phenylethyl alcohol, phenylmercuric nitrate and thimerosal); antioxidants (e.g., ascorbic acid, ascorbyl palmitate, butylated hydroxyanisole, butylated hydroxytoluene, hypophosphorus acid, monothioglycerol, propyl gallate, sodium ascorbate, sodium bisulfite, sodium formaldehyde sulfoxylate, sodium metabisulfite); binding materials (e.g., block polymers, natural and synthetic rubber, polyacrylates, polyurethanes, silicones and styrene-butadiene copolymers); buffering agents (e.g., potassium metaphosphate, potassium phosphate monobasic, sodium acetate, sodium citrate anhydrous and sodium citrate dihydrate); carrying agents (e.g., acacia syrup, aromatic syrup, aromatic elixir, cherry syrup, cocoa syrup, orange syrup, syrup, corn oil, mineral oil, peanut oil, sesame oil, bacteriostatic sodium chloride injection and bacteriostatic water for injection); chelating agents (e.g., edetate disodium and edetic acid); colorants (e.g., FD&C Red No. 3, FD&C Red No. 20, FD&C Yellow No. 6, FD&C Blue No. 2, D&C Green No. 5, D&C Orange No. 5, D&C Red No. 8, caramel and ferric oxide red); clarifying agents (e.g., bentonite); emulsifying agents (but are not limited to, acacia, cetomacrogol, cetyl alcohol, glyceryl monostearate, lecithin, sorbitan monooleate, polyethylene 50 stearate); encapsulating agents (e.g., gelatin and cellulose acetate phthalate); flavorants (e.g., anise oil, cinnamon oil, cocoa, menthol, orange oil, peppermint oil and vanillin); humectants (e.g., glycerin, propylene glycol and sorbitol); levigating agents (e.g., mineral oil and glycerin); oils (e.g., arachis oil, mineral oil, olive oil, peanut oil, sesame oil and vegetable oil); ointment bases (e.g., lanolin, hydrophilic ointment, polyethylene glycol ointment, petrolatum, hydrophilic petrolatum, white ointment, yellow ointment, and rose water ointment); penetration enhancers (transdermal delivery) (e.g., monohydroxy or polyhydroxy alcohols, saturated or unsaturated fatty alcohols, saturated or unsaturated fatty esters, saturated or unsaturated dicarboxylic acids, essential oils, phosphatidyl derivatives, cephalin, terpenes, amides, ethers, ketones and ureas); plasticizers (e.g., diethyl phthalate and glycerin); solvents (e.g., alcohol, corn oil, cottonseed oil, glycerin, isopropyl alcohol, mineral oil, oleic acid, peanut oil, purified water, water for injection, sterile water for injection and sterile water for irrigation); stiffening agents (e.g., cetyl alcohol, cetyl esters wax, microcrystalline wax, paraffin, stearyl alcohol, white wax and yellow wax); suppository bases (e.g., cocoa butter and polyethylene glycols (mixtures)); surfactants (e.g., benzalkonium chloride, nonoxynol 10, oxtoxynol 9, polysorbate 80, sodium lauryl sulfate and sorbitan monopalmitate); suspending agents (e.g., agar, bentonite, carbomers, carboxymethylcellulose sodium, hydroxyethyl cellulose, hydroxypropyl cellulose, hydroxypropyl methylcellulose, kaolin, methylcellulose, tragacanth and veegum); sweetening e.g., aspartame, dextrose, glycerin, mannitol, propylene glycol, saccharin sodium, sorbitol and sucrose); tablet anti-adherents (e.g., magnesium stearate and talc); tablet binders (e.g., acacia, alginic acid, carboxymethylcellulose sodium, compressible sugar, ethylcellulose, gelatin, liquid glucose, methylcellulose, povidone and pregelatinized starch); tablet and capsule diluents (e.g., dibasic calcium phosphate, kaolin, lactose, mannitol, microcrystalline cellulose, powdered cellulose, precipitated calcium carbonate, sodium carbonate, sodium phosphate, sorbitol and starch); tablet coating agents (e.g., liquid glucose, hydroxyethyl cellulose, hydroxypropyl cellulose, hydroxypropyl methylcellulose, methylcellulose, ethylcellulose, cellulose acetate phthalate and shellac); tablet direct compression excipients (e.g., dibasic calcium phosphate); tablet disintegrants (e.g., alginic acid, carboxymethylcellulose calcium, microcrystalline cellulose, polacrillin potassium, sodium alginate, sodium starch glycollate and starch); tablet glidants (e.g., colloidal silica, corn starch and talc); tablet lubricants (e.g., calcium stearate, magnesium stearate, mineral oil, stearic acid and zinc stearate); tablet/ capsule opaquants (e.g., titanium dioxide); tablet polishing agents (e.g., carnuba wax and white wax); thickening agents (e.g., beeswax, cetyl alcohol and paraffin); tonicity agents (e.g., dextrose and sodium chloride); viscosity increasing agents (e.g., alginic acid, bentonite, carbomers, carboxymethylcellulose sodium, methylcellulose, povidone, sodium alginate and tragacanth); and wetting agents (e.g., heptadecaethylene oxycetanol, lecithins, polyethylene sorbitol monooleate, polyoxyethylene sorbitol monooleate, and polyoxyethylene stearate).

The compounds described herein may be administered as the sole pharmaceutical agent or in combination with one or more other pharmaceutical agents where the combination causes no unacceptable adverse effects. For example, the compounds of this invention can be combined with known anti-obesity, or with known antidiabetic or other indication agents, and the like, as well as with admixtures and combinations thereof.

The compounds described herein may also be utilized, in free base form or in compositions, in research and diagnostics, or as analytical reference standards, and the like. Therefore, the present invention includes compositions which are comprised of an inert carrier and an effective amount of a compound identified by the methods described herein, or a salt or ester thereof. An inert carrier is any material which does not interact with the compound to be carried and which lends support, means of conveyance, bulk, traceable material, and the like to the compound to be carried. An effective amount of compound is that amount which produces a result or exerts an influence on the particular procedure being performed.

Formulations suitable for subcutaneous, intravenous, intramuscular, and the like; suitable pharmaceutical carriers; and techniques for formulation and administration may be prepared by any of the methods well known in the art (see, e.g., Remington's Pharmaceutical Sciences, Mack Publishing Co., Easton, Pa., 20$^{th}$ edition, 2000).

The following examples are presented to illustrate the invention described herein, but should not be construed as limiting the scope of the invention in any way.

Capsule Formulation

A capsule formula is prepared from:

| | |
|---|---|
| Compound of this invention | 10 mg |
| Starch | 109 mg |
| Magnesium stearate | 1 mg |

The components are blended, passed through an appropriate mesh sieve, and filled into hard gelatin capsules.

Tablet Formulation

A tablet is prepared from:

| | |
|---|---|
| Compound of this invention | 25 mg |
| Cellulose, microcrystalline | 200 mg |
| Colloidal silicon dioxide | 10 mg |
| Stearic acid | 5.0 mg |

The ingredients are mixed and compressed to form tablets. Appropriate aqueous and non-aqueous coatings may be applied to increase palatability, improve elegance and stability or delay absorption.

Sterile IV Solution

A mg/mL solution of the desired compound of this invention is made using sterile, injectable water, and the pH is adjusted if necessary. The solution is diluted for administration with sterile 5% dextrose and is administered as an IV infusion.

Intramuscular Suspension

The following intramuscular suspension is prepared:

| | |
|---|---|
| Compound of this invention | 50 μg/mL |
| Sodium carboxymethylcellulose | 5 mg/mL |
| TWEEN 80 | 4 mg/mL |
| Sodium chloride | 9 mg/mL |
| Benzyl alcohol | 9 mg/mL |

The suspension is administered intramuscularly.

Hard Shell Capsules

A large number of unit capsules are prepared by filling standard two-piece hard galantine capsules each with powdered active ingredient, 150 mg of lactose, 50 mg of cellulose, and 6 mg of magnesium stearate.

Soft Gelatin Capsules

A mixture of active ingredient in a digestible oil such as soybean oil, cottonseed oil, or olive oil is prepared and injected by means of a positive displacement pump into molten gelatin to form soft gelatin capsules containing the active ingredient. The capsules are washed and dried. The active ingredient can be dissolved in a mixture of polyethylene glycol, glycerin and sorbitol to prepare a water miscible medicine mix.

Immediate Release Tablets/Capsules

These are solid oral dosage forms made by conventional and novel processes. These units are taken orally without water for immediate dissolution and delivery of the medication. The active ingredient is mixed in a liquid containing ingredient such as sugar, gelatin, pectin, and sweeteners. These liquids are solidified into solid tablets or caplets by freeze drying and solid state extraction techniques. The drug compounds may be compressed with viscoelastic and thermoelastic sugars and polymers or effervescent components to produce porous matrices intended for immediate release, without the need of water.

It should be apparent to one of ordinary skill in the art that changes and modifications can be made to this invention without departing from the spirit or scope of the invention as it is set forth herein.

Evaluation of Compounds

Demonstration of the activity of the compounds of the present invention may be accomplished through in vitro, ex vivo, and in vivo assays that are well known in the art. For example, to demonstrate the efficacy of a pharmaceutical agent for the treatment of diabetes and related disorders such as Syndrome X, impaired glucose tolerance, impaired fasting glucose, and hyperinsulinemia or atherosclerotic disease and related disorders such as hypertriglyceridemia and hypercholesteremia, the following assays may be used.

Insulin Receptor Binding in 3T3-L1 Cells Treated with Compounds

3T3-L1 cells were seeded at 9300 cells per well in Costar flat bottom TC and incubated for 1 week until they were 2 days post-confluent (e.g., cells have reached maximum density). The cells were then treated for 2 days with differentiation media (Dulbecco's Modified Eagle Medium (DMEM), 100 μg/ml Penicillin/Streptomycin, 2 mM L-Glutamine, 10% Fetal Bovine Serum) containing 0.5 μM human Insulin-like Growth Factor (IGF-1) and test compounds. After treatment, the media was replaced with differentiation media, and the cells were incubated for 4 days. The cells were then assayed for insulin receptor activity. After washing the cells with buffer, they were incubated with 0.1 nM $^{125}$I-insulin and (+/−) 100 nM unlabeled insulin, and incubated at rt for 1 hour. The cells were then washed 3× with buffer, dissolved with 1 N NaOH, and counted on a gamma counter. An EC50 value was determined if a plateau was attained and percent maximum stimulation was assessed.

In Vivo Assays

Method for Measuring Blood Glucose Levels db/db mice (obtained from Jackson Laboratories, Bar Harbor, Me.) are bled (by either eye or tail vein) and grouped according to equivalent mean blood glucose levels. They are dosed orally (by gavage in a pharmaceutically acceptable vehicle) with the test compound once daily for 14 days. At this point, the animals are bled again by eye or tail vein and blood glucose levels are determined. In each case, glucose levels are measured with a Glucometer Elite XL (Bayer Corporation, Elkhart, Ind.).

Method for Measuring Triglyceride Levels hApoA1 mice (obtained from Jackson Laboratories, Bar Harbor, Me.) are bled (by either eye or tail vein) and grouped according to equivalent mean serum triglyceride levels. They are dosed orally (by gavage in a pharmaceutically acceptable vehicle) with the test compound once daily for 8 days. The animals are then bled again by eye or tail vein, and serum triglyceride levels are determined. In each case, triglyceride levels are measured using a Technicon Axon Autoanalyzer (Bayer Corporation, Tarrytown, N.Y.).

Method for Measuring HDL-Cholesterol Levels

To determine plasma HDL-cholesterol levels, hApoA1 mice are bled and grouped with equivalent mean plasma HDL-cholesterol levels. The mice are orally dosed once daily with vehicle or test compound for 7 days, and then bled again on day 8. Plasma is analyzed for HDL-cholesterol using the Synchron Clinical System (CX4) (Beckman Coulter, Fullerton, Calif.).

Method for Measuring Total Cholesterol, HDL-Cholesterol, Triglycerides, and Glucose Levels In another in vivo assay, obese monkeys are bled, then orally dosed once daily with vehicle or test compound for 4 weeks, and then bled again. Serum is analyzed for total cholesterol, HDL-cholesterol, triglycerides, and glucose using the Synchron Clinical System (CX4) (Beckman Coulter, Fullerton, Calif.). Lipoprotein subclass analysis is performed by NMR spectroscopy as described by Oliver et al., (Proc. Natl. Acad. Sci. USA 98:5306-5311, 2001).

Method for Measuring an Effect on Cardiovascular Parameters

Cardiovascular parameters (e.g., heart rate and blood pressure) are also evaluated. SHR rats are orally dosed once daily with vehicle or test compound for 2 weeks. Blood pressure and heart rate are determined using a tail-cuff method as described by Grinsell et al., (Am. J. Hypertens. 13:370-375, 2000). In monkeys, blood pressure and heart rate are monitored as described by Shen et al., (J. Pharmacol. Exp. Therap. 278:1435-1443, 1996).

Evaluation of Compound Efficacy on the Reduction of Body Weight in Diet-Induced Obese Mice The purpose of this protocol is to determine the effect of chronic administration of a compound on the body weight of mice made obese by exposure to a 45% kcal/g high fat diet for more than 10 weeks. The body weight of mice selected for these studies is generally higher than three standard deviations from the weight of a control group of mice fed standard low fat (5-6% fat) mouse chow. Diet-induced obese (DIO) animals have been used frequently in the determination of compound efficacy in the reduction of body weight (see, e.g., Brown, et al., Brit. J. Pharmacol. 132:1898-1904, 2001; Guerre-Millo, et al. J. Biol. Chem. 275(22):16638-42, 2000; Han, et al., Intl. J. Obesity and Related Metabolic Disorders 23(2):174-79, 1999, Surwit, et al., Endocrinol. 141(10):3630-37, 2000).

This animal model has been successfully used in the identification and characterization of the efficacy profile of compounds that are or have been used in the management of body weight in obese humans (see, e.g., Brown, et al., 2001; Guerre-Millo, et al., 2000; Han, et al., 1999).

A typical study includes 60-80 male C57bl/J6 mice (n=10/treatment group) with an average body weight of approximately 45 g. Mice are kept in standard animal rooms under controlled temperature and humidity and a 12 hour/12 hour light/dark cycle. Water and food are continuously available. Mice are individually housed. Animals are sham dosed with study vehicle for at least four days before the recording of two-day baseline measurements of body weight and 24-hour food and water consumption. Mice are assigned to one of 6-8 treatment groups based upon their body weight on baseline. The groups are set up so that the mean and standard error of the mean of body weight are similar.

Animals are orally gavaged (5 ml/kg) daily before the dark phase of the light/dark cycle for a pre-determined number of days (typically 8-14 days) with their assigned dose/compound. Compounds are typically dosed at 5 or 10 mg/kg p.o. q.d. Body weight, and food and water consumption are measured. Data is analyzed using appropriate statistics following the research design. Compounds are considered to be active if a statistically significant reduction in weight is observed for the treated animals, relative to vehicle-treated control animals.

The structures, materials, compositions, and methods described herein are intended to be representative examples of the invention, and it will be understood that the scope of the invention is not limited by the scope of the examples. Those skilled in the art will recognize that the invention may be practiced with variations on the disclosed structures, materials, compositions and methods, and such variations are regarded as within the ambit of the invention.

We claim:

1. A compound of Formula (I)

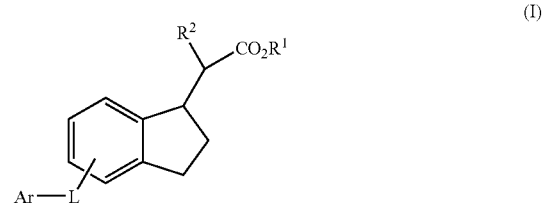

wherein $R^1$ and $R^2$ are independently H, $C_1$-$C_6$ alkyl, or $C_3$-$C_6$ cycloalkyl;

L is a linker and selected from the group consisting of:

—$(CH_2)_m$—X—,

—Y—$(CH_2)_n$—X—,
and

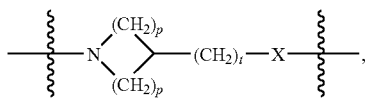

wherein
X is selected from the group consisting of O, S, S(=O), and S(O)$_2$, wherein L can be

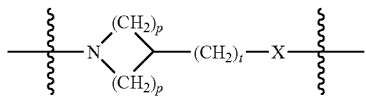

only when X is O,
Y is selected from the group consisting of O, NR$^5$, S, S(=O), and S(=O)$_2$,
m is 2, or 3,
n is 2, 3, or 4,
t is 0 or 1,
p is 0, 1, 2, or 3,
q is 1, 2, 3, or 4,
wherein the sum of p and q is 1,2, 3, or 4;
Ar is selected from the group consisting of phenyl and a 6-membered heteroaryl ring containing up to three N atoms, said Ar being optionally substituted at any available position by 1 to 5 independently selected R$^3$ groups, and
optionally fused to a 5- or 6-membered saturated carbocyclic ring,
a 5- or 6-membered unsaturated carbocyclic ring, or
a 5- or 6-membered heterocyclic ring containing up to 3 additional heteroatoms selected from the group consisting of N, O, and S,
wherein
said fused ring may be optionally substituted at any available position by 1 to 4 independently selected R$^4$ groups;
R$^3$ is selected from the group consisting of:
hydroxy,
SH,
halo,
CN,
NO$_2$,
C(=O)OH,
C(=O)—OC$_1$-C$_6$ alkyl,
CO(=O)—OC$_3$-C$_6$ cycloalkyl,
NR$^6$R$^7$,
C(=O)NR$^6$R$^7$,
C(=S)NR$^6$R$^7$,
C$_1$-C$_6$ alkyl optionally substituted with halo, OH, NR$^6$R$^7$, or C$_1$-C$_6$ alkoxy,
C$_1$-C$_6$ haloalkyl,
C$_1$-C$_6$ alkoxy,
C$_1$-C$_6$ thioalkyl,
C$_2$-C$_6$ alkenyl,
C$_1$-C$_6$ haloalkoxy,
C$_3$-C$_8$ cycloalkyl,
C$_3$-C$_8$ cycloalkoxy,
phenoxy optionally substituted on the phenyl ring with halo, C$_1$-C$_6$ alkyl, or C$_1$-C$_6$ alkoxy, and
a mono or bicyclic ring radical selected from the group consisting of
a) phenyl optionally fused to
a 5- or 6-membered saturated or partially unsaturated carbocyclic ring, or
a 5- or 6-membered saturated or partially unsaturated heterocyclic ring containing from 1-3 heteroatoms selected from the group consisting of N, O, and S,
b) a 5- or 6-membered heterocyclic ring radical containing up to 4 heteroatoms selected from N, O, or S, optionally fused to
a 5- or 6-membered saturated or partially unsaturated carbocyclic ring, or
a 5- or 6-membered saturated or partially unsaturated heterocyclic ring containing from 1-3 heteroatoms selected from the group consisting of N, O, and S,
said mono or bicyclic ring radical being optionally substituted with up to 5 groups independently selected from the group consisting of
halo,
hydroxy,
oxo,
CN,
C$_1$-C$_6$ alkyl optionally substituted with halo, OH, NR$^6$R$^7$, or C$_1$-C$_6$ alkoxy,
C$_1$-C$_6$ haloalkyl,
C$_1$-C$_6$ alkoxy,
C$_1$-C$_6$ thioalkyl,
C$_1$-C$_6$ haloalkoxy,
C$_3$-C$_8$ cycloalkyl,
C$_3$-C$_8$ cycloalkoxy,
C$_1$-C$_6$ acyl,
C(=O)OH,
CH$_2$C(=O)OH,
NR$^6$R$^7$,
C(=O)NR$^6$R$^7$,
C(=O)OC$_1$-C$_6$ alkyl, and
C(=O)OC$_3$-C$_6$ cycloalkyl;
R$^4$ is selected from the group consisting of:
oxo,
hydroxy,
halo,
CN
NR$^6$R$^7$,
C$_1$-C$_6$ alkyl optionally substituted with OH, NR$^6$R$^7$, or C$_1$-C$_6$ alkoxy,
C$_1$-C$_6$ haloalkyl,
C$_1$-C$_6$ alkoxy,
C$_1$-C$_6$ thioalkyl,
C$_1$-C$_6$ haloalkoxy,
C$_3$-C$_8$ cycloalkyl, and
C$_3$-C$_8$ cycloalkoxy;
R$^5$ is selected from the group consisting of:
H,
C$_1$-C$_6$ alkyl optionally substituted with C$_3$-C$_6$ cycloalkyl,
C$_1$-C$_6$ acyl,
benzyl optionally substituted with halo, C$_1$-C$_6$ alkoxy, (C$_1$-C$_6$) alkyl, CN, NH$_2$, N[(C$_1$-C$_3$)alkyl]$_2$, NO$_2$, or CF$_3$,
C$_3$-C$_6$ cycloalkyl, and
C(=O)OC$_1$-C$_6$ alkyl;

$R^6$ and $R^7$ are independently selected from the group consisting of:

H, $C_1$-$C_6$ alkyl optionally substituted with $C_3$-$C_6$ cycloalkyl, $C_1$-$C_6$ acyl, benzyl optionally substituted with halo, $C_1$-$C_6$ alkoxy, $(C_1$-$C_6)$alkyl, CN, $NH_2$, $N[(C_1$-$C_3)$alkyl$]_2$, $NO_2$, or $CF_3$, $C_3$-$C_6$ cycloalkyl, and phenyl optionally substituted with halo, $C_1$-$C_6$ alkoxy, $(C_1$-$C_6)$alkyl, CN, $N[(C_1$-$C_3)$alkyl$]_2$, $NO_2$, or $CF_3$, or $R^6$ and $R^7$ may be taken together with the nitrogen atom to which they are attached to form a 5- or 6-membered heterocyclic ring optionally interrupted by $NR^5$ or O;

and pharmacologically acceptable esters and salts thereof.

2. The compound of claim 1, wherein $R^1$ and $R^2$ are independently H or $C_1$-$C_6$ alkyl;

L is a linker and selected from the group consisting of:

—(CH$_2$)$_m$—X—, and

—Y—(CH$_2$)$_n$—X—, wherein

X is selected from the group consisting of O, S, S(O), and S(O)$_2$,

Y is selected from the group consisting of O, $NR^5$, S, S(=O), and S(=O)$_2$, m is 2, or 3, n is 2, 3, or 4;

Ar is a 6-membered heteroaryl ring containing up to three N atoms, optionally substituted at any available position by 1 to 5 independently selected $R^3$ groups, and optionally fused to a 5- or 6-membered saturated carbocyclic ring, a 5- or 6-membered unsaturated carbocyclic ring, or a 5- or 6-membered heterocyclic ring containing up to 3 additional heteroatoms selected from the group consisting of N, O, and S, wherein said fused ring may be optionally substituted at any available position by 1 to 4 independently selected $R^4$ groups;

and m, n, $R^3$, $R^4$, $R^5$, $R^6$, and $R^7$ are as defined in claim 1.

3. The compound of claim 1, wherein $R^1$ and $R^2$ are independently H or $C_1$-$C_6$ alkyl;

L is —Y—(CH$_2$)$_n$—X—, wherein

X is O,

Y is O;

Ar is phenyl optionally substituted at any available position by 1 to 5 independently selected $R^3$ groups;

and n, $R^3$, $R^6$, and $R^7$ are as defined in claim 1.

4. The compound of claim 1, wherein $R^1$ and $R^2$ are independently H or $C_1$-$C_6$ alkyl;

L is —Y—(CH$_2$)$_n$—X—, wherein

X is O,

Y is O;

Ar is phenyl optionally substituted at any available position by 1 to 5 independently selected $R^3$ groups;

and fused to a 5- or 6-membered saturated carbocyclic ring, a 5- or 6-membered unsaturated carbocyclic ring, or a 5- or 6-membered heterocyclic ring containing up to 3 additional heteroatoms selected from N, O, and S, wherein said fused ring may be optionally substituted at any available position by 1 to 4 independently selected $R^4$ groups;

and n, $R^3$, $R^4$, $R^6$, and $R^7$ are as defined in claim 1.

5. The compound of claim 1, wherein $R^1$ and $R^2$ are independently H or $C_1$-$C_6$ alkyl;

L is —Y—(CH$_2$)$_n$—X—, wherein

X is O,

Y is $NR^5$;

Ar is a 6-membered heteroaryl ring containing up to three N atoms, optionally substituted at any available position by 1 to 5 independently selected $R^3$ groups; and n, $R^3$, $R^5$, $R^6$, and $R^7$ arc as defined in claim 1.

6. The compound of claim 1, wherein $R^1$ and $R^2$ are independently H or $C_1$-$C_6$ alkyl;

L is —(CH$_2$)$_m$—X—, wherein

X is O;

Ar is a 6-membered heteroaryl ring containing up to three N atoms, optionally substituted at any available position by 1 to 5 independently selected $R^3$ groups, and optionally fused to a 5- or 6-membered saturated carbocyclic ring, a 5- or 6-membered unsaturated carbocyclic ring, or a 5- or 6-membered heterocyclic ring containing up to 3 additional heteroatoms selected from N, O, and S, wherein said fused ring may be optionally substituted at any available position by 1 to 4 independently selected $R^4$ groups;

and m, $R^3$, $R^4$, $R^6$, and $R^7$ are as defined in claim 1.

7. A compound selected from the group consisting oil ((1S)-5-{2-[(3-methyl-7-propyl-1,2-benzisoxazol-6-yl) oxy]ethoxy}-2,3-dihydro-1H-inden-1-yl)acetic acid;

2-((1S)-5-{2-[6-(4-acetylphenyl)(2-pyridyl)] ethoxy}indanyl)acetic acid;

2-{(1S)-5-[3-(3,7-dimethylbenzo[d]isoxazol-6-yloxy) propoxy]indanyl}acetic acid;

2-{(1S)-5-[3-(3-methyl-7-propylbenzo [d]isoxazol-6-yloxy)propoxy]indanyl}acetic acid;

2-{5-[2-(6-(2H-benzo[3,4-d]1,3-dioxolan-5-yl)(2-pyridyl))ethoxy](1S)indanyl}(2S)butanoic acid;

(2S)-2-((1S)-5-{2-[6-(4-ethylphenyl)(2-pyridyl)1] ethoxy}indanyl)butanoic acid;

2-[(1S)-5-(3-{[2-(4-ethylphenyl)-5-methylpyrimidin-4-yl]methylamino}propoxy) indanyl]acetic acid;

2-((1S)-5-{3-[(2-(21-1-benzo[3,4-d]1,3-dioxolen-5-yl)-5-methylpyrimidin-4-yl)methylamino] propoxy}indanyl)acetic acid;

2-[(1S)-5-[3-{2-methyl-4-[3-(trifluoromethyl)(1,2,4-thiadiazol-5-yl)]phenoxy}propoxy)indanyl]acetic acid;

2-{(1S)-5-[3-({2-[4-(tert-butyl)phenyl]-5-methylpyrimidin-4-yl}methylamino) propoxylindanyl}acetic acid:

2-((1S)-5-{3-[2-propyl-4-(trifluoromethyl)phenoxy] propoxy}indanyl)acetic acid;
2-{(1S)-5-[3-(methyl {5-methyl-2-[4-(methylethyl)phenyl]pyrimidin-4-yl}amino) propoxy]indanyl}acetic acid;
2-[(1S)-5-(3-{[2-(4-ethoxyphenyl)-5-methylpyrimidin-4-yl]methylamino}propoxy)indanyl]acetic acid;
2-[(1S)-5-(3-{[2-(4-ethoxyphenyl)-5-methylpyrimidin-4-yl]methylamino}propoxy)indanyl]acetic acid;
2-[(1S)-5-(3-{[5-fluoro-2-(4-methoxyphenyl)pyrimidin-4-yl]methylamino}propoxy)indanyl]acetic acid;
2-{(1S)-5-[3-({5-fluoro-2-[4-(methylethyl)phenyl]pyrimidin-4-yl}methylamino) propoxy]indanyl}acetic acid;
2-((1S)-5-{3-[(2-(2H-benzo [3,4-d]1,3-dioxolan-5-yl)-5-fluoropyrimidin-4-yl)methylamino]propoxy}indanyl)acetic acid;
((1S)-5-{3-[4-(4-ethyl-1,3-thiazol-2-yl)-2-propylphenoxy]propoxy}-2,3-dihydro-1H-inden-1-yl)acetic acid;
2-((1S)-5-{3-[4-(5-acetyl-4-methyl(1,3-thiazol-2-yl))-2-propylphenoxy]propoxy}indanyl)acetic acid;
2-[(1S)-5-(3-{4-[4-(tert-butyl)(1,3-thiazol-2-yl)]-2-propylphenoxy}propoxy) indanyl]acetic acid;
2-(4-{3-[(1S)-1-(carboxymethyl)indan-5-yloxy]propoxy}-3-propylphenyl)-4-methyl-1,3-thiazole-5-carboxylic acid;
2-[(1S)-5-(3-{2-propyl-4-[4-(trifluoromethyl)(1,3-thiazol-2-yl)]phenoxy}propoxy) indanyl]acetic acid;
2-{(1S)-5-[3-(2-propyl-4-(4,5,6-trihydrocyclopenta[1,2-d]1,3-thiazol-2-yl)phenoxy) propoxy]indanyl}acetic acid;
2-(4-{3-[(1S)-1-(carboxymethyl)indan-5-yloxy]propoxy}phenyl)-4-methyl-1,3-thiazole-5-carboxylic acid;
2-((1S)-5-{3-[4-(4,5-dimethyl(1,3-thiazol-2-yl))phenoxy]propoxy}indanyl)acetic acid;
2-((1S)-5-{3-[4-(4-methoxy(1,3-thiazol-2-yl))phenoxy]propoxy}indanyl)acetic acid;
2-{(1S)-5-[3-(4-(4,5,6,7-tetrahydrobenzothiazol-2-yl) phenoxy)propoxy]indanyl}acetic acid;
2-((1S)-5-{3-[4-(4-ethoxy(1,3-thiazol-2-yl))-2-propylphenoxy]propoxy}indanyl)acetic acid;
2-{(1S)-5-[3-(2-propyl-4-(4,5,6,7-tetrahydrobenzothiazol-2-yl)phenoxy) propoxy]indanyl}acetic acid;
2-((1S)-5-{3-[4-(4-ethoxy(1,3-thiazol-2-yl))-2-methoxyphenoxy]propoxy}indanyl)acetic acid;
2-((1S)-5-{3-[4-(4,5-dimethyl(1,3-thiazol-2-yl))-2-methoxyphenoxy]propoxy}indanyl)acetic acid;
2-{(1S)-5-[3-(2-methoxy-4-(4,5,6-trihydrocyclopenta[1,2-d]1,3-thiazol-2-yl)phenoxy)propoxy]indanyl}acetic acid;
2-[(1S)-5-(3-{2-methoxy-4-[4-(methylethoxy)(1,3-thiazol-2-yl)]phenoxy}propoxy)indanyl]acetic acid;
[(1S)-5-(3-{[5-(4,5-dimethyl-1,3-thiazol-2-yl)-2-pyridinyl]oxy}propoxy)-2,3-dihydro-1H-inden-1-yl]acetic acid;
2-[(1S)-5-{3-1,4-(4-ethyl(1,3-thiazol-2-yl))-2-methoxyphenoxy]propoxy}indanyl)acetic acid;
2-{(1S)-5-[3-(2-methoxy-4-(4,5,6,7-tetrahydrobenzothiazol-2-yl)phenoxy)propoxy]indanyl}acetic acid;
2-((1S)-5-{3-[4-(5-acetyl-4-methyl(1,3-thiazol-2-yl))-2-methoxyphenoxy]propoxy}indanyl)acctic acid;
2-((1S)-5-{3-[5-(5-acetyl-4-methyl(1,3-thiazol-2-yl))(2-pyridyloxy)]propoxy}indanyl)acetic acid;
2-((1S)-5-{3-[5-(4-ethyl(1,3-thiazol-2-yl))(2-pyridyloxy)]propoxy}indanyl)acetic acid;
2-{(1S)-5-[3-(4-(4,5,6,7-tetrahydrobenzoxazol-2-yl)phenoxy)propoxy]indanyl}acetic acid;
2-((1S )-5-{3-[2-methoxy-4-(4-methoxy(1,3-thiazol-2-yl))phenoxy]propoxy}indanyl)acetic acid;
2-[(1S)-5-(3-{[2-(4-fluorophenyl)-6-methylpyrimidin-4-yl]methylamino]propoxy}indanyl)acetic acid;
2-[2-(4-{3-[(1S)-1-(carboxymethyl)indan-5-yloxyl]propoxy}-3-propylphenyl)-1,3-thiazol-4-yl]acetic acid;
2-((1S)-5-{3-[4-(4-ethoxy-5-methyl(1,3-thiazol-2-yl))-2-propylphenoxy]propoxy}indanyl)acetic acid;
2-((1S)-5-[3-{4-[5-(N,N-dimethylcarbamoyl)-4-methyl(1,3-thiazol-2-yl)]-2-propylphenoxy}propoxy)indanyl]acetic acid;
2-{(1S)-5-[3-(2-propyl-4-(5,6,7-trihydro-2H-pyrano[2,3-d]1,3-thiazol-2-yl)phenoxy)propoxy]indanyl}acetic acid;
2-[(1S)-5-(3-{[2-(4-cyclohexylphenyl)-6-methylpyrimidin-4-yl]methylamino}propoxy)indanyl]acetic acid;
2-{(1S)-5-[3-(2-methoxy-4-(4,5,6,7-tetrahydrobenzoxazol-2-yl)phenoxy) propoxy]indanyl}acetic acid;
2-((1S)-5-{3-[4-(4-ethyl(1,3-oxazol-2-yl))-2-propylphenoxy]propoxy}indanyl)acetic acid;
2-{(1S)-5-[3-(2-propyl-4-(4,5,6,7-tetrahydrobenzoxazol-2-yl)phenoxy) propoxy]indanyl}acetic acid;
2-[(1S)-5-(3-{4-[4-(methylethoxy)(1,3-thiazol-2-yl)]-2-propylphenoxy}propoxy)indanyl]acetic acid;
2-{(1S)-5-[3-(2-propyl-4-(1,3-thiazol-2-yl)phenoxy)propoxy]indanyl}acetic acid;
2-((1S)-5-{3-[4-(5-acetyl-4-methyl(1,3-oxazol-2-yl))-2-propylphenoxy]propoxy}indanyl)acetic acid;
2-((1S)-5-{3-[4-(4-ethyl(1,3-oxazol-2-yl))-2-methoxyphenoxy]propoxy}indanyl)acetic acid;
2-{(1S)-5-[3-(2-methoxy-4-(1,3-thiazol-2-yl)phenoxy) propoxy]indanyl}acetic acid;
2-((1S)-5-{3-[4-(4-ethoxy-5-methyl(1,3-thiazol-2-yl))-2-methoxyphenoxy]propoxy}indanyl)acetic acid;
2-{(1S)-5-[3-(2-methoxy-4-(5,6,7-trihydro-2H-pyrano[2,3-d]1,3-thiazol-2-yl)phenoxy)propoxy]indanyl}acetic acid;
2-{(1S)-5-[3-(4-phenoxy-2-propylphenoxy)propoxyl]indanyl}acetic acid;
2-((1S)-5-{3-[4-(5,5-dimethyl-7-oxo(4,5,6-trihydrobenzothiazol-2-yl))-2-propylphenoxy]propoxy}indanyl) acetic acid;
2-{(1S)-5-[3-(4-benzothiazol-2-yl-2-methoxyphenoxy) propoxy]indanyl}acetic acid;
2-{(1S)-5-[3-(2-ethoxy-4-(4,5,6,7-tetrahydrobenzothiazol-2-yl)phenoxy) propoxy]indanyl}acetic acid;
2-{(1S)-5-[3-(2-propoxy-4-(4,5,6,7-tetrahydrobenzothiazol-2-yl)phenoxy) propoxy]indanyl}acetic acid;
2-{(1R)-5-[3-(2-propyl-4-(5,6,7-trihydro-2H-pyrano[2,3-d]1,3-thiazol-2-yl)phenoxy)propoxy]indanyl}acetic acid; and
[(1S)-5-({3-[4-(6,7-dihydro-5H-pyrano[3,2-d][1,3]thiazol-2-yl)-2-propylphenoxy]propyl}sulfanyl)-2,3-dihydro-1H-inden-1-yl]acetic acid.
or a pharmaceutically acceptable salt thereof.

8. A pharmaceutical composition comprising a therapeutically effective amount of one or more compounds of claim 1 in combination with a pharmaceutically acceptable carrier.

9. A pharmaceutical composition comprising a therapeutically effective amount of one or more compounds of claim 1, in combination with a pharmaceutically acceptable carrier and one or more pharmaceutical agents.

10. The pharmaceutical composition of claim 9, wherein said pharmaceutical agent is selected from the group consisting of PPAR agonists, sulfonylurea drugs, non-sulfonylurea secretagogues, α-glucosidase inhibitors, insulin sensitizers, insulin secretagogues, hepatic glucose output lowering compounds, insulin, anti-obesity agents, HMG CoA reductase inhibitors, nicotinic acid, bile acid sequestrants, fibric acid derivatives, and anti-hypertensive agents.

11. A composition comprising an effective amount of one or more compounds of claim 1 in combination with an inert carrier.

12. A method of treating diabetes comprising the step of administering to a subject in need thereof a therapeutically effective amount of a compound of claim 1, wherein said diabetes is selected from the group consisting of type 1 diabetes, type 2 diabetes, maturity-onset diabetes of the young, latent autoimmune diabetes adult, and gestational diabetes.

13. A method of treating Syndrome X comprising the step of administering to a subject in need thereof a therapeutically effective amount of a compound of claim 1.

14. A method of treating diabetes-related disorders comprising the step of administering to a subject in need thereof a therapeutically effective amount of a compound of claim 1, wherein said diabetes-related disorder is selected from the group consisting of hyperglycemia, hyperinsulinemia, impaired glucose tolerance, impaired fasting glucose, dyslipidemia, hypertriglyceridemia, and insulin resistance.

15. A method of treating obesity comprising the step of administering to a subject in need thereof a therapeutically effective amount of a compound of claim 1.

16. A method of treating cardiovascular diseases comprising the step of administering to a subject in need thereof a therapeutically effective amount of a compound of claim 1, wherein said cardiovascular disease is selected from the group consisting of atherosclerosis, coronary heart disease, coronary artery disease and hypertension.

17. A method of treating diabetes comprising the step of administering to a subject in need thereof a therapeutically effective amount of a compound of claim 1 in combination with one or more pharmaceutical agents, wherein said diabetes is selected from the group consisting of type 1 diabetes, type 2 diabetes, maturity-onset diabetes of the young, latent autoimmune diabetes adult, and gestational diabetes.

18. The method of claim 17, wherein said pharmaceutical agent is selected from the group consisting of PPAR agonists, sulfonylurea drugs, non-sulfonylurea secretagogues, α-glucosidase inhibitors, insulin sensitizers, insulin secretagogues, hepatic glucose output lowering compounds, insulin, and anti-obesity agents.

19. A method of treating Syndrome X comprising the step of administering to a subject in need thereof a therapeutically effective amount of a compound of claim 1 in combination with one or more pharmaceutical agents.

20. The method of claim 19, wherein said pharmaceutical agent is selected from the group consisting of PPAR agonists, sulfonylurea drugs, non-sulfonylurea secretagogues, α-glucosidase inhibitors, insulin sensitizers, insulin secretagogues, hepatic glucose output lowering compounds, insulin, and anti-obesity agents.

21. A method of treating diabetes-related disorders comprising the step of administering to a subject in need thereof a therapeutically effective amount of a compound of claim 1 in combination with one or more pharmaceutical agents, wherein said diabetes-related disorder is selected from the group consisting of hyperglycemia, hyperinsulinemia, impaired glucose tolerance, impaired fasting glucose, dyslipidemia, hypertriglyceridemia, and insulin resistance.

22. The method of claim 21, wherein said pharmaceutical agent is selected from the group consisting of PPAR agonists, sulfonylurea drugs, non-sulfonylurea secretagogues, α-glucosidase inhibitors, insulin sensitizers, insulin secretagogues, hepatic glucose output lowering compounds, insulin, and anti-obesity agents.

23. A method of treating diabetes, Syndrome or diabetes-related disorders comprising the step of administering to a subject in need thereof a therapeutically effective amount of a compound of claim 1 in combination with one or more agents selected from the group consisting of HMG CoA reductase inhibitors, nicotinic acid, bile acid sequestrants, fibric acid derivatives, and anti-hypertensive agents, wherein said diabetes is selected from the group consisting of type 1 diabetes, type 2 diabetes, maturity-onset diabetes of the young, latent autoimmune diabetes adult, and gestational diabetes, and said diabetes-related disorder is selected from the group consisting of hyperglycemia, hyperinsulinemia, impaired glucose tolerance, impaired fasting glucose, dyslipidemia, hypertriglyceridemia, and insulin resistance.

24. The method of any one of claims 17, 18, 19 to 21, 22 and 23, wherein the compound of claim 1 and one or more pharmaceutical agents are administered as a single pharmaceutical dosage formulation.

25. A method of stimulating insulin secretion in a subject in need thereof by administering to said subject a compound of claim 1.

26. Compounds according to claim 1 for the treatment of diabetes and diabetes-related disorders, wherein said diabetes is selected from the group consisting of type 1 diabetes, type 2 diabetes, maturity-onset diabetes of the young, latent autoimmune diabetes adult, and gestational diabetes, and said diabetes-related disorder is selected from the group consisting of hyperglycemia, hyperinsulinemia, impaired glucose tolerance, impaired fasting glucose, dyslipidemia, hypertriglyceridemia, and insulin resistance.

27. Medicaments containing at least one or more compounds according to claim 1 in combination with at least one pharmaceutically acceptable, pharmaceutically safe carrier or excipient.

28. Medicaments according to claim 27 for the treatment of diabetes, wherein said diabetes is selected from the group consisting of type 1 diabetes, type 2 diabetes, maturity-onset diabetes of the young, latent autoimmune diabetes adult, and gestational diabetes.

29. A compound having the structure of

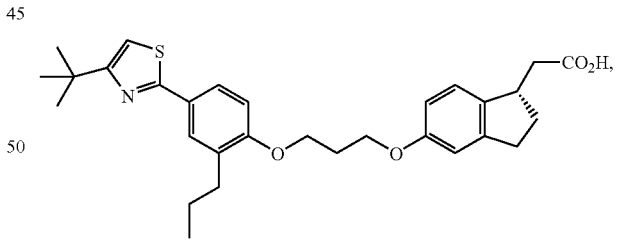

or a pharmaceutically acceptable salt thereof.

30. A method of treating diabetes comprising the step of administering to a subject in need thereof a therapeutically effective amount of a compound of claim 29, wherein said diabetes is selected from the group consisting of type 1 diabetes, type 2 diabetes, maturity-onset diabetes of the young, latent autoimmune diabetes adult, and gestational diabetes.

31. A method of treating Syndrome X comprising the step of administering to a subject in need thereof a therapeutically effective amount of a compound of claim 29.

32. A method of treating diabetes-related disorders comprising the step of administering to a subject in need thereof a therapeutically effective amount of a compound of claim 29, wherein said diabetes-related disorder is selected from the group consisting of hyperglycemia, hyperinsulinemia, impaired glucose tolerance, impaired fasting glucose, dyslipidemia, hypertriglyceridemia, and insulin resistance.

33. A method of treating obesity comprising the step of administering to a subject in need thereof a therapeutically effective amount of a compound of claim 29.

34. A method of treating cardiovascular diseases comprising the step of administering to a subject in need thereof a therapeutically effective amount of a compound of claim 29, wherein said cardiovascular disease is selected from the group consisting of atherosclerosis, coronary heart disease, coronary artery disease and hypertension.

* * * * *